(12) United States Patent  
Tyndall et al.

(10) Patent No.: US 9,060,515 B2
(45) Date of Patent: Jun. 23, 2015

(54) HETEROCYCLIC UREA COMPOUNDS

(71) Applicant: BIOTA EUROPE LTD, Yarntown (GB)

(72) Inventors: Edward Malcolm Tyndall, Notting Hill (AU); Lloyd George Czaplewski, Abingdon (GB); Colin William Gordon Fishwick, Leeds (GB); Andrew Ian Yule, Leeds (GB); Jeffrey Peter Mitchell, Notting Hill (AU); Kelly Helen Anderson, Notting Hill (AU); Gary Robert William Pitt, Notting Hill (AU)

(73) Assignee: Biota Europe Ltd., Yarnton, Oxfordshire (GB)

( * ) Notice: Subject to any disclaimer, the term of this patent is extended or adjusted under 35 U.S.C. 154(b) by 0 days.

(21) Appl. No.: 14/365,948

(22) PCT Filed: Dec. 21, 2012

(86) PCT No.: PCT/AU2012/001579
§ 371 (c)(1),
(2) Date: Jun. 16, 2014

(87) PCT Pub. No.: WO2013/091011
PCT Pub. Date: Jun. 27, 2013

(65) Prior Publication Data
US 2014/0323486 A1 Oct. 30, 2014

Related U.S. Application Data

(60) Provisional application No. 61/578,385, filed on Dec. 21, 2011.

(51) Int. Cl.
| | |
|---|---|
| *C07D 401/12* | (2006.01) |
| *C07D 213/80* | (2006.01) |
| *C07D 233/96* | (2006.01) |
| *A61K 31/44* | (2006.01) |
| *A61K 31/495* | (2006.01) |
| *A01N 47/36* | (2006.01) |
| *C07D 401/14* | (2006.01) |
| *C07D 413/14* | (2006.01) |
| *C07F 9/58* | (2006.01) |
| *C07D 413/12* | (2006.01) |
| *C07D 417/12* | (2006.01) |
| *C07D 213/75* | (2006.01) |
| *C07D 213/82* | (2006.01) |
| *C07D 237/24* | (2006.01) |
| *C07D 405/12* | (2006.01) |
| *C07D 239/42* | (2006.01) |
| *C07D 239/48* | (2006.01) |
| *C07D 471/04* | (2006.01) |
| *A01N 47/30* | (2006.01) |

(52) U.S. Cl.
CPC .............. *A01N 47/36* (2013.01); *C07D 401/14* (2013.01); *C07D 413/14* (2013.01); *C07D 213/80* (2013.01); *C07F 9/588* (2013.01); *C07D 401/12* (2013.01); *C07D 413/12* (2013.01); *C07D 417/12* (2013.01); *C07D 213/75* (2013.01); *C07D 213/82* (2013.01); *C07D 237/24* (2013.01); *C07D 405/12* (2013.01); *C07D 239/42* (2013.01); *C07D 239/48* (2013.01); *C07D 471/04* (2013.01); *A01N 47/30* (2013.01)

(58) Field of Classification Search
None
See application file for complete search history.

(56) References Cited

U.S. PATENT DOCUMENTS 6,727,250 B2   4/2004   Hauel et al.
7,262,220 B2   8/2007   Defossa et al.

OTHER PUBLICATIONS

International Search Report and Written Opinion mailed Feb. 4, 2013, for PCT/AU2012/001579.

*Primary Examiner* — Zinna Northington Davis
(74) *Attorney, Agent, or Firm* — Banner & Witcoff, Ltd.

(57) ABSTRACT

The present invention provides a compound of the following formula, racemates, enantiomers and salts thereof. Also provided is the use of these compounds as antibacterials, compositions comprising them and processes for their manufacture.

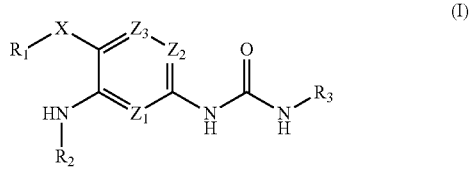

(I)

18 Claims, No Drawings

HETEROCYCLIC UREA COMPOUNDS

CROSS-REFERENCE TO RELATED APPLICATIONS

The present application is a U.S. National Phase filing of International Application No. PCT/AU2012/001579, filed on Dec. 21, 2012, designating the United States of America and claiming priority to U.S. provisional application 61/578,385 filed Dec. 21, 2011, and this application claims priority to and the benefit of the above-identified applications, which are both incorporated by reference herein in their entireties.

FIELD OF THE INVENTION

The present invention relates to a novel class of compounds, their use as antibacterials, compositions comprising them and processes for their manufacture.

BACKGROUND

Type II topoisomerases catalyse the interconversion of DNA topoisomers by transporting one DNA segment through another. Bacteria encode two type II topoisomerase enzymes, DNA gyrase and DNA topoisomerase IV. Gyrase controls DNA supercoiling and relieves topological stress. Topoisomerase IV decatenates daughter chromosomes following replication and can also relax supercoiled DNA. Bacterial type II topoisomerases form a heterotetrameric complex composed of two subunits. Gyrase forms an $A_2B_2$ complex comprised of GyrA and GyrB whereas topoisomerase forms a $C_2E_2$ complex comprised of ParC and ParE. In contrast eukaryotic type II topoisomerases are homodimers. Ideally, an antibiotic based on the inhibition of bacterial type II topoisomerases would be selective for the bacterial enzymes and be relatively inactive against the eukaryotic type II isomerases. The type II topoisomerases are highly conserved enzymes allowing the design of broad-spectrum inhibitors. Furthermore, the GyrB and ParE subunits are functionally similar, having an ATPase domain in the N-terminal domain and a C-terminal domain that interacts with the other subunit (GyrA and ParC respectively) and the DNA. The conservation between the gyrase and topoisomerase IV active sites suggests that inhibitors of the sites might simultaneously target both type II topoisomerases. Such dual-targeting inhibitors are attractive because they have the potential to reduce the development of target-based resistance.

Type II topoisomerases are the target of a number of antibacterial agents. The most prominent of these agents are the quinolones. The original quinolone antibiotics included nalidixic acid, cinoxacin and oxolinic acid. The addition of fluorine yielded a new class of drugs, the fluoroquinolones, which have a broader antimicrobial spectrum and improved pharmacokinetic properties. The fluoroquinolones include norfloxacin, ciprofloxacin, and fourth generation quinolones gatifloxacin and moxifloxacin. The coumarins and the cyclothialidines are further classes of antibiotics that inhibit type II topoisomerases, however they are not widely used because of poor permeability in bacteria, eukaryotic toxicity, and low water solubility. Examples of such antibiotics include novobiocin and coumermycin A1, cyclothialidine, cinodine, and clerocidin. However, the continual emergence of antibiotic resistance demands that novel classes of antibiotics continue to be developed and alternative compounds that inhibit bacterial topoisomerases are required.

SUMMARY

According to a first aspect there is provided a compound of formula (I), racemates, enantiomers and salts thereof:

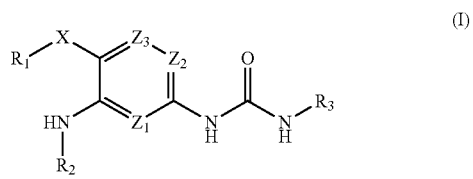

wherein
X is selected from $C(=X_1)$, $S(=O)$ and $SO_2$;
$X_1$ is selected from O, S and $NR_4$;
$R_1$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl, $CR_5(R_6)_2$, $NR_4SO_2R_5$, $OR_6$, $SR_6$, $NH_2$, $NR_5R_6$ and $NR^aR^b$ where $R^a$ and $R^b$ join with the N to which they are attached to form an optionally substituted 5-10 membered heterocyclic ring;
$R_2$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;
$R_3$ is an optionally substituted $C_{1-6}$alkyl;
$R_4$ is H or an optionally substituted $C_{1-6}$alkyl;
$R_5$ is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;
Each $R_6$ is H or is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;
t is an integer selected from 0, 1, 2 and 3 preferably 0, 1 or 2 and wherein each $(CH_2)_t$ when present may be independently optionally substituted;
$Z_1$, $Z_2$ and $Z_3$ are each independently selected from $CR_7$ and N where $R_7$ is selected from H, halo or an optional substituent and further where at least one of $Z_1$, $Z_2$ or $Z_3$ is N; and
each cycloalkyl, cycloalkenyl, aryl, heterocyclyl and heteroaryl ring may be a monocyclic or fused bicyclic ring system.

In one embodiment X is $C(=X_1)$, $X_1$ is selected from O, S and $NR_4$, preferably O, and $R_1$ is selected from $NH_2$, $NR_5R_6$ and $NR^aR^b$, preferably $NR_5R_6$ and $NR^aR^b$. In a particularly preferred embodiment, $R_1$ is $NR_5R_6$ and in an even more preferred embodiment $R_6$ is H or $C_{1-6}$alkyl.

In another embodiment, $R_3$ is optionally substituted $C_{1-3}$alkyl with unsubstituted ethyl being particularly preferred.

According to a second aspect there is provided a method for the treatment of a bacterial infection comprising administration of a compound of Formula I, racemates, enantiomers or pharmaceutically acceptable salts thereof to a subject suffering from said infection. In one embodiment, the infection is a Gram positive bacterial infection. In a further embodiment the Gram positive infection is caused by a bacterial strain selected from *S. aureus*, *E. faecalis* and *S. pyogenes*, even more preferably *S. aureus*. In another embodiment, the infection is a Gram negative bacterial infection. In a further embodiment the Gram negative infection is caused by a bacterial strain of *H. influenzae*. According to a third aspect there is provided a compound of Formula I, racemates, enantiomers or pharmaceutically acceptable salts thereof for use in the treatment of a bacterial infection.

According to a fourth aspect there is provided an antibacterial agent comprising a compound of Formula I, racemates, enantiomers or pharmaceutically acceptable salts thereof.

According to a fifth aspect there is provided a composition comprising a compound of Formula I, racemates, enantiomers or salts thereof and an excipient or carrier. In one embodiment the composition is a pharmaceutical composition, the salt is a pharmaceutically acceptable salt and the excipient or carrier is a pharmaceutically acceptable excipient or carrier.

According to a sixth aspect there is provided a compound of Formula I, racemates, enantiomers or pharmaceutically acceptable salts thereof for use as a gyrase inhibitor. In one embodiment the compound of formula I is active against the ATPase enzyme. According to a seventh aspect there is provided a process for the manufacture of a compound of Formula I via an intermediate of general formula (II):

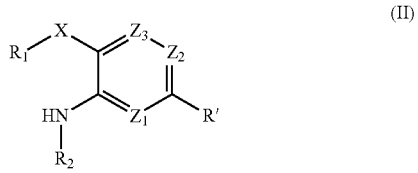

where R' is a halo or $NH_2$ group; or
via an intermediate of general formula (III):

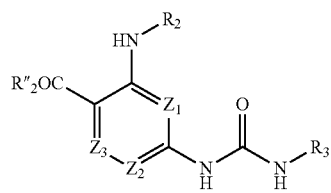

where R" is H or $C_{1-6}$alkyl; or
via an intermediate of general formula (IV):

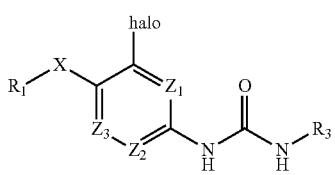

wherein X, $R_1$, $R_2$, $R_3$, $Z_1$, $Z_2$ and $Z_3$ in the case of formulae (II), (III) and (IV) are as defined for formula (I).

According to an eighth aspect, there is provided a method of treating bacterial contamination of a substrate comprising applying to the site of such contamination an amount of a compound of Formula I racemates, enantiomers or pharmaceutically acceptable salts thereof sufficient to inhibit bacterial growth.

According to a ninth aspect, there is provided the use of a compound of Formula I, racemates, enantiomers or pharmaceutically acceptable salts thereof in the preparation of a medicament for the treatment of a bacterial infection in a subject.

DETAILED DESCRIPTION

The present invention is predicated on the discovery of a new class of compounds that have shown on-target gyrase enzyme activity. Accordingly, in one embodiment the compounds of Formula I are useful in modulating the activity of gyrase, more particularly as gyrase inhibitors.

Compounds of this class also exhibit antibacterial activity more particularly antibacterial activity against strains of Gram-positive and/or Gram-negative classes, such as staphylococci, enterococci, streptococci and haemophili for example *Staphylococcus aureus, Enterococcus faecalis, Streptococcus pyogenes* and *Haemophilus influenzae*. The compounds with which the invention is concerned are therefore useful for the treatment of bacterial infection or contamination, for example in the treatment of, inter alia, Gram-positive infections and community acquired pneumonias. Accordingly, in one embodiment the compounds of Formula (I) are useful in the treatment of bacterial infections caused by Gram positive bacterial strains.

In another embodiment, the compounds of Formula (I) are useful in the treatment of bacterial infections caused by Gram negative bacterial strains.

The development of antibacterial resistance is particularly common in a hospital setting. Hospital patients are therefore especially at risk of infection by resistant strains of bacteria.

DEFINITIONS

The term "$C_{1-6}$alkyl" encompasses optionally substituted straight chain or branched chain hydrocarbon groups having from 1, 2, 3, 4, 5 or 6 carbon atoms or a range comprising any of two of those integers. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. Such groups are also referred to as "$C_{1-6}$alkylene" groups. $C_{1-3}$alkyl and $C_{1-3}$alkylene groups are preferred. The term "$C_{2-6}$ alkenyl" refers to optionally substituted straight chain or branched chain hydrocarbon groups having at least one double bond of either E or Z stereochemistry where applicable and 2, 3, 4, 5 or 6 carbon atoms or a range comprising any of two of those integers. Examples include vinyl, 1-propenyl, 1- and 2-butenyl, 2-methyl-2-propenyl, hexenyl, butadienyl, hexadienyl, hexatrienyl and the like. Unless the context requires otherwise, the term "$C_{1-6}$ alkenyl" also encompasses alkenyl groups containing one less hydrogen atom such that the group is attached via two positions i.e. divalent. Such groups are also referred to as "$C_{2-6}$alkenylene" groups. $C_{2-3}$alkenyl and $C_{2-3}$alkenylene groups are preferred.

The term "$C_{2-6}$ alkynyl" refers to optionally substituted straight chain or branched chain hydrocarbon groups having at least one triple bond and 2, 3, 4, 5 or 6 carbon atoms or a range comprising any of two of those integers. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and the like. Unless the context indicates otherwise, the term "$C_{2-6}$alkynyl" also encompasses alkynyl groups containing one less hydrogen atom such that the group is attached via two positions i.e.

divalent. Such groups are also referred to as "$C_{2-6}$alkynylene" groups. $C_{2-3}$alkynyl and $C_{2-3}$alkynylene groups are preferred.

The term "$C_{3-8}$cycloalkyl" refers to non-aromatic cyclic hydrocarbon groups having from 3, 4, 5, 6, 7 or 8 carbon atoms or a range comprising any of two of those integers including cyclopropyl, cyclobutyl, cyclopentyl, cyclohexyl, cyclohexenyl, cycloheptyl and the like. It will be understood that cycloalkyl groups may be saturated such as cyclohexyl or unsaturated such as cyclohexenyl. $C_{3-6}$cycloalkyl groups are preferred.

The terms "hydroxy" and "hydroxyl" refer to the group —OH.

The term "oxo" refers to the group =O.

The term "$C_{1-6}$alkoxyl" refers to the group $OC_{1-6}$alkyl. Examples include methoxy, ethoxy, propoxy, isoproxy, butoxy, tert-butoxy, pentoxy and the like. The oxygen atom may be located along the hydrocarbon chain, and need not be the atom linking the group to the remainder of the compound. $C_{1-3}$alkoxyl groups are preferred.

The term "aryloxy" refers to the group —Oaryl and may include variations thereof such as "alkoxyaryl", wherein aryl is defined herein. Examples include, but are not limited to, phenoxy and naphthoxy and benzyloxy.

The terms "halo", "halogen", "halogenated" and similar terms refers to fluoro, chloro, bromo and iodo (F, Cl, Br, I).

The term "$C_{1-6}$alkylhalo" refers to a $C_{1-6}$alkyl which is substituted with one or more halogens. $C_{1-3}$alkylhalo groups are preferred, such as for example, —$CHF_2$ and —$CF_3$.

The term "$C_{1-6}$alkoxylhalo" refers to a $C_{1-6}$alkoxyl which is substituted with one or more halogens. $C_{1-3}$alkoxylhalo groups are preferred, such as for example, —$OCHF_2$ and —$OCF_3$.

The term "carboxylate" or "carboxyl" refers to the group —COO⁻ or —COOH.

The term "ester" refers to a carboxyl group having the hydrogen replaced with, for example a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "cyano" refers to the group —CN.

The term "nitro" refers to the group —$NO_2$.

The term "amino" refers to the group —$NH_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino", "aralkylamino") and so on. $C_{1-3}$alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_{1-6}$alkyl group, which may be the same or different ("dialkylamino"), an aryl and alkyl group ("aryl(alkyl)amino") and so on. Di($C_{1-3}$alkyl)amino groups are preferred, such as for example, dimethylamino ($NMe_2$), diethylamino ($NEt_2$), dipropylamino ($NPr_2$) and variations thereof (e.g. N(Me)(Et) and so on).

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "alkylketone" or "ketoalkyl"), an aryl group ("arylketone"), an aralkyl group ("aralkylketone") and so on. $C_{1-3}$alkylacyl groups are preferred.

The term "amido" or "amide" refers to the group —C(O)$NH_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyl)amido") or "di($C_{1-6}$alkyl)amide"), an aralkyl and alkyl group ("alkyl(aralkyl)amido") and so on. Di($C_{1-3}$alkyl)amide groups are preferred, such as for example, dimethylamide (—C(O)$NMe_2$), diethylamide (—C(O)$NEt_2$) and dipropylamide (—C(O)$NPr_2$) and variations thereof (e.g. —C(O)N(Me)Et and so on) and includes reverse amides thereof.

The term "thiol" refers to the group —SH.

The term "$C_{1-6}$alkylthio" refers to a thiol group having the hydrogen replaced with a $C_{1-6}$ alkyl group. $C_{1-3}$alkylthio groups are preferred, such as for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —$SO_2NH_2$.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2Me$, —$SO_2Et$ and —$SO_2Pr$.

The term "sulfonylamido" or "sulfonamide" refers to the group —$SO_2NH_2$.

The term "substituted sulfonamido" or "substituted sulphonamide" refers to a sulfonylamido group having a hydrogen replaced with, for example a $C_{1-6}$alkyl group ("sulfonylamido$C_{1-6}$alkyl"), an aryl ("arylsulfonamide"), aralkyl ("aralkylsulfonamide") and so on. Sulfonylamido$C_{1-3}$alkyl groups are preferred, such as for example, —$SO_2NHMe$, —$SO_2NHEt$ and —$SO_2NHPr$ and includes reverse sulfonamides thereof (e.g. —$NHSO_2Me$, —$NHSO_2Et$ and —$NHSO_2Pr$).

The term "disubstituted sulfonamido" or "disubstituted sulphonamide" refers to a sulfonylamido group having the two hydrogens replaced with, for example a $C_{1-6}$alkyl group, which may be the same or different ("sulfonylamidodi($C_{1-6}$alkyl)"), an aralkyl and alkyl group ("sulfonamido(aralkyl)alkyl") and so on. Sulfonylamidodi($C_{1-3}$alkyl) groups are preferred, such as for example, —$SO_2NMe_2$, —$SO_2NEt_2$ and —$SO_2NPr_2$ and variations thereof (e.g. $SO_2N(Me)Et$ and so on) and includes reserve sulfonamides thereof.

The term "sulfate" refers to the group $OS(O)_2OH$ and includes groups having the hydrogen replaced with, for example a C$_{1-6}$alkyl group ("alkylsulfates"), an aryl ("arylsulfate"), an aralkyl ("aralkylsulfate") and so on. C$_{1-3}$sulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a C$_{1-6}$alkyl group ("alkylsulfonate"), an aryl ("arylsulfonate"), an aralkyl ("aralkylsulfonate") and so on. C$_{1-3}$sulfonates are preferred, such as for example, SO$_3$Me, SO$_3$Et and SO$_3$Pr.

The term "phosphate" refers to a group OP(O)(OH)$_2$ and includes groups having each hydrogen independently replaced with, for example a C$_{1-6}$alkyl group ("alkylphosphate"), an aryl ("arylphosphate"), an aralkyl ("aralkylphosphate") and so on.

The term "phosphonate" refers to a group P(O)(OH)$_2$ and includes groups having each hydrogen independently replaced with, for example a C$_{1-6}$alkyl group ("alkylphosphonate"), an aryl ("arylphosphonate"), an aralkyl ("aralkylphosphpmate") and so on.

The term "aryl" refers to any group containing a carbocyclic (non-heterocyclic) aromatic ring and may be a mono-, bi- or tri-cyclic ring system. The aromatic ring or ring system is generally composed of 6 or 10 carbon atoms. Such groups may contain fused ring systems (such as naphthyl, tetrahydronaphthyl, fluorenyl, indenyl, azulenyl, anthracenyl and the like), linked ring systems (such as biphenyl groups), and may be substituted or unsubstituted. Examples of aryl groups include, but are not limited to, phenyl, biphenyl, naphthyl and tetrahydronaphthyl. Phenyl is preferred.

The term "aralkyl" refers to an aryl group substituted with a C$_{1-6}$alkyl group. Examples include benzyl and phenethyl.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixs 3-, 4-, 5-, 6-, 7-, 8-, 9- and 10-membered denote the number of ring atoms, or range of ring atoms, whether carbon atoms or heteroatoms. For example, the term "3-10 membered heterocylyl", as used herein, pertains to a heterocyclyl group having 3, 4, 5, 6, 7, 8, 9 or 10 ring atoms or a range comprising any of two of those integers. Examples of heterocylyl groups include 5-6-membered monocyclic heterocyclyls and 9-10 membered fused bicyclic heterocyclyls. Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulfur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like. Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered heteroaryl groups containing nitrogen include pyridyl (1 nitrogen), pyrazinyl, pyrimidinyl and pyridazinyl (2 nitrogens). It will be understood that, such as in the case of pyridyl when substituted with an oxo (=O) substituted the group may be interchangably referred to as a pyridinone group.

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphthyl, indenyl, azulenyl, fluorenyl, anthracenyl and the like, such as 5- or 6-membered aromatic heterocyclyls fused to a phenyl ring including 5-membered aromatic heterocyclyls containing nitrogen fused to a phenyl ring, 5-membered aromatic heterocyclyls containing 1 or 2 nitrogens fused to a phenyl ring and such as 5- or 6-membered aromatic heteroaryls fused to a 6-membered aromatic or non-aromatic heterocyclyls.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring i.e. 8-membered fused bicyclic rings include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring i.e. 9-membered fused bicyclic rings include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, imidazopyridine (e.g. imidazo[1,2-a]pyridine and imidazo[4,5-b]pyridine], pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings i.e. 10-membered fused bicyclic rings include but are not limited to quinoline, isoquinoline, chroman, thiochroman, chromene (including optionally substituted with oxo (=O) i.e. oxochromene), isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]-dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered monocyclic rings. The term "3-7 membered monocyclic", as used herein, pertains to a mono-cyclic group having 3, 4, 5, 6 or 7 ring atoms or a range comprising any of two of those integers. Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, naphthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl (including straight chain and branched $C_{1-6}$alkyl and further including $C_{1-6}$alkyl incorporating a $C_{3-6}$cycloalkyl moiety within the chain or as a spiro substituent), $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, mono substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, phosphates, phosphonates, aryl, arylC$_{1-6}$alkyl, heterocyclyl and heteroaryl wherein each alkyl, alkenyl, alkynyl, cycloalkyl, aryl and heterocyclyl and groups containing them may be further optionally substituted.

Optional substituents in the case of heterocycles containing N may also include but are not limited to alkyl i.e. N—C$_{1-3}$alkyl, more preferably methyl, particularly N-methyl. It will be understood that suitable derivatives of aromatic heterocyclyls containing nitrogen include N-oxides thereof.

Embodiments will now be described.

In one embodiment C$_{3-10}$cycloalkyl groups (and groups comprising them) are selected from optionally substituted cyclopropyl, optionally substituted cyclobutyl, optionally substituted cyclopentyl and optionally substituted cyclohexyl.

In one embodiment C$_{6-10}$aryl groups (and groups comprising them) are selected from optionally substituted phenyl and optionally substituted naphthyl with optionally substituted phenyl being particularly preferred.

In one embodiment, 5-10 membered heterocycles (and groups comprising them) are selected from optionally substituted 5-membered moncyclic heterocyclyls, optionally substituted 6-membered monocyclic heterocyclyls, optionally substituted 9-membered fused bicyclic heterocyclyls and optionally substituted 10-membered fused bicyclic heterocyclyls and in each case the heterocyclyl contains at least one heteroatom selected from O, N or S. Examples of 5-, 6-, 9- and 10-membered heterocyclyls includes those as previously defined.

In one embodiment, 5-10 membered heteroaryls (and groups comprising them) are selected from optionally substituted 5-membered moncyclic heteroaryls, optionally substituted 6-membered monocyclic heteroaryls, optionally substituted 9-membered fused bicyclic heteroaryls and optionally substituted 10-membered fused bicyclic heteroaryls and in each case the heteroaryl contains at least one heteroatom selected from O, N or S. Examples of 5-, 6-, 9- and 10-membered heteroaryls include those as previously defined.

In one embodiment the compound is of formula (Ia):

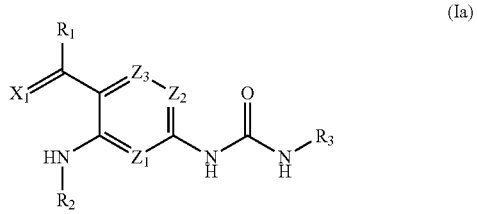

(Ia)

wherein
$X_1$ is selected from O, S or NR$_4$, preferably $X_1$ is O;
$R_1$ is selected from NH$_2$, NR$_5$R$_6$ and NR$^a$R$^b$ where R$^a$ and R$^b$ join with the N to which they are attached to form an optionally substituted 5-10 membered heterocyclic ring, preferably a 5- or 6-membered heterocyclic ring;
$R_2$ is optionally substituted and selected from C$_{1-6}$alkyl, C$_{2-6}$alkenyl, C$_{2-6}$alkynyl, (CH$_2$)$_t$C$_{3-10}$cycloalkyl, (CH$_2$)$_t$C$_{3-10}$cycloalkenyl, (CH$_2$)$_t$C$_{6-10}$aryl, (CH$_2$)$_t$3-10-membered heterocyclyl and (CH$_2$)$_t$5-10-membered heteroaryl;
$R_3$ is an optionally substituted C$_{1-6}$alkyl, preferably C$_{1-3}$alkyl, particularly ethyl;
$R_4$ is H or an optionally substituted C$_{1-6}$alkyl;

$R_5$ is optionally substituted and selected from C$_{1-6}$alkyl, C$_{1-6}$alkoxyl, C$_{2-6}$alkenyl, C$_{2-6}$alkynyl, (CH$_2$)$_t$C$_{3-10}$cycloalkyl, (CH$_2$)$_t$C$_{3-10}$cycloalkenyl, (CH$_2$)$_t$C$_{6-10}$aryl, (CH$_2$)$_t$3-10-membered heterocyclyl and (CH$_2$)$_t$5-10-membered heteroaryl;
$R_6$ is H or is optionally substituted and selected from C$_{1-6}$alkyl, C$_{1-6}$alkoxyl, C$_{2-6}$alkenyl, C$_{2-6}$alkynyl, (CH$_2$)$_t$C$_{3-10}$cycloalkyl, (CH$_2$)$_t$C$_{3-10}$cycloalkenyl, (CH$_2$)$_t$C$_{6-10}$aryl, (CH$_2$)$_t$3-10-membered heterocyclyl and (CH$_2$)$_t$5-10-membered heteroaryl; preferably $R_6$ is H or optionally substituted C$_{1-6}$alkyl, more preferably H or optionally substituted C$_{1-3}$alkyl and most preferably H;
t is an integer selected from 0, 1, 2 and 3 preferably 0, 1 or 2 and wherein each (CHA when present may be independently optionally substituted;
$Z_1$, $Z_2$ and $Z_3$ are each independently selected from CR$_7$ and N where each $R_7$ is independently selected from H, halo or an optional substituent and further where at least one of $Z_1$, $Z_2$ or $Z_3$ is N.

In a further embodiment one of $Z_1$, $Z_2$ or $Z_3$ is N and the two remaining are each CR$_7$ where each $R_7$ is independently selected from selected from H, halo or an optional substituent and in a particularly preferred embodiment each $R_7$ is H.

In a further preferred embodiment $Z_1$ or $Z_2$ is N, preferably $Z_2$ is N.

In yet another particular embodiment $Z_2$ is N and $Z_1$ and $Z_3$ are each CR$_7$ where each $R_7$ is independently selected from selected from H, halo or an optional substituent and in a particularly preferred embodiment each $R_7$ is H. In an alternative embodiment, $Z_1$ is CH, $Z_2$ is CH and $Z_3$ is N.

In still another embodiment, two of $Z_1$, $Z_2$ or $Z_3$ are N and the one remaining is CR$_7$ where $R_7$ is independently selected from selected from H, halo or an optional substituent and in a particularly preferred embodiment $R_7$ is H. In a further embodiment, $Z_1$ and $Z_2$ are both N and $Z_3$ is CH. In an alternative embodiment, $Z_1$ is N, $Z_2$ is CH and $Z_3$ is N. In still another alternative embodiment, $Z_1$ is CH, $Z_2$ is N and $Z_3$ is N.

In one embodiment $R_2$ is optionally substituted and selected from (CH$_2$)$_t$C$_{3-10}$cycloalkyl, (CH$_2$)$_t$C$_{3-10}$cycloalkenyl, (CH$_2$)$_t$C$_{6-10}$aryl, (CH$_2$)$_t$3-10-membered heterocyclyl and (CH$_2$)$_t$5-10-membered heteroaryl where t is 0 or 1. In a particular embodiment $R_2$ is selected from an optionally substituted C$_{3-10}$cycloalkyl (preferably C$_{3-6}$cycloalkyl more preferably C$_{5-6}$cycloalkyl), optionally substituted (CH$_2$)$_t$C$_{6-10}$aryl (preferably phenyl), optionally substituted 3-10-membered heterocyclyl (preferably 5-6-membered monocyclic rings and 9-10-membered bicyclic rings) and optionally substituted (CH$_2$)$_t$5-10-membered heteroaryl (preferably 5-6-membered monocyclic rings and 9-10 membered bicyclic rings) where t is 0 or 1.

In yet a further embodiment $R_2$ is selected from an optionally substituted cyclohexyl, an optionally substituted (CH$_2$)$_t$phenyl, an optionally substituted 5-6-membered heterocyclyl and an optionally substituted (CH$_2$)$_t$5-6-membered heteroaryl ring where t is 0 or 1.

In still another embodiment $R_2$ is an optionally substituted (CH$_2$)$_t$phenyl or an optionally substituted (CH$_2$)$_t$5-6-membered heteroaryl ring where t in each case is independently 0 or 1.

Particularly preferred (CH$_2$)$_t$5-membered heteroaryl rings include an optionally substituted pyrazolyl or an optionally substituted isoxazolyl.

Particularly preferred (CH$_2$)$_t$6-membered heteroaryl rings include an optionally substituted pyridyl, an optionally substituted CH$_2$pyridyl, an optionally substituted pyrimidinyl or an optionally substituted pyridinonyl.

In a particularly preferred embodiment $R_2$ is an optionally substituted phenyl.

In one embodiment $R_1$ is $NR_5R_6$.

In a further embodiment $R_5$ is optionally substituted and selected from $C_{1-3}$alkyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl where t is an integer 0, 1 or 2.

In another further embodiment $R_5$ is selected from an optionally substituted $C_{3-10}$cycloalkyl (preferably $C_{3-6}$cycloalkyl), optionally substituted $(CH_2)_tC_{6-10}$aryl (preferably $(CH_2)_t$phenyl), optionally substituted 3-10-membered heterocyclyl (preferably 5-6-membered monocyclic rings and 9-10-membered fused bicyclic rings) and optionally substituted $(CH_2)_t$5-10-membered heteroaryl (preferably $(CH_2)_t$5-6-membered monocyclic rings and $(CH_2)_t$9-10 membered fused bicyclic rings) where t is an integer 0, 1 or 2.

In yet a further embodiment $R_5$ is selected from an optionally substituted $C_{1-3}$alkyl, an optionally substituted $C_{3-6}$cycloalkyl, an optionally substituted $(CH_2)_t$phenyl, an optionally substituted 5-6-membered heterocyclyl, an optionally substituted $(CH_2)_t$5-6-membered heteroaryl ring and an optionally substituted 9-10-membered heteroaryl ring where t is an integer 0, 1 or 2.

In a particular embodiment $R_5$ is optionally substituted and is selected from phenyl, $CH_2$-phenyl, $CH_2CH_2$-phenyl, 5-membered heterocyclyl, 6-membered heterocyclyl, 5-membered heteroaryl, 6-membered heteroaryl, $CH_2$6-membered heteroaryl, 9-membered heteroaryl and 10-membered heteroaryl.

In still another embodiment $R_2$ and $R_5$ are each independently selected from an optionally substituted $(CH_2)_t$phenyl, an optionally substituted $(CH_2)_t$5-6-membered heterocyclyl, an optionally substituted $(CH_2)_t$5-6-membered heteroaryl ring and an optionally substituted $(CH_2)_t$9-10-membered heteroaryl ring where t is an integer 0, 1 or 2 preferably 0 or 1 and $R_6$ is H.

In another embodiment $R_1$ is $NR^aR^b$.

In a further embodiment when $R_1$ is $NR^aR^b$, $R^a$ and $R^b$ join with the N to which they are attached to form an optionally substituted 5- or 6-membered heterocyclic ring. In a particular embodiment $NR^aR^b$ forms an optionally substituted 6-membered heterocyclic ring, for example, such as an optionally substituted piperidine, an optionally substituted piperazine or an optionally substituted morpholine.

Suitable optional substituents in the case of $R_1$ (including $R_5$, $R_6$ and $NR^aR^b$) and $R_2$ include, but are not limited to 1, 2, 3 or 4, preferably 1, 2 or 3 more preferably 1 or 2 optional substituents selected from $C_{1-6}$alkyl (including methyl, ethyl, propyl, isopropyl, butyl, iso-butyl, sec-butyl, tert-butyl, and the like, particularly methyl). $C_3$-$C_6$cycloalkyl, $C_{2-6}$alkenyl (including ethenyl, propenyl, butenyl and the like, particularly ethenyl), $C_{1-6}$alkoxy (including methoxy), aryloxy (including phenoxy), oxo (=O), hydroxy, halo (particularly Cl and F), $C_{1-6}$alkylhalo (including $CF_3$), $SF_5$, $C_1$-6alkoxyhalo (including $OCF_3$), $CO_2H$, $CO_2C_{1-6}$alkyl, $C(O)C_{1-6}$alkyl, cyano, $N_3$, $P(O)(OH)_2$, $P(O)(OC_{1-3}$alkyl$)_2$, $NHSO_2C_{1-3}$alkyl, $SO_2NH_2$, $SO_2NHC_{1-3}$alkyl, amino, substituted amino (including $NHC_{1-6}$alkyl), disubstituted amino (including $N(C_{1-6}$alkyl$)_2$), amido, substituted amido (including $C(O)NHC_{1-6}$alkyl and $NHC(O)C_{1-6}$alkyl), disubstituted amido (including $C(O)N(C_{1-6}$alkyl$)_2$ and $NC_{1-6}$alkyl$C(O)C_{1-6}$alkyl), $C(O)C_{1-6}$alkyl, phenyl, 4-6-membered heterocyclyl (particularly azetidinyl, pyrrolidinyl, morpholinyl, piperidinyl, piperazinyl and dioxidothiomorpholinyl) and 5-6-membered heteroaryl (particularly pyrrolyl, triazolyl, tetrazolyl, and pyridinyl) wherein each alkyl, alkenyl, alkoxy, aryloxy, phenyl, heterocyclyl and heteroaryl and groups containing them may be further optionally substituted with any one or more of the optional substituents as previously defined.

In one embodiment each alkyl, cycloalkyl, alkenyl, alkoxy, aryloxy, phenyl, heterocyclyl and heteroaryl and groups containing them may be further optionally substituted with one or more optional substituents, preferably 1, 2 or 3, more preferably 1 or 2 optional substituents, independently selected from $C_{1-3}$alkyl, halo (particularly Cl and F), hydroxyl, $CO_2H$, $CO_2C_{1-6}$alkyl (particularly $CO_2CH_3$ and $CO_2CH_2CH_3$), amido ($C(O)NH_2$), substituted amido (particularly $C(O)NHCH_3$) and disubstituted amido groups (particularly $C(O)N(CH_3)_2$).

In one embodiment the optional substituent is a straight chain or branched $C_{1-6}$alkyl (preferably $C_{1-4}$alkyl), a $C_{1-6}$alkyl incorporating a $C_{3-6}$cycloalkyl within the chain (preferably —CH-cyclopropyl-CH—), $NHC_{1-6}$alkyl, $C_{2-6}$alkenyl (preferably $C_{2-4}$alkenyl) or $C_{2-6}$alkynyl (preferably $C_3$alkenyl) which in each case may be further optionally substituted with a $C_{1-3}$alkyl, $C_{3-6}$cycloalkyl (preferably spirocycloalkyl such as spirocylobutyl), halo, hydroxyl, $CO_2H$, $CO_2C_{1-6}$alkyl, tetrazolyl, amido ($C(O)NH_2$), substituted amido (particularly $C(O)NHCH_3$) or disubstituted amido group (particularly $C(O)NH(CH_3)_2$). Particularly preferred examples of such optional substituents include the following: $(CH_2)_qOH$, $(CH_2)_qCO_2H$, $(CH_2)_qCO_2C_{1-3}$alkyl (particularly $(CH_2)_qCO_2CH_3$ and $(CH_2)_qCO_2CH_2CH_3$), $(CH_2)_q$tetrazolyl, $(CH_2)_qC(O)NH_2$, $(CH_2)_qC(O)NHCH_3$, $(CH_2)_qC(O)N(CH_3)_2$, $(CH_2)_qC(O)CH_3$, $(CH_2)_qC(O)N(CH_3)OCH_3$, $CH=CHCO_2H$, $CH=CHCO_2C_{1-3}$alkyl (particularly $CH=CHCO_2CH_3$ and $CH=CHCO_2CH_2CH_3$), $(CH_2)_qC(CH_3)_2CO_2H$, $(CH_2)_qC(CH_3)_2CO_2C_{1-3}$alkyl (particularly $(CH_2)_qC(CH_3)_2CO_2CH_3$ and $(CH_2)_qC(CH_3)_2CO_2CH_2CH_3$), $C≡CCH_2OH$ and $C≡CCHC_{1-3}$alkylOH (particularly $C≡CCHCH_3OH$); $C≡CC(C_{1-3}$alkyl$)_2OH$ (particularly $C≡CC(CH_3)_2OH$); $C_{1-3}$alkyl incorporating a $C_{3-6}$cycloalkyl substituted with $CO_2H$ or $CO_2C_{1-3}$alkyl (particularly

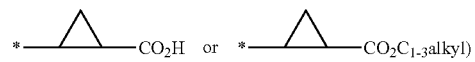

and $NHC_{1-6}$alkyl optionally substituted with a $C_{3-6}$cycloalkyl and $CO_2H$ or $CO_2C_{1-3}$alkyl (particularly

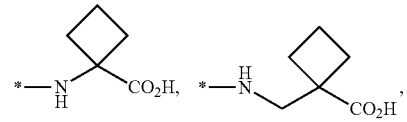

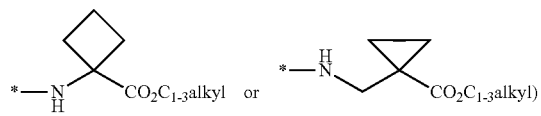

where * represents the point of attachment;

and where q is an integer independently selected from 1, 2 or 3, preferably 1 or 2.

Accordingly, in a further embodiment the compound is of formula (Ib)

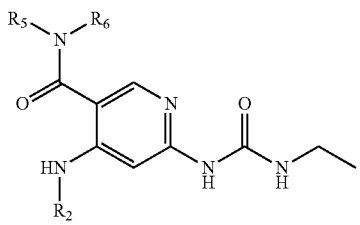

(Ib)

wherein $R_2$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_t$ $C_{3-10}$cycloalkenyl, $(CH_2)_tC_{6-10}$aryl, $(CH_2)_t$3-10-membered heterocyclyl and $(CH_2)_t$5-10-membered heteroaryl;

$R_5$ is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_6$ is H or is optionally substituted and selected from $C_{1-6}$alkyl, $C_{1-6}$alkoxyl, $C_{2-6}$alkenyl, $C_{2-6}$alkynyl, $(CH_2)_t$ $C_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl; preferably $R_6$ is H or optionally substituted $C_{1-6}$alkyl, more preferably H or optionally substituted $C_{1-3}$alkyl and most preferably H; and t is an integer selected from 0, 1, 2 and 3 preferably 0, 1 or 2 and wherein each $(CH_2)_t$ when present may be independently optionally substituted.

In one embodiment $R_2$ is optionally substituted and selected from $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl where t is 0 or 1.

In a particular embodiment $R_2$ is selected from an optionally substituted $C_{3-10}$cycloalkyl (preferably $C_{3-6}$cycloalkyl, more preferably $C_{5-6}$cycloalkyl such as cyclohexyl), optionally substituted $(CH_2)_tC_{6-10}$aryl (preferably phenyl), optionally substituted 3-10-membered heterocyclyl (preferably 5-6-membered monocyclic rings and 9-10-membered bicyclic rings) and optionally substituted $(CH_2)_t$5-10-membered heteroaryl (preferably 5-6-membered monocyclic rings and 9-10 membered bicyclic rings) where t is 0 or 1.

In yet a further embodiment $R_2$ is selected from an optionally substituted $(CH_2)_t$phenyl, an optionally substituted 5-6-membered heterocyclyl and an optionally substituted $(CH_2)_t$ 5-6-membered heteroaryl ring where t is 0 or 1.

In still another embodiment $R_2$ is an optionally substituted $(CH_2)_t$phenyl or an optionally substituted $(CH_2)_t$5-6-membered heteroaryl ring where t in each case is independently 0 or 1.

Particularly preferred $(CH_2)_t$5-membered heteroaryl rings include an optionally substituted pyrazolyl or an optionally substituted isoxazolyl.

Particularly preferred $(CH_2)_t$6-membered heteroaryl rings include an optionally substituted pyridyl, an optionally substituted $CH_2$pyridyl, an optionally substituted pyrimidinyl or an optionally substituted pyridinonyl.

In a particularly preferred embodiment $R_2$ is an optionally substituted phenyl.

In one embodiment $R_5$ is optionally substituted and selected from $C_{1-3}$alkyl, $(CH_2)_tC_{3-10}$cycloalkyl, $(CH_2)_t$ $C_{3-10}$cycloalkenyl, $(CH_2)_tC_{6-10}$aryl, $(CH_2)_t$3-10-membered heterocyclyl and $(CH_2)_t$5-10-membered heteroaryl where t is an integer 0, 1 or 2.

In a particular embodiment $R_5$ is selected from an optionally substituted $C_{3-10}$cycloalkyl (preferably $C_{3-6}$cycloalkyl), optionally substituted $(CH_2)_tC_{6-10}$aryl (preferably $(CH_2)_t$ phenyl), optionally substituted 3-10-membered heterocyclyl (preferably 5-6-membered monocyclic rings and 9-10-membered fused bicyclic rings) and optionally substituted $(CH_2)_t$ 5-10-membered heteroaryl (preferably $(CH_2)_t$5-6-membered monocyclic rings and $(CH_2)_t$9-10 membered fused bicyclic rings) where t is an integer 0, 1 or 2.

In yet a further embodiment $R_5$ is selected from an optionally substituted $C_{1-3}$alkyl, an optionally substituted $C_{3-6}$cycloalkyl, an optionally substituted $(CH_2)_t$phenyl, an optionally substituted 5-6-membered heterocyclyl, an optionally substituted $(CH_2)_t$5-6-membered heteroaryl ring and an optionally substituted 9-10-membered heteroaryl ring where t is an integer 0, 1 or 2.

In a particular embodiment $R_5$ is optionally substituted and is selected from phenyl, $CH_2$phenyl, $CH_2CH_2CH_2$phenyl, 5-membered heterocyclyl, 6-membered heterocyclyl, 5-membered heteroaryl, 6-membered heteroaryl, $CH_2$6-membered heteroaryl, 9-membered heteroaryl and 10-membered heteroaryl.

In a particularly preferred embodiment $R_5$ is an optionally substituted phenyl.

In still another embodiment $R_2$ and $R_5$ are each independently selected from an optionally substituted $(CH_2)_t$phenyl, an optionally substituted $(CH_2)_t$5-6-membered heterocyclyl, an optionally substituted $(CH_2)_t$5-6-membered heteroaryl ring and an optionally substituted $(CH_2)_t$9-10-membered heteroaryl ring where t is an integer 0, 1 or 2 preferably 0 or 1 and $R_6$ is H.

In a particularly preferred embodiment, $R_2$ is an optionally substituted phenyl or an optionally substituted pyridinyl and $R_5$ is an optionally substituted $C_{3-6}$cycloalkyl, an optionally substituted phenyl, an optionally substituted $CH_2$phenyl, an optionally substituted $CH_2CH_2$phenyl, an optionally substituted 5-membered heteroaryl (preferably thiazolyl, isoxazolyl, pyrrolyl, pyrazolyl), an optionally substituted 6-membered heteroaryl (preferably pyridinyl, pyridinonyl, pyridazinyl and pyrimidinyl), an optionally substituted $CH_2$6-membered heteroaryl (preferably $CH_2$pyridinyl), an optionally substituted 9-membered heteroaryl (preferably indolyl, benzothiazolyl and imidazopyridinyl) or an optionally substituted 10-membered heteroaryl (preferably quinolinyl and oxochromenyl).

In a further preferred embodiment $R_2$ is an optionally substituted phenyl and $R_5$ is an optionally substituted phenyl.

Suitable optional substituents for $R_2$ and $R_5$ are as previously defined.

In one embodiment suitable optional substituents for $R_2$ include 1, 2 or 3 preferably 1 or 2 optional substituents independently selected from the group consisting of $C_{1-3}$alkyl (particularly methyl which may be further optionally substituted with OH, $CO_2H$, $CO_2C_{1-3}$alkyl (particularly $CO_2CH_3$ and $CO_2CH_2CH_3$), $C(O)NH_2$, $C(O)NHC_{1-3}$alkyl (particularly $C(O)NHCH_3$) and $C(O)N(C_{1-3}$alkyl$)_2$ (particularly $C(O)N(CH_3)_2$)); halo (particularly Cl and F); halo$C_{1-3}$alkyl (particularly $CF_3$); halo$C_{1-3}$alkoxyl (particularly $OCF_3$); $SF_5$; $C_{1-3}$ alkoxyl (particularly methoxy); CN; OH; $CO_2H$; $CO_2C_{1-3}$alkyl (particularly $CO_2CH_3$ and $CO_2CH_2CH_3$); $C(O)NH_2$; $C(O)NHC_{1-3}$alkyl (particularly $C(O)NHCH_3$); and $C(O)N(C_{1-3}$alkyl$)_2$ (particularly $C(O)N(CH_3)_2$).

In one embodiment suitable optional substituents for $R_5$ include 1, 2 or 3 preferably 1 or 2 optional substituents independently selected from the group consisting of $C_{1-6}$alkyl; $C_{2-6}$alkenyl, $C_{2-6}$alkynyl; halo (particularly Cl and F); halo$C_{1-3}$alkyl (particularly $CF_3$); halo$C_{1-3}$alkoxyl (particularly $OCF_3$); $SF_5$; $C_{1-3}$alkoxyl (particularly methoxy); aryloxy (particularly phenoxy); CN; $N_3$; OH; $CO_2H$; $CO_2C_{1-3}$ alkyl (particularly $CO_2CH_3$ and $CO_2CH_2CH_3$); $C(O)NH_2$; $C(O)NHC_{1-3}$alkyl (particularly $C(O)NHCH_3$); and $C(O)N$ $(C_{1-3}$alkyl$)_2$ (particularly $C(O)N(CH_3)_2$); $P(O)(OH)_2$; $P(O)$ $(OC_{1-3}$alkyl$)_2$; $NHSO_2C_{1-3}$alkyl; $SO_2NH_2$; $SO_2NHC_{1-3}$ alkyl; amino; substituted amino (including NHC$_{1-6}$alkyl); disubstituted amino (including N(C$_{1-6}$alkyl)$_2$); amido; substituted amido (including C(O)NHC$_{1-6}$alkyl and NHC(O) C$_{1-6}$alkyl); disubstituted amido (including C(O)N(C$_{1-6}$ alkyl)$_2$ and NC$_{1-6}$alkylC(O)C$_{1-6}$alkyl); C(O)C$_{1-6}$alkyl; phenyl; 4-6-membered heterocyclyl (particularly azetidinyl, pyrrolidinyl, morpholinyl, piperidinyl, piperazinyl and dioxidothiomorpholinyl); and 5-6-membered heteroaryl (particularly pyrrolyl, triazolyl, tetrazolyl, and pyridinyl) wherein each alkyl, alkenyl, alkoxy, aryloxy, phenyl, heterocyclyl and heteroaryl and groups containing them may be further optionally substituted with any one or more of the optional substituents as previously defined.

In one embodiment R$_5$ is optionally substituted with a substituent selected from the group consisting of (CH$_2$)$_q$OH, (CH$_2$)$_q$CO$_2$H, (CH$_2$)$_q$CO$_2$C$_{1-3}$alkyl (particularly (CH$_2$)$_q$CO$_2$CH$_3$ and (CH$_2$)$_q$CO$_2$CH$_2$CH$_3$), (CH$_2$)$_q$tetrazolyl, (CH$_2$)$_q$C(O)NH$_2$, (CH$_2$)$_q$C(O)NHCH$_3$, (CH$_2$)$_q$C(O)N (CH$_3$)$_2$, (CH$_2$)$_q$C(O)CH$_3$, (CH$_2$)$_q$C(O)N(CH$_3$)OCH$_3$, CH=CHCO$_2$H, CH=CHCO$_2$C$_{1-3}$alkyl (particularly CH=CHCO$_2$CH$_3$ and CH=CHCO$_2$CH$_2$CH$_3$), (CH$_2$)$_q$C (CH$_3$)$_2$CO$_2$H, (CH$_2$)$_q$C(CH$_3$)$_2$CO$_2$C$_{1-3}$alkyl (particularly (CH$_2$)$_q$C(CH$_3$)$_2$CO$_2$CH$_3$ and (CH$_2$)$_q$C(CH$_3$)$_2$CO$_2$CH$_2$CH$_3$), C≡CCH$_2$OH and C≡CCHC$_{1-3}$alkylOH (particularly C≡CCHCH$_3$OH) and C≡CC(C$_{1-3}$ alkyl)$_2$OH (particularly C≡CC(CH$_3$)$_2$OH); C$_{1-3}$alkyl incorporating a C$_{3-6}$cycloalkyl substituted with CO$_2$H or CO$_2$C$_{1-3}$alkyl (particularly

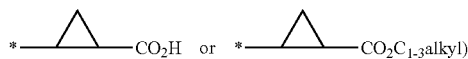

and NHC$_{1-6}$alkyl optionally substituted with a C$_{3-6}$cycloalkyl and CO$_2$H or CO$_2$C$_{1-3}$alkyl (particularly

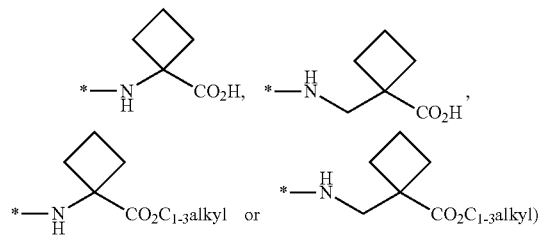

where * represents the point of attachment; and where q is an integer independently selected from 1, 2 or 3, preferably 1 or 2.

In one embodiment the compound is selected from the group consisting of:

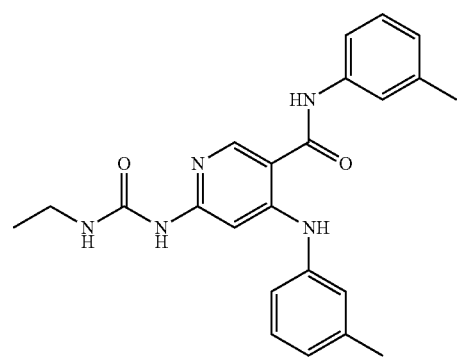

1

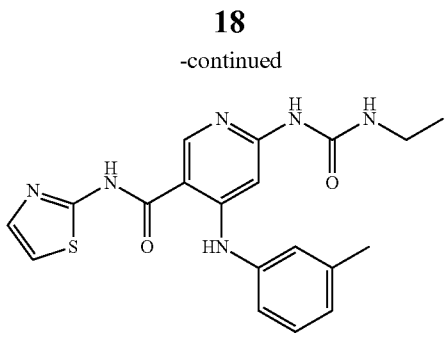

2

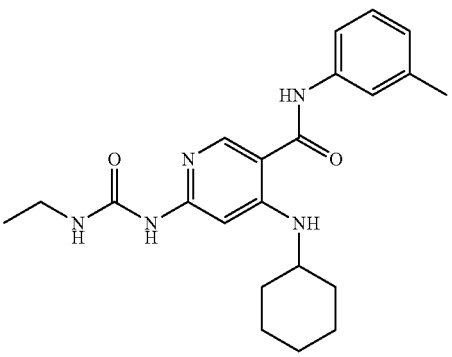

3

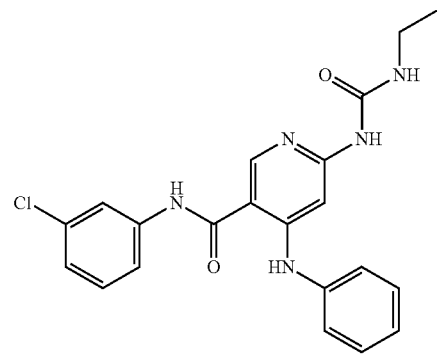

4

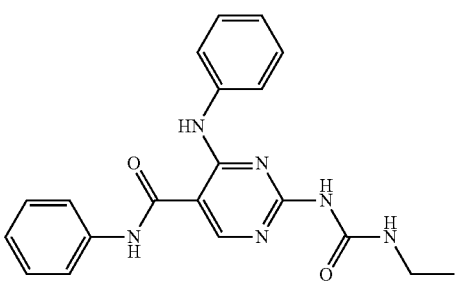

5

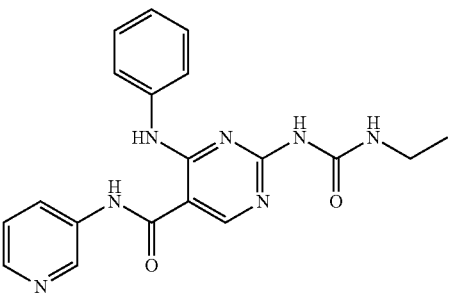

6

-continued
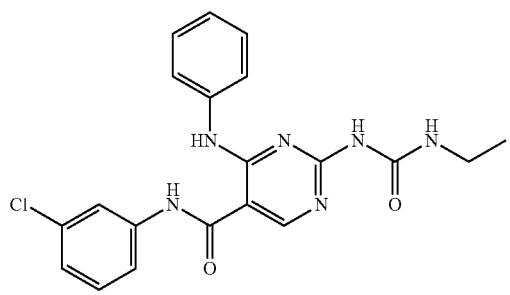
7
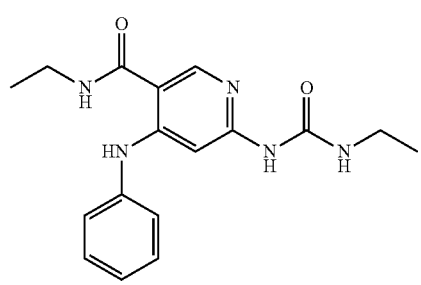
8
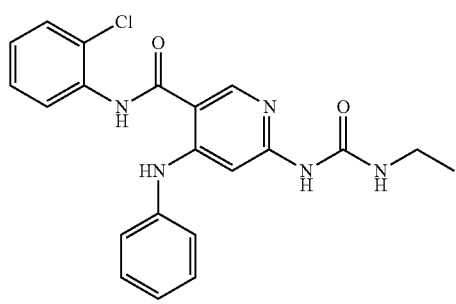
9
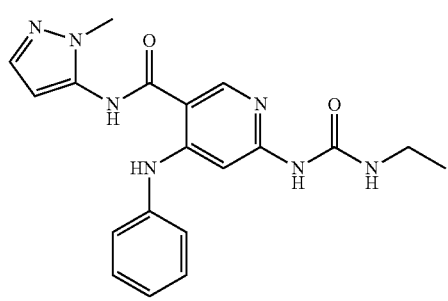
10
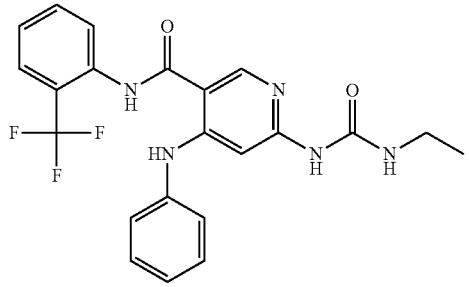
11
-continued
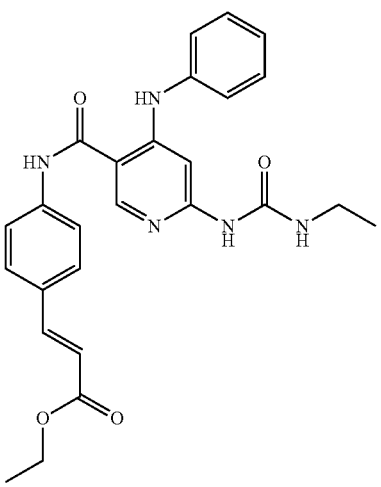
12
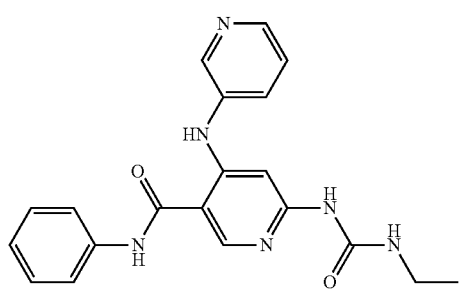
13
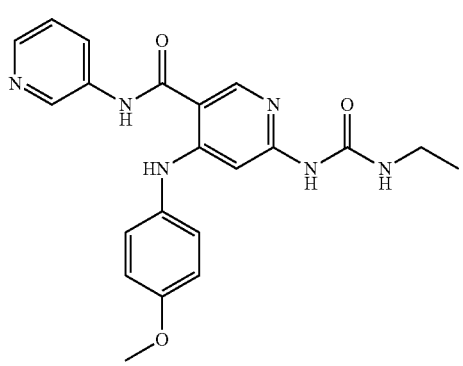
14
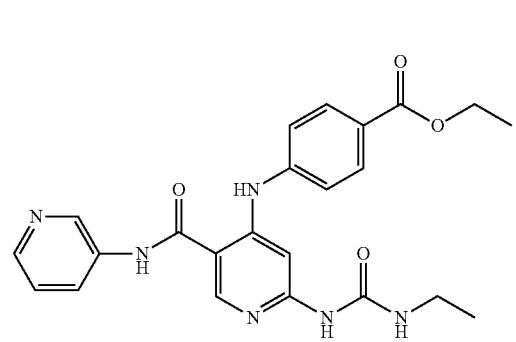
15

-continued
16
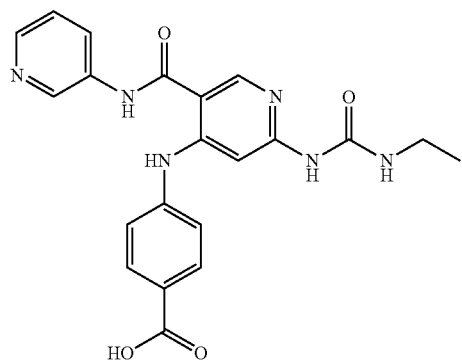
17
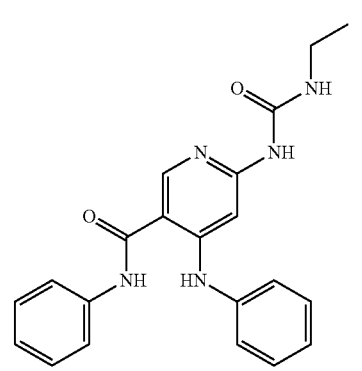
18
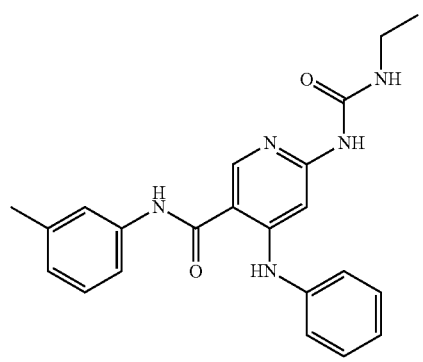
19
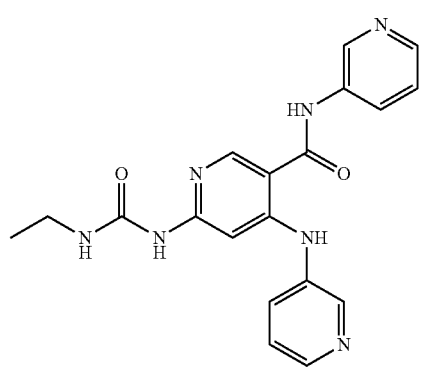
-continued
20
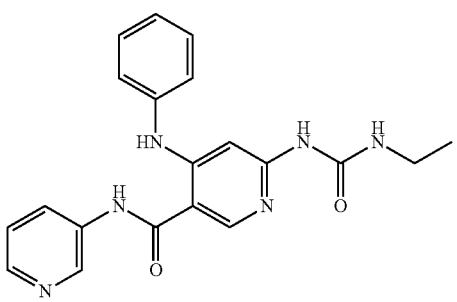
21
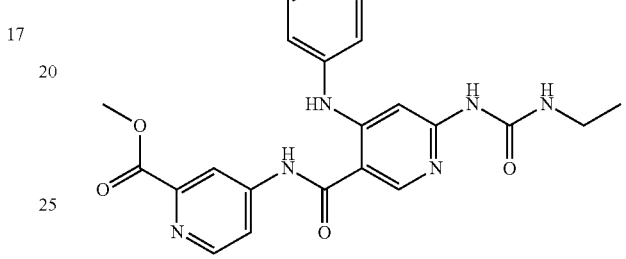
22
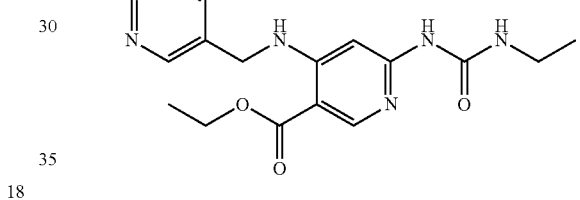
23
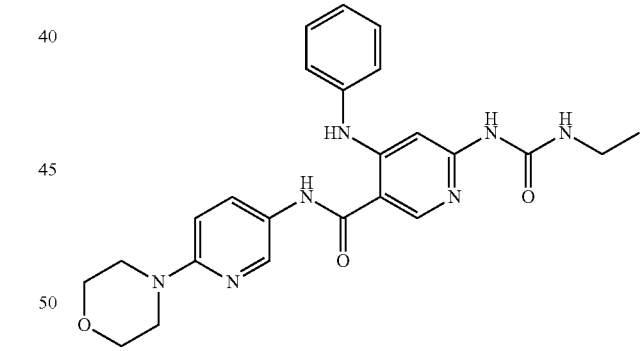
24
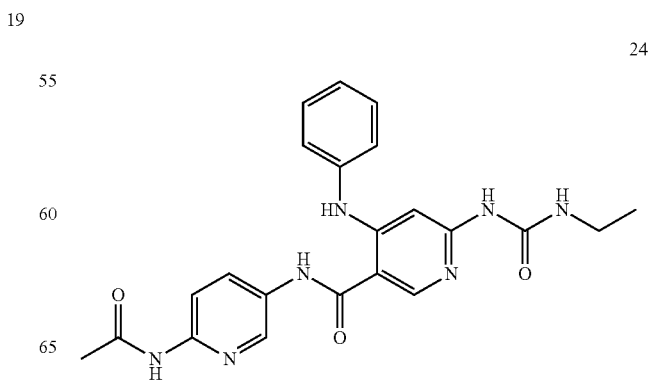

23
-continued
25
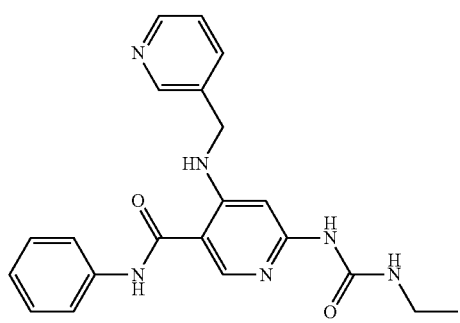
26
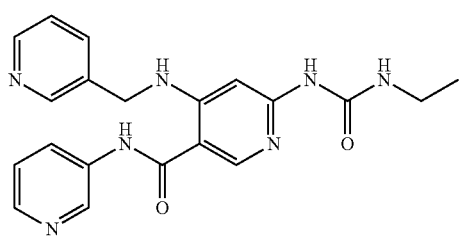
27
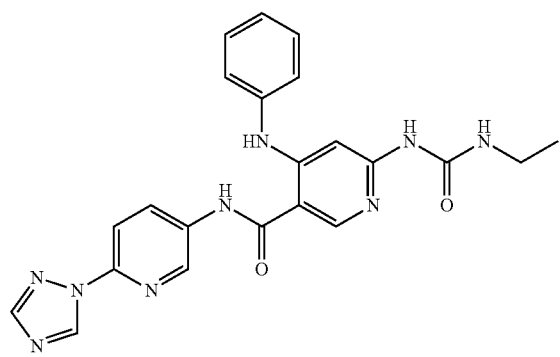
28
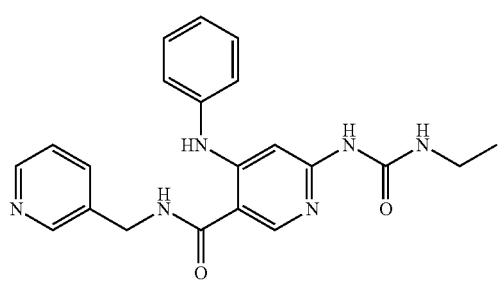
29
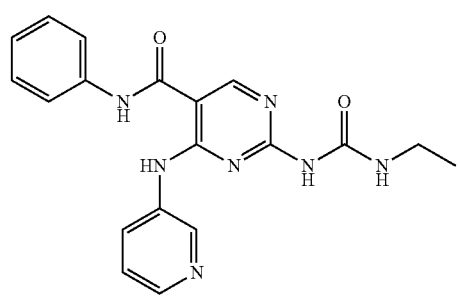
24
-continued
30
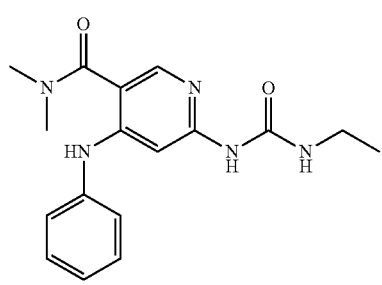
31
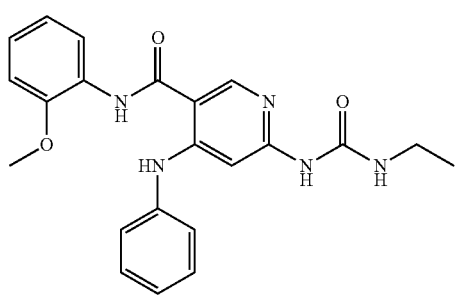
32
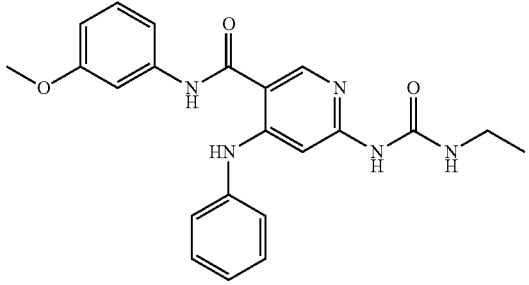
33
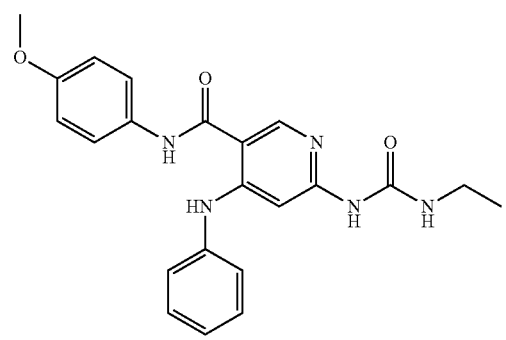
34
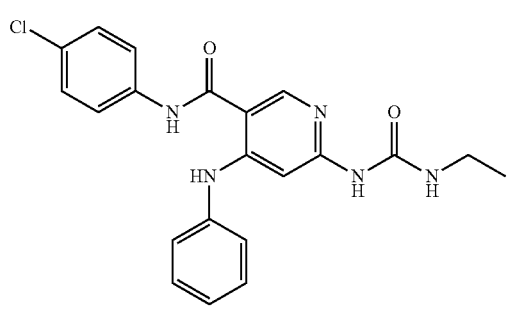

25
-continued
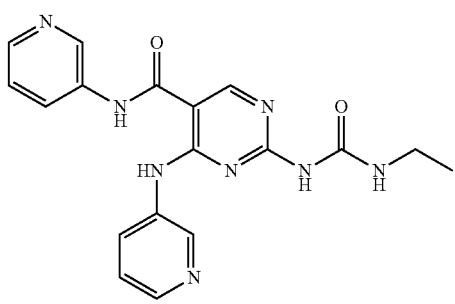
35
36
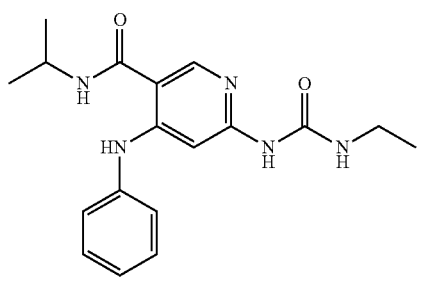
37
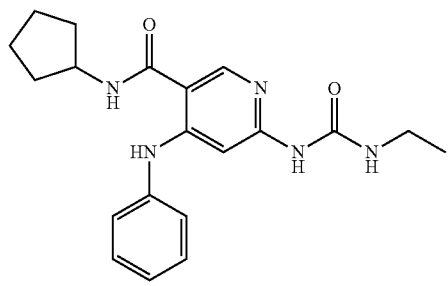
38
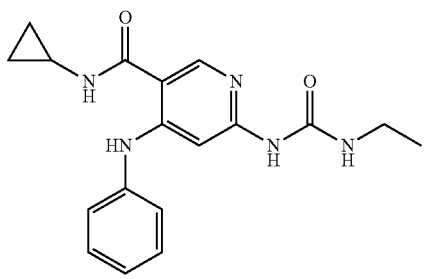
39
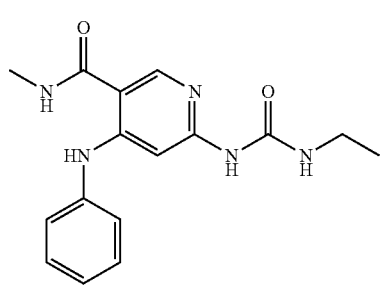
26
-continued
40
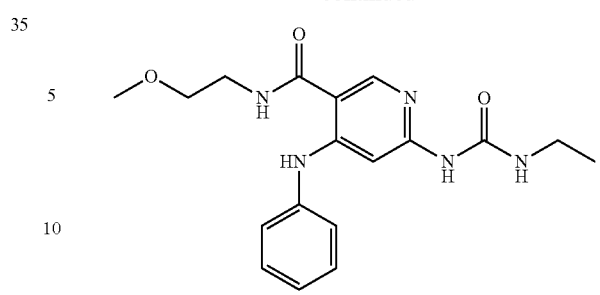
41
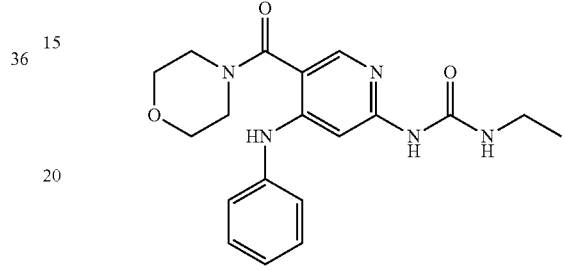
42
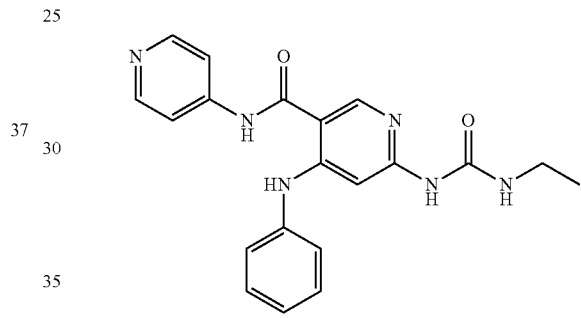
43
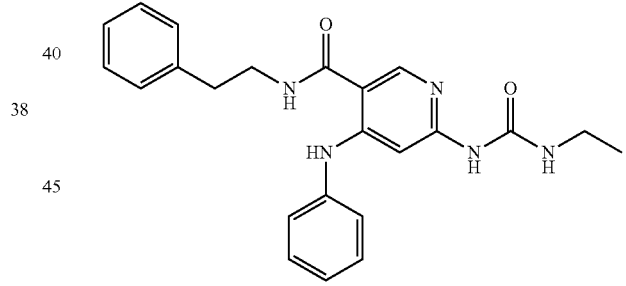
44
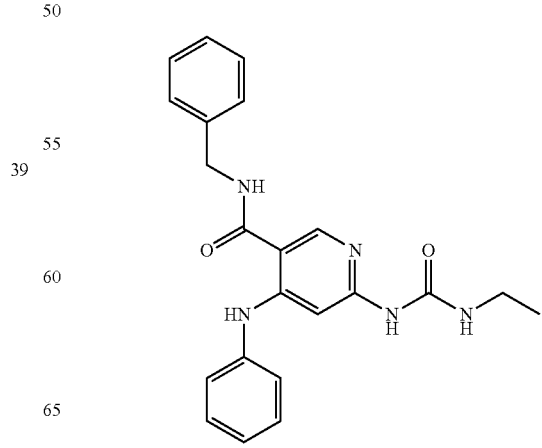

45
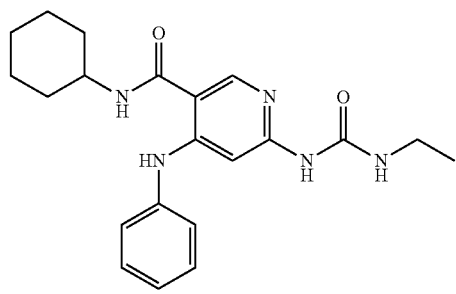
46
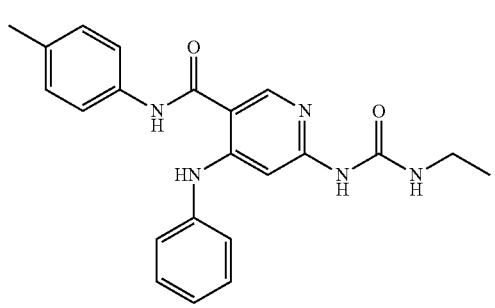
47
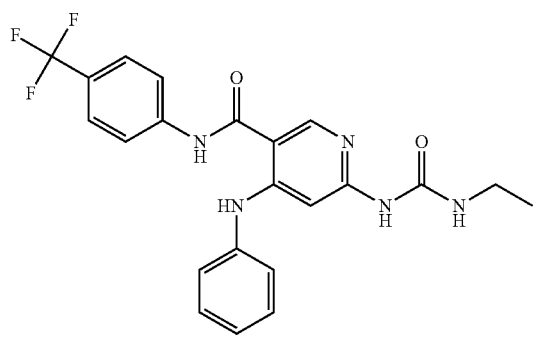
48
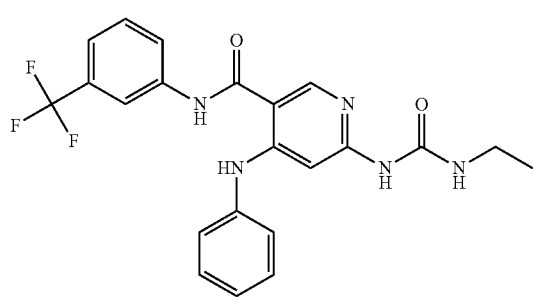
49
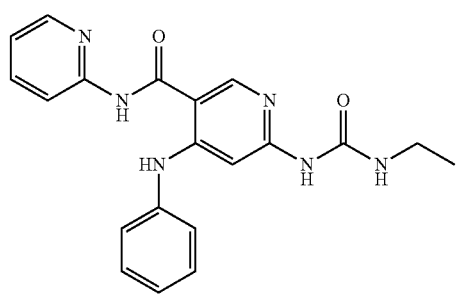
50
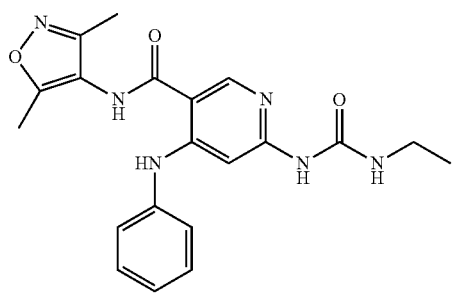
51
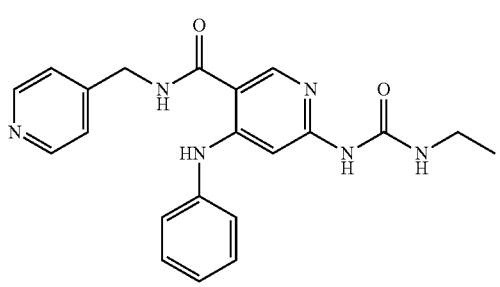
52
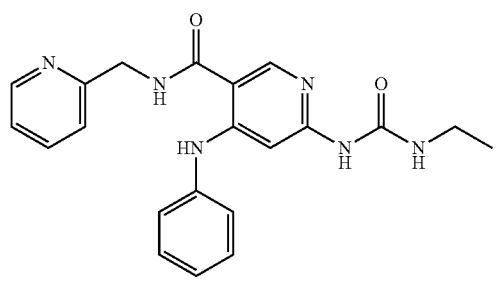
53
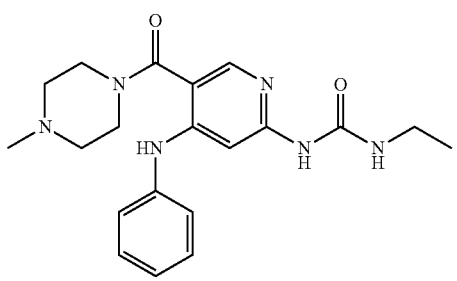
54
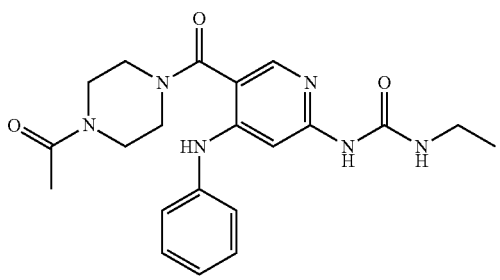

55
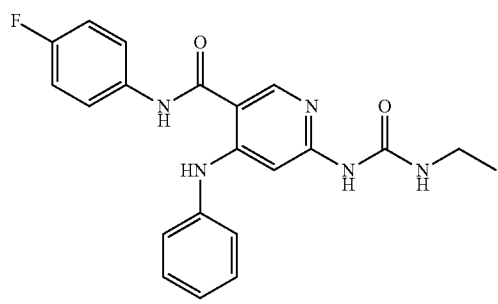
56
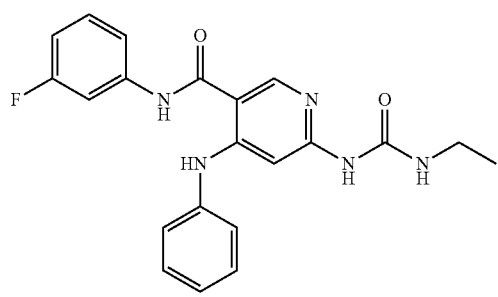
57
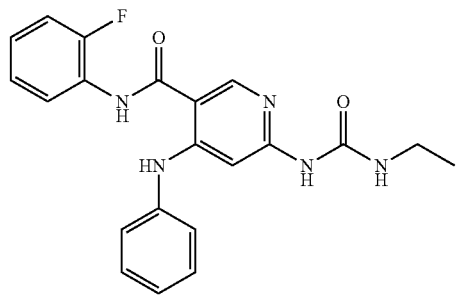
58
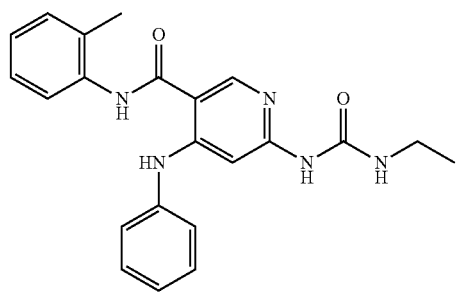
59
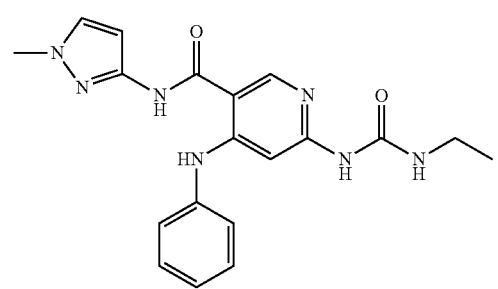
60
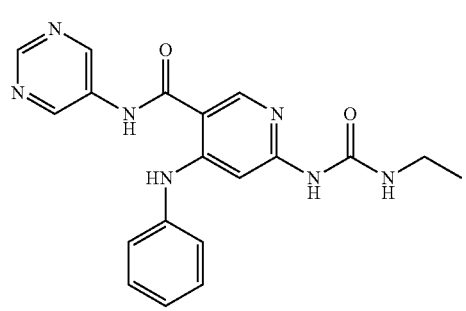
61
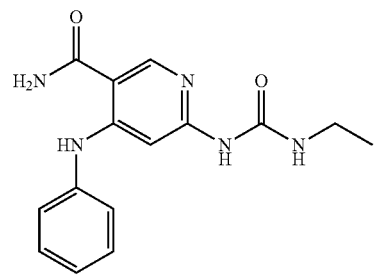
62
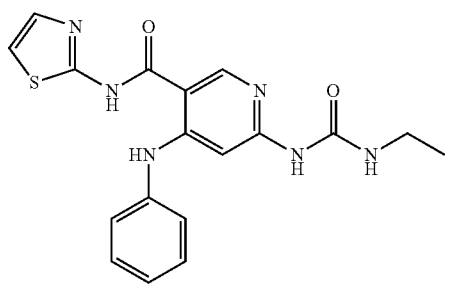
63
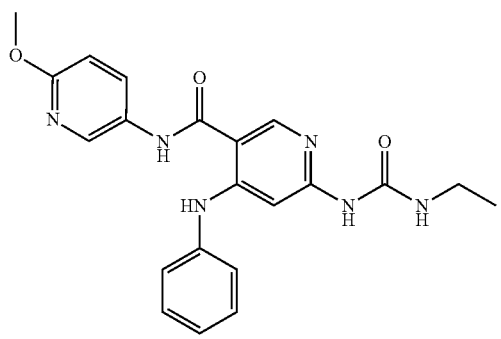
64
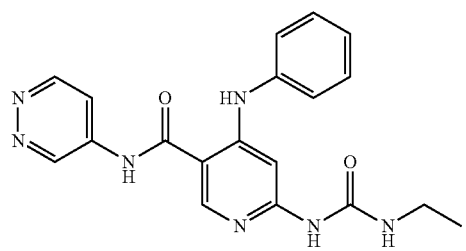

65
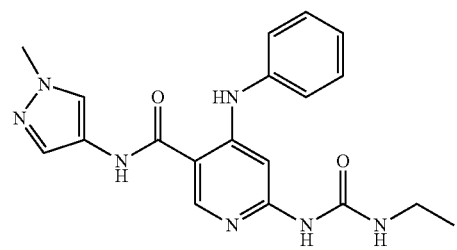
66
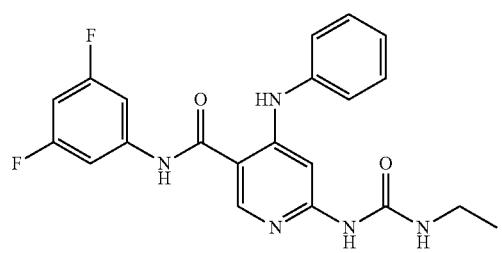
67
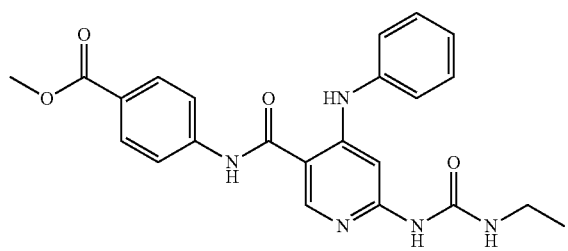
68
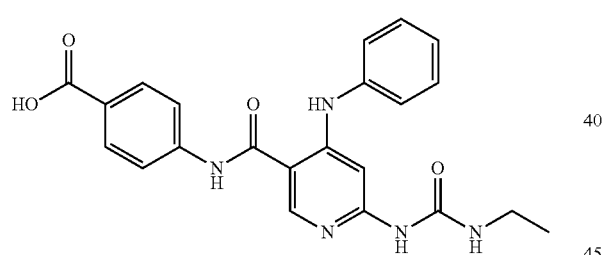
69
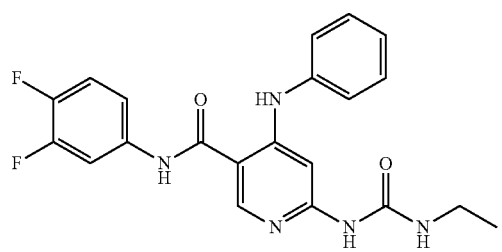
70
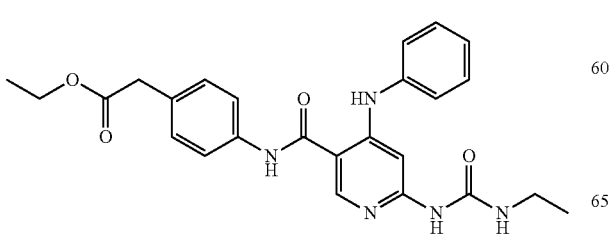
71
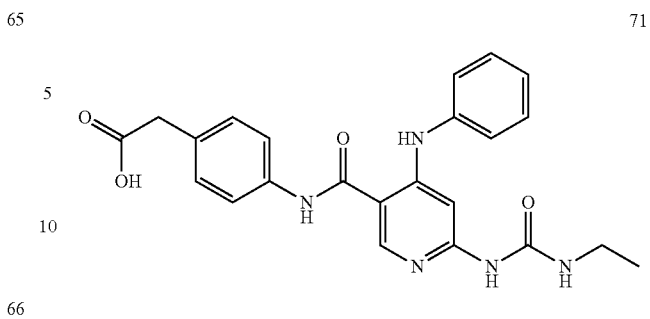
72
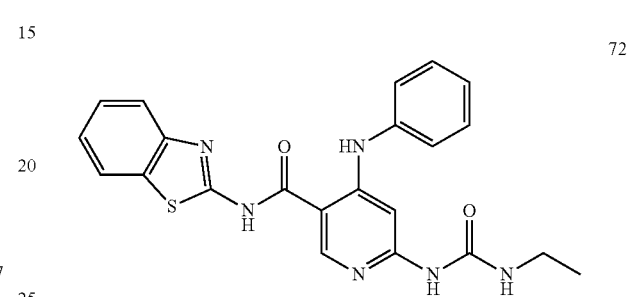
73
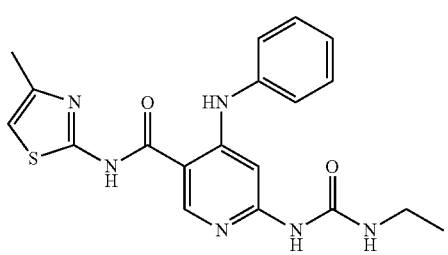
74
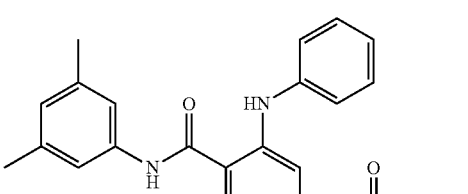
75
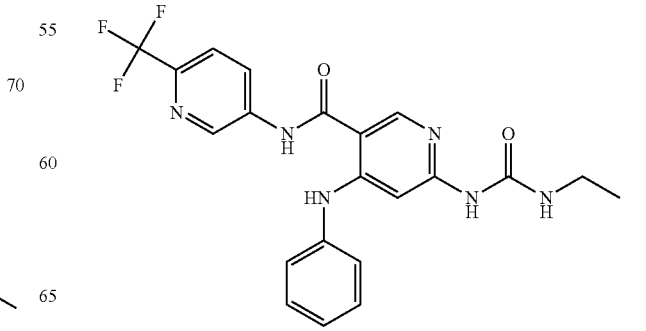

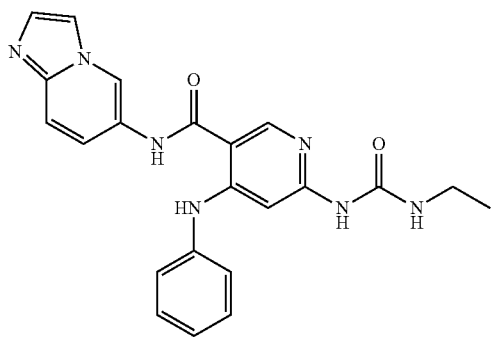
76
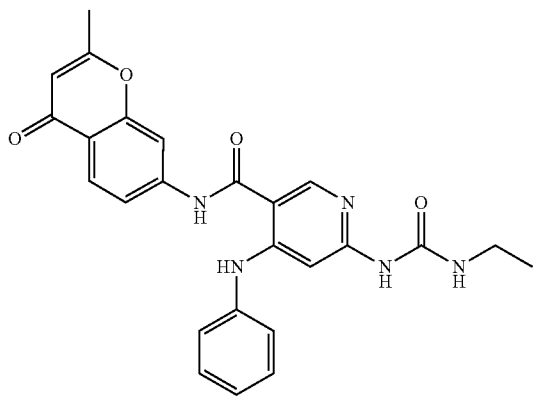
80
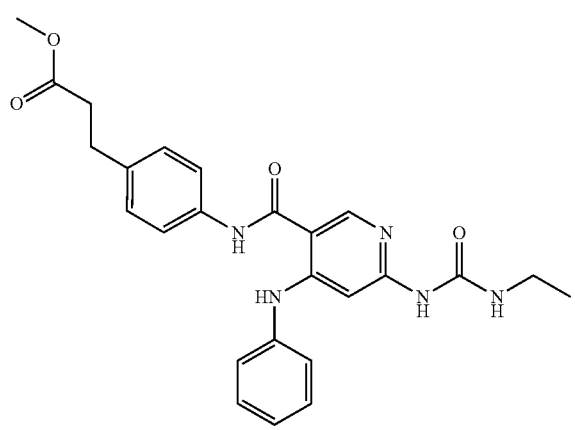
77
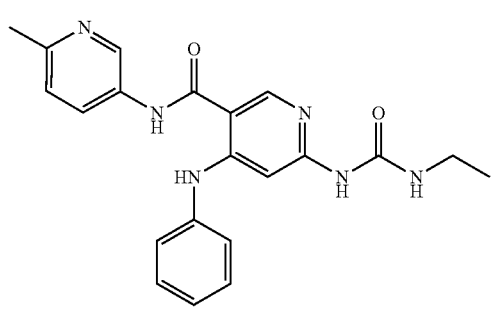
81
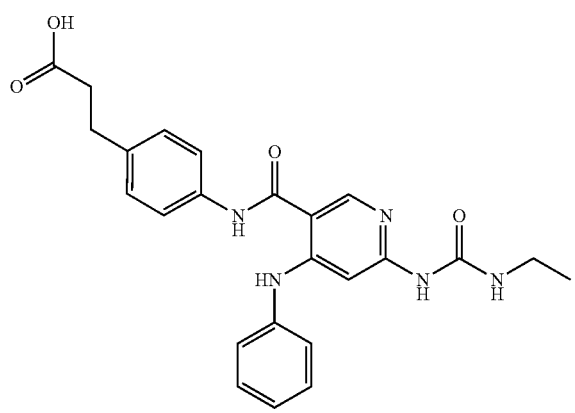
78
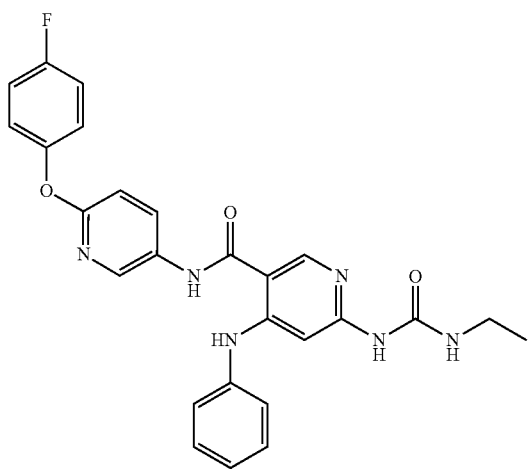
82
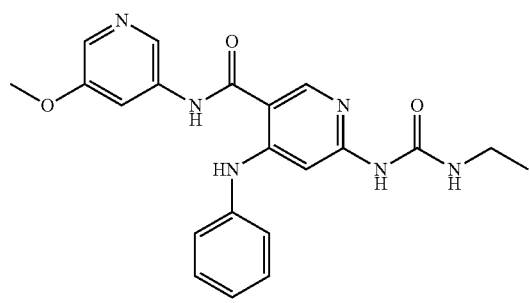
79
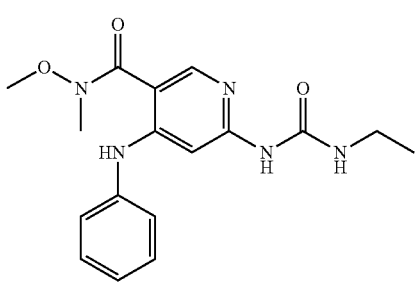
83

35
-continued
84
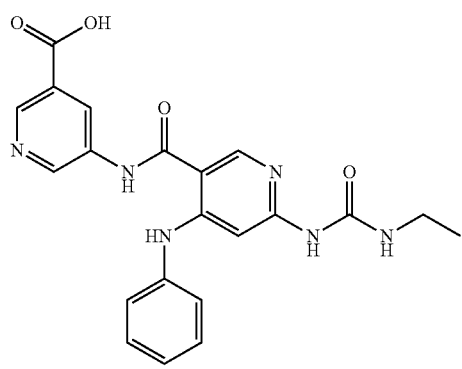
85
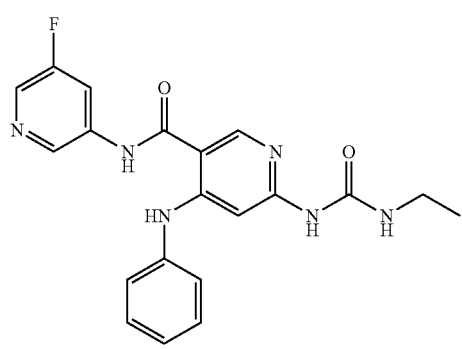
86
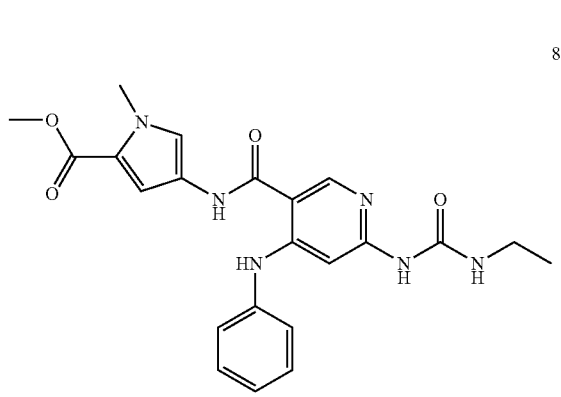
87
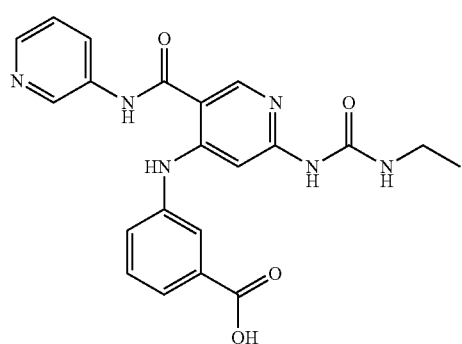
36
-continued
88
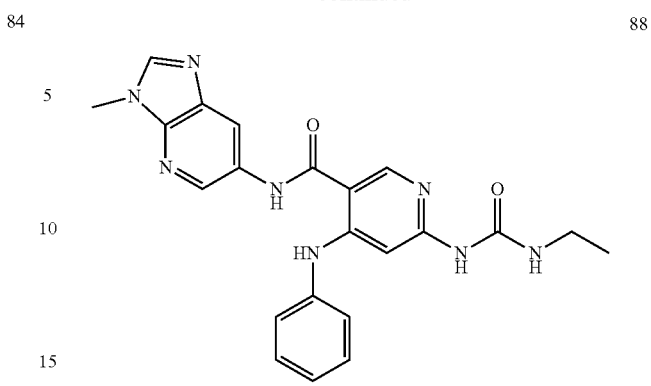
89
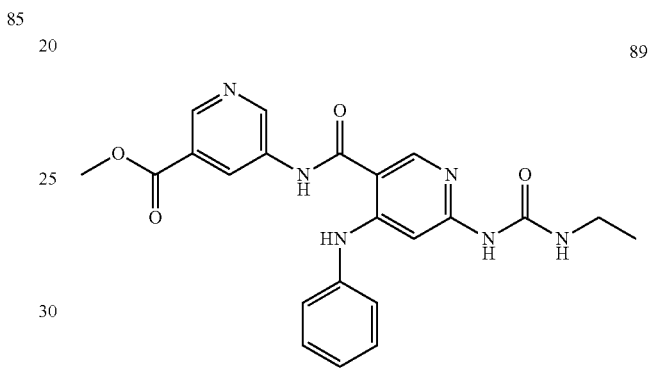
90
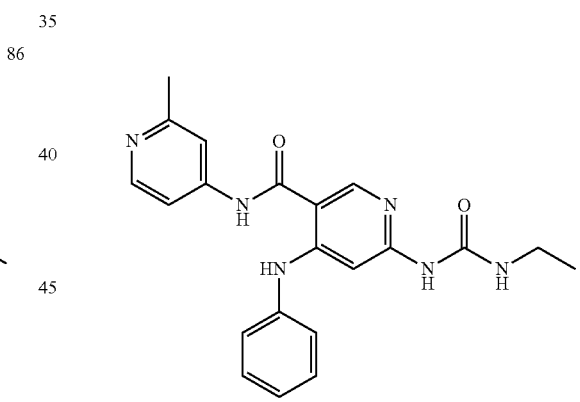
91
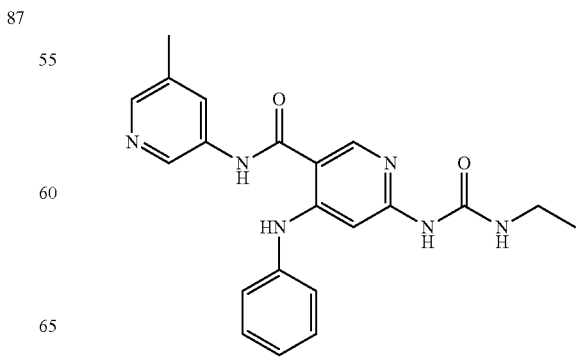

| 37 | 38 |
|---|---|
| -continued | -continued |
| 92 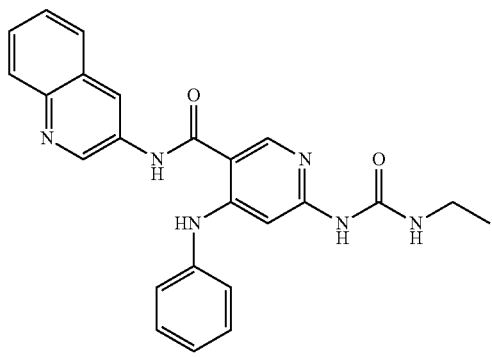 | 96 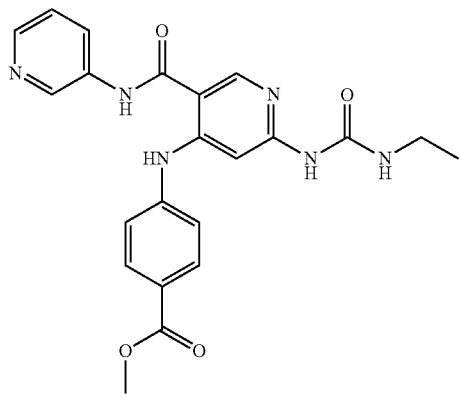 |
| 93 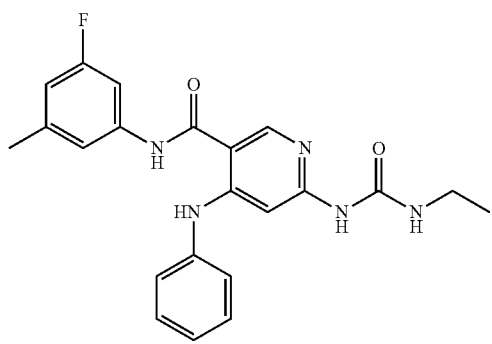 | 97 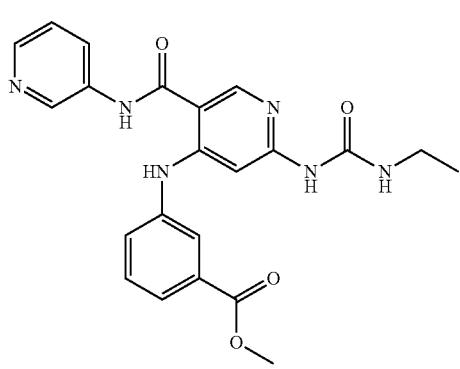 |
| 94 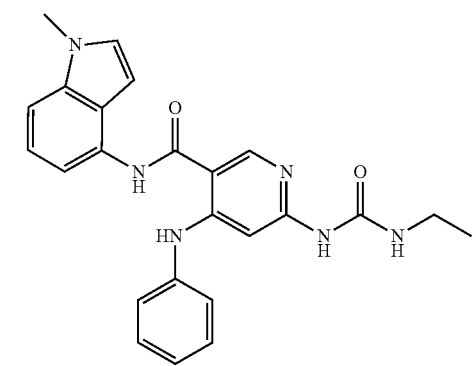 | 98 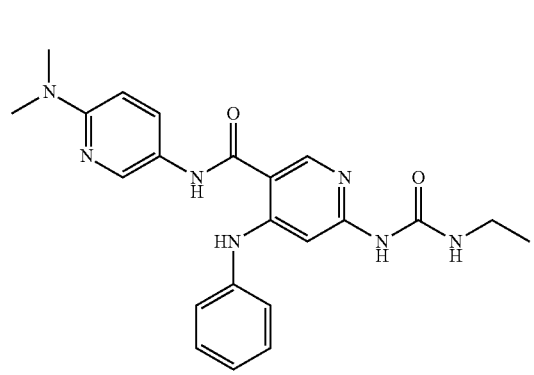 |
| 95 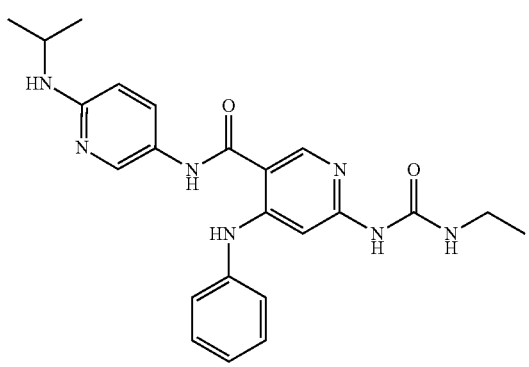 | 99 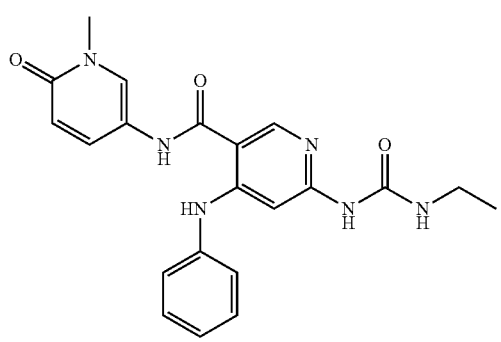 |

-continued
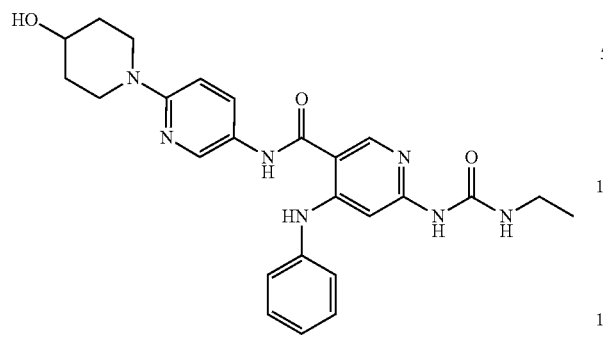 100
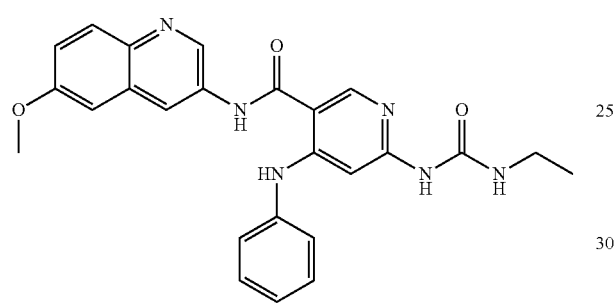 101
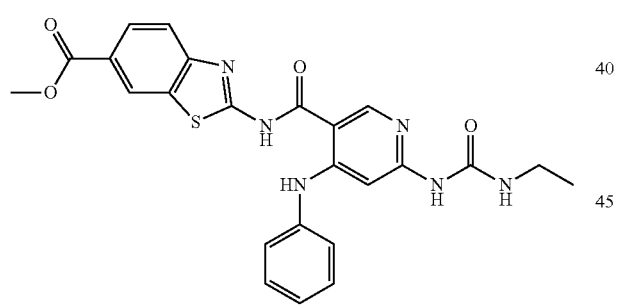 102
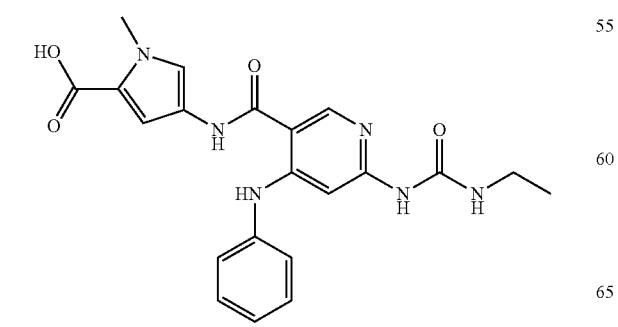 103
-continued
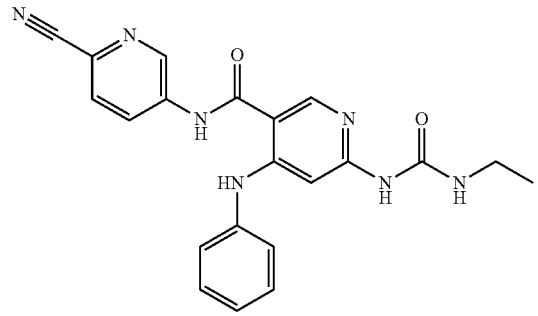 104
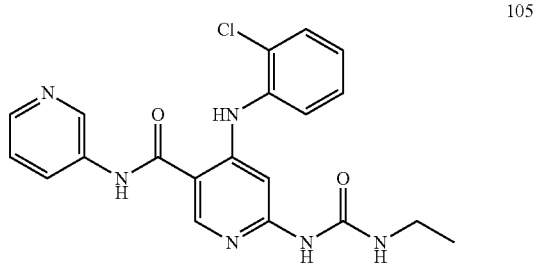 105
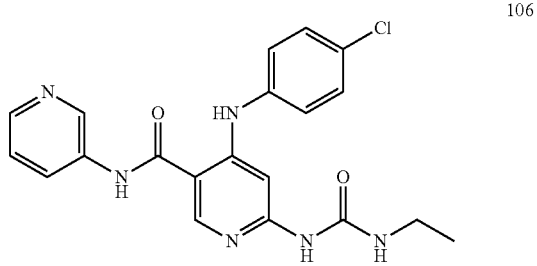 106
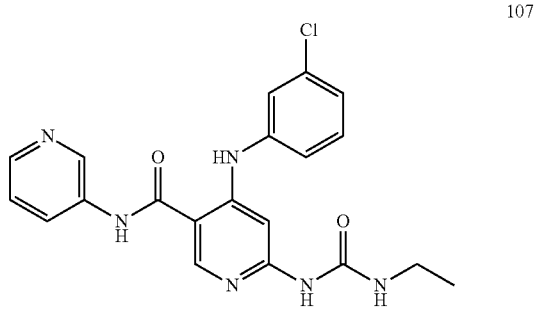 107
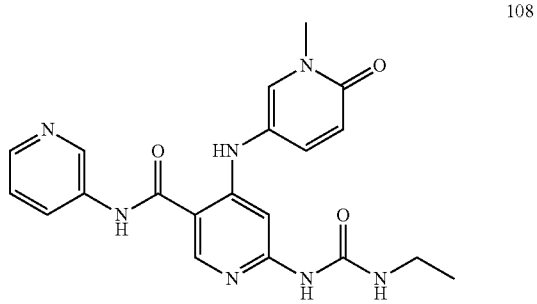 108

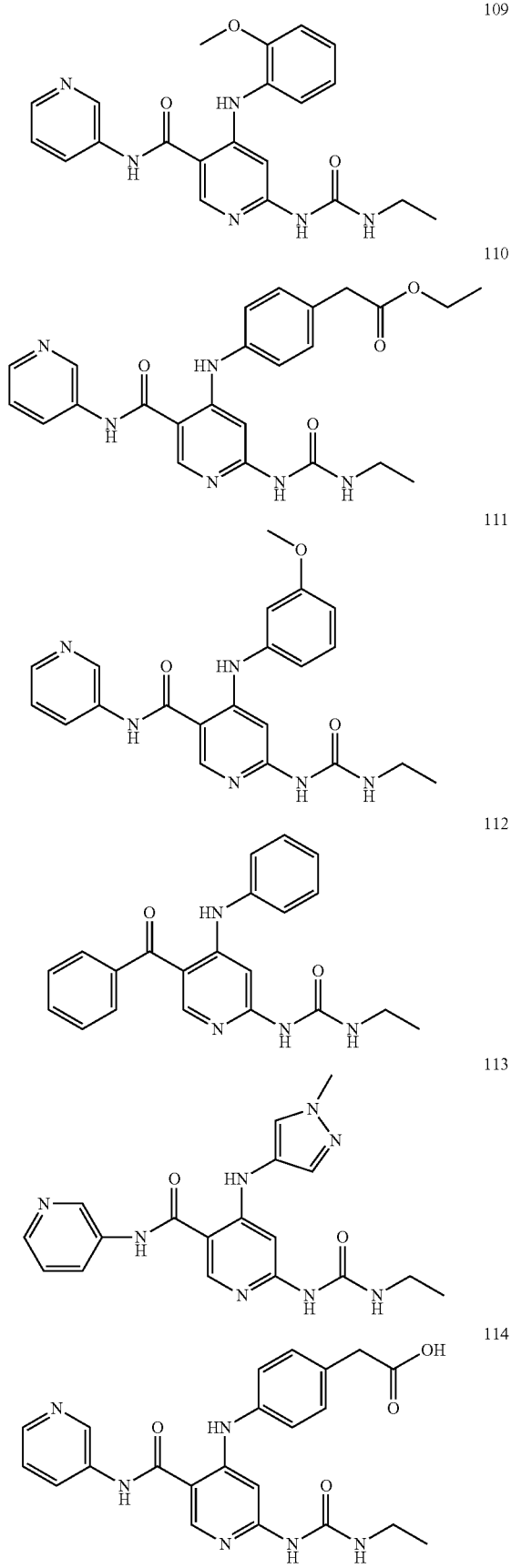
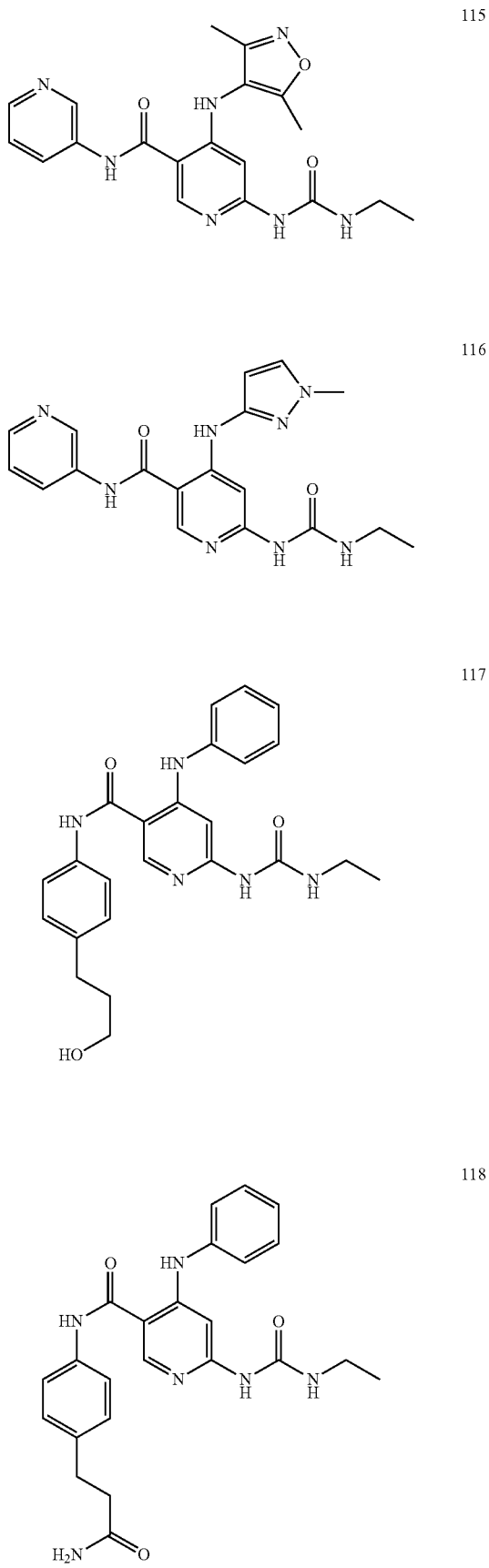

119
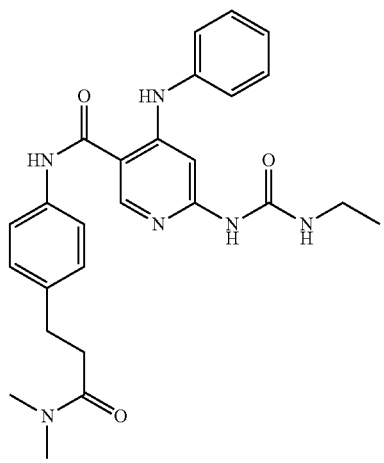
120
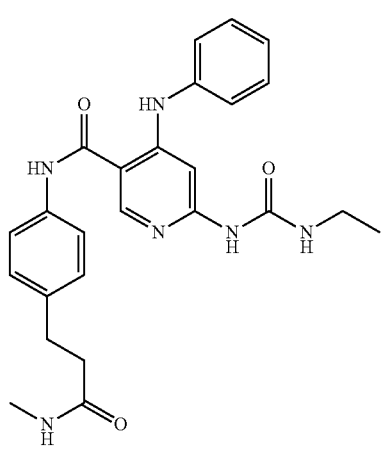
121
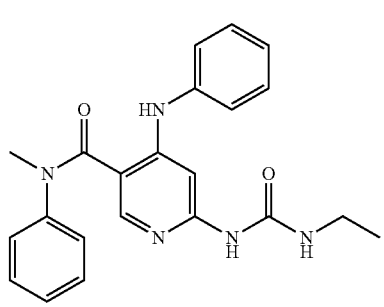
122
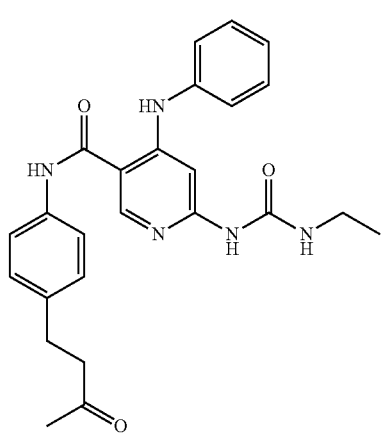
123
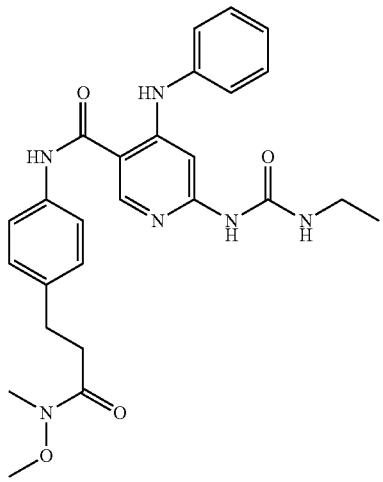
124
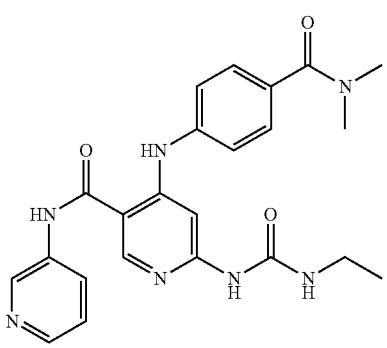
125
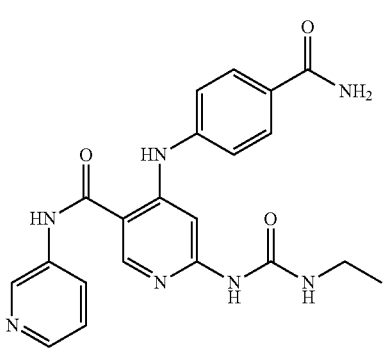
126
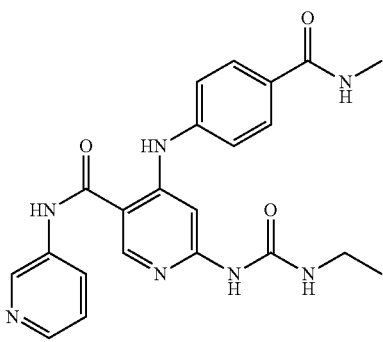

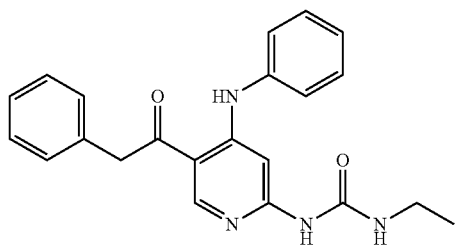
127
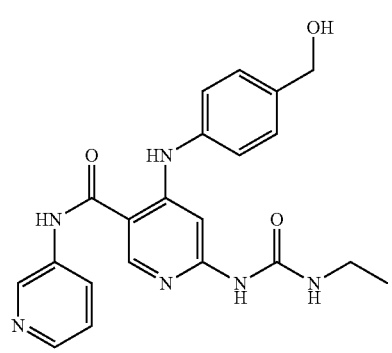
128
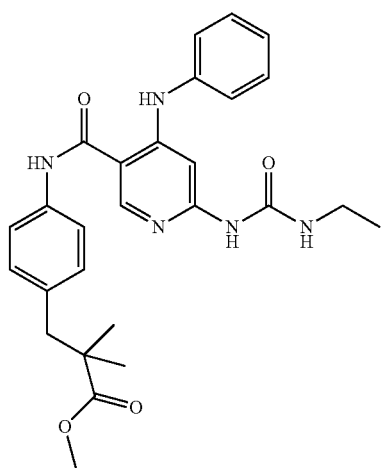
129
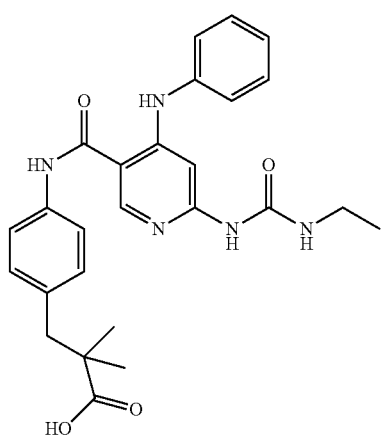
130
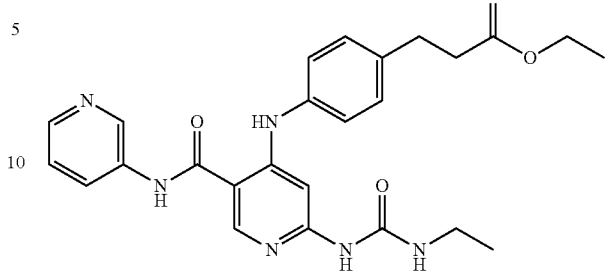
131
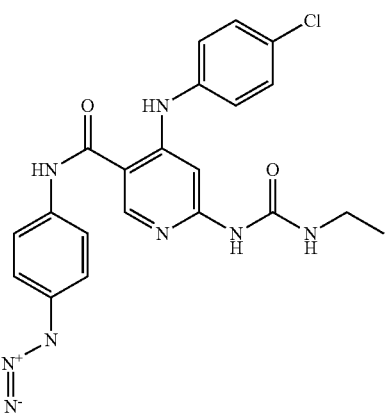
132
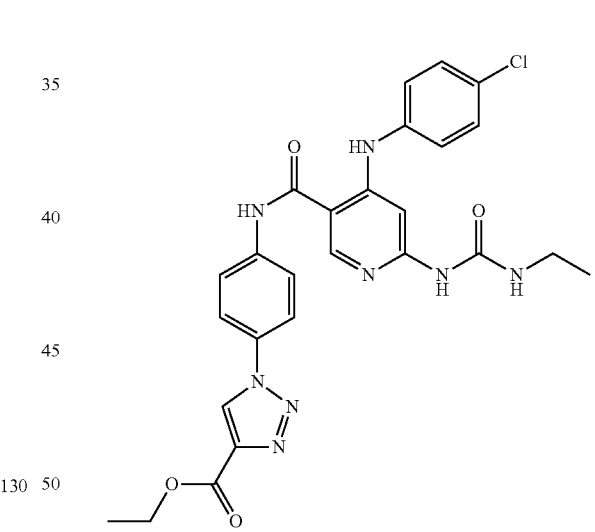
133
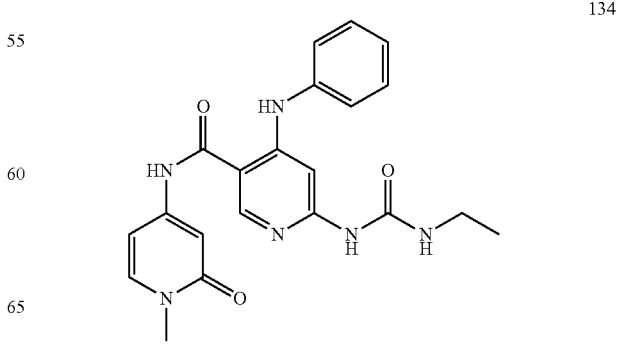
134

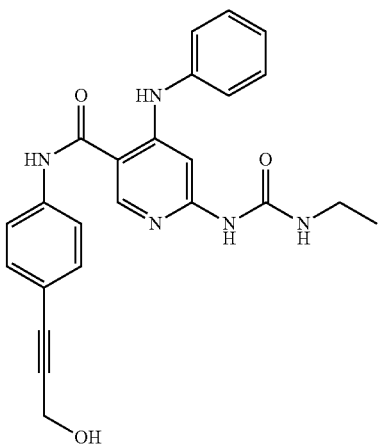
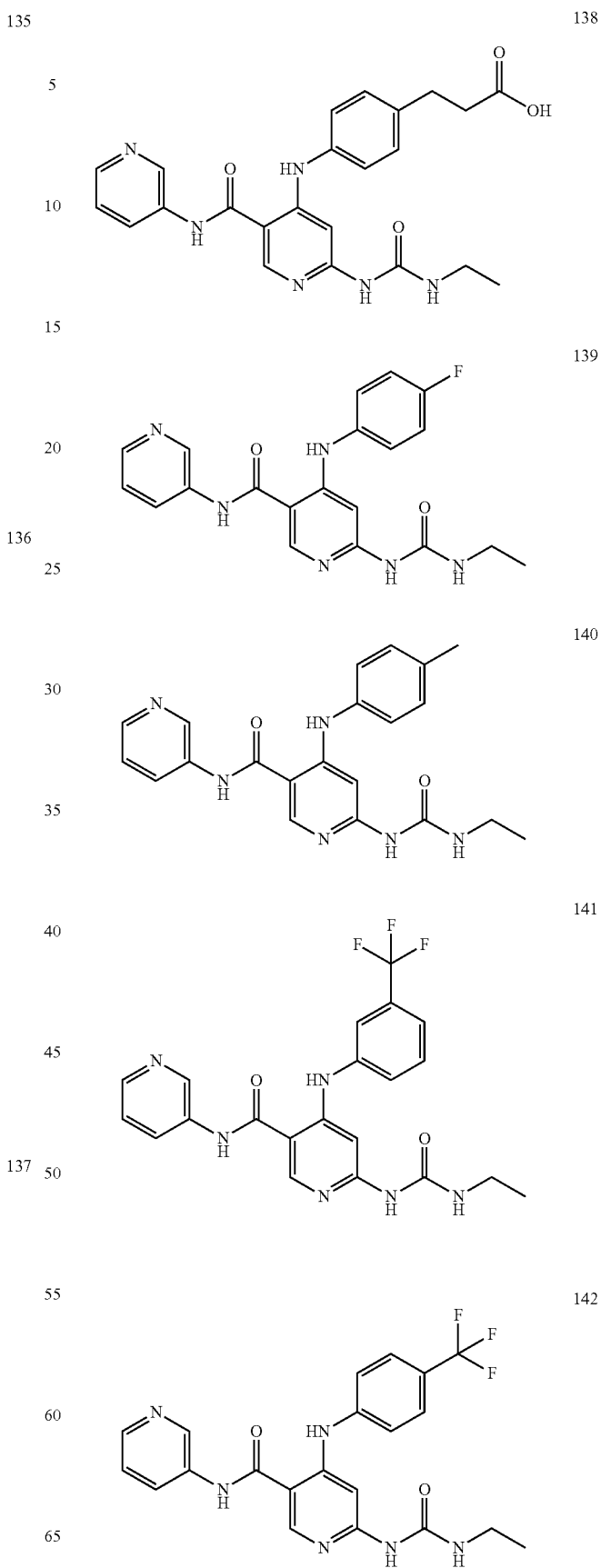

-continued
143
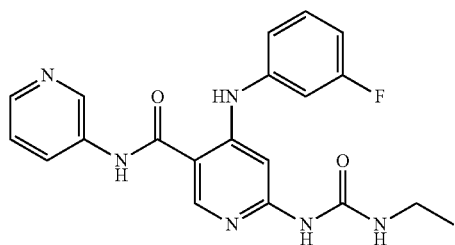
144
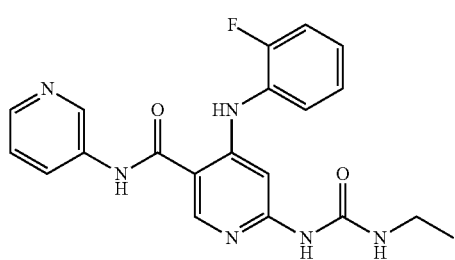
145
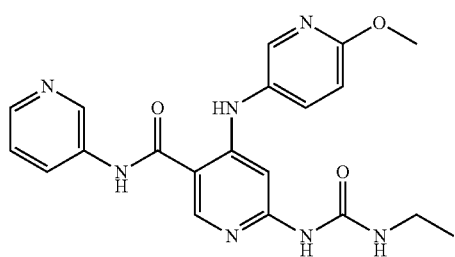
146
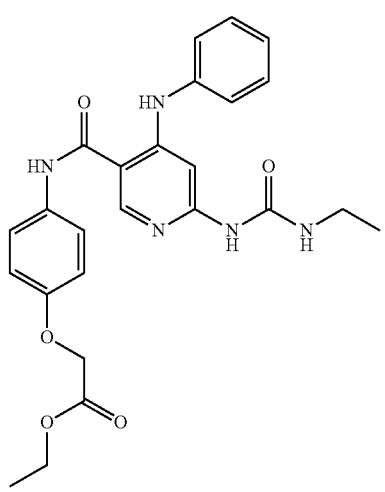
147
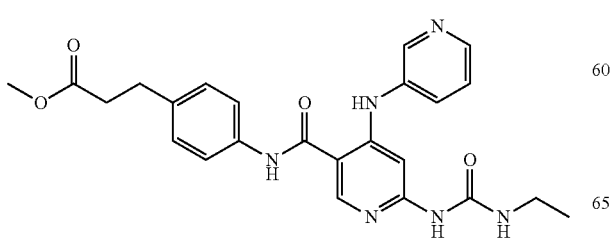
-continued
148
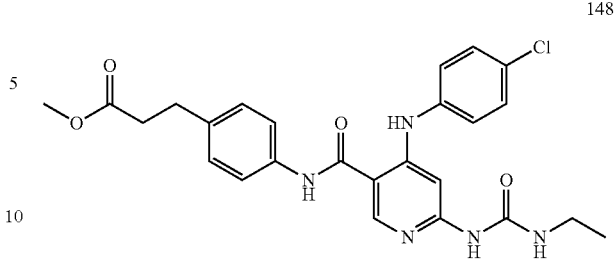
149
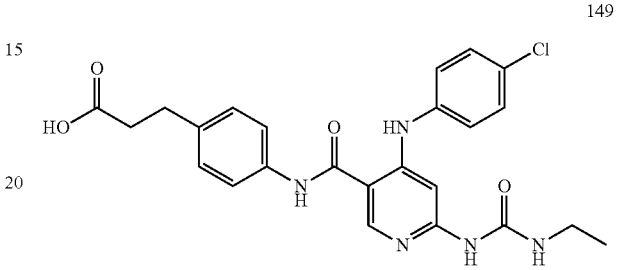
150
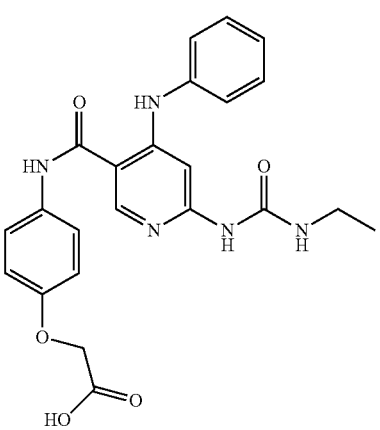
151
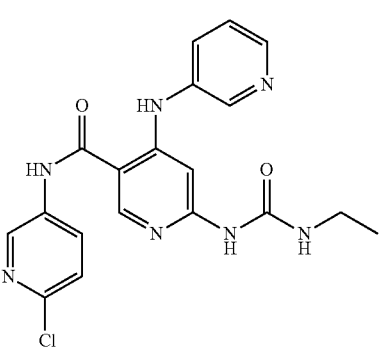
152
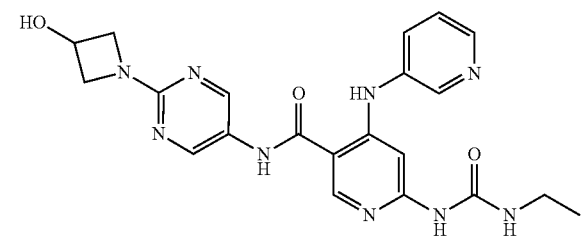

153
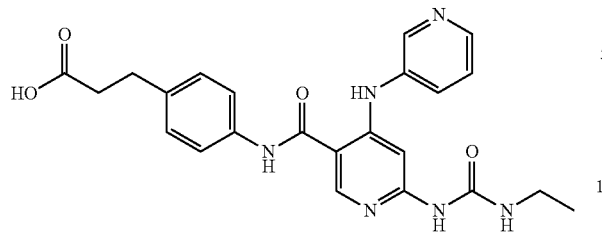
154
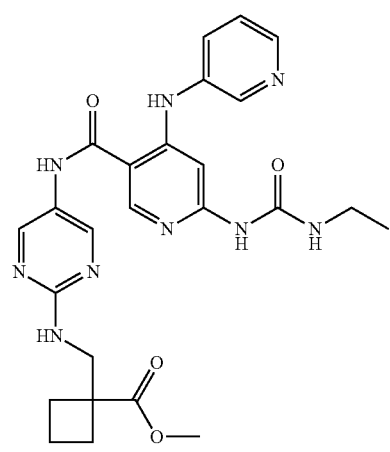
155
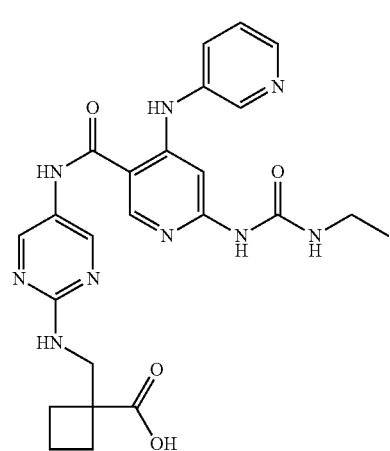
156
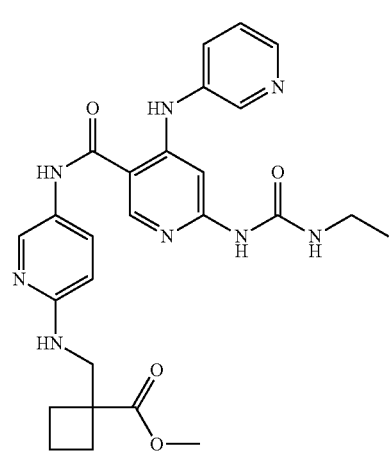
157
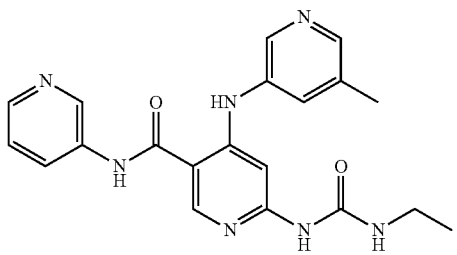
158
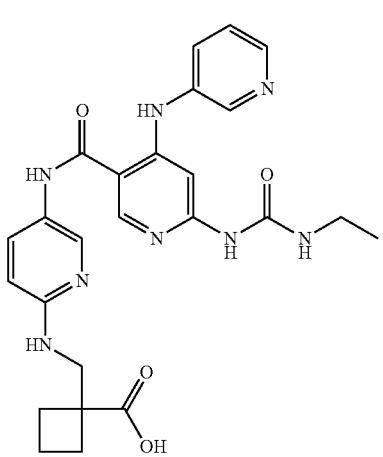
159
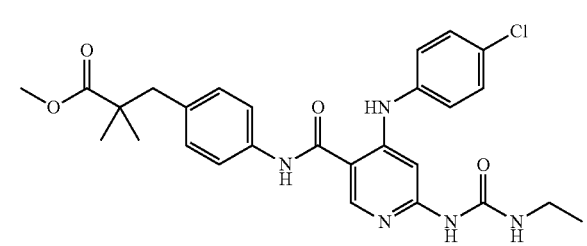
160
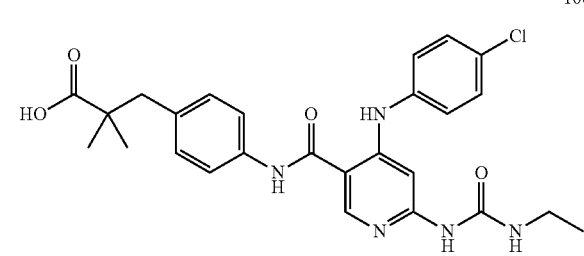
161
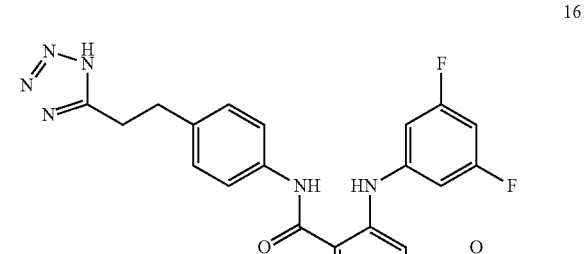

162 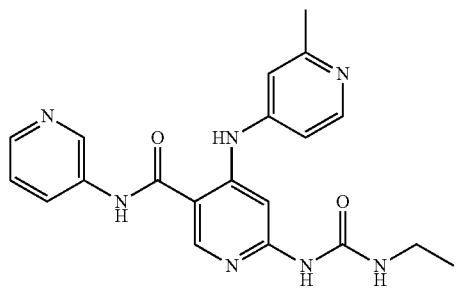
163 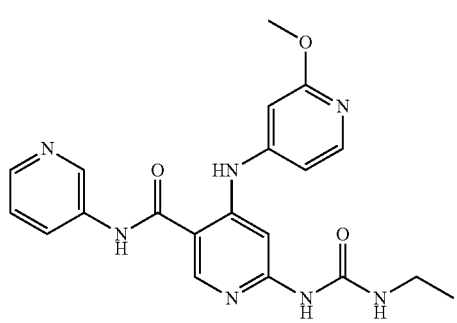
164 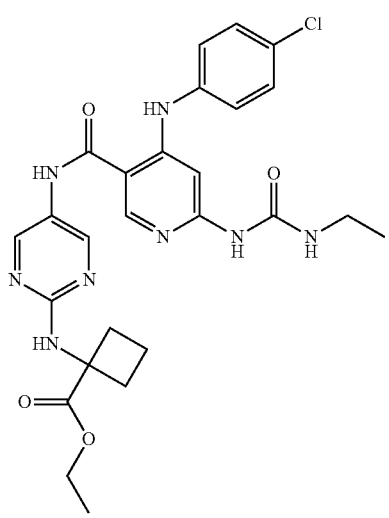
165 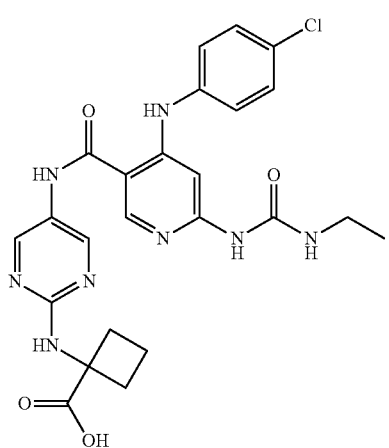
166 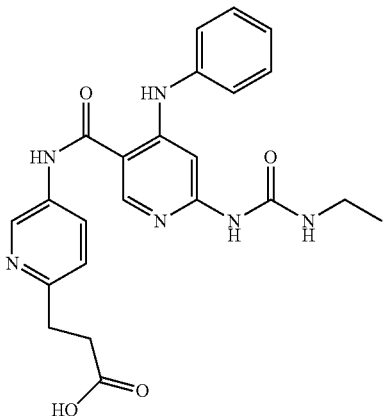
167 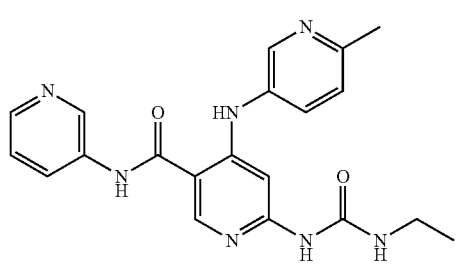
168 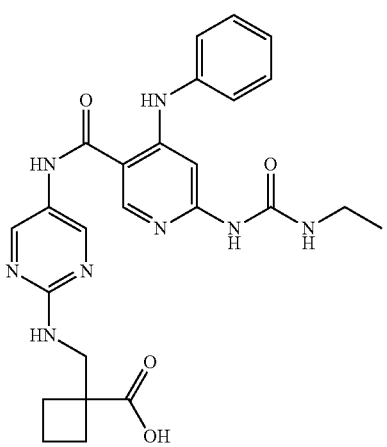
169 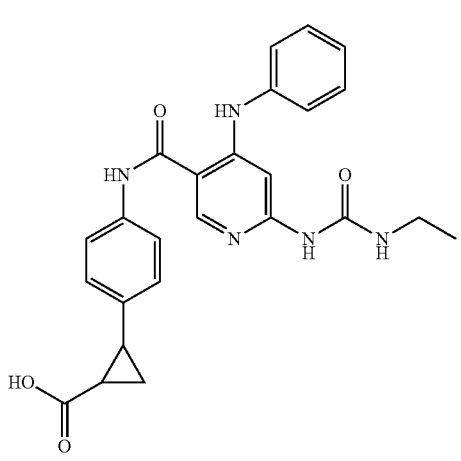

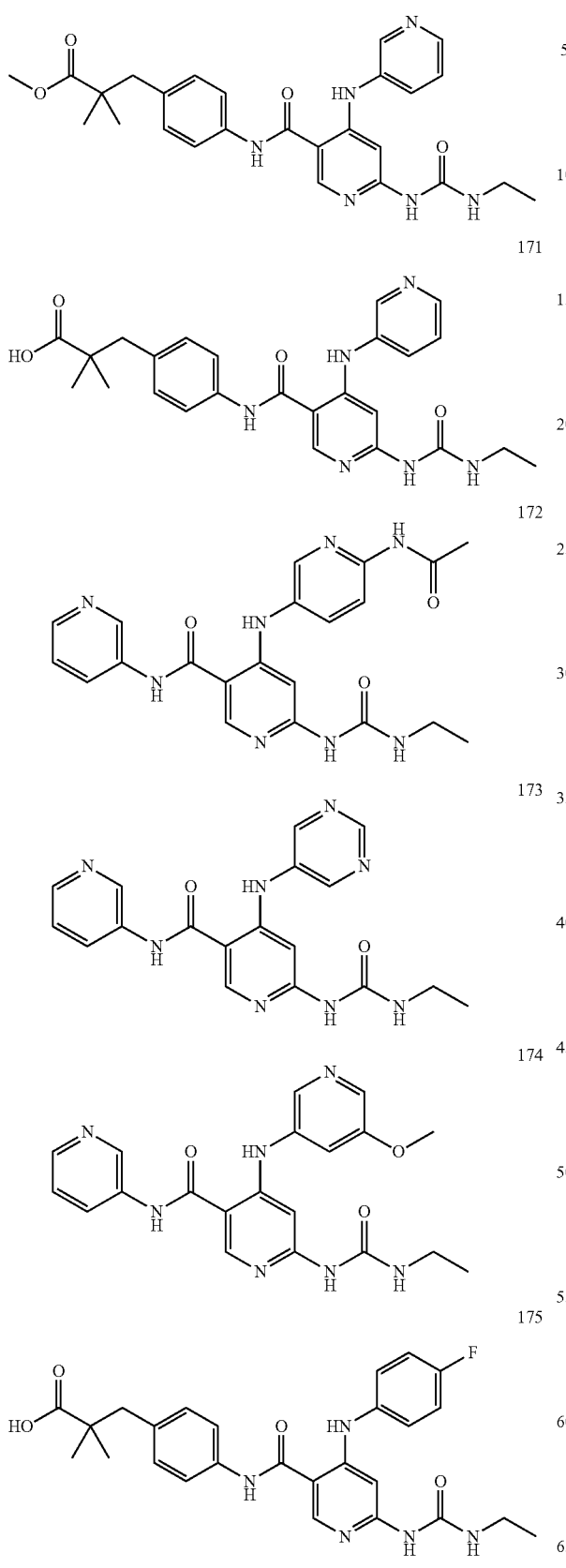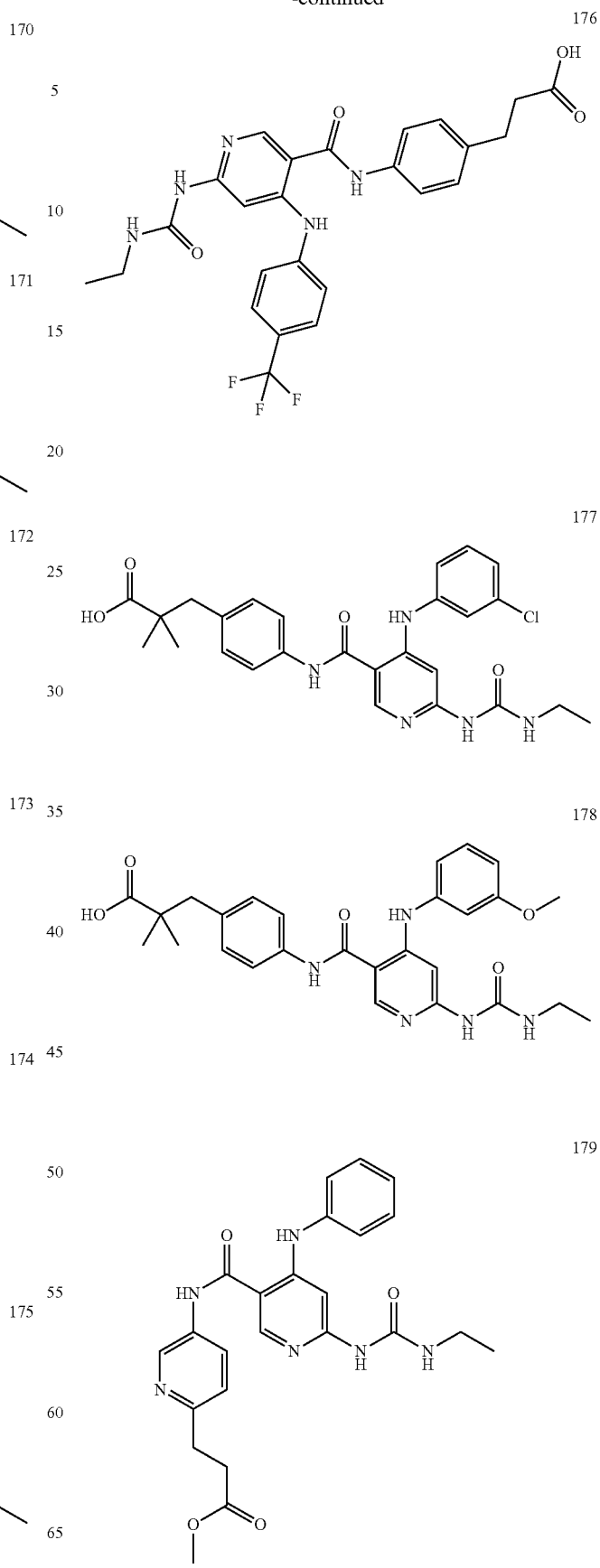

180
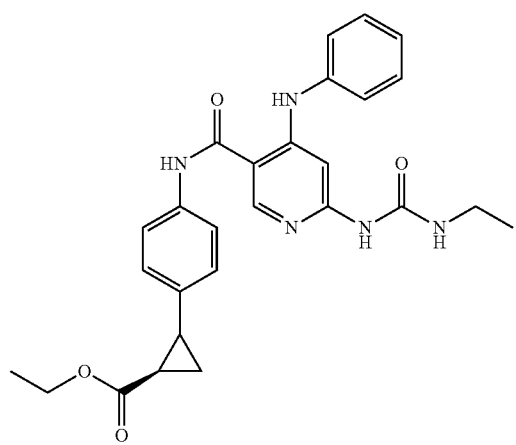
181
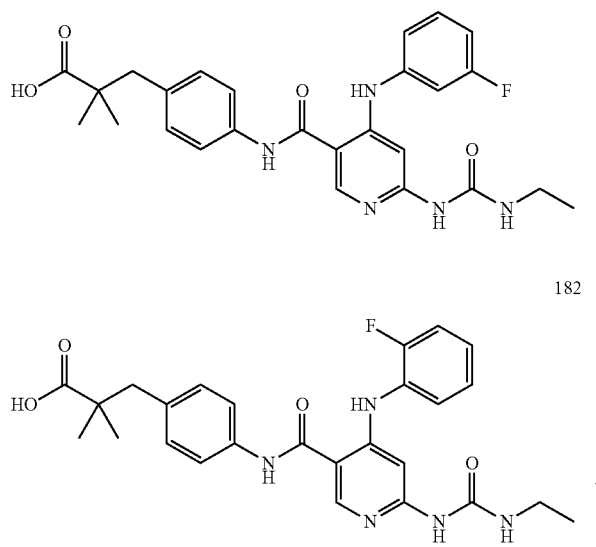
182
183
184
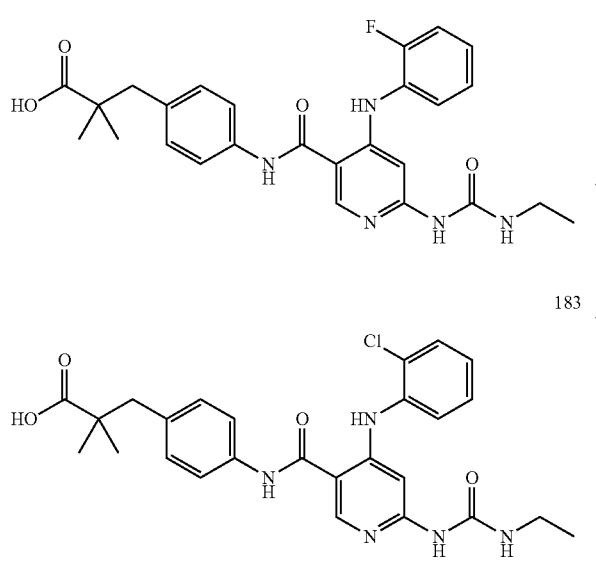
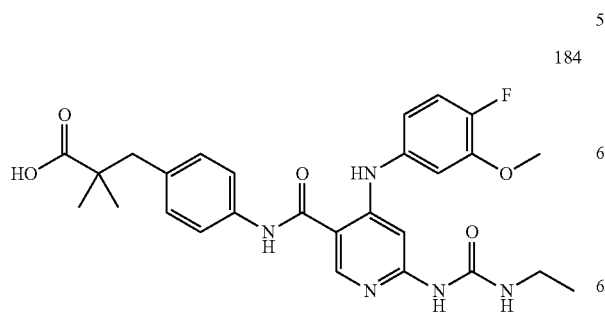
185
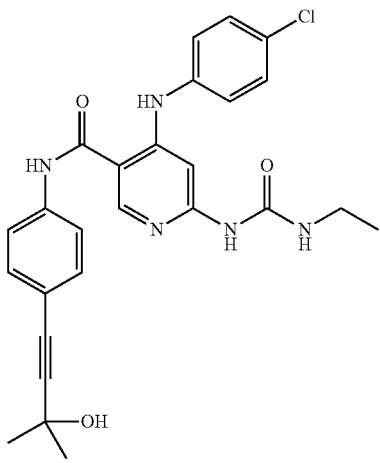
186
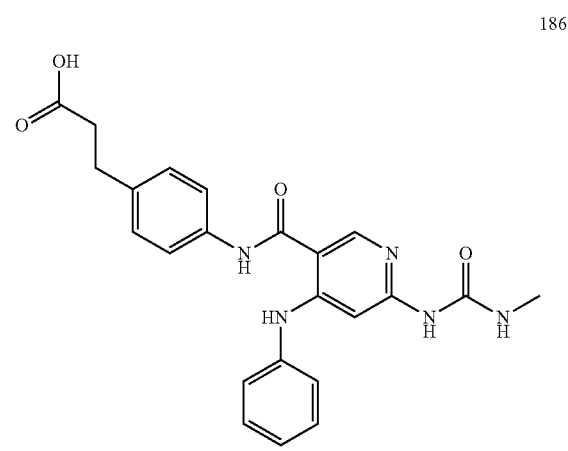
187
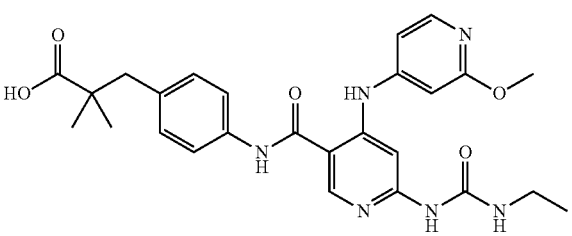
188
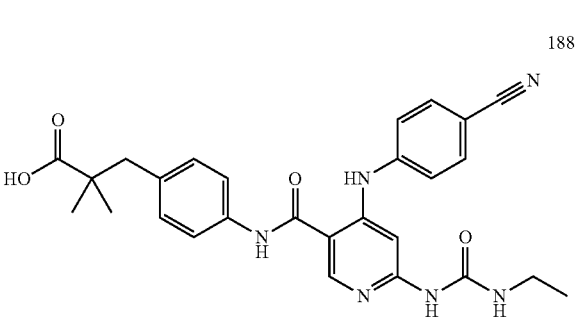

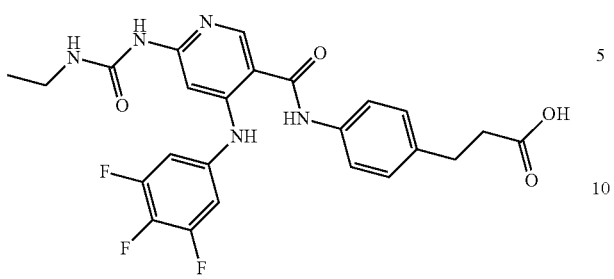
189
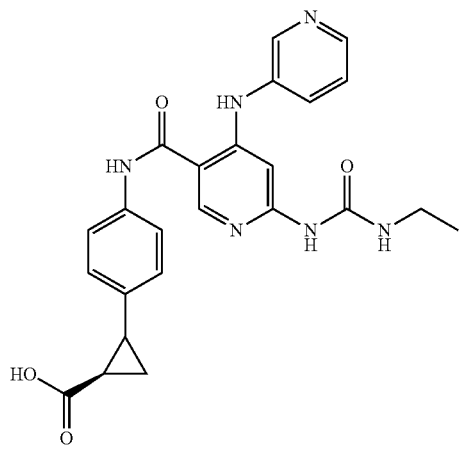
193
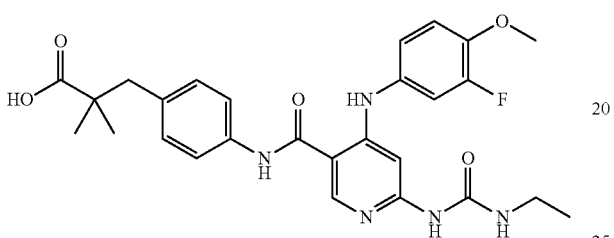
190
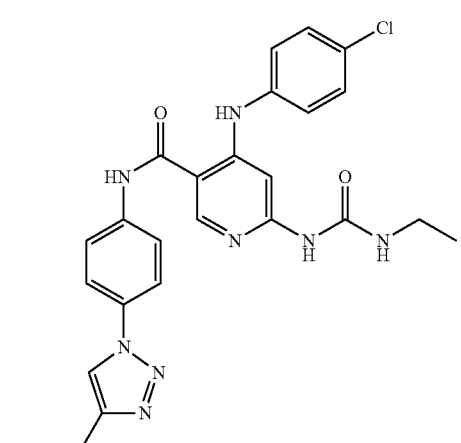
194
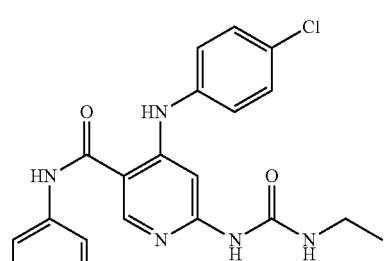
191
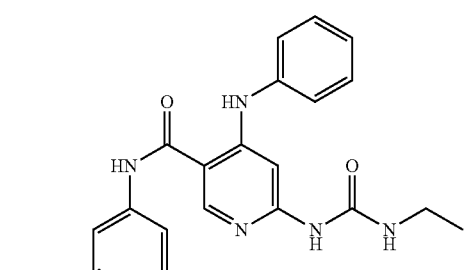
195
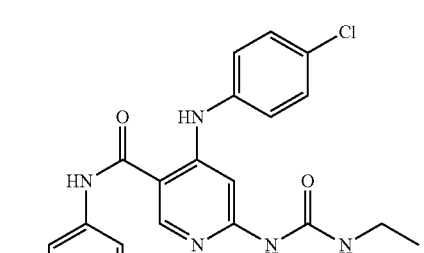
192
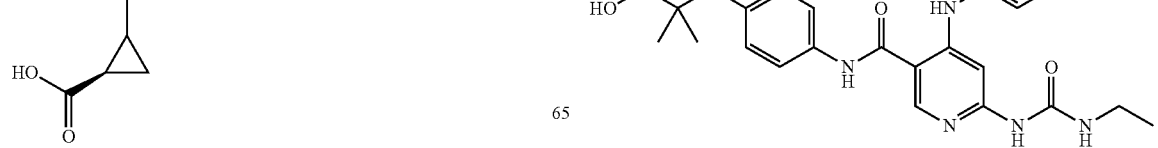
196

-continued
197
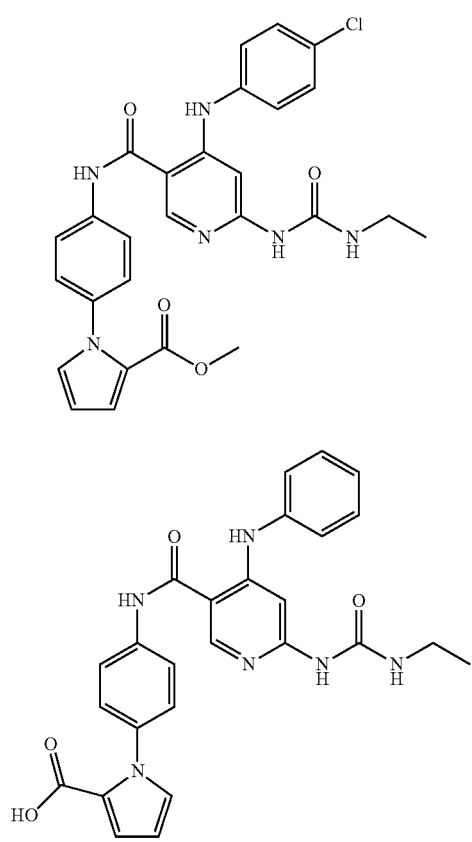
198
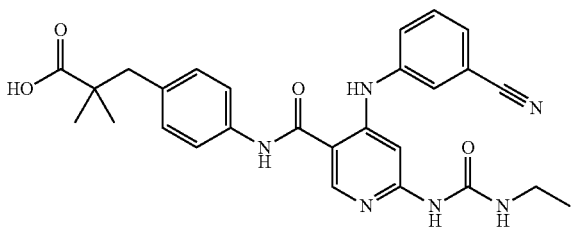
199
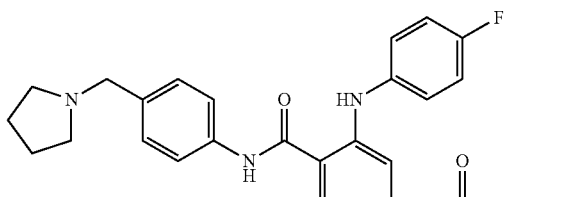
200
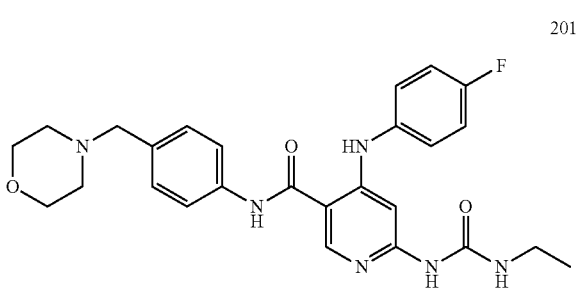
201
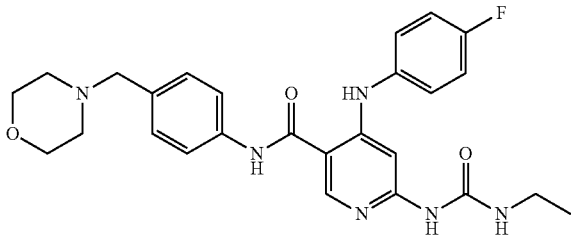
-continued
202
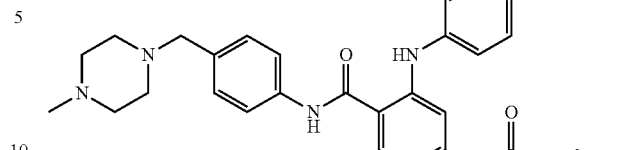
203
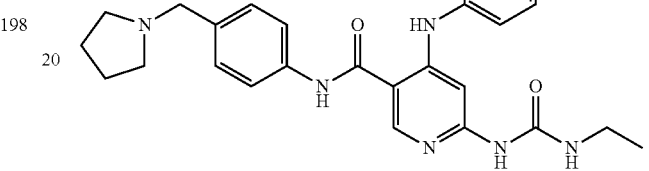
204
205
206
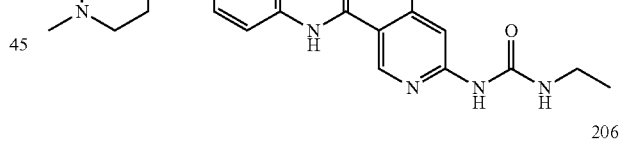

207
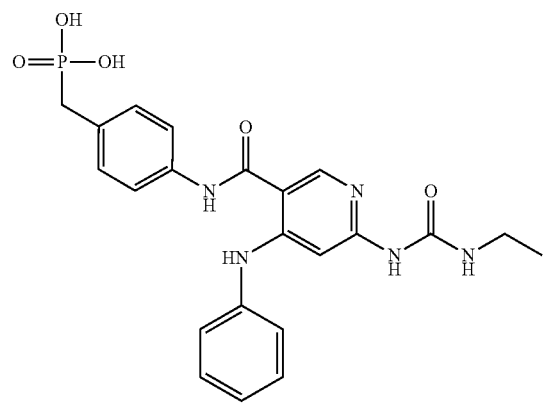
208
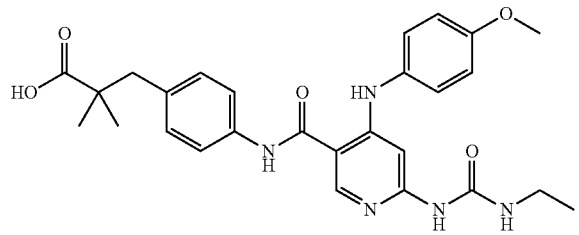
209
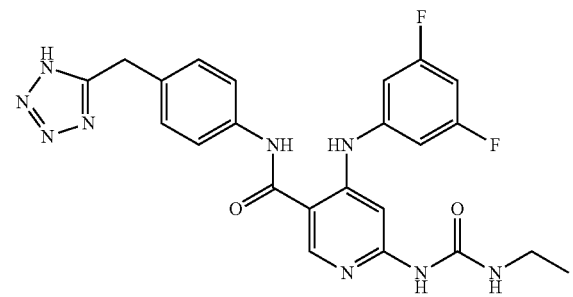
210
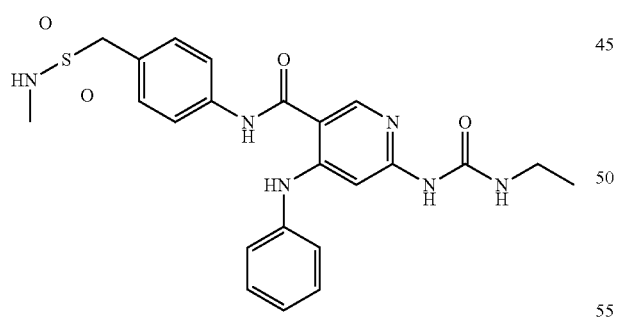
211
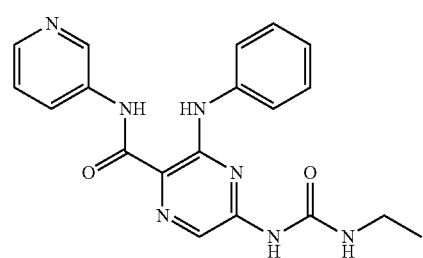
212
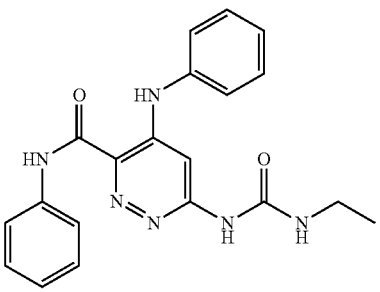
213
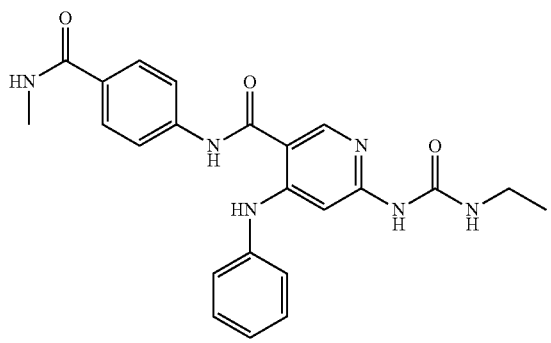
214
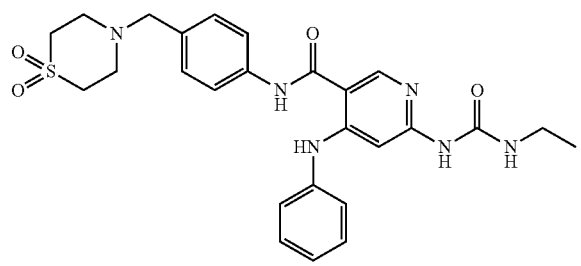
215
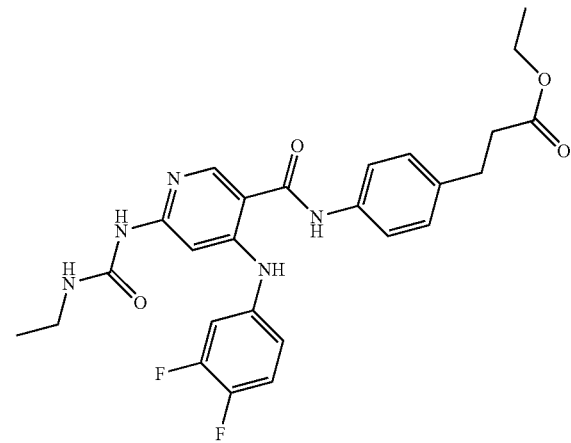

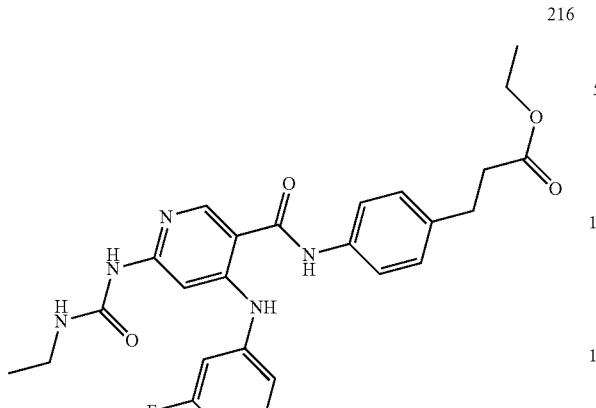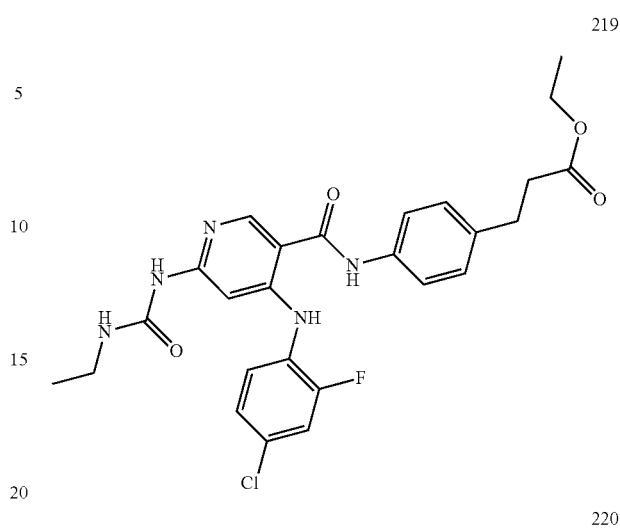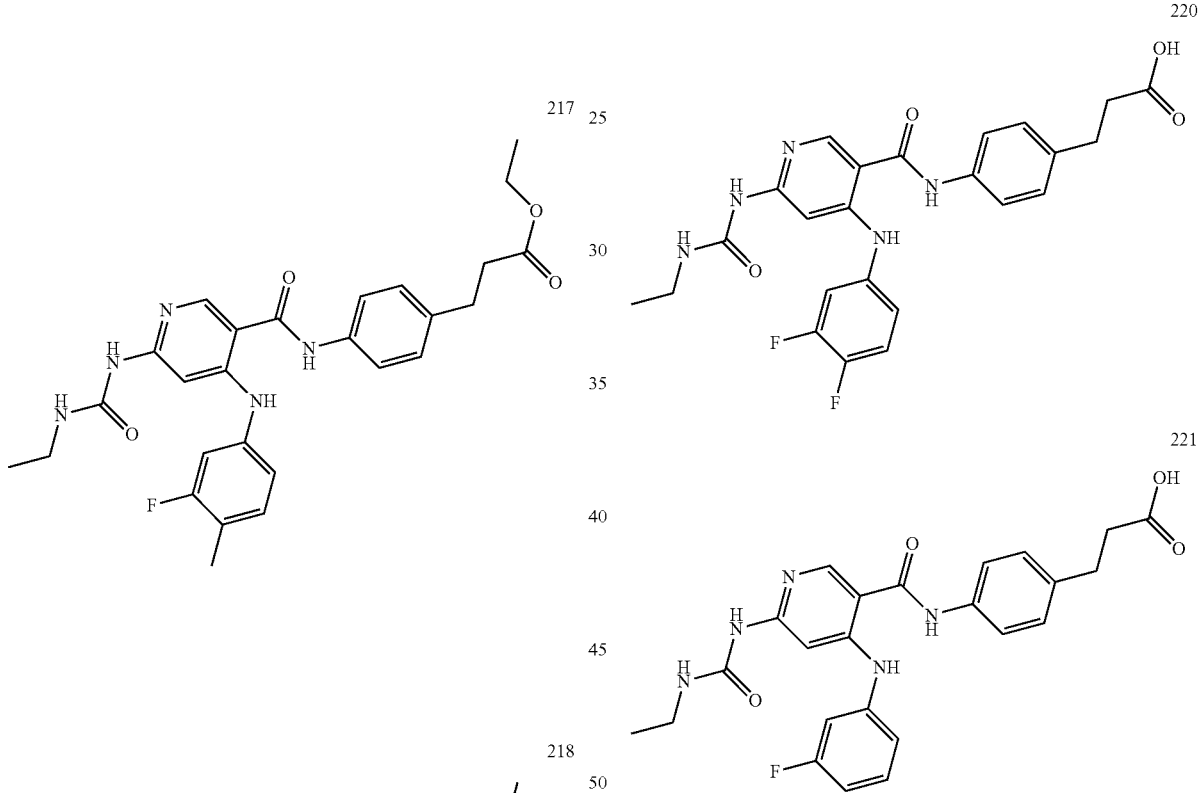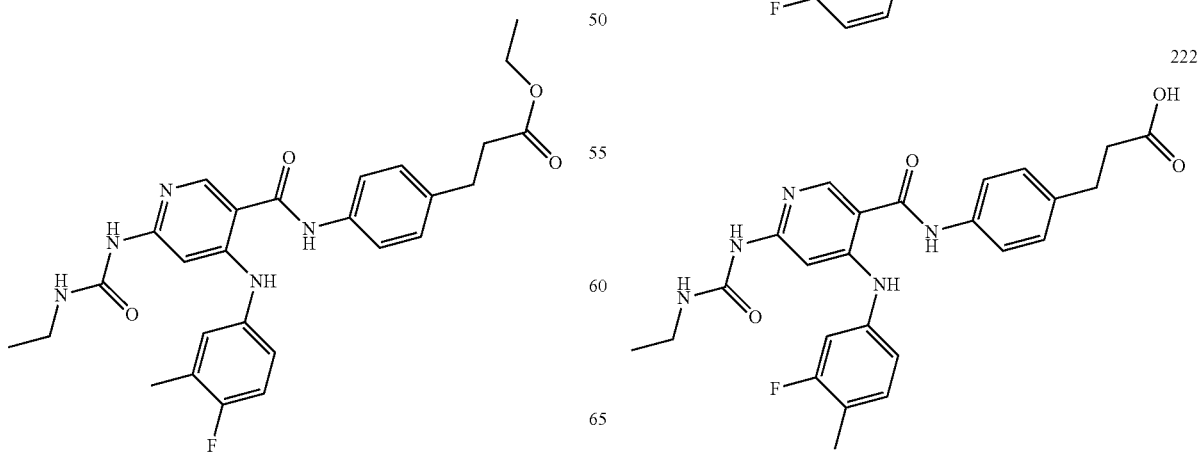

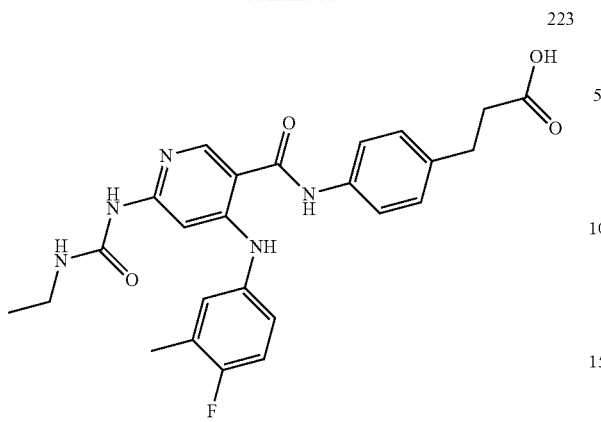
223
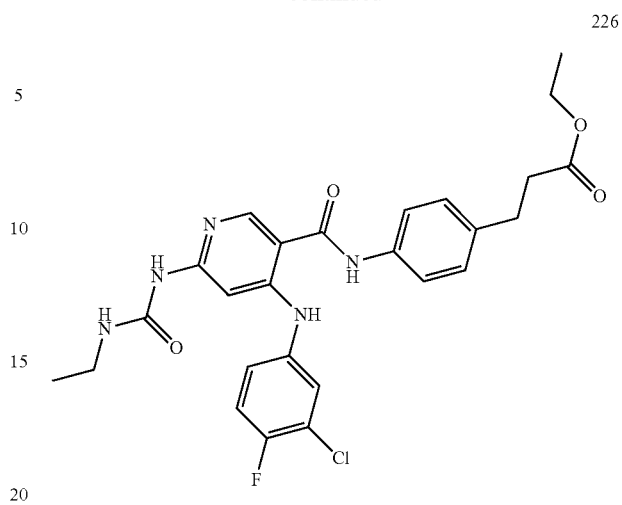
226
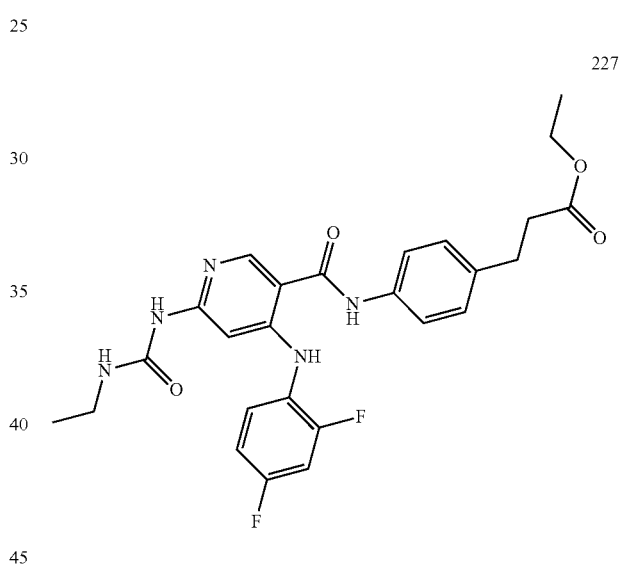
227
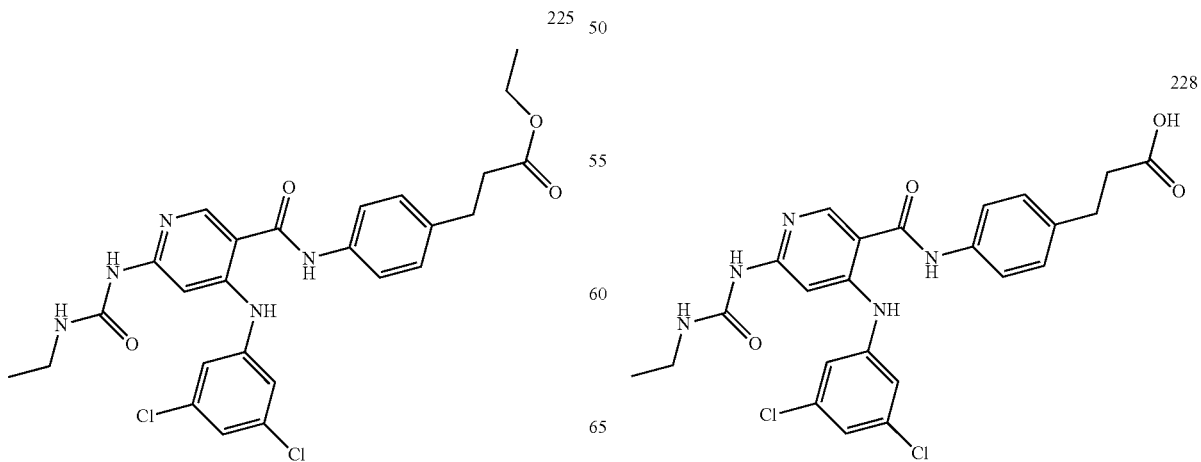

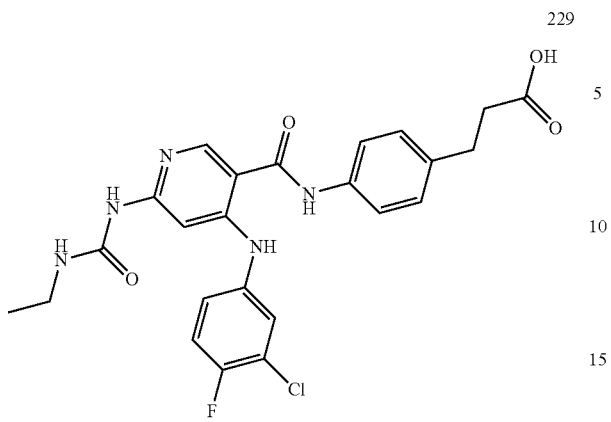
229
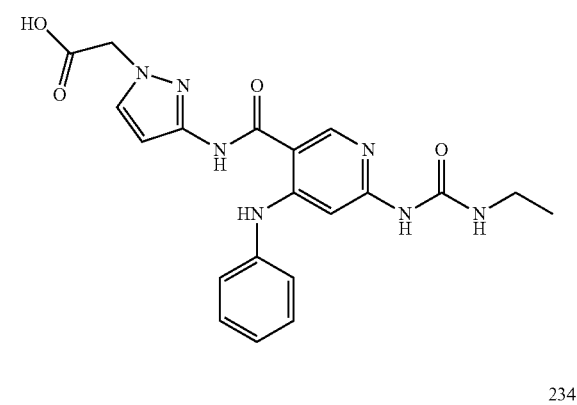
233
230
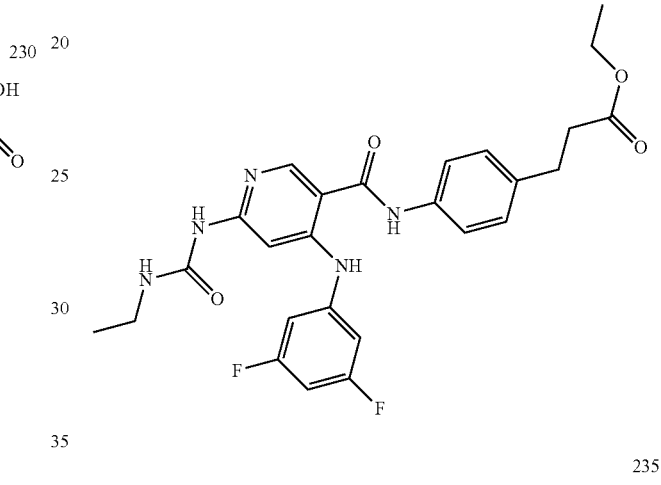
234
231
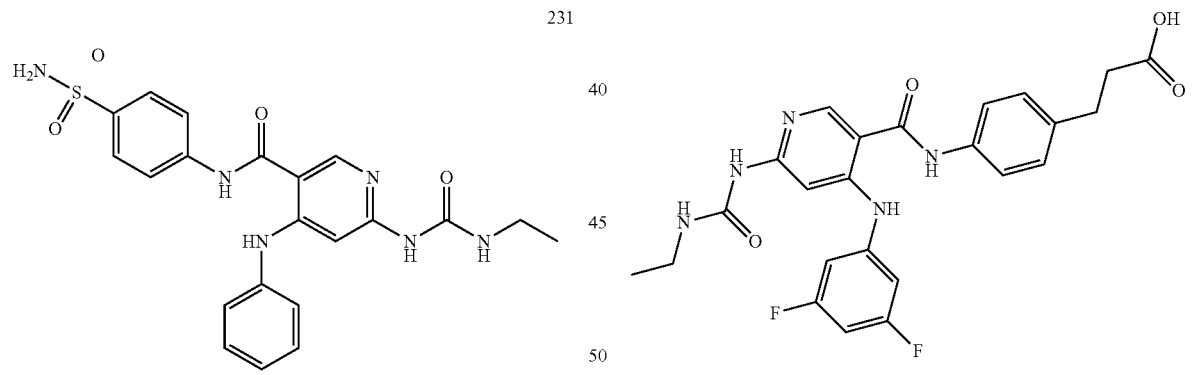
235
232
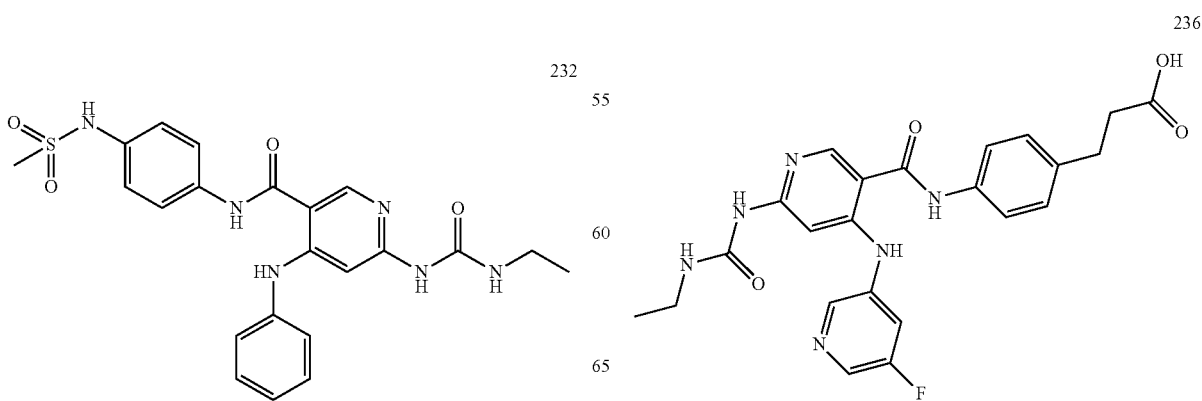
236

237
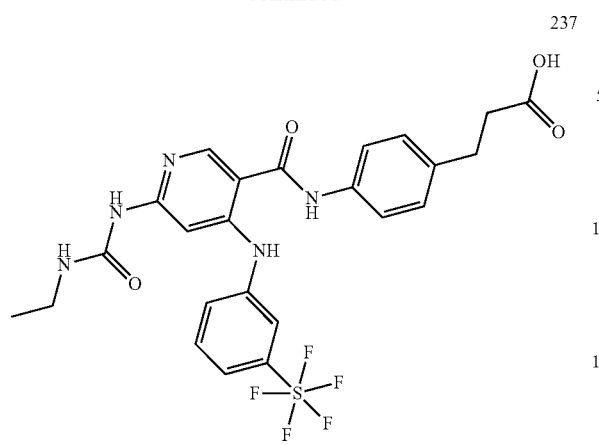
241
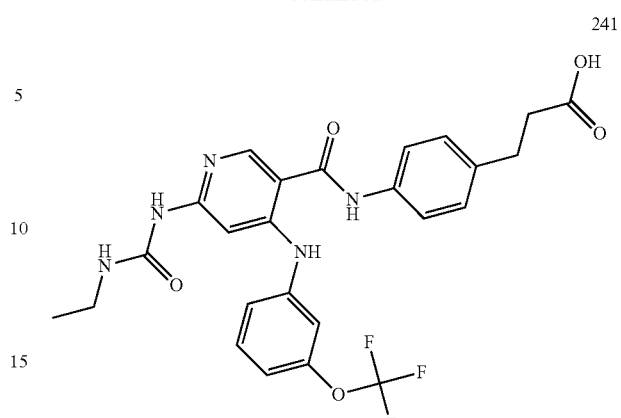
238
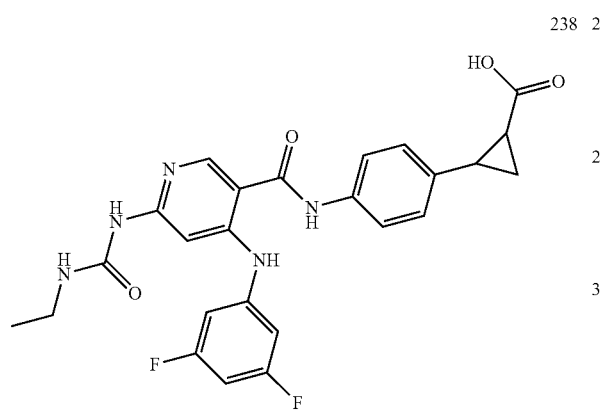
242
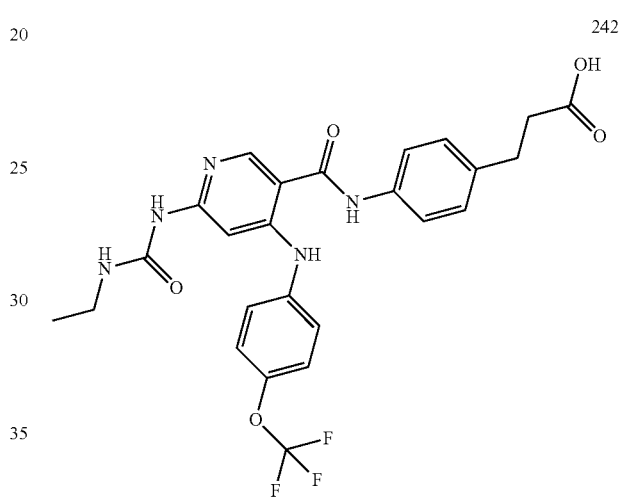
239
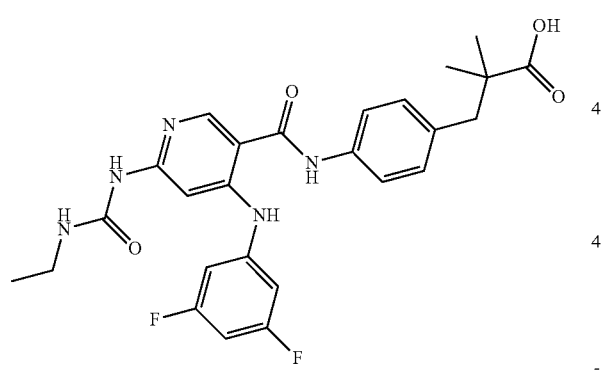
243
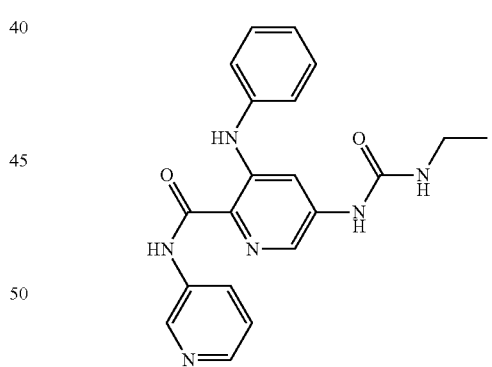
240
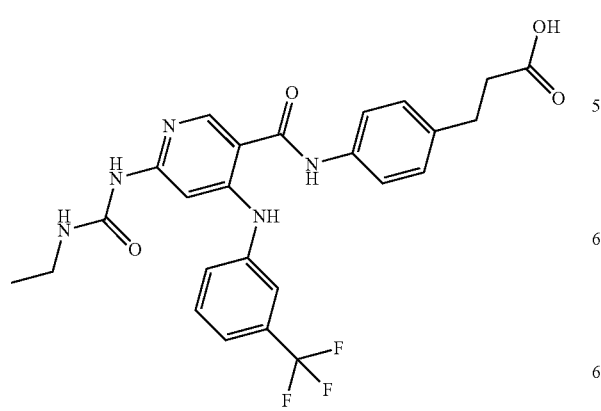
244
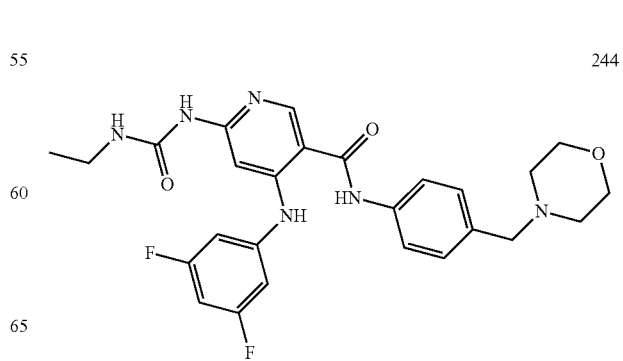

245

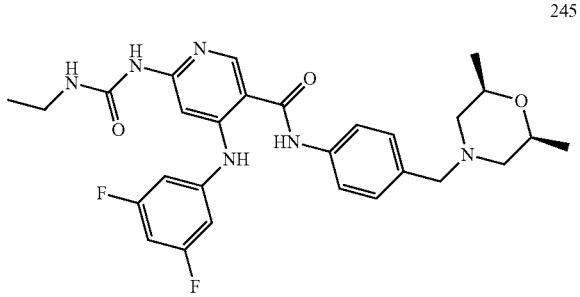

246

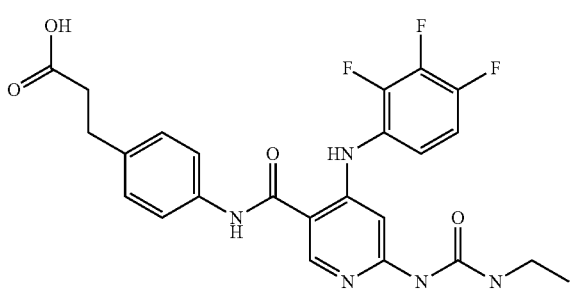

247

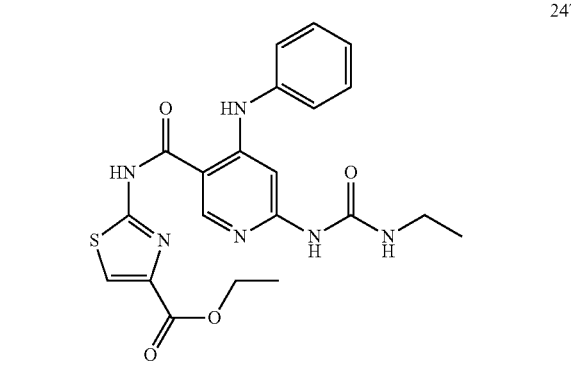

248

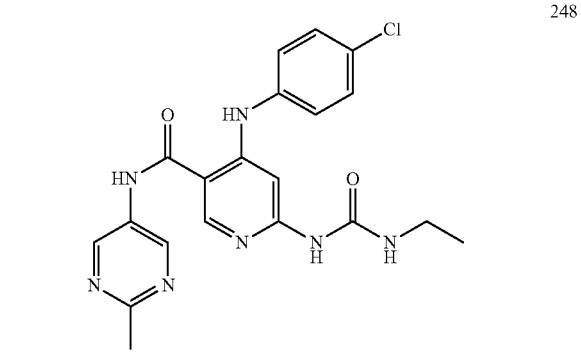

249

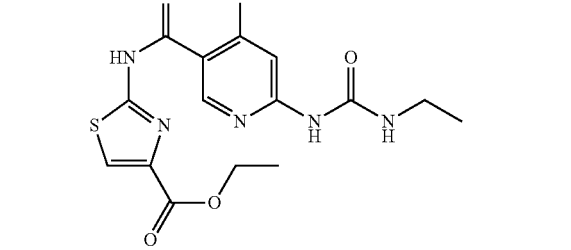

250

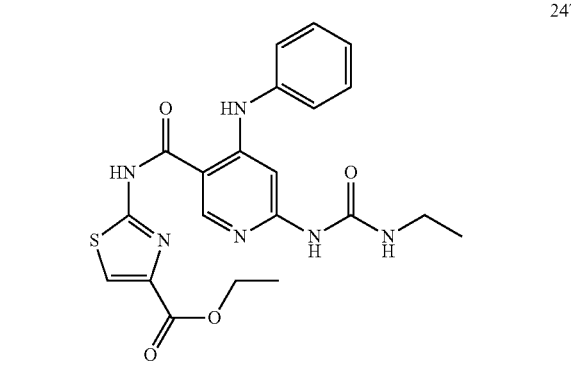

251

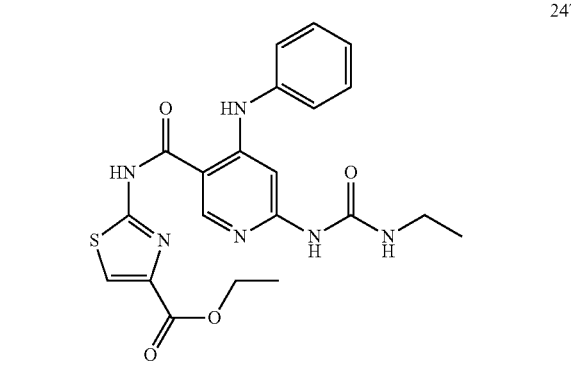

and racemates, enantiomers and salts thereof.

The salts of the compound of Formula I are preferably pharmaceutically acceptable, but it will be appreciated that non-pharmaceutically acceptable salts also fall within the scope of the present invention, since these are useful as intermediates in the preparation of pharmaceutically acceptable salts.

Suitable pharmaceutically acceptable salts include, but are not limited to, salts of pharmaceutically acceptable inorganic acids such as hydrochloric, sulfuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1$^{st}$ edition, 2002, Wiley-VCH. Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others such as alkylphosphonates or phosphoramidates.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid or phosphorylated with groups including alkylphosphonic acids, such as methylenephosphonic acid, or directly attached to phosphonate esters, phosphinate esters, or phosphate esters.

It will be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

This invention also encompasses prodrugs of compounds of formula I. Compounds of formula I having free amino, amido, hydroxy or carboxylic groups can be converted into prodrugs.

The present invention provides a method for the treatment of an antibacterial infection comprising administration of a compound of Formula I or a pharmaceutically acceptable salt thereof to a subject suffering from said infection.

The compounds of the present invention may be administered by any suitable means, for example, orally, parenterally, such as by subcutaneous, intravenous, intramuscular, or intracisternal injection or infusion techniques (e.g., as sterile injectable aqueous or non-aqueous solutions or suspensions).

The present invention also provides compound of Formula I or a pharmaceutically acceptable salt thereof for use in the treatment of an antibacterial infection.

There is also provided a composition comprising a compound of Formula I or a salt thereof. Preferably, the composition further comprises a pharmaceutically acceptable carrier, diluent or excipient.

The compositions of the present invention may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use. In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated.

However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In the treatment or prevention of bacterial infections, an appropriate dosage level will generally be about 0.01 to 500 mg per kg patient body weight per day which can be administered in single or multiple doses. For oral administration, the compositions are preferably provided in the form of tablets containing 1.0 to 1000 milligrams of the active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the invention may be generally prepared by the following general method(s).

General Method A

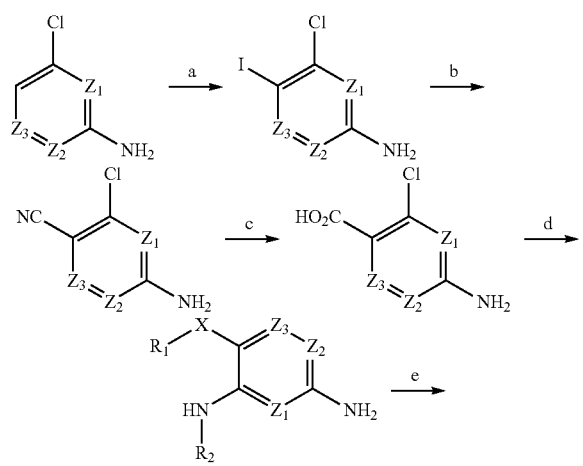

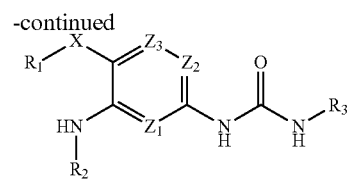

Step a: The chloro-amino analogue was subjected to standard iodination conditions (eg. NIS) in an organic solvent (eg. DMF).

Step b: The iodo-chloro-amino analogue was subjected to cyanation condition using a metal cyanide (eg. $Zn(CN)_2$), a palladium catalyst (eg. $Pd(PPh_3)_4$) in a suitable organic solvent (eg. NMP).

Step c: The cyano analogue was subjected to standard hydrolysis using an aqueous acid (eg. $H_2SO_4$).

Step d: The acid was subjected to amide coupling conditions using common coupling reagents (eg. EDCI+HOBt) with a suitable amine (eg. m-toluidine) in an organic solvent (eg. DMF).

Step e: The free amine analogue was reacted with a suitable isocyanate (eg. ethyl isocyanate) in an organic solvent (eg. 1,4-dioxane).

General Method B

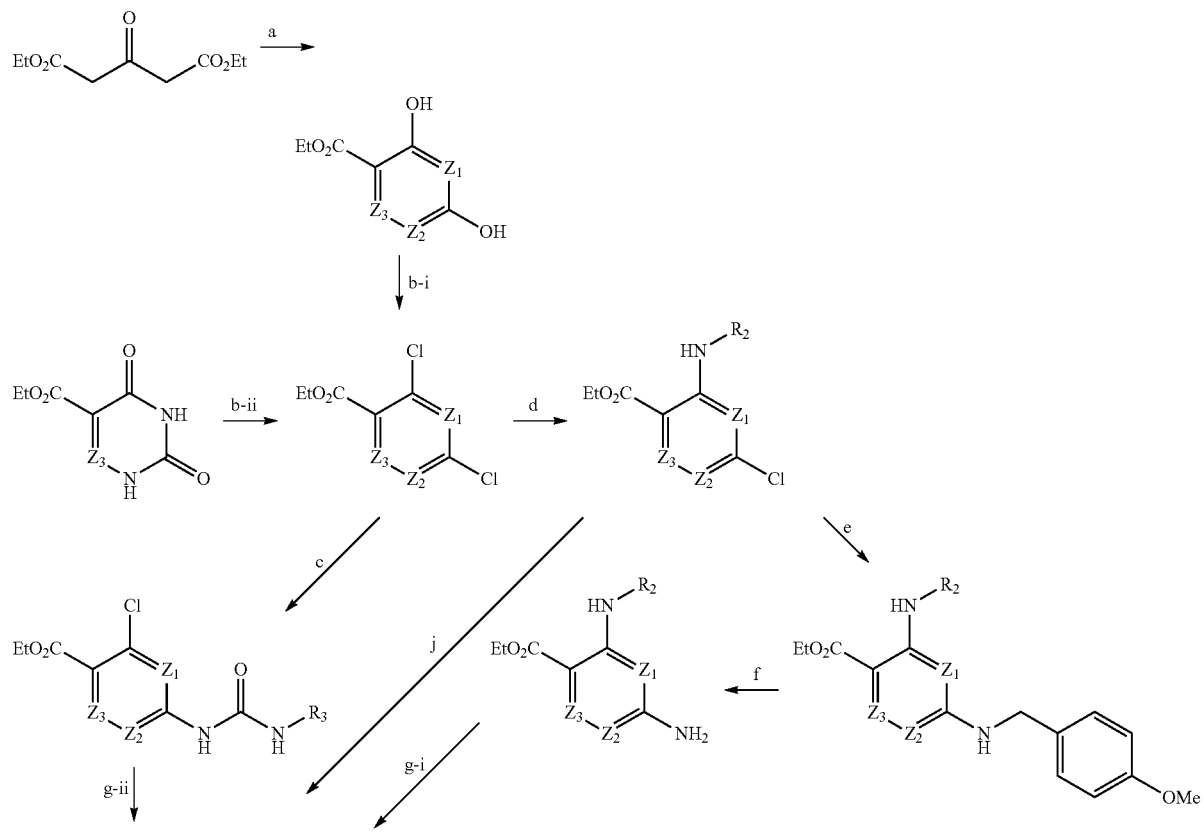

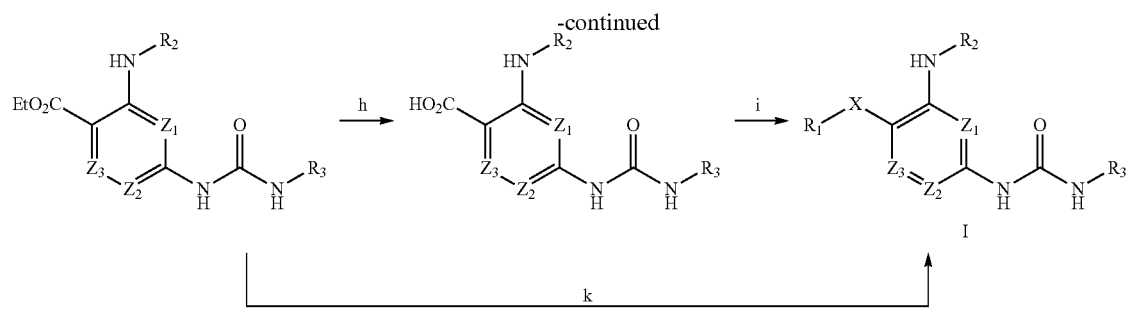

Step a: The heterocyclic ester was formed by the condensation of 1,3-acetonedicarboxylate with an orthoformate (eg. trimethylorthoformate) in acetic anhydride followed by treatment with ammonia.

Step b: (i)/(ii) The dihydroxy analogue (i) or pyrimidine analogue (ii) was subjected to dehydrative chlorination using a suitable reagent (eg. $POCl_3$).

Step c: The dichloro analogue was subjected to Buchwald coupling conditions with a suitable urea (eg. N-ethyl urea) in the presence of a palladium catalyst (eg. $Pd(OAc)_2$), a co-catalyst (eg. Xantphos) and a base (eg. KOtBu) in a suitable organic solvent (eg. 1,4-dioxane).

Step d: The dichloro analogue was subjected to selective displacement by a suitable amine (eg. aniline), in the presence of a base (eg. NaH) or an acid (eg. HCl) in an organic solvent (eg. DMF).

Step e: The amino-chloro analogue was subjected to displacement conditions with a suitable protected amine (eg. p-methoxybenzylamine) in a suitable organic solvent (eg. toluene).

Step f: The protected amine was deprotected using standard conditions (eg. $TFA+Et_3SiH$ in DCM for a PMB group).

Step g (i): The amino analogue was reacted with a suitable isocyanate (eg. N-ethyl isocyanate) to form a urea analogue.

Step g (ii): The chloro-urea analogue was subjected to selective displacement by a suitable amine (eg. m-toluidine) in the presence of a base (eg. NaH) or an acid (eg. HCl) in an organic solvent (eg. DMF).

Step h: The ester analogue was hydrolysed to an acid with a suitable aqueous base (eg. NaOH) in a suitable solvent (eg. EtOH).

Step i: The acid was subjected to amide coupling conditions using common coupling reagents (eg. EDCI+HOBt) with a suitable amine (eg. m-toluidine) in an organic solvent (eg. DMF).

Step j: The chloro-amino analogue was subjected to Buchwald coupling conditions with a suitable urea (eg. N-ethyl urea) in the presence of a palladium catalyst (eg. $Pd(OAc)_2$), a co-catalyst (eg. Xantphos) and a base (eg. KOtBu) in a suitable organic solvent (eg. 1,4-dioxane).

Step k: The ester was reacted with a suitable amine (eg aniline) in the presence of a Lewis acid (eg. trimethylaluminium) in a suitable solvent (eg. THF).

General Method C

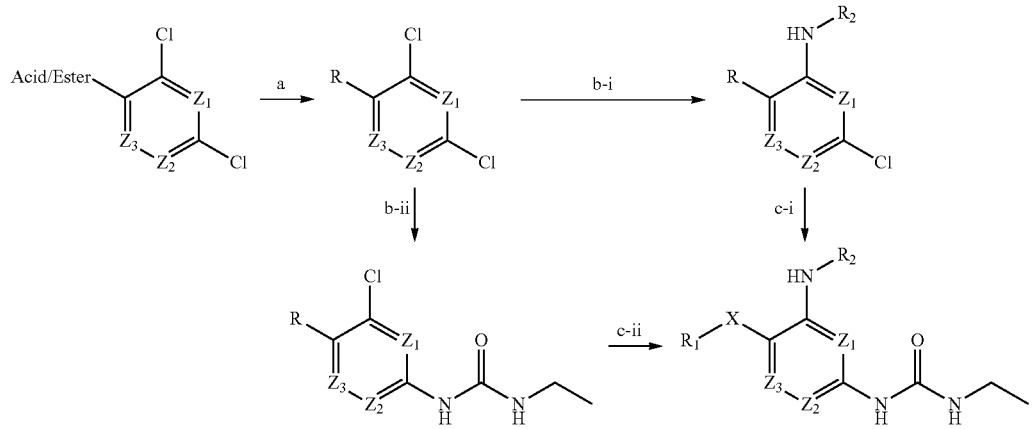

where R in the general reaction scheme represents an acid ($CO_2H$), an ester ($CO_2$alkyl) or the group —X—$R_1$ where X and $R_1$ are as previously defined.

Step a: The dichloro acid was converted to an amide by activation to the acid chloride with a suitable reagent (eg. thionyl chloride) in an organic solvent (eg. THF) with catalytic DMF, followed by reaction with a suitable amine (eg. 3-aminopyridine) in the presence of a base (eg. TEA) in an organic solvent (eg. THF).

Step b: (i) The dichloro analogue was subjected to selective displacement by a suitable amine (eg. aniline), in the presence of a base (eg. NaH) or an acid (eg. HCl) in an organic solvent (eg. DMF).

Step b (ii): The dichloro analogue was subjected to Buchwald coupling conditions with a suitable urea (eg. N-ethyl urea) in the presence of a palladium catalyst (eg. Pd(OAc)$_2$), a co-catalyst (eg. Xantphos) and a base (eg. KOtBu) in a suitable organic solvent (eg. 1,4-dioxane).

Step c (i): The chloro-amino analogue was subjected to Buchwald coupling conditions with a suitable urea (eg. N-ethyl urea) in the presence of a palladium catalyst (eg. Pd(OAc)$_2$), a co-catalyst (eg. Xantphos) and a base (eg. KOtBu) in a suitable organic solvent (eg. 1,4-dioxane).

Step c (ii): The chloro-urea analogue was subjected to selective displacement by a suitable amine (eg aniline), in the presence of a base (eg. NaH) or an acid (eg. HCl) in an organic solvent (eg. DMF).

In one embodiment there is provided an intermediate of general formula (II):

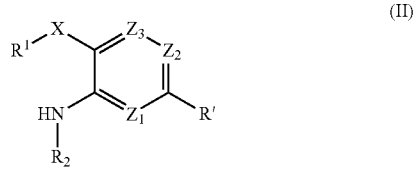

(II)

where R' is a halo or NH$_2$ group and R$_1$, R$_2$, X, Z$_1$, Z$_2$ and Z$_3$ are as previously defined for formula (I).

Accordingly, there is provided a process for the manufacture of a compound of formula (I) via an intermediate of formula (II). In one embodiment, R' is halo and the process comprises the step of coupling said intermediate of formula (II) with an N—C$_{1-6}$alkyl urea under Buchwald coupling conditions. In another embodiment, R' is NH$_2$ and the process comprises the step of reacting said intermediate of formula (II) with a C$_{1-6}$alkyl isocyanate under suitable reaction conditions.

In another embodiment there is provided an intermediate of general formula (III):

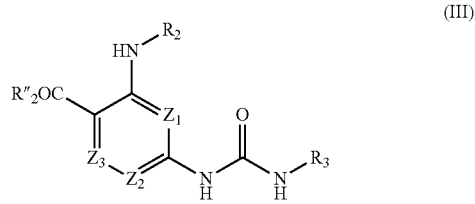

(III)

where R" is H or C$_{1-6}$alkyl and R$_2$, R$_3$, Z$_1$, Z$_2$ and Z$_3$ are as previously defined for formula (I).

Accordingly, there is provided a process for the manufacture of a compound of formula (I) wherein X—R$_1$ is C(=O)NR$^5$R$^6$ or C(=O)NR$^a$R$^b$, via an intermediate of formula (III) wherein the process comprises the step of reacting said intermediate of formula (III) with a reagent of formula NHR$^5$R$^6$ or NHR$^a$R$^b$ under amide formation conditions such as amide coupling (e.g. using coupling reagents such as HOBt/EDCI, HATU, HBTU) or acid catalysis (e.g. Lewis acid); or alternatively, activating the —CO$_2$R" group of formula (III) to form an acid chloride or acid anhydride thereof then reacting with said reagent of formula NHR$^5$R$^6$ or NHR$^a$R$^b$.

In another embodiment there is provided an intermediate of general formula (IV):

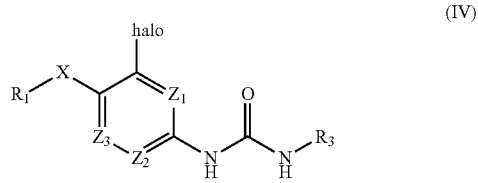

(IV)

wherein X, R$_1$, R$_3$, Z$_1$, Z$_2$ and Z$_3$ are as previously defined for formula (I).

Accordingly, there is provided a process for the manufacture of a compound of formula (I) via an intermediate of formula (IV) wherein the process comprises the step of reacting said intermediate of formula (IV) under nucleophilic displacement/substitution conditions (e.g. in the presence of base or acid/base or acid catalysed) with a reagent of formula NH$_2$R$_2$.

EXAMPLES

Those skilled in the art will appreciate that the invention described herein is susceptible to variations and modifications other than those specifically described. The invention will now be described without limitation by reference to the examples which follow.

Compound Synthesis $^1$H NMR spectra were recorded on either a Brüker Avance DRX 400, AC 200 or AM 300 spectrometer. Spectra were recorded in deuterated solvents (CDCl$_3$, MeOD, DMSO-d$_6$, CD$_3$CN, or Acetone-d$_6$) using the residual solvent peak as a reference. Chemical shifts are reported on the δ scale in parts per million (ppm) using the following conventions to assign the multiplicity: s (singlet), d (doublet), t (triplet), q (quartet), p (pentet), m (multiplet) and prefixed br (broad). Mass spectra (ESI) were recorded on either a Micromass Platform QMS or Thermo Finnigan LCQ Advantage spectrometer. Flash chromatography was performed on 40-63 μm silica gel 60 (Merck No. 9385). Automated flash chromatography was performed either on a Combi-Flash™ purification system using Combi-Flash™ silica gel columns or on a Biotage SP4 purification system using either GraceResolv™ silica gel cartridges, Grace Reveleris™ C-18 reverse phase silica gel cartridges or Biotage SNAP™ C-18 reverse phase silica gel cartridges. Preparative HPLC was carried out using either a Gilson 322 pump with a Gilson 215 liquid handler and a HP1100 PDA detector or an Agilent 1200 Series mass detected preparative LCMS using a Varian XRs C-18 100×21.2 mm column. Unless otherwise specified, the HPLC systems employed Phenomenex C8(2) columns using either acetonitrile or acetonitrile containing 0.06% TFA in water, water containing 0.1 TFA or water containing 0.1% formic acid.

During the reactions a number of the moieties may need to be protected. Suitable protecting groups are well known in industry and have been described in many references such as Protecting Groups in Organic Synthesis, Greene T W, Wiley-Interscience, New York, 1981.

The abbreviations used in the Examples are as follows unless indicated otherwise:
Ac: acetyl
ACN: acetonitrile
conc.: concentrated
DCM: dichloromethane
DIPEA: N,N-diisopropylethylamine
DMAP: N,N-dimethylpyridin-4-amine
DMF: N,N-dimethylformamide
DMSO: dimethylsulfoxide
EDCI: 1-Ethyl-3-(3-dimethylaminopropyl) carbodiimide
EtOAc: ethyl acetate
Et$_2$O: diethylether
EtOH: ethanol
ESI: electrospray ionisation
Eq: equivalents
h: hour(s)

HATU: 2-(7-Aza-1H-benzotriazole-1-yl)-1,1,3,3-tetramethyluronium hexafluorophosphate
HBTU: N-[(1H-Benzotriazol-1-yloxy)(dimethylamino)methylidene]-N-methylmethanaminium hexafluorophosphate
HOBt: N-hydroxybenzotriazole
HPLC: high performance liquid chromatography
IPA: propan-2-ol
LCMS: liquid chromatography coupled mass spectrometry
LDA: lithium diisopropylamide
LHMDS: lithium bis(trimethylsilyl)amide
min. minute(s)
MeOH: methanol
MS: mass spectrometry
NBS: N-bromosuccinimide
NIS: N-iodosuccinimde
NMP: 1-methylpyrrolidin-2-one
NMR: nuclear magnetic resonance
NOE: nuclear Overhauser effect
PTFE: poly(tetrafluoroethylene)
PMB: p-methoxybenzyl
s: second(s)
RT: room temperature
THF: tetrahydrofuran
TLC: thin-layer chromatography
TMEDA: N,N,N',N'-tetramethylethylenediamine
Xantphos: 4,5-bis(diphenylphosphino)-9,9-dimethylxanthene
X-phos: 2-(dicyclohexylphosphino)-2',4',6'-tri-1-propyl-1,1'-biphenyl All amines used were commercially available unless otherwise stated. The following amines were prepared synthetically.

Methyl 3-(4-aminophenyl)-2,2-dimethyl-propanoate

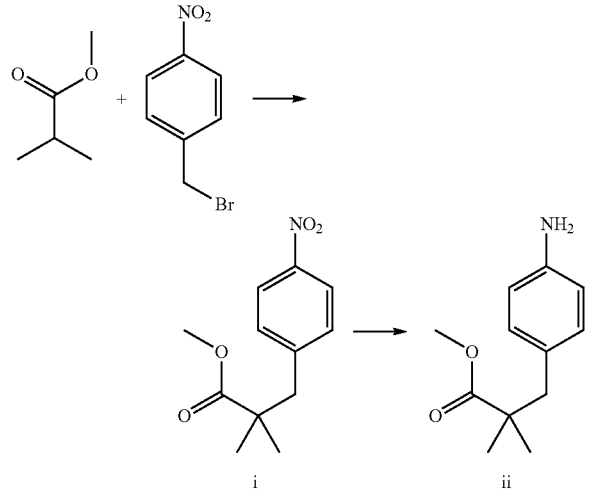

Methyl 2,2-dimethyl-3-(4-nitrophenyl)propanoate (i)

n-BuLi (1.15M in hexane) (10.1 mL, 11.6 mmol) was added dropwise to a solution of diisopropylamine (1.64 mL, 11.6 mmol) in THF (20 mL) in a dry ice/acetone bath. The mixture was stirred and warmed to ~−50° C. before being cooled again and methyl 2-methylpropanoate (1.3 mL, 11 mmol) was added over 5 min. The mixture was stirred for 30 min before a solution of the nitrobenzyl bromide (2 g in 15 mL THF) was added dropwise over 20 min. The temperature was kept below −65° C. during the addition then left in the cool bath to warm slowly to RT and stirred for 16 hr. The mixture was quenched with NH$_4$Cl (sat.) and left at RT for 9 days. The quenched reaction mixture was diluted with water and EtOAc and extracted into EtOAc (3×40 mL). The organics were combined, dried with brine, then solid MgSO$_4$, filtered and the solvent removed to afford a crude oil. The oil was dissolved in ~2 mL DCM and applied to a silica column to afford (i) 1.4 g (64%). $^1$H NMR (400 MHz, CDCl$_3$) δ 8.13 (d, J=8.8 Hz, 2H), 7.27 (d, J=9.6 Hz, 2H), 3.67 (s, 3H), 2.96 (s, 2H), 1.21 (s, 6H).

Methyl 3-(4-aminophenyl)-2,2-dimethyl-propanoate (ii)

Compound (i) (736 mg, 3.06 mmol) was dissolved in MeOH (15 mL) at RT and this solution degassed with N$_2$. Palladium on carbon (10%) (25 mg) was suspended in water/MeOH (0.5 mL/2 mL) and added to the substrate solution. The mixture was again degassed with N$_2$ and then vacuum/flushed with H$_2$. The mixture was stirred under a H$_2$ balloon overnight at RT. The mixture was filtered through celite, washed with MeOH and the filtrate evaporated to dryness to afford a clear oil which was placed under high vacuum for 1 h to afford the desired product (ii), 620 mg. $^1$H NMR (400 MHz, CDCl$_3$) δ 6.88 (d, J=8.3 Hz, 2H), 6.60 (d, J=8.3 Hz, 2H), 3.64 (s, 3H), 2.74 (s, 2H), 1.15 (s, 6H).

Ethyl (1R,2R)-2-(4-aminophenyl)cyclopropanecarboxylate

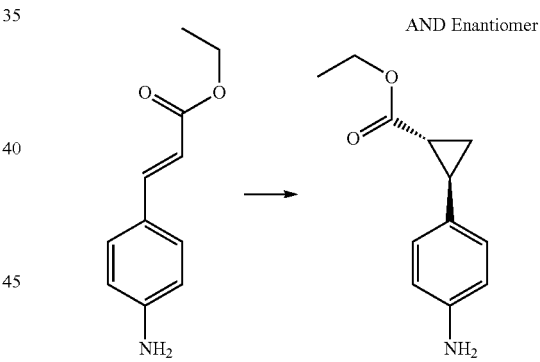

To a suspension of sodium hydride (36 mg, 0.89 mmol) in DMSO (2 mL) was added the solid trimethyl sulfoxonium iodide (185 mg, 1.05 mmol). The mixture was stirred for 25 min before a solution of ethyl (E)-3-(4-aminophenyl)prop-2-enoate (100 mg, 0.52 mmol) in DMSO (2 mL) was added quickly at RT. The mixture was left to stir overnight. The bulk mixture was quenched with NH$_4$Cl (sat.) and the mixture diluted with water and EtOAc. The layers were separated and the aqueous layer extracted into EtOAc (3×30 mL). The organic fractions were combined, dried with brine then MgSO$_4$ and the solvent removed. Flash chromatography on silica gel, eluting with 20-50% ethyl acetate gradient in n-heptane, gave ethyl (1R,2R)-2-(4-aminophenyl)cyclopropanecarboxylate, 70 mg. $^1$H NMR (400 MHz, CDCl$_3$) δ 6.96-6.89 (m, 2H), 6.68-6.61 (m, 2H), 4.17 (q, J=7.1 Hz, 2H), 2.44 (ddd, J=9.2, 6.6, 4.2 Hz, 1H), 1.80 (ddd, J=8.4, 5.2, 4.2 Hz, 1H), 1.53 (ddd, J=9.2, 5.2, 4.5 Hz, 1H), 1.28 (t, J=7.1 Hz, 3H), 1.24 (ddd, J=8.3, 6.6, 4.5 Hz, 1H).

Methyl 1-(4-aminophenyl)pyrrole-2-carboxylate

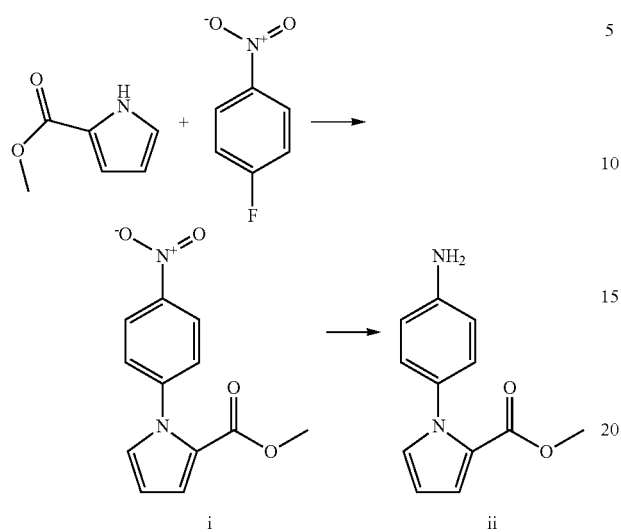

Methyl 1-(4-nitrophenyl)pyrrole-2-carboxylate (i)

Methyl 1H-pyrrole-2-carboxylate (1 g, 8.0 mmol) was dissolved in DMF (14 mL). The mixture was cooled down at 0° C. and sodium hydride (350 mg, 8.8 mmol) was added. After 5 min 1-fluoro-4-nitro-benzene (1.13 mmol, 7.99 mmol) was added and the mixture stirred at 80° C. for 3 hours. Water was added, the solid collected by filtration and washed with water to give (i) (1.85 g). $^1$H NMR (400 MHz, DMSO) δ 8.30 (d, J=9.0 Hz, 2H), 7.87-7.49 (m, 2H), 7.38 (dd, J=2.7, 1.8 Hz, 1H), 7.13 (dd, J=3.9, 1.7 Hz, 1H), 6.41 (dd, J=3.8, 2.8 Hz, 1H), 3.66 (s, 3H).

Methyl 1-(4-aminophenyl)pyrrole-2-carboxylate (ii)

Sodium hydrosulphite (2.08 g, 10.15 mmoll) in water (7.5 mL) was added to a refluxing solution of (i) (1 g, 4.06 mmol) in EtOH (15 mL). After 5 minutes another solution of sodium hydrosulphite (2.08 g, 10.15 mmoll) in water (7.5 mL) was added. The mixture refluxed for 5 min After that time the mixture was poured onto water. The reaction mixture was extracted with EtOAc and DCM/iPrOH. The organic fractions were dried (MgSO$_4$), filtered and concentrated in vacuo to give a residue that was purified by flash chromatography on silica gel, eluting with a MeOH gradient in DCM to afford the desired product (ii) (480 mg). $^1$H NMR (400 MHz, DMSO) δ 7.06 (dd, J=2.5, 1.9 Hz, 1H), 6.96-6.90 (m, 3H), 6.59-6.53 (m, 2H), 6.22 (dd, J=3.9, 2.6 Hz, 1H), 5.25 (s, 2H), 3.60 (s, 3H).

1-(5-Aminopyrimidin-2-yl)azetidin-3-ol

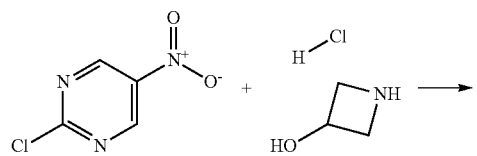

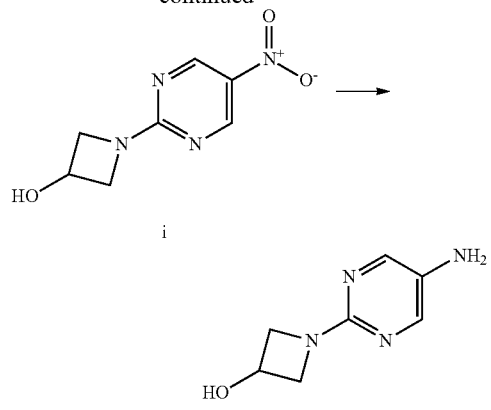

1-(5-nitropyrimidin-2-yl)azetidin-3-ol (i)

2-chloro-5-nitro-pyrimidine (100 mg, 0.63 mmol), azetidin-3-ol hydrochloride (137 mg, 1.25 mmol), DIPEA (0.44 mL, 2.51 mmol) and DMSO (2 mL) were combined and stirred at it for 1 hr. The reaction mixture was partitioned with brine (50 mL) and THF (50 mL). The organic (THF) layer was separated, and the aqueous layer was extracted with a further portion of THF (50 mL). The organic fractions were combined, dried (MgSO$_4$) and concentrated in vacuo to give an oil. The oil was taken up in a mixture of water and acetonitrile and freeze-dried to give (i) as a light yellow solid (130 mg). $^1$H NMR (400 MHz, Acetone) δ 9.03 (s, 2H), 4.91-4.64 (m, 1H), 4.49 (ddd, J=10.5, 6.6, 1.7 Hz, 2H), 4.04 (ddd, J=10.4, 4.3, 1.7 Hz, 2H).

1-(5-aminopyrimidin-2-yl)azetidin-3-ol (ii)

Compound (i) (130 mg, 0.66 mmol), 10% Pd on activated carbon (10 mg) and EtOH (5 mL) were combined and stirred under molecular hydrogen for 18 hrs at it. The reaction mixture was filtered to remove Pd/C residues and concentrated in vacuo to give crude (ii) as a yellow oil (104 mg). $^1$H NMR (400 MHz, Acetone) δ 7.83 (s, 2H), 4.68 (s, 1H), 4.24 (dd, J=9.8, 6.2 Hz, 2H), 3.83 (dd, J=10.1, 4.3 Hz, 2H).

Ethyl 2-(4-aminophenoxy)acetate

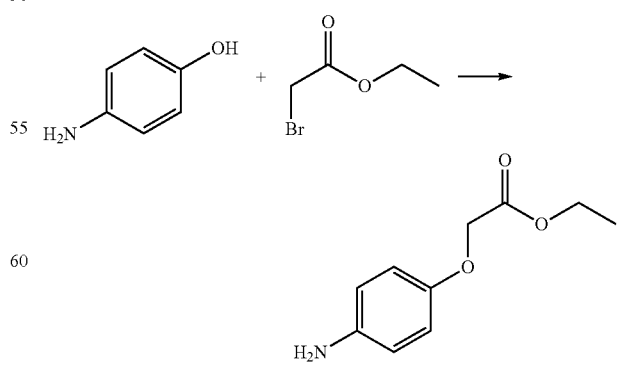

4-amino phenol (500 mg, 4.58 mmol) was suspended in acetonitrile (60 mL), the mixture cooled to 0° C. and ethyl 2-bromoacetate (0.53 mL, 4.81 mmol) added. CsCO₃ (1.9 g, 10 mmol) was added in portions and the mixture stirred for 16 h, allowing to warm to RT. The mixture was filtered, the residue washed with acetonitrile and the filtrate evaporated to dryness. The crude product was suspended in DCM (~30 mL), filtered and this filtrate evaporated to dryness to afford ethyl 2-(4-aminophenoxy)acetate (860 mg) as a dark oil that solidified on standing. ¹H NMR (400 MHz, CDCl₃) δ 6.79-6.74 (m, 2H), 6.66-6.60 (m, 2H), 4.53 (s, 2H), 4.26 (q, J=7.1 Hz, 2H), 1.29 (t, J=7.1 Hz, 3H).

4-(Morpholinomethyl)aniline

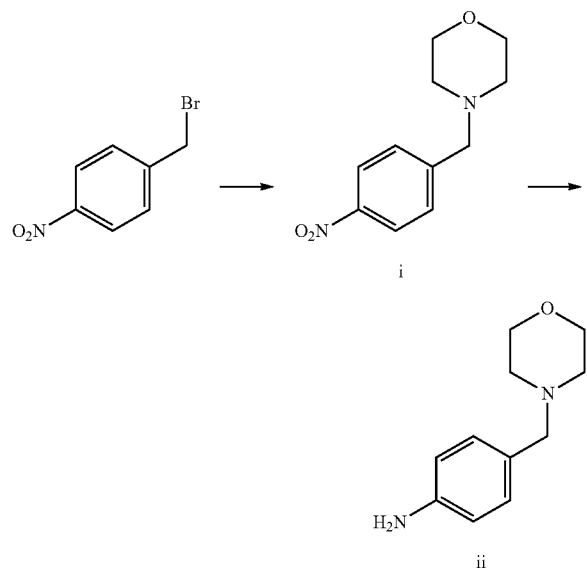

4-[(4-nitrophenyl)methyl]morpholine (i)

A suspension of 1-(bromomethyl)-4-nitro-benzene (250 mg, 1.157 mmol) in dichloromethane (5 mL) was treated with triethylamine (200 μL, 1.39 mmol) and morpholine (110 μL, 1.27 mmol) then stirred at room temperature for 1.5 hrs. The solution was diluted with dichloromethane (20 mL) then washed with water (2×20 mL). The organic extract was dried (MgSO₄), filtered and concentrated to give (i) which was used in subsequent reactions without further purification. ¹H NMR (400 MHz, CDCl₃) δ 8.21-8.16 (m, 2H), 7.56-7.50 (m, 2H), 3.76-3.69 (m, 4H), 3.59 (s, 2H), 2.49-2.42 (m, 4H).

4-(morpholinomethyl)aniline (ii)

A solution of (i) (205 mg, 0.92 mmol) in 50:50 acetic acid:ethanol (10 mL) was treated with zinc dust (370 mg, 5.53 mmol) then stirred at RT under N₂ for 4 hr. The mixture was concentrated under vacuum and the residue suspended in EtOAc (20 mL). The solution was filtered to remove undissolved zinc, and then washed with water (50 mL). The aqueous layer was neutralised then extracted with EtOAc (3×20 mL). The organic extracts were combined and concentrated to give (ii). Sample was used in subsequent reactions without further purification. ¹H NMR (400 MHz, CDCl₃) δ 8.20-8.15 (m, 2H), 7.55-7.50 (m, 2H), 3.76-3.70 (m, 4H), 3.59 (s, 2H), 2.49-2.42 (m, 4H).

4-Azidoaniline

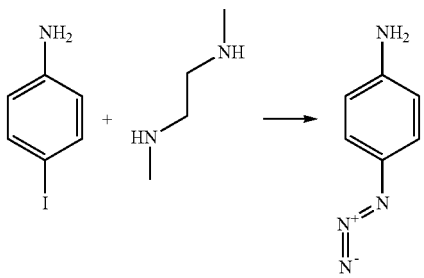

4-iodoaniline (400 mg, 1.8263 mmol) was mixed with sodium L-ascorbic acid (90 mg, 0.46 mmol) in DMSO (25 mL). A solution of sodium azide (241 mg, 3.65 mmol) in water (6.5 mL) was added followed by N,N'-dimethylethane-1,2-diamine (30 mg, 0.4 mmol) and copper iodide (30 mg, 0.2 mmol). The mixture was then heated at 100° C. for 6 h. The mixture was then mixed with a large amount of water (80 mL) and then extracted with EtOAc (3 times). The organics were dried (MgSO4), filtered and concentrated in vacuo to give a residue that was purified by flash chromatography (silica, eluting with MeOH in DCM) to give 4-azidoaniline (150 mg). ¹H NMR (400 MHz, DMSO) δ 6.81-6.75 (m, 2H), 6.63-6.57 (m, 2H), 5.13 (s, 2H).

Example(s) of General Method A 6-(3-ethylureido)-N-m-tolyl-4-(m-tolylamino)nicotinamide (1)

Scheme 1.

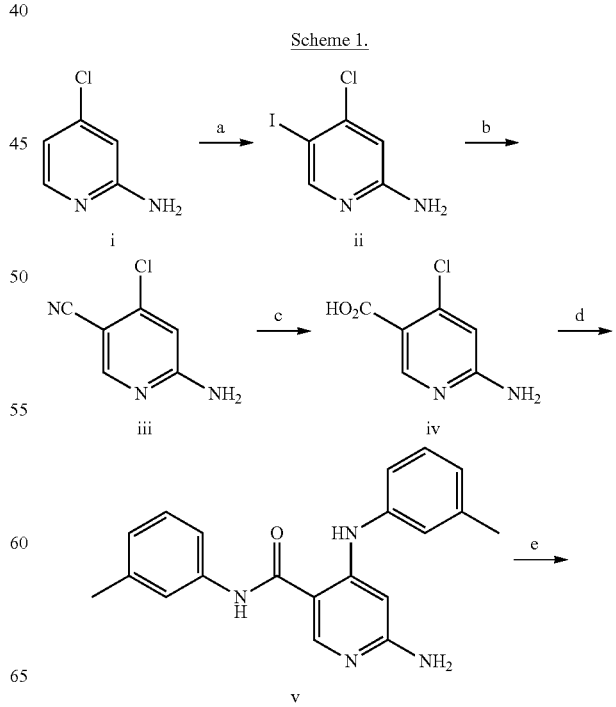

-continued

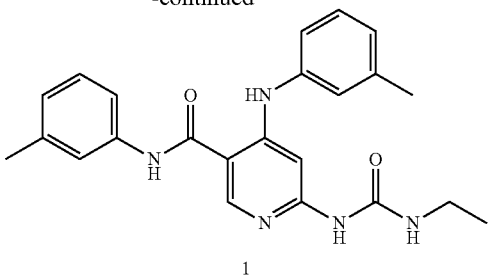

1

Reagents and conditions; (a) NIS, DMF, rt, 18 h, 60%; (b) Zn(CN)₂, Pd(PPh₃)₄, NMP, 135° C., 2 h, 60%; (c) 1:2 conc. H₂SO₄—H₂O, 100° C., 18 h, 81%; (d) m-toluidine, HOBt, EDCl·HCl, DMF, rt, 5 h; (e) EtNCO, 1,4-dioxane, 80° C., 16 h, 17%.

4-Chloro-5-iodopyridin-2-amine (ii)

(A. Tsuruoka, T. Matsushima, K. Miyazaki, J. Kamata, Y. Fukuda, K. Takahashi and M. Matsukura, Int. Pat. Appl. WO 200420434, 2005) N-iodosuccinimide (9.10 g, 40.4 mmol) was added to a solution of 2-amino-4-chloropyridine (i) (4.00 g, 31.1 mmol) in DMF (40 mL). The reaction mixture was stirred at room temperature for 18 h and partitioned between EtOAc (150 mL) and aqueous sodium thiosulfate solution (1M, 100 mL). The organic fraction was separated, washed successively with water (2×100 mL) and brine (50 mL), dried (MgSO₄) and reduced in vacuo to give the crude product as a light orange solid. Column chromatography (SiO₂), eluting with 5:1 Petrol-EtOAc to 2:1 Petrol-EtOAc, afforded compound ii. (4.65 g, 18.4 mmol, 60%) as colourless needles, [M+H]⁺ m/z=254.8.

6-Amino-4-chloronicotinonitrile (iii)

(Tsuruoka, A., et. al. ibid) Zinc cyanide (0.254 g, 2.17 mmol) and tetrakistriphenylphosphine palladium (0) (0.460 g, 0.394 mmol) were added to a solution of compound ii (1.00 g, 3.94 mmol) in NMP (10 mL). The reaction mixture was heated under N₂(g) to 135° C. for 2 h, cooled to room temperature and partitioned between EtOAc (30 mL) and aqueous ammonia solution (0.35%, 50 mL). The organic fraction was separated, washed successively with water (2×100 mL) and brine (30 mL), dried (MgSO₄) and reduced in vacuo onto SiO₂. Column chromatography (SiO₂), eluting with 2:1 Petrol-EtOAc to 1:1 Petrol-EtOAc, afforded compound iii. (0.360 g, 2.35 mmol, 60%) as an off-white solid.

6-Amino-4-chloronicotinic acid (iv)

Concentrated sulfuric acid (98%, 0.5 mL) was added dropwise to a stirred suspension of compound iii (0.020 g, 0.130 mmol) in water (1 mL). The reaction mixture was heated to 100° C. for 18 h, cooled to room temperature and added dropwise to a slurry of ice in saturated sodium bicarbonate solution (2 mL). The pH after addition was pH-2. The resulting precipitate was filtered, washed with water (2 mL) and air-dried to give compound iv. (0.019 g, 0.110 mmol, 84%) as a colourless powder, [M+H]⁺ m/z=173.0.

6-amino-N-(3-methylphenyl)-4-[(3-methylphenyl)amino]pyridine-3-carboxamide (v)

Ethyl-3-(3-dimethylaminopropyl) carbodiimide hydrochloride and 1-hydroxybenzotriazole monohydrate were added to a stirred solution of compound iv in DMF (3 mL) at room temperature. After 15 min, the m-toluidine was added and the reaction mixture stirred at the specified temperature for 24 h. The mixture was cooled to room temperature, poured onto water and extracted with EtOAc (3×30 mL). The combined organic phase was washed with water (20 mL), saturated aqueous sodium bicarbonate (20 mL) and brine (2×20 mL), dried (MgSO₄), and reduced in vacuo to give the v as a crude brown gum, which was used in the next step without further purification.

6-(3-ethylureido)-N-m-tolyl-4-(m-tolylamino)nicotinamide (1)

Compound v (crude product) was suspended in 1,4-dioxane (2 mL), treated with ethyl isocyanate (23 μL, 0.300 mmol) and heated to 80° C. for 18 h. The reaction mixture was cooled to room temperature, diluted with EtOAc (5 mL) and reduced in vacuo directly onto SiO₂. Column chromatography (SiO₂), eluting with 30% EtOAc in hexanes to 100% EtOAc, afforded the desired Compound 1 (0.029 g, 0.072 mmol, 17% over 2 steps from iv) as a tan solid, ¹H NMR (300 MHz, DMSO-d₆): δ 10.22 (1H, br s), 9.92 (1H, br s), 9.16 (1H, br s), 8.56 (1H, s), 8.12 (1H, br t), 7.57 (1H, s), 7.48 (1H, d, J 8.2), 7.31-7.21 (3H, m), 7.11-7.05 (2H, m), 6.97 (1H, d, J 8.7), 6.94 (1H, d, J 8.7), 3.21-3.12 (2H, m), 2.32 (3H, s), 2.31 (3H, s), 1.07 (3H, t, J 7.2); [M+H]⁺ m/z=404.2.

Example(s) of General Method B 6-(3-ethylureido)-N-(thiazol-2-yl)-4-(m-tolylamino)nicotinamide (2)

Scheme 2.

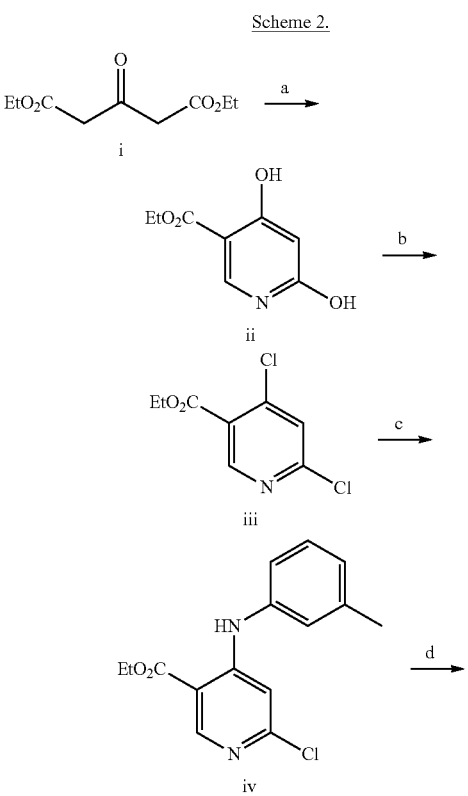

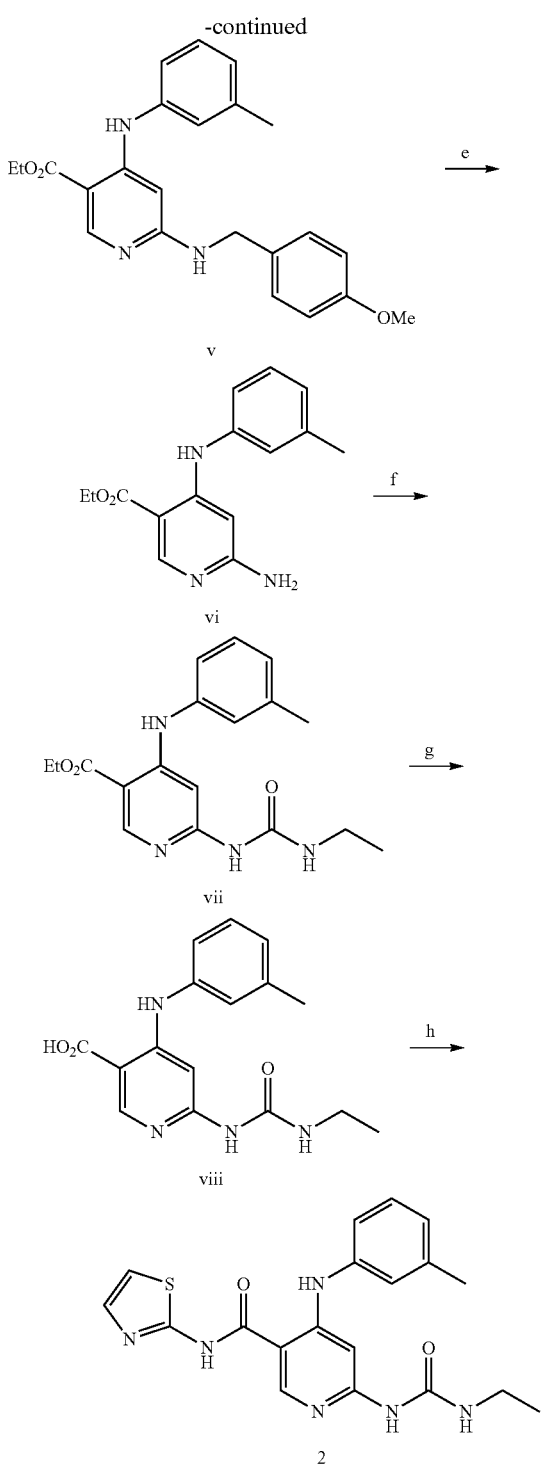

Reagents and conditions; (a) HC(OEt)₃, Ac₂O, NH₃(aq), 120° C., 2 h, 55%; (b) POCl₃, 110° C., 2.5 h, 79%; (c) m-toluidine, conc. HCl, EtOH, 80° C., 3 h, 51%; (d) p-methoxybenzylamine, PhMe, reflux, 72 h, 62%; (e) TFA, Et₃SiH, DCM, RT, 4 h, 98%; (f) EtNCO, 1,4-dioxane, 100° C., 48 h, 43%; (g) 2M NaOH(aq), 75° C., 48 h, 90%; (h) EDCI·HCl, HOBt, 2-aminothiazole, DMF, 40° C., 18 h, 35%.

Ethyl 4,6-dihydroxynicotinate (ii)

(E. Wallace, B. Hurley, H. W. Yang, J. Lyssikatos and J. Blake. Int. Pat. App. WO200523759, 2005) Trimethylorthoformate (5.95 mL, 54.4 mmol) was added to a solution of diethyl 1,3-acetonedicarboxylate (i) (8.98 mL, 49.5 mmol) in acetic anhydride (9.34 mL, 99.0 mmol). The reaction mixture was heated under N₂(g) to 120° C. for 2 h, cooled to room temperature and the excess solvent removed in vacuo. The resulting dark orange residue was cooled to 0° C. and treated with an aqueous solution of ammonia (33%, 4 mL) followed by water (15 mL). The mixture was stirred at room temperature for 18 h and the resulting heavy tan precipitate filtered, washed with water (20 mL) and air dried to give compound ii. (5.00 g, 27.3 mmol, 55%) as a light tan solid, [M+H]⁺ m/z=184.1.

Ethyl 4,6-dichloronicotinate (iii)

(Wallace, E., et. al., ibid.) A stirred suspension of compound ii (1.40 g, 7.67 mmol) in phosphorus (V) oxychloride (15 mL) was heated to 110° C. for 2.5 h with a guard tube (CaCl₂) fitted. The reaction mixture was cooled to room temperature, reduced in vacuo and the resulting dark brown residue taken up in a small volume of DCM (~5 mL) and transferred dropwise onto a slurry of ice in water (250 mL) whilst stirring vigorously. The aqueous mixture was extracted with EtOAc (3×100 mL), the organic extracts combined, dried (MgSO₄) and evaporated to dryness to afford the crude product as an orange gum. Column chromatography (SiO₂), eluting with 15:1 Hexanes-EtOAc, afforded compound iii. (1.33 g, 6.14 mmol, 79%) as a colourless oil; [M+H]⁺ m/z=220.0.

Ethyl 6-chloro-4-(m-tolylamino)nicotinate (iv)

(Wallace, E., et. al., ibid.) m-toluidine (0.47 mL, 4.34 mmol) and conc. HCl (1 drop) were added to a solution of compound iii (1.00 g, 4.57 mmol) in ethanol (10 mL). The reaction mixture was heated at 80° C. for 3 h, cooled to room temperature and partitioned between water (15 mL) and EtOAc (20 mL). The aqueous phase was extracted with EtOAc (3×20 mL). The combined organic phase was dried (MgSO₄) and reduced in vacuo to give the crude product as a brown oil. Column chromatography (SiO₂), eluting with 12:1 Hexanes-EtOAc, gave compound iv. (0.670 g, 2.31 mmol, 51%) as a light orange oil, which solidified on standing, [M+H]⁺ m/z=291.0.

Ethyl-6-(4-methoxybenzylamino)-4-(m-tolylamino)nicotinate (v)

(Wallace, E., et. al., ibid.) 4-Methoxybenzylamine (1.12 mL, 8.60 mmol) was added to a suspension of compound iv (0.50 g, 1.72 mmol) in toluene (10 mL). The reaction mixture was heated under reflux for 72 h, cooled, and reduced in vacuo to give the crude product as an orange oil. Column chromatography (SiO₂), eluting with 10:1 Hexanes-EtOAc, gave the desired compound v. (0.415 g, 1.06 mmol, 62%) as a tan solid, ¹H NMR (300 MHz, DMSO-d₆): δ 9.46 (1H, br s), 8.52 (1H, s), 7.48 (1H, br t), 7.48-7.26 (2H, m), 7.20 (2H, d, J 9.0), 7.00-6.94 (2H, m), 6.86 (2H, d, J 6.0), 6.03 (1H, s), 4.33 (2H, br), 4.24 (2H, q, J 7.2), 3.71 (3H, s), 2.28 (3H, s), 1.30 (3H, t, J 7.2); [M+H]⁺ m/z=392.2.

Ethyl 6-amino-4-(m-tolylamino)nicotinate (vi)

Trifluoroacetic acid (6 mL) and triethylsilane (0.49 mL, 3.06 mmol) were added to a stirred solution of compound v (0.40 g, 1.02 mmol) in DCM (6 mL). The reaction mixture was stirred at room temperature for 4 h, reduced in vacuo and the resulting residue mixed with water (5 mL). The pH was adjusted to pH ~11 using 2M aqueous sodium carbonate solution and the mixture extracted with EtOAc (3×20 mL). The combined organic fraction was dried (MgSO₄) and reduced in vacuo to give the crude product as a light yellow gum. Column chromatography (SiO₂), eluting with 100% EtOAc, gave the desired compound vi. (0.280 g, 1.02 mmol, quantitative) as a colourless glass; $^1$H NMR (300 MHz, DMSO-d₆): δ 9.54 (1H, br s), 8.46 (1H, s), 7.32 (1H, t, J 7.5), 7.09-7.02 (3H, m), 6.68 (2H, br s), 6.02 (1H, s), 4.26 (2H, q, J 6.9), 2.33 (3H, s), 1.31 (3H, t, J 6.9); [M+H]⁺ m/z=272.1.

Ethyl 6-(3-ethylureido)-4-(m-tolylamino)nicotinate (vii)

Ethyl isocyanate (0.898 mL, 1.49 mmol), was added to a solution of compound vi (0.270 g, 0.99 mmol) in 1,4-dioxane (5 mL). The reaction mixture was warmed to 100° C. for 48 h, cooled to room temperature and reduced in vacuo. The resulting orange residue was re-dissolved in EtOAc (15 mL) and reduced in vacuo on to SiO₂. Column chromatography (SiO₂), eluting with 2:1 Hexanes-EtOAc, gave the desired compound vii. (0.145 g, 0.424 mmol, 43%) as an off-white solid, $^1$H NMR (300 MHz, DMSO-d₆): δ 9.62 (1H, br s), 9.19 (1H, br s), 8.62 (1H, s), 7.85 (1H, br t), 7.31 (1H, t, J 7.7), 7.23 (1H, s), 7.13-7.07 (2H, m), 7.03 (1H, d, J 7.2), 4.31 (2H, q, J 7.2), 3.13 (2H, dq, J 6.7 and 7.2), 2.33 (3H, s), 1.33 (3H, t, J 7.2), 1.05 (3H, t, J 7.2); [M+H]⁺ m/z=343.1.

6-(3-Ethylureido)-4-(m-tolylamino)nicotinic acid (viii)

A suspension of compound vii (0.140 g, 0.410 mmol) in aqueous sodium hydroxide solution (2M, 3 mL) was heated to 75° C. for 48 h, cooled to 0° C. and acidified to pH ~2 using concentrated hydrochloric acid (35%). The resulting colourless precipitate was filtered, washed with water (3 mL) and air dried to give the desired compound viii. (0.116 g, 0.369 mmol, 90%) as a colourless powder, $^1$H NMR (300 MHz, DMSO-d₆): δ 9.98 (1H, br s), 9.17 (1H, br s), 8.58 (1H, s), 7.94 (1H, br t), 7.30 (1H, t, J 7.7), 7.20 (1H, s), 7.12-7.06 (2H, m), 7.01 (1H, d, J 7.7), 3.13 (2H, dq, J 6.7 and 7.7), 1.05 (3H, t, J 7.2); [M+H]⁺ m/z=315.1.

6-(3-ethylureido)-N-(thiazol-2-yl)-4-(m-tolylamino) nicotinamide (2)

1-Ethyl-3-(3-dimethylaminopropyl) carbodiimide hydrochloride (0.031 g, 0.16 mmol) and 1-hydroxybenzotriazole monohydrate (0.024 g, 0.16 mmol) were added to a stirred solution of the viii (0.050 g, 0.16 mmol) in DMF (3 mL) at room temperature. After 15 min, the m-toluidine (0.16 mmol) was added and the reaction mixture stirred at the specified temperature for 24 h. The mixture was treated with water (5 mL) and the resulting colourless precipitate filtered, washed with water, air-dried and recrystallized from EtOH to afford Compound 2 (0.022 g, 0.056 mmol, 35%) as a light beige powder. $^1$H NMR (300 MHz, DMSO-d₆): δ 10.02 (1H, br s), 9.14 (1H, br s), 8.73 (1H, s), 7.91 (1H, br t), 7.56 (1H, d, J 3.6), 7.30 (1H, t, J 7.7), 7.27-7.22 (3H, m), 7.15-7.09 (2H, m), 7.00 (1H, d, J 7.7), 3.15 (2H, dq, J 6.1 and 7.2), 2.33 (3H, s), 1.06 (3H, t. J 7.2); [M+H]⁺ m/z=397.1.

4-(cyclohexylamino)-6-(3-ethylureido)-N-m-tolylnicotinamide (3); and N-(3-chlorophenyl)-4-(3-ethylureido)-2-(phenylamino)benzamide (4)

Scheme 3:

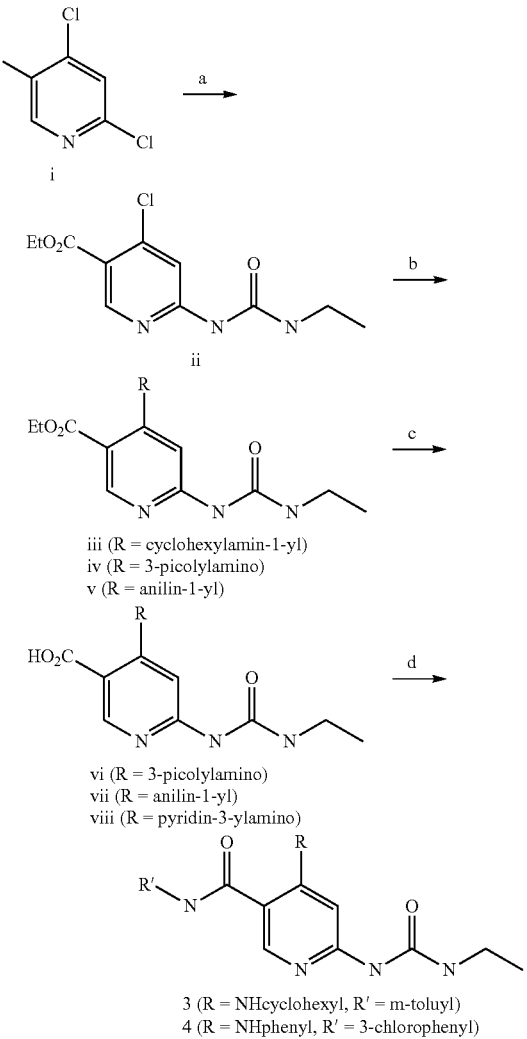

3 (R = NHcyclohexyl, R' = m-toluyl)
4 (R = NHphenyl, R' = 3-chlorophenyl)

Reagents and conditions; (a) Pd(OAc)₂, Xanpthos, KOt-Bu, N-ethylurea, 1,4-dioxane, H₂O, 100° C., 16 h, 40%; (b) NaH, NuH, DMF, 0° C.-70° C., 48 h, 21-32%, or RNH₂, EtOH, reflux, 68-71%, or ArNH₂, HCl, EtOH, 60° C., 16 h, 93%, or Pd(OAc)₂, Xanpthos, KOt-Bu, ArNH₂, 1,4-dioxane, H₂O, 100° C., 3 h; (c) 2M NaOH(aq), RT-70° C., 47%-quantitative or LiOH (aq), THF, EtOH, 60° C., 3 h, 95%; (d) ArNH₂, EDCI·HCl, HOBt, DMF, RT-40° C., 22-55%.

Ethyl 4-(cyclohexylamino)-6-(3-ethylureido)nicotinate (iii)

Cyclohexylamine (0.63 mL, 5.50 mmol) was added to a stirred suspension of ii (prepared from i) (0.300 g, 1.11 mmol) in EtOH (3 mL) at room temperature. The mixture was heated under reflux for 16 h, cooled to room temperature and treated with a further 2 eq. cyclohexylamine (25 µL) and heated under reflux for 3 h. The clear solution was cooled to 0° C. and the resulting colourless needles filtered, washed with cold EtOH and dried in vacuo to give iii as colourless needles. (0.250 g, 0.749 mmol, 68%) $^1$H NMR (300 MHz, DMSO-$d_6$): δ 9.04 (1H, s), 8.50 (1H, s, 2H), 7.93 (1H, app. t), 7.91 (1H, d, J 6.8, 4H), 6.80 (1H, s, 5H), 4.25 (2H, q, J 6.8), 3.32-3.30 (1H, m, 1-H), 3.17 (2H, dq, J 5.9 and 7.7), 1.97-1.91 (2H, m), 1.74-1.67 (2H, m), 1.62-1.57 (1H, m), 1.44-1.34 (2H, m), 1.33-1.25 (6H, m), 1.08 (3H, t, J 6.8); [M+H]$^+$ m/z=335.1.

Ethyl 6-(3-ethylureido)-4-(pyridin-3-ylmethylamino) nicotinate (iv)

3-picolylamine (0.56 mL, 5.50 mmol) was added to a solution of ii (0.300 g, 1.11 mmol) in EtOH (1.5 mL). The mixture was heated to reflux for 18 h. cooled to room temperature and the resulting crystalline precipitate filtered, washed with ice-cold EtOH and air dried to give ii (0.266 g, 0.776 mmol, 71%) as colourless microcrystals, $^1$H NMR (300 MHz, DMSO-$d_6$): δ 9.14 (1H, br s), 8.59 (1H, d, J 1.5), 8.51-8.41 (3H, m), 7.99 (1H, br), 7.75 (1H, d, J 8.2), 7.38 (1H, dd, J 7.2 and 4.6), 6.70 (1H, s), 4.45 (2H, d, J 5.6), 4.26 (2H, q, J 7.2), 3.14 (2H, dq, J 7.2 and 6.1), 1.30 (3H, q, J 7.2), 1.05 (3H, q, J 7.2); [M+H]$^+$ m/z=344.1.

Ethyl 6-(3-ethylureido)-4-(phenylamino)nicotinate (v)

Aniline (0.140 mL, 1.55 mmol) and conc. HCl (1 drop) were added to a suspension of ii (0.350 g, 1.29 mmol) in EtOH (5 mL). The mixture was stirred at 60° C. for 16 h, cooled to room temperature and reduced in vacuo. The resulting residue was partitioned between EtOAc (20 mL) and saturated aqueous sodium bicarbonate solution (10 mL). The layers were separated and the aqueous phase extracted with EtOAc (20 mL). The combined organic fraction was dried (MgSO$_4$) and reduced in vacuo to give the crude product as a light orange gum. Column chromatography (SiO$_2$), eluting with 3:1 Hexanes-EtOAc to 1:1 Hexanes EtOAc gave v. (0.392 g, 1.20 mmol, 93%) as an off-white solid, $^1$H NMR (300 MHz, DMSO-$d_6$): δ 9.73 (1H, s), 9.29 (1H, app. t), 8.70 (1H, s), 8.48 (1H, s), 7.39 (2H, t, J 7.7), 7.25 (2H, d, J 7.7), 7.19 (1H, t, J 6.8), 6.37 (1H, s), 4.36 (2H, q, J 6.8), 3.30 (2H, dq, J 5.1 and 6.8), 1.40 (3H, t, J 6.8), 1.18 (3H, t, J 6.8); [M+H]$^+$ m/z=329.1.

6-(3-Ethylureido)-4-(pyridin-3-ylmethylamino)nico-tinic acid (vi)

Lithium hydroxide (0.310 g, 7.29 mmol) dissolved in water (2 mL) was added to a solution of iv (0.250 g, 0.730 mmol) in EtOH (2 mL) THF (5 mL). The mixture was warmed to 60° C. for 3 h, cooled to room temperature and reduced in vacuo. The resulting residue was re-dissolved in water (2 mL) and the pH adjusted to pH 2-3 using conc. HCl (35%). The resulting colourless precipitate was filtered, washed with water and dried in vacuo to give vi (0.219 g, 0.695 mmol, 95%) as a colourless powder. $^1$H NMR (300 MHz, DMSO-$d_6$): δ 9.10 (1H, s), 8.65-8.57 (2H, m), 8.07 (1H, br), 7.75 (1H, dt, J 8.2 and 1.5), 7.38 (1H, dd, J 7.7 and 4.6), 6.64 (1H, s), 4.45 (2H, d, J 6.1), 3.14 (2H, dq, J 7.2 and 5.6), 1.05 (3H, t, J 7.2); [M+H]$^+$ m/z=316.1.

6-(3-Ethylureido)-4-(phenylamino)nicotinic acid (vii)

A suspension of v (0.355 g, 1.08 mmol) in aqueous sodium hydroxide solution (2M, 6 mL) was stirred at 75° C. for 48 h, cooled to 0° C. and acidified to pH ~2 using conc. HCl (35%). The resulting off-white precipitate was filtered, washed with water, and air-dried to give vii (0.328 g, 1.08 mmol, quantitative) as an off-white solid. $^1$H NMR (300 MHz, DMSO-$d_6$): δ 10.12 (1H, br s), 9.64 (1H, br s), 8.58 (1H, s), 7.69 (1H, b), 7.49-7.42 (2H, m), 7.38-7.21 (3H, m), 7.07 (1H, s), 3.13 (2H, dq, J 7.2 and 6.6), 1.04 (3H, t, J 7.2); [M+H]$^+$ m/z=301.1.

6-(3-Ethylureido)-4-(pyridin-3-ylamino)nicotinic acid (viii)

Palladium (II) acetate (0.074 g, 0.33 mmol) was added to a solution of Xantphos (0.270 g, 0.470 mmol) in degassed 1,4-dioxane (5 mL) at room temperature. The mixture was stirred under N$_2$(g) for 1 h and treated with ii (0.30 g, 1.11 mmol), 3-aminopyridine (0.150 g, 1.65 mmol), potassium tert-butoxide (0.190 g, 1.65 mmol) and degassed water (29 µL, 1.65 mmol). The mixture was warmed to 100° C. for 3 h, cooled to room temperature, poured onto water (15 mL) and extracted with DCM (2×50 mL). The combined organic phase was dried (MgSO$_4$), reduced in vacuo and the residue purified by column chromatography (SiO$_2$) eluting with 100% EtOAc to give the crude ethyl nicotinate. The crude product was suspended directly in aqueous sodium hydroxide solution (2M, 5 mL) and stirred at 70° C. for 16 h. The mixture was cooled to 0° C. and acidified to pH 5 using conc. HCl (35%). The resulting off-white solid was filtered, washed with water and air-dried to give viii (0.155 g, 0.515 mmol, 47%) as an off-white solid. $^1$H NMR (300 MHz, DMSO-$d_6$): δ 9.99 (1H, br s), 9.16 (1H, br s), 8.60 (1H, s), 8.59 (1H, d, J 2.6), 8.41 (1H, d, J 4.6), 7.81 (1H, br), 7.76 (1H, dd, J 8.2 and 1.0), 7.46 (1H, dd, J 8.2 and 4.6), 7.20 (1H, s), 3.18-3.07 (2H, m), 1.05 (3H, t, J 7.2); [M+H]$^+$ m/z=302.1.

Amide Coupling Methods

All amines used were commercially available unless otherwise stated.

General Amide Coupling Method 1

1-Ethyl-3-(3-dimethylaminopropyl) carbodiimide hydrochloride (0.092 g, 0.480 mmol) and 1-hydroxybenzotriazole monohydrate (0.073 g, 0.480 mmol) were added to a stirred solution of the appropriate acid (0.100 g, 0.320 mmol) in DMF or DMA (3 mL) at room temperature. After 15 min, the appropriate amine (0.480 mmol) was added and the reaction mixture stirred at the specified temperature for 24 h. The mixture was treated with water (5 mL) and the resulting colourless precipitate filtered, washed with water, air-dried and recrystallized from EtOH to give the desired nicotinamide. Alternatively, the mixture was cooled to room temperature, poured onto water and extracted with DCM or EtOAc (3×30 mL). The combined organic phase was washed successively with water (20 mL), saturated aqueous sodium bicarbonate (20 mL) and brine (2×20 mL), dried (MgSO$_4$), and reduced in vacuo to give the crude product which could be purified by column chromatography, trituration or recrystallization as required.

General Amide Coupling Method 1 was used to make Compounds 3 and 4 as follows.

4-(cyclohexylamino)-6-(3-ethylureido)-N-m-tolylnicotinamide (3)

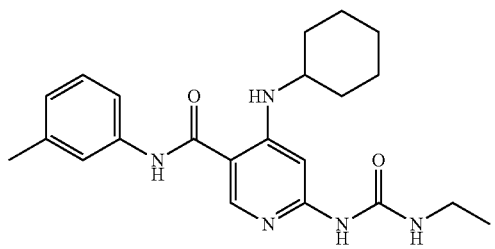 [SMILES: CCNC(=O)Nc1cc(NC2CCCCC2)c(C(=O)Nc2cccc(C)c2)cn1]

EDCI.HCl (1-Ethyl-3-(3-dimethylaminopropyl) carbodiimide hydrochloride, 0.092 g, 0.480 mmol) and 1-hydroxybenzotriazole monohydrate (0.073 g, 0.480 mmol) were added to a stirred solution of ethyl 4-(cyclohexylamino)-6-(3-ethylureido)nicotinate iii (0.100 g, 0.320 mmol) in DMF (3 mL) at room temperature. After 15 min, m-toluidine (0.052 g, 0.480 mmol) was added and the reaction mixture stirred at room temperature for 24 h. The mixture was treated with water (5 mL) and the resulting colourless precipitate filtered, washed with water, air-dried and recrystallized from EtOH to afford Compound 3 (0.030 g, 0.076 mmol, 29%) as colourless microcrystals. $^1$H NMR (300 MHz, DMSO-$d_6$): δ 10.00 (1H, s), 9.01 (1H, s), 8.44 (1H, s), 8.28 (1H, br), 8.10 (1H, d, J 9.0), 7.52 (1H, s), 7.42 (1H, d, J 9.0), 7.20 (1H, t, J 6.0), 6.90 (1H, d, J 6.0), 6.66 (1H, s), 3.25-3.13 (3H, m), 2.29 (3H, s), 1.94-1.91 (2H, m), 1.67-1.57 (3H, m), 1.42-1.23 (5H, m), 1.08 (3H, t, J 7.2); [M+H]$^+$ m/z=396.2.

N-(3-chlorophenyl)-4-(3-ethylureido)-2-(phenylamino)benzamide (4)

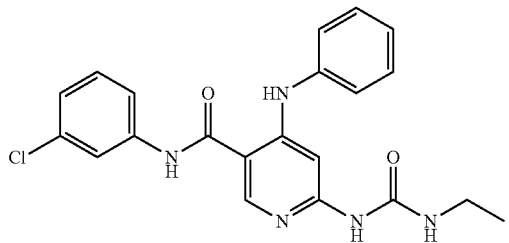 [SMILES: CCNC(=O)Nc1cc(Nc2ccccc2)c(C(=O)Nc2cccc(Cl)c2)cn1]

1-Ethyl-3-(3-dimethylaminopropyl) carbodiimide hydrochloride (0.092 g, 0.480 mmol) and 1-hydroxybenzotriazole monohydrate (0.073 g, 0.480 mmol) were added to a stirred solution of 6-(3-ethylureido)-4-(phenylamino)nicotinic acid, vi (0.100 g, 0.320 mmol) in DMF (3 mL) at room temperature. After 15 min, 3-chloroaniline (0.061 g, 0.480 mmol) was added and the reaction mixture stirred at 40° C. for 24 h. The mixture was cooled to room temperature, poured onto water and extracted with EtOAc (3×30 mL). The combined organic phase was washed successively with water (20 mL), saturated aqueous sodium bicarbonate (20 mL) and brine (2×20 mL), dried (MgSO$_4$), and reduced in vacuo to give the crude product. This was triturated with EtOAc to afford Compound 4 (0.021 g, 0.051 mmol, 16%) as a colourless powder. $^1$H NMR (300 MHz, DMSO-$d_6$): δ 10.44 (1H, s), 9.83 (1H, s), 9.16 (1H, s), 8.58 (1H, s), 7.96-7.90 (2H, m), 7.63 (1H, d, J 8.2), 7.45-7.36 (3H, m), 7.32-7.27 (3H, m), 7.20-7.13 (2H, m), 3.15 (2H, dq, J 7.2 and 6.1), 1.07 (311, t, J 7.2); [M+H]$^+$ m/z=410.1

2-(3-Ethylureido)-N-phenyl-4-(phenylamino)pyrimidine-5-carboxamide (5); 2-(3-ethylureido)-4-(phenylamino)-N-(pyridin-3-yl)pyrimidine-5-carboxamide (6); and N-(3-chlorophenyl)-2-(3-ethylureido)-4-(phenylamino)pyrimidine-5-carboxamide (7)

Scheme 4:

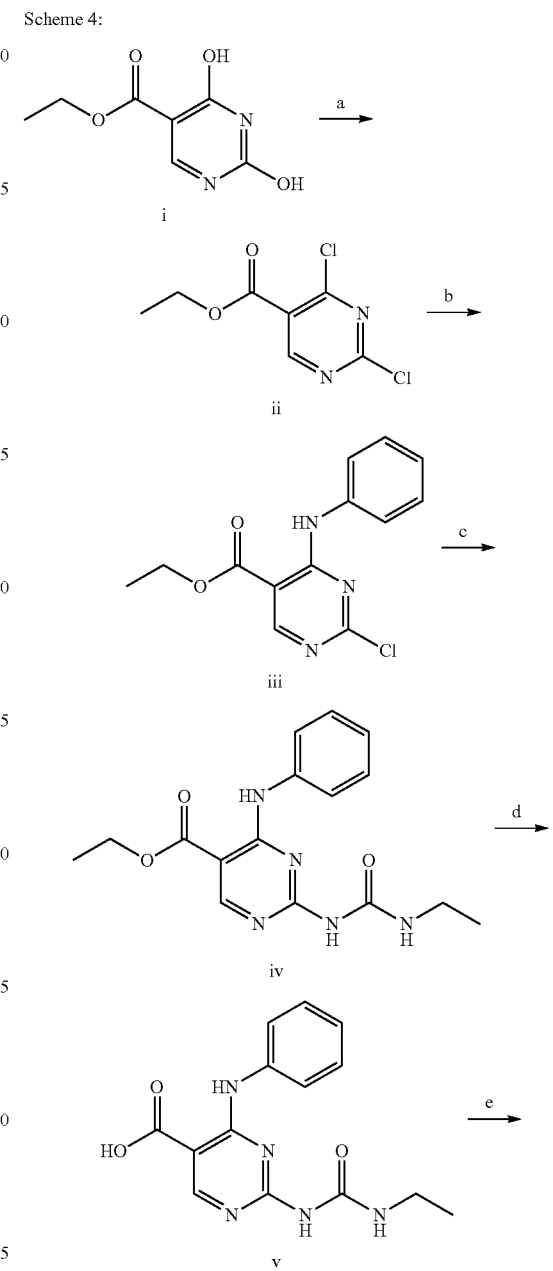

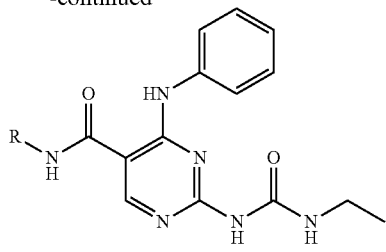

5 (R = Phenyl)
6 (R = Pyridyl-3-yl)
7 (R = 3-chlorophenyl)

Reagents and conditions: (a) POCl₃, PhNEt₂, 110° C., 2 h, 81%; (b) aniline, DIPEA, MeCN, RT, 1 h, 94%; (c) Pd(OAc)₂, Xantphos, KOt-Bu, N-ethylurea, 1,4-dioxane, H₂O, 100° C., 2 h, 43%; (d) 2M NaOH (aq), THF, 65° C., 24 h, 73%; ArNH₂, EDCl•HCl, HOBt, DMF, 35-40° C., 16 h, 43-56%.

Ethyl 2,4-dichloropyrimidine-5-carboxylate (ii)

N,N-Diethylaniline (1.5 mL, 9.45 mmol) was added to a suspension of 5-carbethoxyuracil, i (1.00 g, 5.43 mmol), in phosphorus (V) oxychloride (10 mL). The mixture was heated under reflux for 2 h, cooled to room temperature and reduced in vacuo. The resulting syrupy residue was transferred carefully onto stirred ice water (50 mL). After 1 h, the resulting beige solid was collected by filtration, washed with water (10 mL) and air-dried to give compound ii (0.97 g, 4.41 mmol, 81%) as a light beige powder. $^1$H NMR (300 MHz, CDCl₃): δ 9.04 (1H, s), 4.46 (2H, q, J 7.2), 1.43 (3H, t, J 7.2); [M+H]⁺ m/z=221.0.

Ethyl 2-chloro-4-(phenylamino)pyrimidine-5-carboxylate (iii)

Diisoprolylethylamine (1.38 mL, 7.72 mmol) and aniline (0.35 mL, 3.86 mmol) were added sequentially to a stirred solution of ii (0.850 g, 3.86 mmol) in acetonitrile (15 mL). The mixture was stirred at room temperature for 1 h, poured onto water (20 mL) and extracted with EtOAc (3×30 mL). The combined organic fraction was dried (MgSO₄) and reduced in vacuo to give the crude product as a beige crystalline solid. Column chromatography (SiO₂), eluting with 9:1 Hexanes-EtOAc afforded compound iii (1.00 g, 3.61 mmol, 94%) as a colourless crystalline solid. $^1$H NMR (300 MHz, CDCl₃): δ 10.45 (1H, br s, 4-NH), 8.83 (1H, s), 7.66 (2H, d, J 8.2), 7.40 (2H, t, J 7.7), 7.20 (1H, t, J 7.7), 4.43 (2H, q, J 7.2), 1.44 (3H, t, J 7.2); [M+H]⁺ m/z=278.0.

Ethyl 2-(3-ethylureido)-4-(phenylamino)pyrimidine-5-carboxylate (iv)

Palladium (II) acetate (0.240 g, 1.06 mmol) was added to a solution of Xantphos (0.88 g, 1.52 mmol) in degassed 1,4-dioxane (40 mL) at room temperature. The mixture was stirred under N₂(g) for 1 h and treated with iii (0.98 g, 3.54 mmol), N-ethylurea (0.470 g, 5.31 mmol), potassium tert-butoxide (0.600 g, 5.31 mmol) and degassed water (96 μL, 5.31 mmol). The mixture was warmed to 100° C. for 2 h, cooled to room temperature and diluted with EtOAc (50 mL). The mixture was poured onto water (50 mL), and the layers separated. The aqueous phase was further extracted with EtOAc (2×50 mL). The combined organic phase was washed with brine (50 mL), dried (MgSO₄) and reduced in vacuo to give the crude product as a brown solid. Column chromatography (SiO₂), eluting with 1% MeOH in DCM, afforded compound iv (0.501 g, 1.52 mmol, 43%) as an orange solid. $^1$H NMR (300 MHz, DMSO-d₆): δ 10.14 (1H, br s), 9.94 (1H, br s), 8.77-8.74 (2H, m), 7.64 (2H, d, J 7.7), 7.43 (2H, t, J 8.2), 7.20 (1H, t, J 7.7), 4.35 (2H, q, J 7.2), 3.03 (2H, dq, J 5.6 and 7.2), 1.34 (3H, t, J 7.2), 0.88 (3H, t, J 7.2); [M+H]⁺ m/z=330.1.

2-(3-Ethylureido)-4-(phenylamino)pyrimidine-5-carboxylic acid (v)

A suspension of iv (0.479 g, 1.46 mmol) in 2M NaOH (aq, 15 mL) and THF (2 mL) was stirred at 65° C. for 24 h. The mixture was cooled to 0° C. and the pH adjusted to pH~2-3 using conc. HCl (35%). The resulting tan precipitate was filtered, washed with water, air-dried and further dried in vacuo to give compound v (0.321 g, 1.07 mmol, 73%) as a tan powder. $^1$H NMR (300 MHz, DMSO-d₆): δ 10.47 (1H, br s), 9.90 (1H, br s), 8.84 (1H, app. t), 8.72 (1H, s), 7.65 (2H, d, J 7.7), 7.42 (2H, t, J 7.7), 7.21 (1H, t, J 7.2), 3.12-3.01 (2H, m), 0.90 (3H, t, J 7.2); [M+H]⁺ m/z=302.2.

2-(3-Ethylureido)-N-phenyl-4-(phenylamino)pyrimidine-5-carboxamide (5)

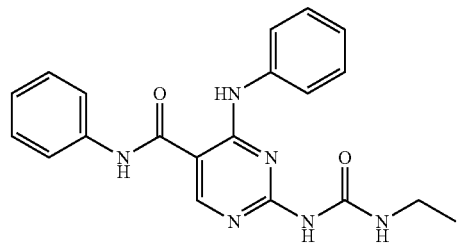 [SMILES: CCNC(=O)Nc1ncc(C(=O)Nc2ccccc2)c(Nc2ccccc2)n1]

1-Ethyl-3-(3-dimethylaminopropyl)carbodiimide hydrochloride (0.096 g, 0.500 mmol) and 1-hydroxybenzotriazole monohydrate (0.077 g, 0.500 mmol) were added to a stirred solution of v (0.100 g, 0.330 mmol) in dimethylformamide (3 mL) at room temperature. After 15 min, aniline (46 μL, 0.500 mmol) was added and the reaction mixture stirred at 35° C. for 3 h. The mixture was cooled to room temperature, treated with water (2 mL) and the resulting colourless precipitate filtered, washed with water, air-dried and triturated with hot EtOH to give Compound 5 (0.070 g, 0.186 mmol, 56%) as a colourless powder. $^1$H NMR (300 MHz, DMSO-d₆): δ 10.77 (1H, br s), 10.34 (1H, br s), 9.86 (1H, br s), 8.90 (1H, br t, J 5.6), 8.86 (1H, s), 7.69 (4H, app. t), 7.44-7.34 (4H, m), 7.22-7.11 (2H, m), 3.11 (2H, dq, J 5.6 and 7.6), 0.95 (3H, t, J 7.2); [M+H]⁺ m/z=377.2.

2-(3-ethylureido)-4-(phenylamino)-N-(pyridin-3-yl)pyrimidine-5-carboxamide (6)

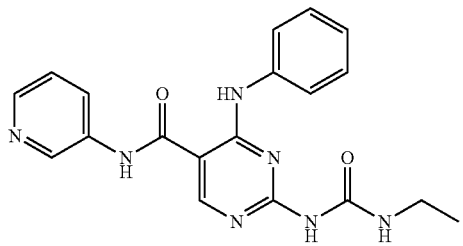 [SMILES: CCNC(=O)Nc1ncc(C(=O)Nc2cccnc2)c(Nc2ccccc2)n1]

1-Ethyl-3-(3-dimethylaminopropyl)carbodiimide hydrochloride (0.096 g, 0.500 mmol) and 1-hydroxybenzotriazole monohydrate (0.077 g, 0.500 mmol) were added to a stirred solution of 2-(3-ethylureido)-4-(phenylamino)pyrimidine-5-carboxylic acid (v) (0.100 g, 0.330 mmol) in dimethylformamide (3 mL) at room temperature. After 15 min, 3-aminopyridine (0.047 g, 0.500 mmol) was added and the reaction mixture stirred at 40° C. for 24 h. The mixture was cooled to room temperature, treated with water (2 mL) and the resulting off-white precipitate filtered, washed with water, air-dried and triturated with hot EtOH to give Compound 6 (0.060 g, 0.159 mmol, 48%) as a colourless powder. ¹H NMR (300 MHz, DMSO-d₆): δ 10.67 (1H, br s), 10.52 (1H, br s), 9.89 (1H, br s), 8.91-8.84 (3H, m), 8.35 (1H, dd, J 1.0 and 4.6), 8.12 (1H, dt, J 2.0 and 8.7), 7.67 (2H, d, J 8.2), 7.46-7.38 (3H, m), 7.20 (1H, t, J 7.2), 3.10 (2H, dq, J 5.6 and 7.2), 0.93 (3H, t, J 7.2); [M+H]⁺ m/z=378.2.

N-(3-chlorophenyl)-2-(3-ethylureido)-4-(phenylamino)pyrimidine-5-carboxamide (7)

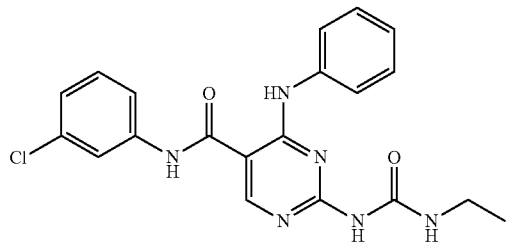 [SMILES: CCNC(=O)Nc1ncc(C(=O)Nc2cccc(Cl)c2)c(Nc2ccccc2)n1]

1-Ethyl-3-(3-dimethylaminopropyl)carbodiimide hydrochloride (0.096 g, 0.500 mmol) and 1-hydroxybenzotriazole monohydrate (0.077 g, 0.500 mmol) were added to a stirred solution of v (0.100 g, 0.330 mmol) in DMF (3 mL) at room temperature. After 15 min, 3-chloroaniline (52 μL, 0.500 mmol) was added and the reaction mixture stirred at 40° C. for 24 h. The mixture now contained a heavy off-white precipitate. The mixture was cooled to room temperature, treated with water (1 mL) and the resulting colourless precipitate filtered, washed with water, air-dried and triturated with hot MeOH to give Compound 7 (0.070 g, 0.170 mmol, 52%) as a white solid. ¹H NMR (300 MHz, DMSO-d₆): δ 10.64 (1H, br s), 10.47 (1H, br s), 9.87 (1H, br s), 8.87 (1H, br t, J 6.1), 8.85 (1H, s), 7.91 (1H, t, J 2.0), 7.68 (2H, d, J 7.7), 7.63 (1H, dd, J 1.0 and 8.2), 7.45-7.38 (3H, m), 7.23-7.17 (2H, m), 3.01 (2H, dq, J 6.1 and 7.2), 0.93 (3H, t, J 7.2); [M+H]⁺ m/z=411.3.

N-Ethyl-6-(3-ethylureido)-4-(phenylamino)nicotinamide (8); N-(2-Chlorophenyl)-6-(3-ethylureido)-4-(phenylamino)nicotinamide (9); 6-(3-Ethylureido)-N-(1-methyl-1H-pyrazol-5-yl)-4-(phenylamino)nicotinamide (10); and 6-(3-Ethylureido)-4-(phenylamino)-N-(2-(trifluoromethyl)phenyl)nicotinamide (11)

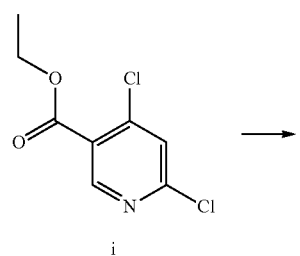

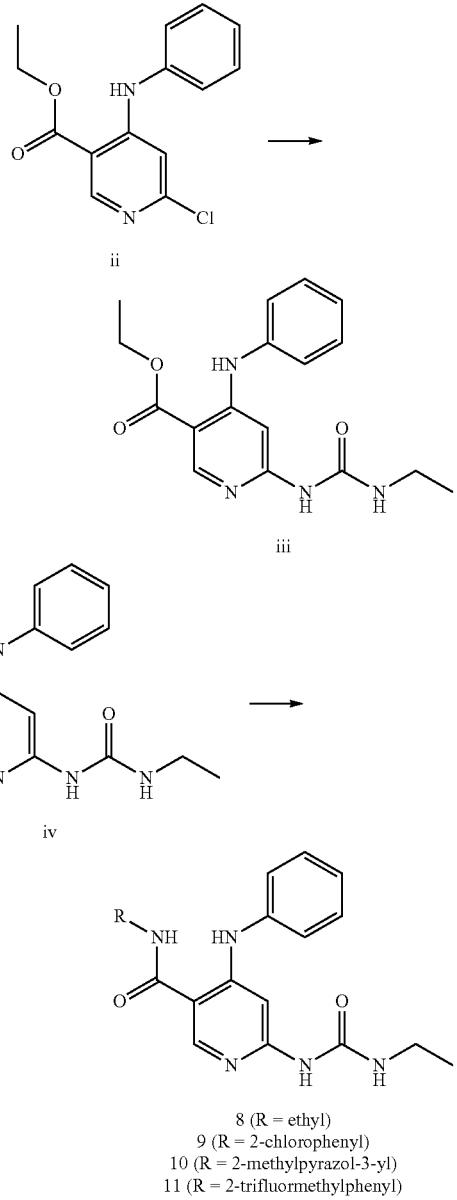

8 (R = ethyl)
9 (R = 2-chlorophenyl)
10 (R = 2-methylpyrazol-3-yl)
11 (R = 2-trifluormethylphenyl)

Ethyl 6-chloro-4-(phenylamino)nicotinate (ii)

Ethyl 4,6-dichloronicotinate (10.0 g, 45.44 mmol) in EtOH (100 mL) was stirred till a clear solution was obtained followed by addition of aniline (3.90 mL, 43.17 mmol) and 10 drops of conc. HCl. The resulting solution was heated to 80° C. for 2-3 h. The reaction mass was cooled to room temperature, poured onto ice-cold water and then extracted with EtOAc (3×250 mL). The combined organic phase was washed with brine, dried (Na₂SO₄), filtered and concentrated under reduced pressure. The crude residue was then purified over silica gel (100-200 M, 2% EtOAc-hexane) to obtain the desired product ii (4.90 g, 39%). ¹H-NMR (400 MHz, DMSO-d₆): δ 9.72 (br s, 1H), 8.66 (s, 1H), 7.28-7.49 (m, 5H), 6.77 (s, 1H), 4.35 (q, J=7.20 Hz, 2H), 1.34 (t, J=7.20 Hz, 3H). [M+H]⁺ m/z=277.17.

Ethyl 6-(3-ethylureido)-4-(phenylamino)nicotinate (iii)

To a solution of ii (6.40 g, 23.18 mmol) in 1,4-dioxane (200 mL) was added N-ethylurea (2.60 g, 29.0 mmol) followed by Cs$_2$CO$_3$ (11.50 g, 34.80 mmol). The resulting solution was purged with nitrogen for 15 min followed by addition of Pd(OAc)$_2$ (0.16 g, 0.70 mmol) and Xantphos (0.81 g, 1.40 mmol). The reaction mixture was again purged with nitrogen for 15 min and then heated at 80° C. for 16 h. The reaction mass was cooled to room temperature and filtered through a celite bed. The celite bed was washed with EtOAc and the combined filtrates concentrated under reduced pressure. Water was added to the residue and extracted with EtOAc (3×20 mL). The combined organic phase was washed with brine, dried (Na$_2$SO$_4$), filtered and concentrated under reduced pressure. The crude residue was purified over silica gel (60-120 M, 50-75% EtOAc-hexane) to obtain a solid residue. This was purified further by trituration with 25% ether-hexane to afford compound iii as an off-white solid (7.0 g, 92%). $^1$H-NMR (400 MHz, DMSO-d$_6$): δ 9.14 (s, 1H) and 9.64 (s, 1H), 8.61 (s, 1H), 7.70 (br s, 1H), 7.27-7.45 (m, 5H), 7.21 (t, J=7.20 Hz, 1H), 4.32 (q, J=7.20 Hz, 2H), 3.11 (m, 2H), 1.34 (t, J=7.20 Hz, 3H), 1.04 (t, J=7.20 Hz, 3H). [M+H]$^+$ m/z=329.14.

6-(3-Ethylureido)-4-(phenylamino)nicotinic acid (iv)

To a solution of iii (0.90 g, 2.74 mmol) in MeOH (25 mL) was added a solution of NaOH (0.55 g, 13.70 mmol) in H$_2$O (5 mL). The resulting solution was heated at 70° C. for 3-4 h then cooled to RT and the solvent removed in vacuo. Water was added to the residue and this mixture extracted with EtOAc (2×50 mL). The organic layer was discarded, and the aqueous portion was carefully acidified (under ice-cooling) with 6N HCl till pH 5. The resulting precipitate was filtered, washed with ice-cold water and ether. The off-white solid thus obtained was dried under high vacuum to obtain compound iv (0.70 g, 85%). $^1$H-NMR (400 MHz, DMSO-d$_6$): δ10.60 (br s, 1H), 9.07 (br s, 1H), 8.55 (s, 1H), 8.0 (br s, 1H), 7.13-7.42 (m, 6H), 3.12 (m, 2H), 1.05 (t, J=7.20 Hz, 3H); [M+H]$^+$ m/z=301.21.

Amide Coupling Methods

All amines used were commercially available unless otherwise stated.

General Amide Coupling Method 1

As described in examples for Scheme 3 was used to make Compound 8 as follows.

N-Ethyl-6-(3-ethylureido)-4-(phenylamino)nicotinamide (8)

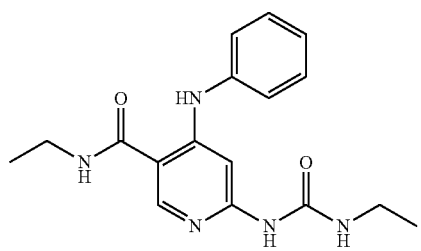 [SMILES: CCNC(=O)Nc1cc(Nc2ccccc2)c(C(=O)NCC)cn1]

To a solution of 6-(3-ethylureido)-4-(phenylamino)nicotinic acid (50 mg, 0.16 mmol, 1.0 eq) in THF (5.0 mL) was added EDCI.HCl (1-ethyl-3-(3-dimethylaminopropyl) carbodiimide hydrochloride, 46 mg, 0.24 mmol, 1.50 eq) followed by HOBt (N-hydroxybenzotriazole, 32 mg, 0.24 mmol, 1.50 eq), DMAP (4-dimethylaminopyridine, 29 mg, 0.24 mmol, 1.50 eq) and finally, ethyl amine (16 mg 70% solution, 0.24 mmol, 1.50 eq). The resulting reaction mixture was stirred overnight at room temperature. The reaction mass was then poured onto ice-cold water followed by extraction with EtOAc (3×20 mL). The organics were combined, washed with brine, dried over anhydrous Na$_2$SO$_4$, filtered and concentrated under reduced pressure. The residue was purified over silica gel (60-120 M, 1-2.5% MeOH-DCM) to obtain Compound 8 (48 mg, 92%), $^1$H NMR (300 MHz, DMSO-d$_6$): δ 10.43 (br s, 1H), 9.03 (br s, 1H), 8.52 (t, J=5.20 Hz, 1H), 8.41 (5, 1H), 7.94 (br s, 1H), 7.39 (m, 2H), 7.22 (m, 3H), 7.13 (m, 1H), 3.26 (m, 2H), 3.13 (m, 2H), 1.12 (t, J=7.20 HZ, 3H) and 1.05 (t, J=7.20 Hz, 3H). [M+H]$^+$ m/z=328.18.

General Amide Coupling Method 2

To an ice-cold solution of 6-(3-ethylureido)-4-(phenylamino)nicotinic acid (50 mg, 0.16 mmol, 1.0 eq) in DMF (2.0 mL) was added HBTU (1.50 eq) followed by DIPEA (3.0 eq) and finally the appropriate amine (1.20 eq). The resulting reaction mixture was stirred overnight at room temperature. The reaction mass was then poured onto the ice-cold water followed by extraction with EtOAc (3 times). The combined organic phase was washed with brine, dried over anhydrous Na$_2$SO$_4$, filtered and concentrated under reduced pressure. The residue was purified over silica gel (60-120 M, 1-2.5% MeOH-DCM) to obtain the desired product. General Amide Coupling Method 2 was used to make Compound 9 as follows.

N-(2-Chlorophenyl)-6-(3-ethylureido)-4-(phenylamino)nicotinamide (9)

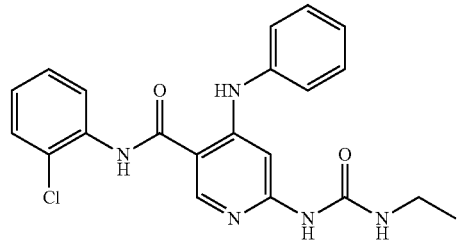 [SMILES: CCNC(=O)Nc1cc(Nc2ccccc2)c(C(=O)Nc2ccccc2Cl)cn1]

To an ice-cold solution of 6-(3-ethylureido)-4-(phenylamino)nicotinic acid (50 mg, 0.16 mmol, 1.0 eq) in DMF (2.0 mL) was added HBTU (91 mg, 0.24 mmol, 1.50 eq) followed by DIPEA (62 mg, 0.48 mmol, 3.0 eq) and finally 2-chloroaniline (24 mg, 0.19 mmol, 1.20 eq). The resulting reaction mixture was stirred overnight at room temperature. The reaction mass was then poured onto ice-cold water followed by extraction with EtOAc (3×20 mL). The organics were combined, washed with brine, dried over anhydrous Na$_2$SO$_4$, filtered and concentrated under reduced pressure. The residue was purified over silica gel (60-120 M, 1-2.5% MeOH-DCM) to obtain Compound 9 (10 mg, 15%). NMR (300 MHz, DMSO-d$_6$): δ 10.17 (br s, 1H), 10.08 (br s, 1H), 9.12 (s, 1H), 8.67 (s, 1H), 7.87 (m, 1H), 7.56 (m, 1H), 7.24-7.40 (m, 8H), 7.15 (m, 1H), 3.14 (m, 2H), 1.06 (t, J=7.20 Hz, 3H). [M+H]$^+$ m/z=410.15.

General Amide Coupling Method 3

To an ice-cold solution of 6-(3-ethylureido)-4-(phenylamino)nicotinic acid (50 mg, 0.16 mmol, 1.0 eq) in DMF (2.0 mL) was added HATU (1.50 eq) followed by HOBt (1.50 eq), DIPEA (1.50 eq) and finally the appropriate amine (1.50 eq). The resulting reaction mixture was stirred overnight at room temperature. The reaction mass was then poured onto the ice-cold water followed by extraction with EtOAc (3 times). The combined organic phase was washed with brine, dried over anhydrous $Na_2SO_4$, filtered and concentrated under reduced pressure. The residue was purified over silica gel (60-120 M, 1-2.5% MeOH-DCM) to obtain the desired product.

General Amide Coupling Method 3 was used to make Compound 10 as follows.

6-(3-Ethylureido)-N-(1-methyl-1H-pyrazol-5-yl)-4-(phenylamino)nicotinamide (10)

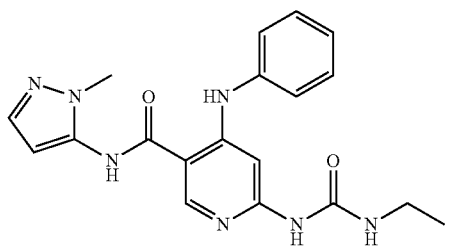 [SMILES: CCNC(=O)Nc1cc(Nc2ccccc2)c(C(=O)Nc2ccnn2C)cn1]

To an ice-cold solution of 6-(3-ethylureido)-4-(phenylamino)nicotinic acid (50 mg, 0.16 mmol, 1.0 eq) in DMF (2.0 mL) was added HATU (0-(7-Azabenzotriazol-1-yl)-N,N,N',N'-tetramethyluronium hexafluorophosphate, 91 mg, 0.24 mmol, 1.50 eq) followed by HOBt (N-hydroxybenzotriazole, 32 mg, 0.24 mmol, 1.50 eq), DIPEA (31 mg, 0.24 mmol, 1.50 eq) and finally the 1-methylpyrazol-3-amine (0.24 mmol, 23 mg, 1.50 eq). The resulting reaction mixture was stirred overnight at room temperature. The reaction mass was then poured onto the ice-cold water followed by extraction with EtOAc (3×20 mL). The reaction mass was then poured onto the ice-cold water followed by extraction with EtOAc (3×20 mL). The organics were combined, washed with brine, dried over anhydrous $Na_2SO_4$, filtered and concentrated under reduced pressure. The residue was purified over silica gel (60-120 M, 1-2.5% MeOH-DCM) to obtain Compound 10 (15 mg, 25%). $^1$H NMR (300 MHz, DMSO-$d_6$): δ 10.31 (br s, 1H), 9.97 (br s, 1H), 9.14 (br s, 1H), 8.64 (s, 1H), 7.85 (m, 1H), 7.40 (m, 3H), 7.27 (m, 3H), 7.17 (m, 1H), 6.23 (s, 1H), 3.71 (s, 3H), 3.13 (m, 2H) and 1.07 (m, 3H); $[M+H]^+$ m/z=380.

General Amide Coupling Method 4

An ice-cold solution of methane sulfonyl chloride (18 µL, 0.23 mmol) in DMA (2.0 mL) was stirred for 10 min followed by sequential drop wise addition of a solution of the appropriate acid (0.16 mmol) in DMA (5.0 mL) and 2,6-lutidine (55.4, 0.46 mmol). The resulting reaction mixture was stirred at 0° C. for 30 min followed by addition of a solution of the appropriate aniline (0.25 mmol) in DMA (1.0 mL). The reaction mass was further stirred at 0° C. for 10 min and then heated at 50° C. for 4 h. The reaction mass was then cooled to 0-5° C. and then quenched with $H_2O$ (5.0 mL) followed by addition of conc. HCl (0.50 mL). The resulting solution was stirred for 5 min followed by extraction with EtOAc (3×50 mL). The combined organics was washed with brine, dried over anhydrous $Na_2SO_4$, filtered and concentrated under reduced pressure. The residue was purified via chromatography or crystallisation as appropriate.

General Amide Coupling Method 4 was used to make Compound 11 as follows.

6-(3-Ethylureido)-4-(phenylamino)-N-(2-(trifluoromethyl)phenyl)nicotinamide (11)

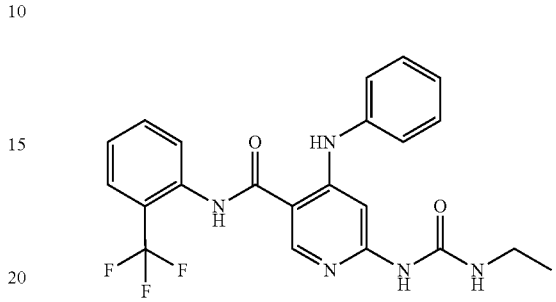

An ice-cold solution of methane sulfonyl chloride (18 µL, 0.23 mmol) in DMA (2.0 mL) was stirred for 10 min followed by sequential drop wise addition of a solution of 6-(3-ethylureido)-4-(phenylamino)nicotinic acid (50 mg, 0.16 mmol) in DMA (5.0 mL) and 2,6-lutidine (55 µL, 0.46 mmol). The resulting reaction mixture was stirred at 0° C. for 30 min followed by addition of a solution of 2-trifluoromethyl aniline (31 µL, 0.25 mmol) in DMA (1.0 mL). The reaction mass was further stirred at RT ° C. for 10 min and then heated at 50° C. for 4 h. The reaction mass was then cooled to 0-5° C. and quenched with $H_2O$ (5.0 mL), followed by addition of conc. HCl (0.50 mL). The resulting solution was stirred for 5 min followed by extraction with EtOAc (3×50 mL). The combined organic phase was washed with brine, dried over anhydrous $Na_2SO_4$, filtered and concentrated under reduced pressure. The residue was purified via preparative TLC to obtain Compound 11 (5.0 mg, 8%). $^1$H NMR (300 MHz, DMSO-$d_6$): δ 10.23 (br s, 1H), 10.07 (br s, 1H), 9.12 (br s, 1H), 8.61 (s, 1H), 7.89 (m, 1H), 7.82 (d, J=8.0 Hz, 1H), 7.74 (m, 1H), 7.57 (m, 2H), 7.38-7.43 (m, 2H), 7.31 (s, 1H), 7.25 (m, 2H), 7.15 (m, 1H), 3.14 (m, 2H) and 1.06 (t, J=7.20 Hz, 3H). $[M+H]^+$ m/z=444.17.

General Amide Coupling Method 5

To an ice-cold suspension of 6-(3-ethylureido)-4-(phenylamino)nicotinic acid (50 mg, 0.16 mmol) in dichloromethane (5 mL) was added oxalyl chloride (0.082 mL, ~6 eq.) followed by a catalytic amount of DMF (0.005 mL). The mixture was allowed to warm to RT and stirred for 16 h. The mixture was concentrated in vacuo and the yellow residue then dissolved in dichloromethane (2.5 mL). This solution was added dropwise to a solution of the appropriate amine in pyridine (1 mL) at 0° C. The mixture was allowed to warm to room temperature and stirred for 3 h. The reaction mixture was quenched with $NH_4Cl$ (sat.), diluted with water and extracted into EtOAc (3×20 mL). The organics were combined, washed with brine, dried over anhydrous $Na_2SO_4$, filtered and concentrated under reduced pressure. The residue was purified by normal or reverse phase chromatography to afford the amide product.

General Amide Coupling Method 5 was used to make Compound 12 as follows.

Ethyl (2E)-3-{4-[({6-[(ethylcarbamoyl)amino]-4-(phenylamino)pyridin-3-yl}carbonyl)amino]phenyl}prop-2-enoate (12)

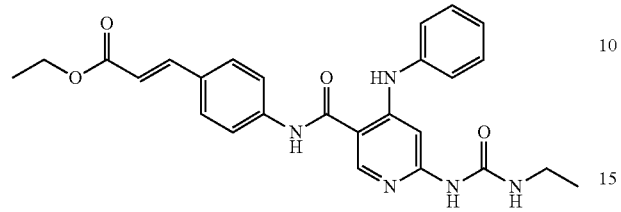

To an ice-cold suspension of 6-(3-ethylureido)-4-(phenylamino)nicotinic acid (50 mg, 0.16 mmol) in dichloromethane (5 mL) was added oxalyl chloride (0.082 mL, ~6 eq.) followed by a catalytic amount of DMF (0.005 mL). The mixture was allowed to warm to RT and stirred for 16 h. The mixture was concentrated in vacuo and the yellow residue then dissolved in dichloromethane (2.5 mL). This solution was added dropwise to a solution of 4-amino ethyl cinnamate in pyridine (1 mL) at 0° C. The mixture was allowed to warm to room temperature and stirred for 3 h. The reaction mixture was quenched with NH$_4$Cl (sat.), diluted with water and extracted into EtOAc (3×20 mL). The organics were combined, washed with brine, dried over anhydrous Na$_2$SO$_4$, filtered and concentrated under reduced pressure. The residue was dissolved in DMSO and purified by reverse phase flash chromatography to afford Compound 12 (12 g Reveleris C18 cartridge, eluting with 0-100% acetonitrile) to afford the desired product. (10 mg, 13%). $^1$H NMR (300 MHz, DMSO-d$_6$): δ 10.44 (s, 1H), 9.86 (s, 1H), 9.13 (s, 1H), 8.59 (s, 1H), 7.93 (s, 1H), 7.75 (dd, J=28.4, 8.8 Hz, 4H), 7.61 (d, J=16.0 Hz, 1H), 7.41 (t, J=7.9 Hz, 2H), 7.28 (d, J=7.4 Hz, 3H), 7.16 (t, J=7.4 Hz, 1H), 6.56 (d, J=16.0 Hz, 1H), 4.19 (q, J=7.1 Hz, 2H), 3.23-3.05 (m, 2H), 1.26 (t, J=7.1 Hz, 3H), 1.07 (t, J=7.2 Hz, 3H). [M+H]$^+$ m/z=474.24.

6-(3-Ethylureido)-N-phenyl-4-(pyridin-3-ylamino)nicotinamide (13)

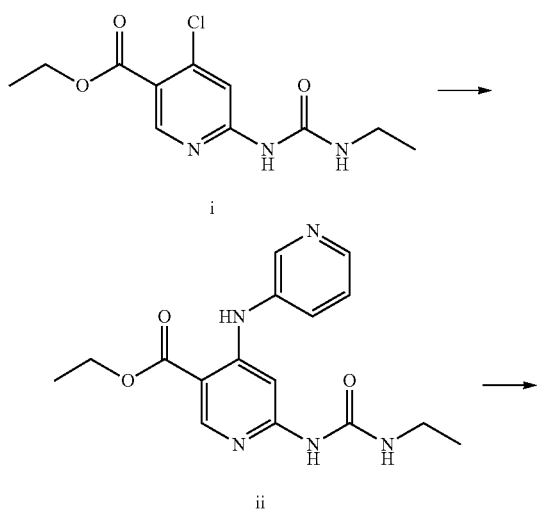

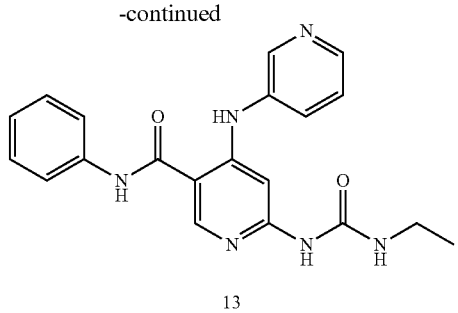

Ethyl 6-(3-ethylureido)-4-(pyridin-3-ylamino)nicotinate (ii)

To a solution of ethyl 4-chloro-6-(3-ethylureido)nicotinate, i (1.0 g, 3.70 mmol), in 1,4-dioxane (25 mL) was added 3-aminopyridine (0.435 g, 4.81 mmol) followed by Cs$_2$CO$_3$ (1.80 g, 5.55 mmol). The resulting solution was purged with nitrogen for 15 min followed by addition of Pd(OAc)$_2$ (0.025 g, 0.11 mmol) and Xantphos (0.13 g, 0.22 mmol). The reaction mixture was again purged with nitrogen for 15 min and then heated at 80° C. overnight. The reaction mixture was cooled to room temperature, filtered through a celite bed, and the bed washed with EtOAc. The combined filtrate was concentrated under reduced pressure. Water was added to the residue and the mixture extracted with EtOAc (3×50 mL). The combined organic phase was washed with brine, dried (Na$_2$SO$_4$), filtered and concentrated under reduced pressure. The crude product thus obtained was triturated with a mixture of 10% MeOH-Et$_2$O to obtain compound ii as an off-white solid (0.80 g, 66%). $^1$H NMR (DMSO-d$_6$, 400 MHz): δ 9.62 (s, 1H), 9.17 (s, 1H), 8.63 (s, 1H), 8.56 (d, J=2.4 Hz, 1H), 8.41 (d, J=4.4 Hz, 1H), 7.77 (m, 1H), 7.75 (br s, 1H), 7.48 (m, 1H), 7.20 (s, 1H), 4.32 (q, J=6.8 Hz, 2H), 3.11 (q, J=7.20 Hz, 2H), 1.33 (t, J=6.8 Hz, 3H) and 1.03 (t, J=7.20 Hz, 3H). [M+H]$^+$ m/z=330.12.

6-(3-ethylureido)-N-phenyl-4-(pyridin-3-ylamino)nicotinamide (13)

A solution of ethyl 6-(3-ethylureido)-4-(pyridin-3-ylamino)nicotinate (0.60 g, 1.82 mmol) and aniline (250 μL, 2.73 mmol) in THF (10 mL) was purged with nitrogen for 15 minutes. To this solution was added trimethylaluminium (2M in toluene, 5.40 mL, 10.80 mmol) dropwise over 10-15 min. The reaction mixture was heated at 125° C. for 30 min in a microwave reactor. The reaction mass was then quenched with water and extracted with EtOAc (3×1000 mL). The organics were combined, washed with brine, dried over anhydrous Na$_2$SO$_4$, filtered and concentrated under reduced pressure. The residue thus obtained was purified by preparative HPLC to afford Compound 13 (0.28 g, 41%) as an off-white solid. $^1$H NMR (300 MHz, DMSO-d$_6$): δ 10.32 (s, 1H), 9.89 (s, 1H), 9.15 (s, 1H), 8.59 (s, 1H), 8.54 (s, 1H), 8.35 (d, J=4.8 Hz, 1H), 7.93 (br s, 1H), 7.73 (t, J=8.0 Hz, 3H), 7.45-7.41 (m, 1H), 7.37 (t, J=7.6 Hz, 2H), 7.23 (s, 1H), 7.13 (t, J=7.6 Hz, 1H), 3.16-3.13 (m, 2H), 1.08 (t, J=7.2 Hz, 3H). [M+H]$^+$ m/z=377.22.

Weinreb Amides

Compound 112 was formed from a Weinreb amide, compound 83, as follows.

6-(3-ethylureido)-N-methoxy-N-methyl-4-(phenylamino)nicotinamide (83) and 1-(5-benzoyl-4-(phenylamino)pyridin-2-yl)-3-ethylurea (112)

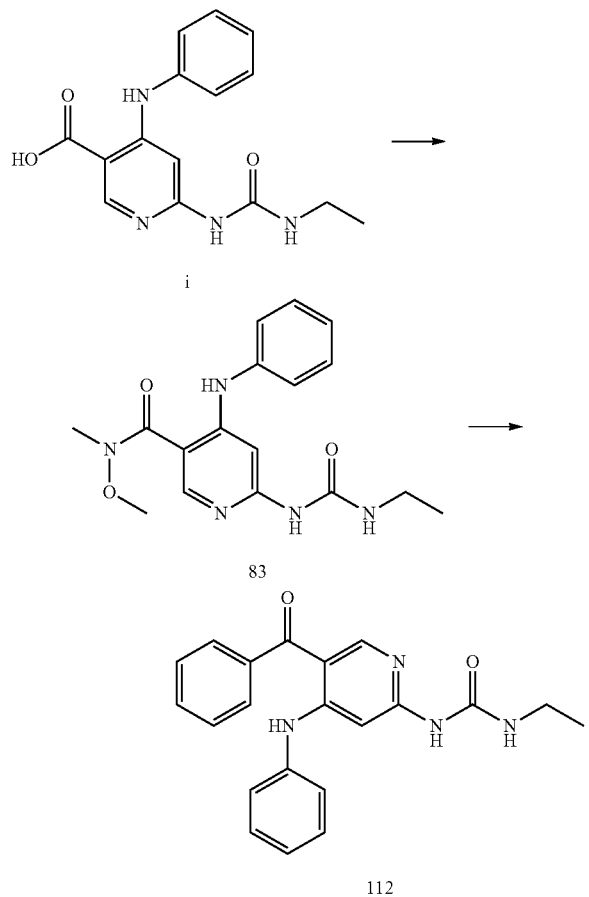

6-(3-ethylureido)-N-methoxy-N-methyl-4-(phenylamino)nicotinamide (83)

4-anilino-6-(ethylcarbamoylamino)pyridine-3-carboxylic acid (i) (200 mg, 0.67 mmol), dimethylhydroxylamine hydrochloride (65 mg, 0.67 mmol), 4-dimethylaminopyridine (81 mg, 0.67 mmol) and N-hydroxybenzotriazole (90 mg, 0.67 mmol) were added to a dry RBF which was flushed with $N_2$. DMF (1.5 mL) was added and the mixture stirred. 3-(ethyliminomethyleneamino)-N,N-dimethyl-propan-1-amine hydrochloride (150 mg, 0.80 mmol) was dissolved in DMF (1.5 mL) in a separate vial and this solution added to the reaction mixture at RT. The mixture was stirred overnight at RT.

After 8 days at RT, the mixture was diluted with water and extracted into EtOAc (3×30 mL) and the organics dried with brine then $Na_2SO_4$. The cloudy EtOAc suspension (conatins some unreacted acid) was filtered and the clear filtrate evaporated to dryness. The residue was dissolved in DCM (2 mL) and applied to a silica column, eluting with EtOAc/heptane, to afford Compound 83 (90 mg).

1-(5-benzoyl-4-(phenylamino)pyridin-2-yl)-3-ethylurea (112)

Compound 83 (15 mg, 0.044 mmol) was dissolved in dry THF (0.8 mL) and this solution added to the phenyl magnesium bromide (1M, 0.2 mL, 0.20 mmol) at 0° C. The mixture was stirred and allowed to warm slowly to RT. The mixture was quenched with MeOH/HCl (2M) (1 mL:0.1 mL) then $NH_4Cl$ (sat.) added and the mixture diluted with water and EtOAc (pH of aqueous ~7). The mixture was extracted into EtOAc and the organics combined and dried with brine then $Na_2SO_4$. The solvent was removed to afford 20 mg crude residue. This was dissolved in DCM (2 mL) and applied to a silica column, eluting with EtOAc/heptane, to afford Compound 112 (13 mg).).

Example(s) of General Method C

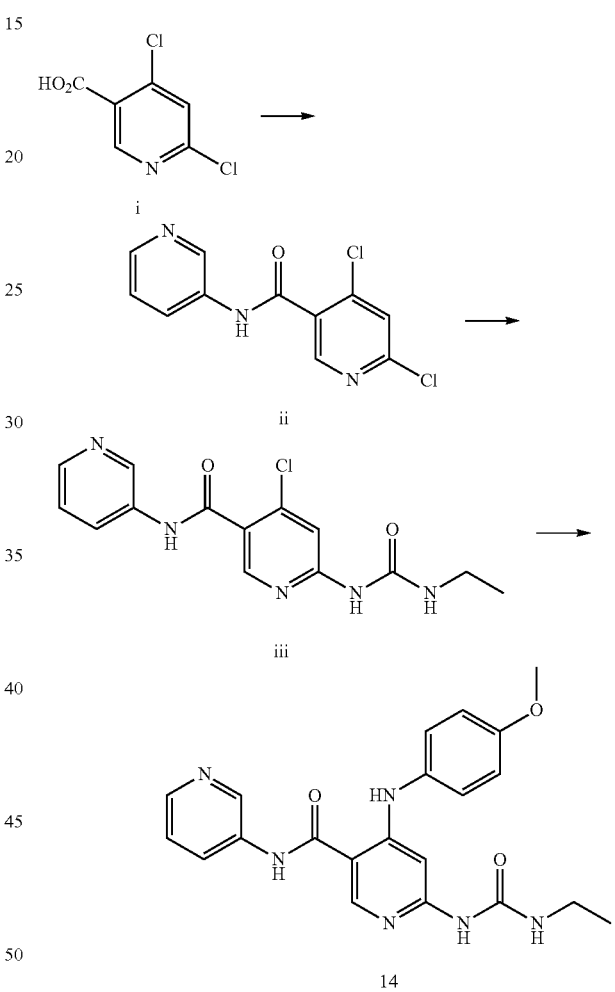

4,6-Dichloro-N-(3-pyridyl)pyridine-3-carboxamide (ii)

To a suspension of 4,6-Dichloropyridine-3-carboxylic acid (5.0 g, 26 mmol) in THF (100 mL) was added thionyl chloride (4 mL, 52 mmol) and catalytic DMF (5 drops). The solution was heated at 60° C. for 20 minutes. The mixture was concentrated in vacuo to afford the acid chloride as a yellow residue. The acid chloride was dissolved in THF (50 mL) was and added to a cooled (icewater bath) solution of triethylamine (11 mL, 78 mmol) and 3-aminopyridine (4.9 g, 52 mmol) in THF (50 mL). The mixture was allowed to warm to room temperature while stirring for 40 h. The reaction mixture was concentrated, diluted with water (100 mL) and washed with DCM (3×100 mL). The organic extracts were combined, washed with brine (2×20 mL), dried over MgSO$_4$ and concentrated. The resultant residue was purified by flash chromatography (120 g GraceResolv silica cartridge, 50-90% EtOAc in cyclohexane) to afford compound ii as a white crystalline solid (3.52 g, 50%).). [M+H]$^+$ m/z=268.13, 270.11.

4-Chloro-6-(ethylcarbamoylamino)-N-(3-pyridyl)pyridine-3-carboxamide (iii)

Compound ii (1.0 g, 3.7 mmol) and N-ethylurea (362 mg, 4.1 mmol) were dissolved in degassed dioxane (50 mL) under an atmosphere of argon. Potassium tert-butoxide (628 mg, 5.6 mmol), Xantphos (129 mg, 0.22 mmol) and palladium(0)bis(dibenzylideneacetone) (65 mg, 0.11 mmol) were added sequentially. The mixture was heated at 100° C. with stirring under argon for 16 h. Additional palladium(0)bis(dibenzylideneacetone) (65 mg, 0.11 mmol) and N-ethylurea (560 mg, 6.4 mmol) were added and the mixture heated at reflux for 5 h. The mixture was cooled to RT, diluted with acetonitrile (100 mL) and then adsorbed on to silica by concentration in vacuo. The crude product was purified by flash chromatography (40 g GraceResolv silica cartridge, 0-10% MeOH in EtOAc) to afford iii as a light brown solid (244 mg, 20%). [M+H]$^+$ m/z=320.05.

6-(3-Ethylureido)-4-(4-methaxyphenylamino)-N-(pyridin-3-yl)nicotinamide (14)

Ethanol (2 mL) was treated with acetyl chloride (22 µL) at room temperature to give an ethanolic solution of HCl (2 eq., 0.31 mmol). To this solution was added iii (50 mg, 0.16 mmol) and p-anisidine (38 mg, 0.31 mmol). The solution was heated in a microwave reactor at 100° C. for 5 minutes and then at 110° C. for a further 5 minutes. The mixture was cooled and concentrated under a stream of nitrogen. The resultant residue was suspended in saturated sodium bicarbonate (2 mL) and washed with EtOAc (6×2 mL) and acetonitrile (2×2 mL). The combined organic extracts were filtered, concentrated and the residue purified by chromatography (4 g Reveleris silica cartridge, 0-5% MeOH in DCM) to afford Compound 14 as an off white solid (19 mg, 30%). $^1$H NMR (400 MHz, DMSO-d$_6$): δ 10.41 (s, 1H), 9.72-9.63 (m, 1H), 9.06 (s, 1H), 8.89 (d, J=2.2 Hz, 1H), 8.61 (s, 1H), 8.33 (dd, J=4.7, 1.5 Hz, 1H), 8.13 (ddd, J=8.4, 2.5, 1.5 Hz, 1H), 7.96-7.90 (m, 1H), 7.41 (dd, J=8.3, 4.7 Hz, 1H), 7.22 (d, J=8.9 Hz, 2H), 7.04 (s, 1H), 7.00 (d, J=8.9 Hz, 2H), 3.80 (s, 3H), 3.19-3.11 (m, 2H), 1.07 (t, J=7.2 Hz, 3H). [M+H]$^+$ m/z=407.17.

Ethyl 4-(2-(3-ethylureido)-5-(pyridin-3-ylcarbamoyl)pyridin-4-ylamino)benzoate (15); and 4-(2-(3-ethylureido)-5-(pyridin-3-ylcarbamoyl)pyridin-4-ylamino)benzoic acid (16)

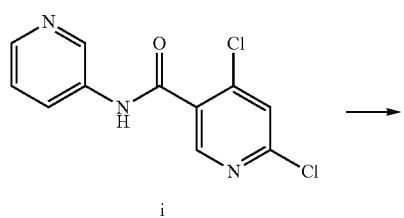

i

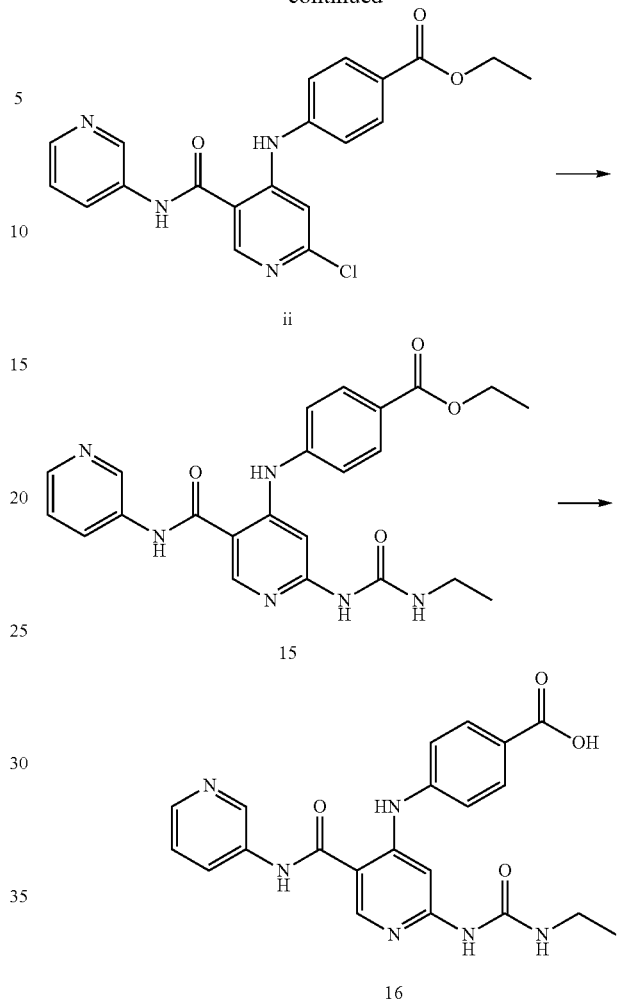

Ethyl 4-[[2-chloro-5-(3-pyridylcarbamoyl)-4-pyridyl]amino]benzoate (ii)

To a suspension of 4,6-dichloro-N-(3-pyridyl)pyridine-3-carboxamide (500 mg, 1.9 mmol) in EtOH (5 mL) was added ethyl 4-aminobenzoate (340 mg, 2.1 mmol) and HCl (0.1 mL, 4M). The mixture was heated in a microwave for 10 min at 100° C. then heated again at 130° C. for 20 min. More ethyl 4-aminobenzoate (100 mg, 0.6 mmol) was added and the mixture heated again at 130° C. for 20 min. The mixture was evaporated to dryness and the residue purified by flash chromatography (40 g Reveleris silica cartridge, 0-10% MeOH in DCM) to afford ii as an off white solid (334 mg, 46%). A 10 mg sample of ii was dissolved in DMSO and purified further using reverse phase preparatory HPLC (20-60% MeCN in water, 0.1% formic acid) to afford 8.74 mg of ii as a white solid. $^1$H NMR (400 MHz, DMSO-d$_6$): δ 8.85 (d, J=2.2 Hz, 1H), 8.65 (s, 1H), 8.33 (d, J=3.7 Hz, 1H), 8.11 (ddd, J=8.3, 2.5, 1.5 Hz, 1H), 7.96 (d, J=8.6 Hz, 2H), 7.40 (dd, J=8.1, 4.4 Hz, 3H), 7.15 (s, 1H), 4.30 (q, J=7.1 Hz, 2H), 1.32 (t, J=7.1 Hz, 31-1). [M+H]$^+$ m/z=397.09.

Ethyl 4-(2-(3-ethylureido)-5-(pyridin-3-ylcarbamoyl)pyridin-4-ylamino)benzoate (15)

Compound ii (210 mg, 0.53 mmol) and N-ethylurea (93 mg, 1.1 mmol) were dissolved in degassed dioxane (2 mL) under an atmosphere of nitrogen. Sodium tert-butoxide (102 mg, 1.1 mmol), X-phos (2-(Dicyclohexylphosphino)-2',4',6'-tri-1-propyl-1,1'-biphenyl, 50 mg, 0.1 mmol) and palladium(0)bis(dibenzylideneacetone) (50 mg, 0.05 mmol) were added sequentially. The mixture was heated at 120° C. in a microwave reactor for 60 min. The mixture was cooled to RT, filtered then evaporated to dryness. The residue was purified by flash chromatography (40 g GraceResolv silica cartridge, 0-15% MeOH in DCM) to yield Compound 15 as an off white solid (160 mg, 68%). $^1$H NMR (400 MHz, DMSO-d6): δ 10.53 (s, 1H), 10.06 (s, 1H), 9.24 (s, 1H), 8.86 (s, 1H), 8.64 (s, 1H), 8.32 (d, J=4.8 Hz, 1H), 8.12 (d, J=7.6 Hz, 1H), 7.95 (d, J=8.4 Hz, 2H), 7.80 (m, 1H), 7.55 (s, 1H), 7.40 (d, J=8.8 Hz, 3H), 4.32-4.27 (m, 2H), 3.17-3.14 (m, 2H), 1.34 (t, J=7.2 Hz, 3H), 1.12-1.09 (m, 3H). [M+H]$^+$ m/z=449.16.

4-(2-(3-Ethylureido)-5-(pyridin-3-ylcarbamoyl)pyridin-4-ylamino)benzoic acid (16)

Methyl 4-[[2-(ethylcarbamoylamino)-5-(3-pyridylcarbamoyl)-4-pyridyl]amino]benzoate (35 mg, 0.07 mmol) was suspended in acetonitrile (3 mL) and water (3 mL) and treated with NaOH (1 mL, 1 M). The mixture was heated to 40° C. for 40 minutes. The mixture was adjusted to pH ~6 by addition of dilute aqueous HCl. The mixture was then freeze-dried. The crude product was dissolved in DMSO/water and purified by reverse phase chromatography (12 g Reveleris C18 cartridge, eluting with 0-100% acetonitrile in 0.1% aqueous formic acid). Compound 16 was isolated as a white solid (23 mg, 68%). $^1$H NMR (400 MHz, DMSO-d$_6$): δ 10.53 (s, 1H), 10.04 (s, 1H), 9.24 (s, 1H), 8.86 (d, J=2.1 Hz, 1H), 8.64 (s, 1H), 8.32 (dd, J=4.7, 1.5 Hz, 1H), 8.12 (ddd, J=8.4, 2.5, 1.5 Hz, 1H), 7.93 (d. J=8.7 Hz, 2H), 7.87 (s, 1H), 7.51 (s, 1H), 7.40 (ddd, J=8.4, 4.7, 0.6 Hz, 1H), 7.36 (d. J=8.8 Hz, 2H), 3.20-3.12 (m, 2H), 1.07 (t, J=7.2 Hz, 3H). [M+H]$^+$ m/z=421.14.

Functionalisation

It will be understood that the particular examples which are described herein may undergo further functionalization using methods known in the art, for example, including, but not limited to the following.

6-(3-Ethylureido)-N-(4-(3-(methoxy(methyl)amino)-3-oxopropyl)phenyl)-4-(phenylamino)nicotinamide (123) and 6-(3-ethylureido)-N-(4-(3-oxobutyl)phenyl)-4-(phenylamino)nicotinamide (122)

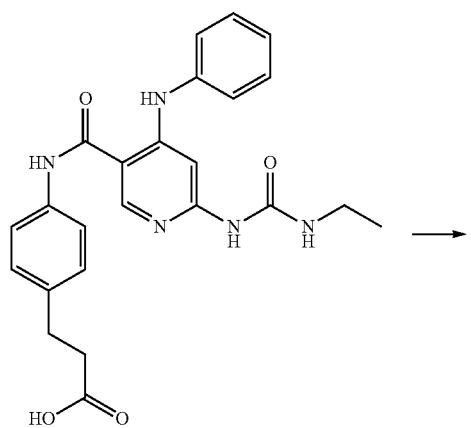

78

-continued

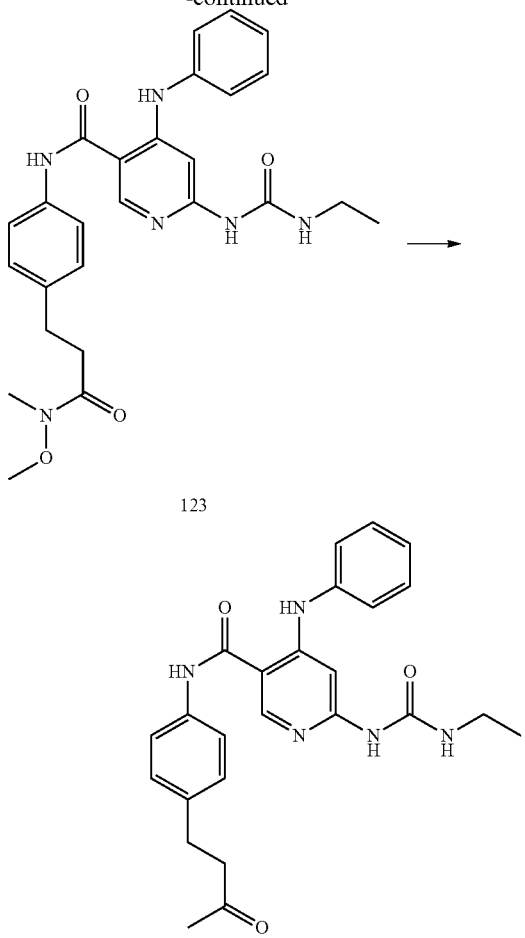

123

122

6-(3-Ethylureido)-N-(4-(3-(methoxy(methyl)amino)-3-oxopropyl)phenyl)-4-(phenylamino)nicotinamide (123)

3-[4-[[4-anilino-6-(ethylcarbamoylamino)pyridine-3-carbonyl]amino]phenyl]propanoic acid (Compound 78) (14.5 mg, 0.032 mmol) and dimethyl hydroxylamine (3.8 mg, 0.039 mmol) were dissolved in DMF (1 mL) and the DIPEA (17 µL, 0.098 mmol) added, followed by [dimethylamino(triazolo[4,5-b]pyridin-3-yloxy)methylene]-dimethyl-ammonium hexafluorophosphate (15 mg, 0.039 mmol). The mixture was stirred at RT. After 1 h the mixture was diluted with EtOAc and evaporated to dryness. The residue was dissolved in DCM and applied to a silica column, eluting with MeOH/DCM, to afford Compound 123 (8 mg).

6-(3-Ethylureido)-N-(4-(3-oxobutyl)phenyl)-4-(phenylamino)nicotinamide (122)

Methylmagnesium chloride (100 µmol, 0.3 mmol) was added to THF (1 mL) and cooled to 0° C. Compound 123 (8 mg, 0.016 mmol) was dissolved in THF (1 mL) and this solution added dropwise to the Grignard at 0° C. The mixture was allowed to warm slowly to RT over 1 h then quenched with NH$_4$Cl and diluted with water and EtOAc. The mixture was extracted into EtOAc and the organics combined and dried with brine then Na$_2$SO$_4$ then evaporated to dryness. The residue was applied to a silica column in DCM (1 mL) and MeOH (2 drops) and eluted with MeOH in DCM to afford Compound 122 (4 mg).

N-(4-Azidophenyl)-4-[(4-chlorophenyl)amino]-6-[(ethylcarbamoyl)amino]pyridine-3-carboxamide (132) and Ethyl 1-{4-[({4-[(4-chlorophenyl)amino]-6-[(ethylcarbamoyl)amino]pyridin-3-yl}carbonyl)amino]phenyl}-1H-1,2,3-triazole-4-carboxylate (133)

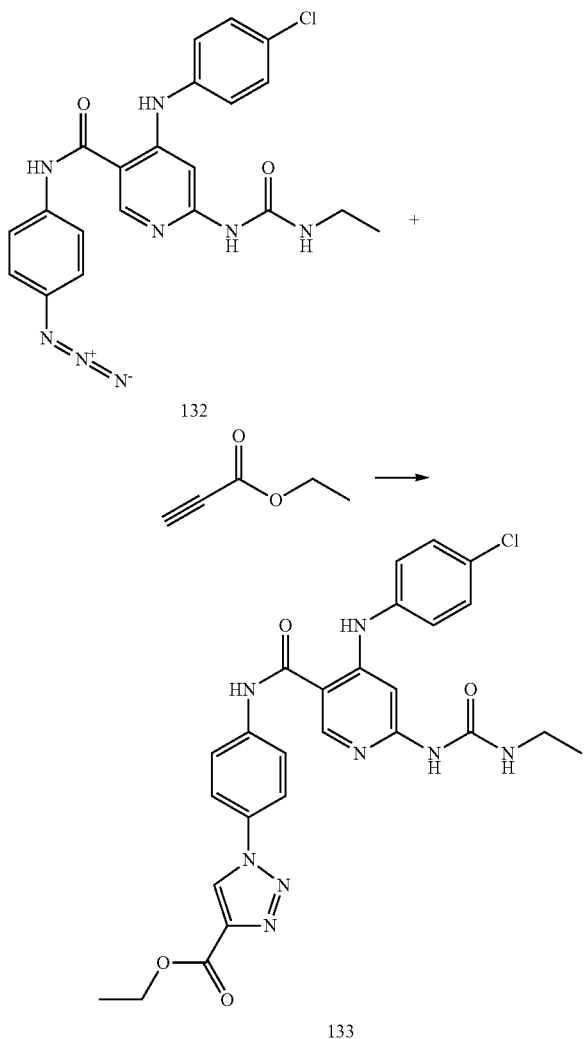

N-(4-azidophenyl)-4-[(4-chlorophenyl)amino]-6-[(ethylcarbamoyl)amino]pyridine-3-carboxamide (132)

Compound 132 was prepared by coupling 4-anilino-6-(ethylcarbamoylamino)pyridine-3-carboxylic acid and 4-azidoaniline. $^1$H NMR (400 MHz, DMSO) δ 10.35 (s, 1H), 9.86 (s, 1H), 9.11 (s, 1H), 8.57 (s, 1H), 7.88 (s, 1H), 7.79-7.72 (m, 2H), 7.47-7.41 (m, 2H), 7.33-7.27 (m, 2H), 7.25 (br s, 1H), 7.15-7.09 (m, 2H), 3.20-3.10 (m, 2H), 1.06 (t, J=7.2 Hz, 3H), [M+H]$^+$ m/z=450.98.

Ethyl 1-{4-[({4-[(4-chlorophenyl)amino]-6-[(ethylcarbamoyl)amino]pyridin-3-yl}carbonyl)amino]phenyl}-1H-1,2,3-triazole-4-carboxylate (133)

To a solution of Compound 132 (50 mg, 0.11 mmol) in DMF (1.8 mL) was added ethyl prop-2-ynoate (21 mg, 0.2218 mmol), followed by ethyl-diiopropylamine (0.023 mL, 0.13 mmol) and cuprous iodide (3.8 mg, 0.020 mmol) at 0° C. The ice bath was removed and the mixture stirred at RT for 2 hours. Water was added and the mixture extracted with EtOAc (4 times). The organic fractions were combined and concentrated in vacuo to give a residue that was purified by medium pressure chromatography (C18 column), eluting with ACN gradient in water, to give target product. The product was triturated with EtOAc to give Compound 133 (5 mg). $^1$H NMR (400 MHz, DMSO) δ 10.55 (s, 1H), 9.82 (5, 1H), 9.43 (s, 1H), 9.12 (s, 1H), 8.62 (s, 1H), 7.94 (t, J=6.4 Hz, 5H), 7.44 (d, J=8.5 Hz, 2H), 7.31 (d, J=8.5 Hz, 2H), 7.26 (s, 1H), 4.37 (q, J=7.1 Hz, 2H), 3.20-3.11 (m, 2H), 1.35 (t, J=7.1 Hz, 3H), 1.07 (t, J=7.2 Hz, 3H), [M+H]$^+$ m/z=549.03.

6-[(Ethylcarbamoyl)amino]-N-(1-methyl-2-oxo-1,2-dihydropyridin-4-yl)-4-(phenylamino)pyridine-3-carboxamide (134)

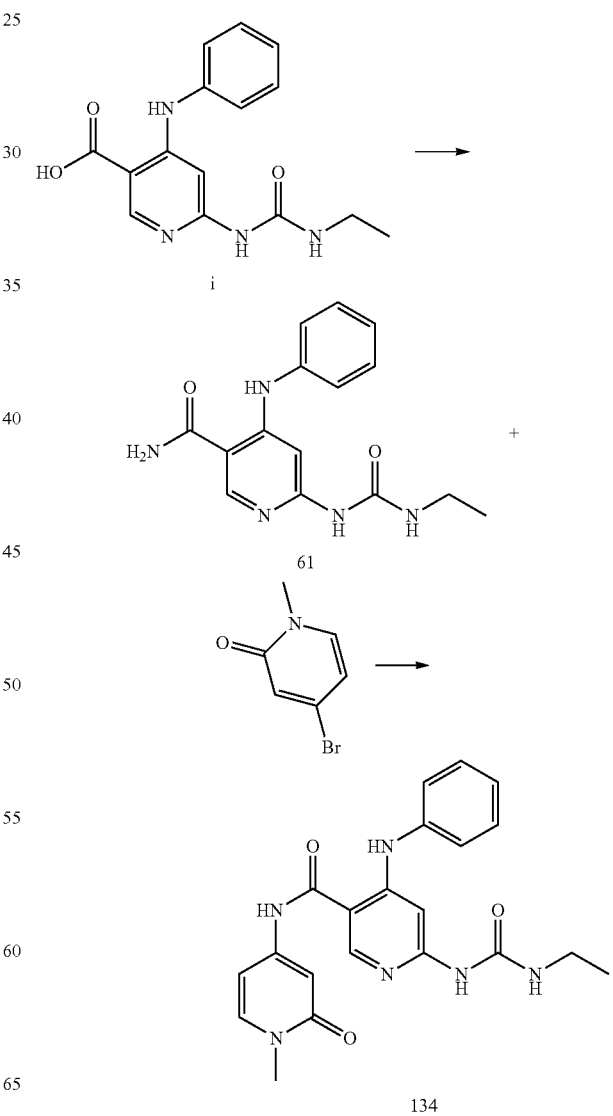

6-(3-Ethylureido)-4-(phenylamino)nicotinamide (61)

4-anilino-6-(ethylcarbamoylamino)pyridine-3-carboxylic acid (i) (70 mg, 0.23 mmol) was suspended in DMF (2 mL) and N,N-diisopropylethyl amine (0.16 mL, 0.93 mmol) was added, causing the solid to dissolve. The [benzotriazol-1-yloxy(dimethylamino)methylene]-dimethyl-ammonium hexafluorophosphate (97 mg, 0.26 mmol) was added. After stirring at RT for 10 min, ammonia (1 mL, 25 mass %, 14.7 mmol) was added. The mixture was stirred overnight at RT. The mixture was quenched with NH$_4$Cl and diluted with water and EtOAc. The mixture was extracted into EtOAc (3×20 mL), the organics combined and dried with brine then over MgSO$_4$. The solvent was removed to afford a crude residue as a white solid. The solid was dissolved in MeOH/DCM and applied to a silica column, eluting with MeOH/DCM, to give Compound 6140 mg. $^1$H NMR (400 MHz, CD$_3$OD) δ 8.46-8.39 (m, 1H), 7.44-7.37 (m, 2H), 7.29-7.23 (m, 2H), 7.22-7.14 (m, 1H), 6.84 (s, 1H), 3.29-3.24 (m, 2H), 1.18 (t, J=7.2 Hz, 3H).

6-[(Ethylcarbamoyl)amino]-N-(1-methyl-2-oxo-1,2-dihydropyridin-4-yl)-4-(phenylamino)pyridine-3-carboxamide (134)

Compound 61 (20 mg, 0.067 mmol) was suspended in dry dioxane (2 mL) with the sodium butoxide (13 mg, 0.13 mmol), dicyclohexyl-[2-(2,4,6-triisopropylphenyl)phenyl] phosphane (6 mg, 0.01 mmol), 4-bromo-1-methyl-pyridin-2-one (25 mg, 0.13 mmol) and tris-(dibenzylidineacetone)dipalladium(0) (6 mg, 0.007 mmol). The mixture was placed under N$_2$ and heated in a microwave for 1 h at 120° C. The mixture was left at RT over 2 days. The mixture was transferred to a flask with MeOH and the solvent removed. The residue was suspended in 10% MeOH/DCM and applied to a silica column, eluting with EtOAc/heptane, followed by MeOH/DCM gradient, to afford Compound 134 (6.8 mg). $^1$H NMR (400 MHz, DMSO) δ 10.27 (s, 1H), 9.70 (s, 1H), 9.14 (s, 1H), 8.54 (s, 1H), 7.88 (s, 1H), 7.62 (d, J=7.5 Hz, 1H), 7.47-7.35 (m, 2H), 7.34-7.21 (m, 3H), 7.21-7.11 (m, 1H), 6.87 (d, J=2.3 Hz, 1H), 6.58 (dd, J=7.5, 2.4 Hz, 1H), 3.37 (s, 3H), 3.19-3.09 (m, 2H), 1.06 (t, J=7.2 Hz, 3H), [M+H]$^+$ m/z=407.13.

6-[(Ethylcarbamoyl)amino]-N-[4-(3-hydroxyprop-1-yn-1-yl)phenyl]-4-(phenylamino)pyridine-3-carboxamide (135)

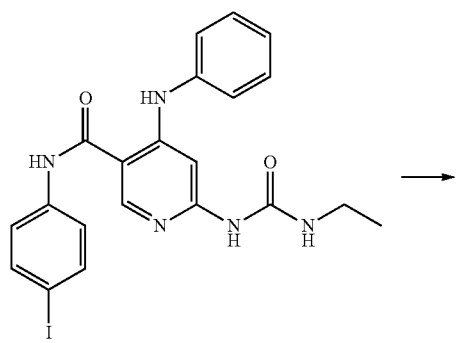

i

→

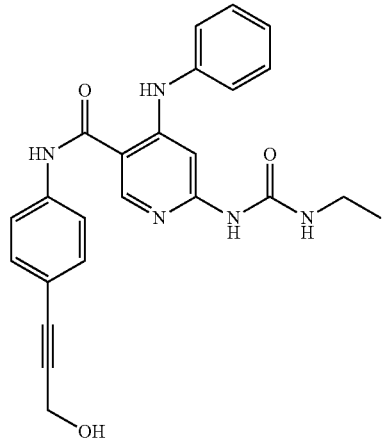

135

4-anilino-6-(ethylcarbamoylamino)-N-(4-iodophenyl)pyridine-3-carboxamide (i) was prepared by coupling 4-anilino-6-(ethylcarbamoylamino)pyridine-3-carboxylic acid and 4-iodoaniline Compound (i) (50 mg, 0.10 mmol) and PdCl$_2$(PPh$_3$)$_2$ (2.8 mg, 4.0 μmol) were placed in a 0.5-1.5 mL microwave vial and anhydrous DMF (1 mL) added, quickly followed by triethylamine (83 wok 0.60 mmol) and propargyl alcohol (17 μmol, 0.30 mmol). The solution was bubbled with argon for ~3 minutes then CuI (0.38 mg, 2.0 μmol) was added. The vial was capped and mixture degassed then heated in the microwave at 100° C. for 30 minutes. The mixture was filtered on celite and then the filtrate concentrated in vacuo to give a residue that was purified by flash chromatography, eluting with methanol and DCM. The resulting product mixture was further purified by chromatography (reverse phase; ACN gradient in water), to afford Compound 135. $^1$H NMR (400 MHz, DMSO) δ 10.40 (br s, 1H), 9.84 (br s, 1H), 9.11 (br s, 1H), 8.57 (s, 1H), 7.94 (br s, 1H), 7.73 (br d, J=8.4 Hz, 2H), 7.45-7.36 (m, 4H), 7.27 (br d, J=7.8 Hz, 3H), 7.15 (m, 1H), 5.33-5.25 (m, 1H), 4.29 (d, J=5.0 Hz, 2H), 3.24-3.04 (m, 2H), 1.06 (t, J=7.2 Hz, 3H), [M+H]$^+$ m/z=430.12.

Ethyl 1-{5-[({6-[(ethylcarbamoyl)amino]-4-(pyridin-3-ylamino)pyridin-3-yl}carbonyl)amino]pyrimidin-2-yl}-4-methylpiperidine-4-carboxylate (136)

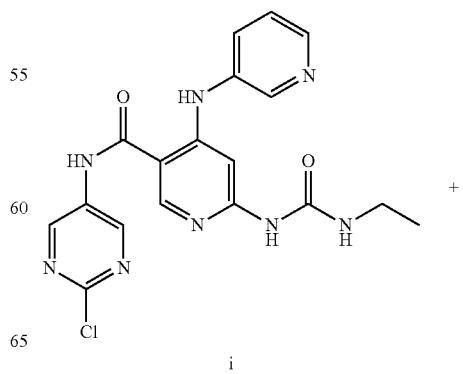

i

+

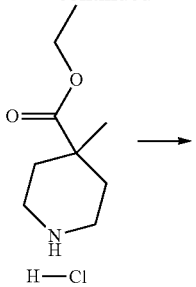

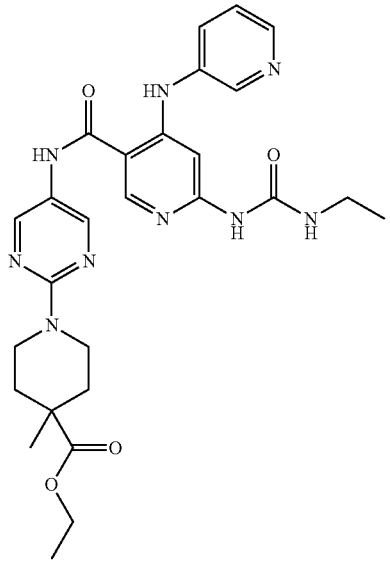

136

N-(2-chloropyrimidin-5-yl)-6-(ethylcarbamoylamino)-4-(3-pyridylamino)pyridine-3-carboxamide (i) was prepared by coupling 4-anilino-6-(ethylcarbamoylamino)pyridine-3-carboxylic acid and 2-chloropyrimidin-5-amine. Compound (i) (30 mg, 73 woe, ethyl 4-methylpiperidine-4-carboxylate hydrochloride (23 mg, 0.11 mmol), N-ethyl-N-isopropyl-propan-2-amine (50 mmol, 0.29 mmol) and DMSO (2 mL) were combined and heated for 2 hr at 80° C. followed by 2 hr at 90° C. The reaction mixture was partitioned between EtOAc (50 mL) and saturated NH$_4$Cl solution (50 mL). The organic layer was separated and further washed with saturated aqueous sodium hydrogen carbonate (50 mL) and brine (50 mL). The organic layer was separated and concentrated to give a crude oil. Flash chromatography on silica, eluting with 0-100% EtOAc gradient in n-heptane, gave crude product. Further flash chromatography (C18 column), eluting with 20-60% acetonitrile gradient in water (containing 0.1% formic acid), afforded Compound 136 (35 mg, 88%). $^1$H NMR (400 MHz, Acetone) δ 10.24 (s, 1H), 9.56 (s, 1H), 8.74-8.68 (m, 3H), 8.62 (d, J=2.6 Hz, 1H), 8.57 (s, 1H), 8.44 (s, 1H), 8.41 (dd, J=4.7, 1.3 Hz, 1H), 7.79 (ddd, J=8.4, 2.5, 1.5 Hz, 1H), 7.45 (dd, J=8.2, 4.7 Hz, 1H), 7.07 (d, J=4.4 Hz, 1H), 4.36 (dt, J=13.9, 4.4 Hz, 2H), 4.21 (q, J=7.1 Hz, 2H), 3.34-3.26 (m, 4H), 2.16 (s, 2H), 1.51-1.43 (m, 2H), 1.29 (dd, J=9.4, 4.8 Hz, 3H), 1.25 (s, 3H), 1.17 (t, J=7.2 Hz, 3H), [M+H]$^+$ m/z=548.29.

The following compounds were similarly prepared with reference to the general method(s) and/or examples previously described.

TABLE 1

Compounds and characterisation data

| No | Name | Observed LCMS [M + H]$^+$ | $^1$H NMR |
|---|---|---|---|
| 17 | 6-(3-ethylureido)-N-phenyl-4-(phenylamino)nicotinamide | 376.1 | (300 MHz, DMSO-d$_6$); δ 10.30 (1H, s), 9.93 (1H, s), 9.14 (1H, s), 8.58 (1H, s), 7.98 (1H, br t, J 5.1), 7.71 (2H, d, J 8.2), 7.45-7.25 (7H, m), 7.19-7.08 (2H, m), 3.16 (2H, h, J 6.1), 1.07 (3H, t, J 7.2) |
| 18 | 6-(3-ethylureido)-4-(phenylamino)-N-m-tolylnicotinamide | 390.1 | (300 MHz, DMSO-d$_6$); δ 10.23 (1H, s), 9.94 (1H, s), 9.13 (1H, s), 8.57 (1H, s), 7.98 (1H, br t, J 5.1), 7.58 (1H, s), 7.48 (1H, d, J 8.7), 7.45-7.37 (2H, m), 7.31-7.20 (4H, m), 7.16 (1H, t, J 7.2), 6.93 (1H, d, J 7.2), 3.15 (2H, dq, J 7.2 and 6.1), 2.31 (3H, s), 1.07 (3H, t, J 7.2) |
| 19 | 6-(3-ethylureido)-N-(pyridin-3-yl)-4-(pyridin-3-ylamino)nicotinamide | 378.2 | (300 MHz, DMSO-d$_6$); δ 10.51 (1H, s), 9.84 (1H, s), 9.19 (1H, s), 8.88 (1H, d, J 2.0), 8.63 (1H, s), 8.55 (1H, d, J 2.6), 8.37 (1H, d, J 4.6), 8.33 (1H, d, J 4.6), 8.13 (1H, d, J 8.7), 7.89 (1H, br), 7.74 (1H, d, J 8.7), 7.47-7.38 (2H, m), 7.25 (1H, s), 3.21-3.10 (2H, m), 1.07 (3H, t, J 7.2) |
| 20 | 6-(3-ethylureido)-4-(phenylamino)-N-(pyridin-3-yl)nicotinamide | 377.2 | (300 MHz, DMSO-d$_6$); δ 10.48 (1H, s), 9.88 (1H, s), 9.17 (1H, s), 8.87 (1H, d, J 2.0), 8.62 (1H, s), 8.32 (1H, dd, J 4.6 and 1.0), 8.13 (1H, d, J 8.2), 7.92 (1H, br), 7.46-7.37 (3H, m), 7.33-7.26 (3H, m), 7.17 (1H, t, J 7.7), 3.15 (2H, dq, J 7.2 and 6.1), 1.07 (3H, t, J 7.2) |
| 21 | methyl 4-(6-(3-ethylureido)-4-(phenylamino)nicotinamido)picolinate | 435.2 | |

TABLE 1-continued

Compounds and characterisation data

| No | Name | Observed LCMS [M + H]+ | 1H NMR |
|---|---|---|---|
| 22 | ethyl 6-(3-ethylureido)-4-(pyridin-3-ylmethylamino)nicotinate | 344.1. | (300 MHz, DMSO-$d_6$); δ 9.14 (1H, br s), 8.59 (1H, d, J 1.5), 8.51-8.41 (3H, m), 7.99 (1H, br), 7.75 (1H, d, J 8.2), 7.38 (1H, dd, J 7.2 and 4.6), 6.70 (1H, s), 4.45 (2H, d, J 5.6), 4.26 (2H, q, J 7.2), 3.14 (2H, dq, J 7.2 and 6.1), 1.30 (3H, q, J 7.2), 1.05 (3H, q, J 7.2). |
| 23 | 6-(3-ethylureido)-N-(6-morpholinopyridin-3-yl)-4-(phenylamino)nicotinamide | 462.1 | (300 MHz, DMSO-$d_6$); δ 10.20 (1H, s), 10.03 (1H, s), 9.13 (1H, s), 8.59 (1H, s), 8.41 (1H, d, J 2.6), 7.95 (1H, br), 7.88 (1H, dd, J 8.7 and 2.6), 7.41 (2H, t, J 8.2), 7.31-7.24 (3H, m), 7.16 (1H, t, J 7.2), 6.87 (1H, d, J 9.2), 3.71 (4H, d, J 4.6), 3.40 (4H, t, J 5.1), 3.15 (2H, dq, J 7.2 and 5.6), 1.07 (3H, t, J 7.2) |
| 24 | N-(6-acetamidopyridin-3-yl)-6-(3-ethylureido)-4-(phenylamino)nicotinamide | 434.2 | (300 MHz, DMSO-$d_6$); δ 10.51 (1H, br s), 10.41 (1H, br s), 9.93 (1H, br s), 9.15 (1H, br s), 8.65 (1H, d, J 2.0), 8.61 (1H, s), 8.08 (1H, d, J 8.7), 8.03 (1H, dd, J 8.7 and 2.0), 7.92 (1H, br), 7.41 (2H, t, J 7.2), 7.32-7.26 (3H, m), 7.16 (1H, t, J 7.2), 3.15 (2H, dq, J 7.2 and 5.6), 2.08 (3H, s), 1.06 (3H, t, J 7.2) |
| 25 | 6-(3-ethylureido)-N-phenyl-4-(pyridin-3-ylmethylamino)nicotinamide | 391.2 | (300 MHz, DMSO-$d_6$); δ 10.14 (1H, br s), 9.12 (1H, br s), 8.61 (1H, d, J 1.5), 8.53-8.46 (2H, m), 8.44 (1H, s), 8.31 (1H, br), 7.76 (1H, br d, J 7.7), 7.70 (2H, d, J 7.7), 7.38 (1H, dd, J 8.2 and 5.1), 7.33 (2H, t, J 7.7), 7.09 (1H, t, J 7.2), 6.59 (1H, s), 4.41 (2H, d, J 6.1), 3.16 (2H, dq, J 7.2 and 5.3), 1.07 (3H, t, J 7.2) |
| 26 | 6-(3-ethylureido)-N-(pyridin-3-yl)-4-(pyridin-3-ylmethylamino)nicotinamide | 392.2 | (300 Hz, DMSO-$d_6$); δ 10.32 (1H, s), 9.14 (1H, br s), 8.86 (1H, d, J 2.0), 8.61 (1H, d, J 1.5), 8.54-8.46 (3H, m), 8.30 (1H, dd, J 4.6 and 1.0), 8.23 (1H, br), 8.10 (1H, ddd, J 8.7, 2.5 and 1.5), 7.77 (1H, dt, J 7.7 and 2.0), 7.41-7.35 (2H, m), 6.62 (1H, s), 4.42 (2H, d, J 5.6), 3.16 (2H, dq, J 7.2 and 5.6), 1.07 (3H, t, J 7.2) |
| 27 | N-(6-(1H-1,2,4-triazol-1-yl)pyridin-3-yl)-6-(3-ethylureido)-4-(phenylamino)nicotinamide | 444.2 | (300 MHz, DMSO-$d_6$); δ 10.69 (1H, s), 9.86 (1H, s), 9.35 (1H, s), 9.18 (1H, s), 8.84 (1H, d, J 2.6), 8.65 (1H, s), 8.42 (1H, dd, J 2.6 and 8.7), 8.30 (1H, s), 7.94-7.86 (2H, m), 7.42 (2H, t, J 7.7), 7.34-7.27 (3H, m), 7.18 (1H, t, J 7.7), 3.20-3.10 (2H, m), 1.07 (3H, t, J 7.2) |
| 28 | 6-(3-ethylureido)-4-(phenylamino)-N-(pyridin-3-ylmethyl)nicotinamide | 391.1 | (300 MHz, DMSO-$d_6$); δ 10.36 (1H, s), 9.19 (1H, t, J 5.6), 9.10 (1H, s), 8.57 (1H, d, J 2.0), 8.51 (1H, s), 8.48 (1H, dd, J 4.6 and 1.0), 7.91 (1H, br t), 7.76 (1H, dt, J 8.2 and 2.0), 7.44-7.35 (3H, m), 7.28-7.22 (3H, m), 7.14 (1H, t, J 7.7), 4.48 (2H, d, J 6.1), 3.13 (2H, dq, J 7.2 and 6.1), 1.05 (3H, t, J 7.2) |
| 29 | 2-(3-ethylureido)-N-phenyl-4-(pyridin-3-ylamino)pyrimidine-5-carboxamide | 378.19 | (400 MHz, DMSO-$d_6$): δ10.81 (br s, 1H), 10.36 (br s, 1H), 9.95 (br s, 1H), 8.88 (s, 1H), 8.85 (br s, 1H), 8.79 (d, J = 2.40 Hz, 1H), 8.33-8.38 (m, 2H), 7.71 (d, J = 8.0 Hz, 2H), 7.36-7.41 (m, 3H), 7.14 (t, J = 7.20 Hz, 1H), 3.14-3.17 (m, 2H) and 1.02 (t, J = 7.20 Hz, 3H). |
| 30 | 6-(3-ethylureido)-N,N-dimethyl-4-(phenylamino)nicotinamide | 328.21 | (400 MHz, DMSO-$d_6$); δ 8.94 (br s, 1H), 8.31 (br s, 1H), 8.06 (m, 1H), 7.90 (s, 1H), 7.33-7.36 (m, 2H), 7.17 (d, J = 8.0 Hz, 2H), 7.13 (s, 1H), 7.08 (t, J = 7.20 Hz, 1H), 3.13 (m, 2H), 2.94 (s, 6H) and 1.05 (t, J = 7.20 Hz, 3H) |
| 31 | 6-(3-ethylureido)-N-(2-methoxyphenyl)-4-(phenylamino)nicotinamide | 404.14 [M − H]− | (400 MHz, DMSO-$d_6$); δ 10.09 (br s, 1H), 9.64 (br s, 1H), 9.10 (br s, 1H), 8.60 (s, 1H), 7.93 (m, 1H), 7.60 (d, J = 8.0 Hz, 1H), 7.37-7.45 (m, 2H), 7.14-7.29 (m, 6H), 7.10 (m, 1H), 3.81 (s, 3H), 3.13 (m, 2H) and 1.06 (t, J = 7.20 Hz, 3H) |
| 32 | 6-(3-ethylureido)-N-(3-methoxyphenyl)-4-(phenylamino)nicotinamide | 406.24 | (400 MHz, DMSO-$d_6$); δ 10.24 (br s, 1H), 9.88 (br s, 1H), 9.11 (br s, 1H), 8.56 (s, 1H), 7.95 (m, 1H), 7.38-7.42 (m, 3H), 7.27-7.31 (m, 5H), 7.15 (t, J = 7.20 Hz, 1H), 6.70 (m, 1H), 3.75 (s, 3H), 3.14 (m, 2H) and 1.06 (t, J = 7.20 Hz, 3H) |
| 33 | 6-(3-ethylureido)-N-(4-methoxyphenyl)-4-(phenylamino)nicotinamide | 406.15 | (400 MHz, TFA-d); δ 8.55 (s, 1H), 7.44 (m, 2H), 7.37 (m, 1H), 7.34 (m, 2H), 7.19 (d, J = 8.0 Hz, 2H), 7.06 (d, J = 8.40 Hz, 2H), 6.28 (s, 1H), 3.93 (s, 3H), 3.28 (m, 2H) and 1.15 (t, J = 7.20 Hz, 3H) |
| 34 | N-(4-chlorophenyl)-6-(3-ethylureido)-4-(phenylamino)nicotinamide | 408.13 [M − H]− | (400 MHz, DMSO-$d_6$); δ 10.39 (br s, 1H), 9.86 (br s, 1H), 9.13 (s, 1H), 8.57 (s, 1H), 7.93 (m, 1H), 7.75 (d, J = 8.80 Hz, 2H), 7.37-7.42 (m, 4H), 7.28 (m, 3H), 7.15 (t J = 7.20 Hz, 1H), 3.14 (m, 2H) and 1.06 (t, J = 7.20 Hz, 3H) |

TABLE 1-continued

Compounds and characterisation data

| No | Name | Observed LCMS [M + H]+ | 1H NMR |
|---|---|---|---|
| 35 | 2-(3-ethylureido)-N-(pyridin-3-yl)-4-(pyridin-3-ylamino)pyrimidine-5-carboxamide | 377.13 [M − H]− | (400 MHz, DMSO-d$_6$): δ 10.71 (br s, 1H), 10.54 (br s, 1H) 9.96 (s, 1H), 8.87-8.90 (m, 2H), 8.80 (m, 2H), 8.35 (m, 3H), 8.10 (m, 1H), 7.41-7.44 (m, 2H), 3.14 (m, 2H) and 1.06 (t, J = 7.20 Hz, 3H). |
| 36 | 6-(3-ethylureido)-N-isopropyl-4-(phenylamino)nicotinamide | 340.17 [M − H]− | (400 MHz, DMSO-d$_6$): δ 10.39 (br s, 1H), 9.06 (br s, 1H), 8.43 (s, 1H), 8.32 (d, J = 7.60 Hz, 1H), 7.99 (br, s, 1H), 7.37-7.40 (m, 2H), 7.23 (m, 3H), 7.12 (t, J = 7.20 Hz, 1H), 4.07 (m, 1H), 3.13 (m, 2H), 1.15 (d, J = 6.40 Hz, 6H) and 1.05 (t, J = 7.20 Hz, 3H) |
| 37 | N-cyclopentyl-6-(3-ethylureido)-4-(phenylamino)nicotinamide | 366.18 [M − H]− | (400 MHz, TFA-d): δ 8.27 (s, 1H), 7.34-7.45 (m, 3H), 7.15 (m, 2H), 6.22 (s, 1H), 4.30 (m, 1H), 3.25 (m, 2H), 2.08 (m, 2H), 1.75 (m, 2H), 1.57-1.68 (m, 4H) and 1.13 (t, J = 7.20 Hz, 3H) |
| 38 | N-cyclopropyl-6-(3-ethylureido)-4-(phenylamino)nicotinamide | 340.12 | (400 MHz, DMSO-d$_6$): δ 10.41 (br s, 1H), 9.05 (br s, 1H), 8.51 (m, 1H), 8.36 (s, 1H), 7.94 (br s, 1H), 7.37-7.41 (m, 2H), 7.22-7.24 (m, 3H), 7.13 (t, J = 7.20 Hz, 1H), 3.12 (m, 2H), 2.82 (m, 1H), 1.04 (t, J = 7.20 Hz, 3H), 0.68 (m, 2H) and 0.57 (m, 2H) |
| 39 | 6-(3-ethylureido)-N-methyl-4-(phenylamino)nicotinamide | 314.08 | (400 MHz, DMSO-d$_6$): δ 10.43 (br s, 1H), 9.02 (br s, 1H), 8.52 (m, 1H), 8.39 (s, 1H), 7.92 (m, 1H), 7.37-7.41 (m, 2H), 7.24 (m, 3H), 7.13 (t, J = 7.20 Hz, 1H), 3.14 (m, 2H), 2.67 (d, J = 4.40 Hz, 3H) and 1.05 (t, J = 7.20 Hz, 3H) |
| 40 | 6-(3-ethylureido)-N-(2-methoxyethyl)-4-(phenylamino)nicotinamide | 358.22 | (400 MHz, DMSO-d$_6$): δ 10.38 (br s, 1H), 9.04 (br s, 1H), 8.61 (br s, 1H), 8.42 (br s, 1H), 7.91 (s, 1H), 7.39 (s, 2H), 7.24 (s, 3H), 7.13 (s, 1H), 3.43 (m, 4H), 3.23 (s, 3H), 3.09 (m, 2H) and 1.02 (s, 3H) |
| 41 | 1-ethyl-3-(5-(morpholine-4-carbonyl)-4-(phenylamino)pyridin-2-yl)urea | 370.22 | (400 MHz, DMSO-d$_6$): δ 8.96 (s, 1H), 8.32 (br s, 1H), 8.04 (br s, 1H), 7.89 (s, 1H), 7.33-7.36 (m, 2H), 7.20 (m, 2H), 7.06-7.12 (m, 2H), 3.57 (br s, 4H), 3.45 (br s, 4H), 3.13 (m, 2H) and 1.04 (t, J = 7.20 Hz, 3H) |
| 42 | 6-(3-ethylureido)-4-(phenylamino)-N-(pyridin-4-yl)nicotinamide | 377.18 | (400 MHz, DMSO-d$_6$): δ 10.58 (br s, 1H), 9.77 (br s, 1H), 9.16 (br s, 1H), 8.60 (s, 1H), 8.47 (d, J = 4.40 Hz, 2H), 7.88 (br s, 1H), 7.72 (d, J = 4.40 Hz, 2H), 7.41 (m, 2H), 7.29 (m, 3H), 7.17 (m, 1H), 3.15 (m, 2H) and 1.05 (t, J = 7.20 Hz, 3H) |
| 43 | 6-(3-ethylureido)-N-phenethyl-4-(phenylamino)nicotinamide | 404.22 | (400 MHz, DMSO-d$_6$): δ 10.35 (br s, 1H), 9.02 (br s, 1H), 8.64 (t, J = 5.20 Hz, 1H), 8.37 (s, 1H), 7.92 (br s, 1H), 7.37-7.41 (m, 2H), 7.31-7.37 (m, 9H), 3.48 (q, J = 6.80 Hz, 2H), 3.13 (m, 2H), 2.86 (m, 2H) and 1.05 (t, J = 7.20 Hz, 3H) |
| 44 | N-benzyl-6-(3-ethylureido)-4-(phenylamino)nicotinamide | 390.21 | (400 MHz, DMSO-d$_6$): δ 10.40 (br s, 1H), 9.12 (t, J = 6.0 Hz, 1H), 9.05 (br s, 1H), 8.51 (s, 1H), 7.91 (br s, 1H), 7.37-7.41 (m, 2H), 7.34 (m, 4H), 7.22-7.26 (m, 4H), 7.13 (m, 1H), 4.46 (d, J = 6.0 Hz, 2H), 3.13 (m, 2H) and 1.05 (t, J = 7.20 Hz, 3H) |
| 45 | N-cyclohexyl-6-(3-ethylureido)-4-(phenylamino)nicotinamide | 382.26 | (400 MHz, DMSO-d$_6$): δ 10.37 (br s, 1H), 9.06 (br s, 1H), 8.42 (br s, 1H), 8.31 (d, J = 7.60 Hz, 1H), 8.0 (br s, 1H), 7.38 (t, J = 8.0 Hz, 2H), 7.22 (m, 3H), 7.12 (t, J = 7.60 Hz, 1H), 3.74 (m, 1H), 3.13 (m, 2H), 1.81 (br s, 2H), 1.74 (br s, 2H), 1.59-1.61 (m, 1H), 1.29-1.32 (m, 4H), 1.13 (m, 1H) and 1.05 (t, J = 7.20 Hz, 3H) |
| 46 | 6-(3-ethylureido)-4-(phenylamino)-N-p-tolylnicotinamide | 390.25 | (400 MHz, DMSO-d$_6$): δ 10.21 (br s, 1H), 9.96 (br s, 1H), 9.12 (s, 1H), 8.56 (s, 1H), 7.97 (m, 1H), 7.59 (d, J = 8.40 Hz, 2H), 7.40 (m, 2H), 7.27 (m, 3H), 7.16 (m, 3H), 3.14 (m, 2H), 2.27 (s, 3H) and 1.06 (t, J = 7.20 Hz, 3H) |
| 47 | 6-(3-ethylureido)-4-(phenylamino)-N-(4-(trifluoromethyl)phenyl)nicotinamide | 444.19 | (400 MHz, DMSO-d$_6$): δ 10.58 (br s, 1H), 9.81 (br s, 1H), 9.15 (br s, 1H), 8.60 (s, 1H), 7.93 (m, 3H), 7.71 (d, J = 8.40 Hz, 2H), 7.41 (m, 2H), 7.29 (m, 3H), 7.16 (t, J = 7.20 Hz, 1H), 3.14 (m, 2H) and 1.06 (t, J = 7.20 Hz, 3H) |
| 48 | 6-(3-ethylureido)-4-(phenylamino)-N-(3-(trifluoromethyl)phenyl)nicotinamide | 444.19 | (400 MHz, DMSO-d$_6$): δ 10.56 (br s, 1H), 9.80 (br s, 1H), 9.14 (br s, 1H), 8.60 (s, 1H), 8.19 (s, 1H), 7.94 (m, 2H), 7.59 (m, 1H), 7.29-7.47 (m, 6H), 7.17 (m, 1H), 3.14 (m, 2H) and 1.06 (t, J = 6.80 Hz, 3H) |
| 49 | 6-(3-ethylureido)-4-(phenylamino)-N-(pyridin-2-yl)nicotinamide | 377.2 | (400 MHz, DMSO-d$_6$): δ 10.79 (br s, 1H), 9.86 (br s, 1H), 9.09 (br s, 1H), 8.61 (s, 1H), 8.39 (m, 1H), 8.05 (s, 1H), 7.82 (m, 2H), 7.48 (m, 2H), 7.28 (m, 3H), 7.16 (m, 2H), 3.13 (m, 2H) and 1.06 (m, 3H) |

TABLE 1-continued

Compounds and characterisation data

| No | Name | Observed LCMS [M + H]+ | $^1$H NMR |
|----|------|------------------------|-----------|
| 50 | N-(3,5-dimethylisoxazol-4-yl)-6-(3-ethylureido)-4-(phenylamino)nicotinamide | 395.23 | (400 MHz, DMSO-$d_6$): δ 10.11 (br s, 1H), 9.86 (br s, 1H), 9.17 (br s, 1H), 8.63 (s, 1H), 7.81 (m, 1H), 7.41 (m, 2H), 7.25 (m, 2H), 7.19 (m, 1H), 3.14 (m, 2H), 2.31 (s, 3H), 2.14 (s, 3H) and 1.05 (t, J = 7.20 Hz, 3H) |
| 51 | 6-(3-ethylureido)-4-(phenylamino)-N-(pyridin-4-ylmethyl)nicotinamide | 391.25 | (400 MHz, DMSO-$d_6$): δ 10.33 (s, 1H), 9.21 (t, J = 5.60 Hz, 1H), 9.08 (br s, 1H), 8.56 (s, 1H), 8.51 (d, J = 6.0 Hz, 2H), 7.89 (m, 1H), 7.38 (m, 2H), 7.32 (d, J = 5.60 Hz,, 2H), 7.27 (s, 1H), 7.24 (d, J = 7.60 Hz, 2H), 7.13 (t, J = 7.60 Hz, 1H), 4.48 (d, J = 5.60 Hz, 2H), 3.13 (m, 2H) and 1.03 (t, J = 7.20 Hz, 3H) |
| 52 | 6-(3-ethylureido)-4-(phenylamino)-N-(pyridin-2-ylmethyl)nicotinamide | 391.26 | (400 MHz, DMSO-$d_6$): δ 10.36 (br s, 1H), 9.19 (br s, 1H), 9.06 (br s, 1H), 8.55 (s, 1H), 8.51 (m, 1H), 7.90 (m, 1H), 7.76 (m, 1H), 7.37 (m, 3H), 7.24 (m, 4H), 7.13 (t, J = 7.20 Hz, 1H), 4.54 (m, 2H), 3.13 (m, 2H) and 1.05 (t, J = 7.20 Hz, 3H) |
| 53 | 1-ethyl-3-(5-(4-methylpiperazine-1-carbonyl)-4-(phenylamino)pyridin-2-yl)urea | 383.26 | (400 MHz, DMSO-$d_6$): δ 8.97 (br s, 1H), 8.28 (br s, 1H), 8.07 (br s, 1H), 7.86 (s, 1H), 7.32-7.36 (m, 2H), 7.19 (m, 2H), 7.06-7.10 (m, 2H), 3.45 (m, 4H), 3.12 (m, 2H), 2.30 (m, 4H), 2.16 (s, 3H) and 1.04 (t, J = 7.20 Hz, 3H) |
| 54 | 1-(5-(4-acetylpiperazine-1-carbonyl)-4-(phenylamino)pyridin-2-yl)-3-ethylurea | 411.28 | (400 MHz, DMSO-$d_6$): δ 8.97 (br s, 1H), 8.32 (br s, 1H), 8.04 (m, 1H), 7.90 (s, 1H), 7.35 (m, 2H), 7.18 (m, 2H), 7.12 (m, 2H), 3.46 (br s, 8H), 3.13 (m, 2H), 1.99 (s, 3H) and 1.05 (t, J = 7.20 Hz, 3H) |
| 55 | 6-(3-ethylureido)-N-(4-fluorophenyl)-4-(phenylamino)nicotinamide | 394.24 | (400 MHz, DMSO-$d_6$): δ 10.34 (br s, 1H), 9.90 (br s, 1H), 9.13 (br s, 1H), 8.56 (s, 1H), 7.95 (m, 1H), 7.70 (m, 2H), 7.40 (m, 2H), 7.13-7.27 (m, 6H), 3.14 (m, 2H) and 1.06 (t, J = 7.20 Hz, 3H |
| 56 | 6-(3-ethylureido)-N-(3-fluorophenyl)-4-(phenylamino)nicotinamide | 394.21 | (400 MHz, DMSO-$d_6$): δ 10.45 (br s, 1H), 9.81 (br s, 1H), 9.14 (br s, 1H), 8.57 (s, 1H), 7.93 (m, 1H), 7.66 (m, 1H), 7.51 (m, 1H), 7.35-7.49 (m, 3H), 7.27 (m, 3H), 7.16 (m, 1H), 6.93 (m, 1H), 3.14 (m, 2H) and 1.06 (t, J = 7.20 Hz, 3H) |
| 57 | 6-(3-ethylureido)-N-(2-fluorophenyl)-4-(phenylamino)nicotinamide | 394.23 | (400 MHz, DMSO-$d_6$): δ 10.19 (br s, 1H), 10.08 (br s, 1H), 9.13 (br s, 1H), 8.64 (s, 1H), 7.86 (m, 1H), 7.53 (t, J = 7.60 Hz, 1H), 7.40 (m, 2H), 7.17-7.31 (m, 6H), 7.15 (m, 1H), 3.14 (m, 2H) and 1.06 (t, J = 6.80 Hz, 3H) |
| 58 | 6-(3-ethylureido)-4-(phenylamino)-N-o-tolylnicotinamide | 390.21 | (400 MHz, DMSO-$d_6$): δ 10.15 (br s, 1H), 9.95 (s, 1H), 9.10 (br s, 1H), 8.65 (s, 1H), 7.95 (m, 1H), 7.39 (t, J = 7.20 Hz, 2H), 7.17-7.32 (m, 8H), 3.15 (m, 2H), 2.24 (s, 3H) and 1.06 (t, J = 7.20 Hz, 3H) |
| 59 | 6-(3-ethylureido)-N-(1-methyl-1H-pyrazol-3-yl)-4-(phenylamino)nicotinamide | 380.24 | (400 MHz, DMSO-$d_6$): δ 10.82 (br s, 1H), 10.11 (br s, 1H), 9.06 (br s, 1H), 8.58 (s, 1H), 7.85 (m, 1H), 7.61 (d, J = 2.40 Hz, 1H), 7.40 (t, J = 8.0 Hz, 2H), 7.24-7.27 (m, 3H), 7.15 (m, 1H), 6.53 (d, J = 2.0 Hz, 1H), 3.78 (s, 3H), 3.12 (m, 2H) and 1.05 (t, J = 7.20 Hz, 3H). |
| 60 | 6-(3-ethylureido)-4-(phenylamino)-N-(pyrimidin-5-yl)nicotinamide | 378.2 | (400 MHz, DMSO-$d_6$): δ 10.62 (br s, 1H), 9.81 (br s, 1H), 9.16 (br s, 1H), 9.11 (s, 2H), 8.93 (br s, 1H), 8.64 (br s, 1H), 7.83 (br s, 1H), 7.39-7.43 (m, 2H), 7.27-7.31 (m, 3H), 7.17 (m, 1H), 3.14 (m, 2H) and 1.06 (t, J = 7.20 Hz, 3H). |
| 61 | 6-(3-ethylureido)-4-(phenylamino)nicotinamide | 300.15 | (400 MHz, DMSO-$d_6$): δ 10.68 (br s, 1H), 9.03 (br s, 1H), 8.47 (br s, 1H), 8.04 (br s, 1H), 7.96 (br s, 1H), 7.39 (m, 3H), 7.22-7.24 (m, 3H), 7.14 (m, 1H), 3.13 (m, 2H), 1.05 (t, J = 6.8 Hz, 3H). |
| 62 | 6-(3-ethylureido)-4-(phenylamino)-N-(thiazol-2-yl)nicotinamide | 383.18 | (400 MHz, DMSO-$d_6$): δ 12.52 (br s, 1H), 9.83 (br s, 1H), 9.12 (br s, 1H), 8.72 (br s, 1H), 7.74 (m, 1H), 7.55 (d, J = 3.60 Hz, 1H), 7.42 (t, J = 7.60 Hz, 2H), 7.30 (m, 4H), 7.18 (m, 1H), 3.13 (m, 2H) and 1.05 (t, J = 7.20 Hz, 3H). |
| 63 | 6-(3-ethylureido)-N-(6-methoxypyridin-3-yl)-4-(phenylamino)nicotinamide | 407.25 | (400 MHz, DMSO-$d_6$): δ 10.31 (s, 1H), 9.96 (s, 1H), 9.13 (s, 1H), 8.59 (s, 1H), 8.43 (s, 1H), 8.00 (d, J = 8.8 Hz, 1H), 7.92 (br s, 1H), 7.40 (t, J = 7.6 Hz, 2H), 7.25- 7.28 (m, 3H), 7.15 (t, J = 7.2 Hz, 1H), 6.85 (d, J = 8.8 Hz, 1H), 3.84 (s, 3H), 3.12-3.17 (m, 2H), 1.06 (t, J = 7.2 Hz, 3H). |
| 64 | 6-(3-ethylureido)-4-(phenylamino)-N-(pyridazin-4-yl)nicotinamide | 378.23 | (400 MHz, DMSO-$d_6$): δ 10.77 (s, 1H), 9.71 (s, 1H), 9.47 (s, 1H), 9.19 (s, 1H), 9.07 (d, J = 6.0 Hz, 1H), 8.63, (s, 1H), 8.03 (d, J = 3.2 Hz, 1H), 7.80 (br, s, 1H), 7.40-7.43 (m, 2H), 7.28-7.30 (m, 3H), 7.20 (m, 1H), 3.12-3.15 (m, 2H), 1.05 (t, J = 7.2 Hz, 3H). |

TABLE 1-continued

Compounds and characterisation data

| No | Name | Observed LCMS [M + H]+ | 1H NMR |
|---|---|---|---|
| 65 | 6-(3-ethylureido)-N-(1-methyl-1H-pyrazol-4-yl)-4-(phenylamino)nicotinamide | 380.24 | (400 MHz, DMSO-d6): δ 10.47(s, 1H), 10.23 (s, 1H), 9.12 (s, 1H), 8.55 (s, 1H), 8.00 (s, 1H), 7.92, (br, s, 1H), 7.55 (s, 1H), 7.38-7.42 (m, 2H), 7.25-7.28 (m, 3H), 7.13-7.17 (m, 1H), 3.81 (s, 3H), 3.12-3.15 (m, 2H), 1.05 (t, J = 6.8 Hz, 3H). |
| 66 | N-(3,5-difluorophenyl)-6-(3-ethylureido)-4-(phenylamino)nicotinamide | 412.22 | (400 MHz, DMSO-$d_6$): δ 10.59 (s, 1H), 9.74 (s, 1H), 9.16 (s, 1H), 8.57 (s, 1H), 7.89 (br, s, 1H), 7.49 (d, J = 8.0 Hz, 2H), 7.41 (t, J = 7.6 Hz, 2H), 7.27-7.29 (m, 3H), 7.16 (t, J = 7.6 Hz, 1H), 6.96 (t, J = 8.8 Hz, 1H), 3.12-3.17 (m, 2H), 1.05 (t, J = 7.2 Hz, 3H). |
| 67 | methyl 4-(6-(3-ethylureido)-4-(phenylamino)nicotinamido)benzoate | 434.22 | (400 MHz, DMSO-$d_6$): δ 10.58 (s, 1H), 9.81 (s, 1H), 9.16 (s, 1H), 8.59 (s, 1H), 7.96 (d, J = 8.4 Hz, 2H), 7.88 (d, J = 8.4 Hz, 3H), 7.40 (t, J = 7.6 Hz, 2H), 7.92 (m, 1H), 7.27-7.29 (m, 2H), 7.16 (t, J = 7.6 Hz, 1H), 3.83 (s, 3H), 3.12-3.16 (m, 2H), 1.06 (t, J = 7.6 Hz, 3H). |
| 68 | 4-(6-(3-ethylureido)-4-(phenylamino)nicotinamido)benzoic acid | 420.22 | (400 MHz, DMSO-$d_6$): δ 12.77 (br s, 1H), 10.54 (s, 1H), 9.82 (s, 1H), 9.15 (s, 1H), 8.59 (s, 1H), 7.92-7.94 (m, 3H), 7.85 (d, J = 8.4 Hz, 2H), 7.41 (t, J = 7.6 Hz, 2H), 7.27-7.29 (m, 3H), 7.16 (t, J = 6.8 Hz, 1H), 3.12-3.14 (m, 2H), 1.06 (t, J = 7.2 Hz, 3H). |
| 69 | N-(3,4-difluorophenyl)-6-(3-ethylureido)-4-(phenylamino)nicotinamide | 412.22 | (400 MHz, DMSO-$d_6$): δ 10.45 (s, 1H), 9.81 (s, 1H), 9.14 (s, 1H), 8.56 (s, 1H), 7.84-7.89 (m, 2H), 7.38-7.46 (m, 4H), 7.26-7.28 (m, 3H), 7.16 (t, J = 7.2 Hz, 1H), 3.12-3.15 (m, 2H), 1.05 (t, J = 7.2 Hz, 3H). |
| 70 | ethyl 2-(4-(6-(3-ethylureido)-4-(phenylamino)nicotinamido)phenyl)acetate | 462.26 | (400 MHz, DMSO-$d_6$): δ 10.28 (s, 1H), 9.94 (s, 1H), 9.12 (s, 1H), 8.57 (s, 1H), 7.97 (br, s, 1H), 7.65 (d, J = 8.0 Hz, 2H), 7.40 (t, J = 8.0 Hz, 2H), 7.22-7.27 (m, 5H), 7.15 (t, J = 7.2 Hz, 1H), 4.07 (q, J = 7.2 Hz, 2H), 3.62 (s, 2H), 3.11-3.16 (m, 2H), 1.18 (t, J = 7.2 Hz, 3H), 1.08 (t, J = 7.2 Hz, 3H). |
| 71 | 2-(4-(6-(3-ethylureido)-4-(phenylamino)nicotinamido)phenyl)acetic acid | 434.25 | (400 MHz, DMSO-$d_6$): δ 12.3 (br, s, 1H), 10.27 (s, 1H), 9.95 (s, 1H), 9.12 (s, 1H), 8.57 (s, 1H), 7.97 (br s, 1H), 7.63 (d, J = 8.0 Hz, 2H), 7.40 (t, J = 7.2 Hz, 2H), 7.22-7.27 (m, 5H), 7.15 (t, J = 7.2 Hz, 1H), 3.53 (s, 2H), 3.13-3.16 (m, 2H), 1.08 (t, J = 7.2 Hz, 3H). |
| 72 | N-(benzo[d]thiazol-2-yl)-6-(3-ethylureido)-4-(phenylamino)nicotinamide | 433.21 | (400 MHz, DMSO-$d_6$): δ 12.77 (br, s, 1H), 9.82 (br, s, 1H), 9.13 (s, 1H), 8.81 (s, 1H), 7.98 (d, J = 7.2 Hz, 1H), 7.65-7.71 (m, 2H), 7.47-7.52 (m, 3H), 7.42-7.44 (m, 4H), 7.20 (m, 1H), 3.11-3.16 (m, 2H), 1.06 (t, J = 7.2 Hz, 3H). |
| 73 | 6-(3-ethylureido)-N-(4-methylthiazol-2-yl)-4-(phenylamino)nicotinamide | 397.08 | (400 MHz, DMSO-$d_6$): δ 12.54 (br, s, 1H), 9.06 (s, 1H), 8.73 (s, 1H), 7.76-7.77 (m, 1H), 7.42 (m, 2H), 7.30-7.31 (m, 3H), 7.18 (m, 1H), 6.76 (m, 1H), 3.13 (m, 2H), 2.29 (s, 3H), 1.05 (m, 3H). |
| 74 | N-(3,5-dimethylphenyl)-6-(3-ethylureido)-4-(phenylamino)nicotinamide | 404.26 | (400 MHz, DMSO-$d_6$): δ 10.14 (s, 1H), 9.94 (s, 1H), 9.11 (s, 1H), 8.55 (s, 1H), 7.96 (br s, 1H), 7.27-7.52 (m, 7H), 7.15 (br, s, 1H), 6.75 (s, 1H), 3.14 (m, 2H), 2.26 (s, 6H), 1.06 (t, J = 7.2 Hz, 3H). |
| 75 | 6-(3-ethylureido)-4-(phenylamino)-N-(6-(trifluoromethyl)pyridin-3-yl)nicotinamide | 445.16 | (400 MHz, DMSO-$d_6$): δ 10.78 (s, 1H), 9.78 (br s, 1H), 9.17 (s, 1H), 9.03 (s, 1H), 8.64 (s, 1H), 8.42 (d, J = 7.6 Hz, 1H), 7.92 (d, J = 8.8 Hz, 1H), 7.85 (br s, 1H), 7.41 (t, J = 7.6 Hz, 2H), 7.27-7.29 (m, 3H), 7.17 (t, J = 7.6 Hz, 1H), 3.12-3.15 (m, 2H), 1.05 (t, J = 7.2 Hz, 3H). |
| 76 | 6-(3-ethylureido)-N-(imidazo[1,2-a]pyridin-6-yl)-4-(phenylamino)nicotinamide | 416.34 | (400 MHz, DMSO-$d_6$): δ 10.39 (s, 1H), 9.33 (s, 1H), 9.25 (s, 1H), 9.15 (s, 1H), 8.62 (s, 1H), 8.04 (s, 1H), 7.91 (br s, 1H), 7.57-7.60 (m, 2H), 7.41-7.43 (m, 3H), 7.27-7.32 (m, 3H), 7.16 (m, 1H), 3.15 (m, 2H), 1.06 (t, J = 6.8 Hz, 3H). |
| 77 | methyl 3-(4-(6-(3-ethylureido)-4-(phenylamino)nicotinamido)phenyl)propanoate | 462.21 | (400 MHz, DMSO-$d_6$): δ 10.23 (s, 1H), 9.46 (s, 1H), 9.12 (s, 1H), 8.56 (s, 1H), 7.97 (br s, 1H), 7.60 (d, J = 8.0 Hz, 2H), 7.40 (t, J = 7.6 Hz, 2H), 7.25-7.27 (m, 3H), 7.19 (d, J = 8.0 Hz, 2H), 7.15 (t, J = 7.2 Hz, 1H), 3.57 (s, 3H), 3.11-3.14 (m, 2H), 2.82 (t, J = 7.2 Hz, 2H), 2.62 (t, J = 7.2 Hz, 2H), 1.06 (t, J = 7.2 Hz, 3H). |

TABLE 1-continued

Compounds and characterisation data

| No | Name | Observed LCMS [M + H]+ | 1H NMR |
|---|---|---|---|
| 78 | 3-(4-(6-(3-ethylureido)-4-(phenylamino)nicotinamido)phenyl)propanoic acid | 448.22 | (400 MHz, DMSO-$d_6$): δ 12.12 (br s, 1H), 10.23 (s, 1H), 9.95 (s, 1H), 9.12 (s, 1H), 8.56 (s, 1H), 7.98 (br s, 1H), 7.60 (d, J = 8.0 Hz, 2H), 7.40 (t, J = 7.6 Hz, 2H), 7.25-7.27 (m 3H), 7.20 (d, J = 8.0 Hz, 2H), 7.15 (t, J = 7.2 Hz, 1H), 3.13-3.16 (m, 2H), 2.79 (t, J = 7.2 Hz, 2H), 2.53 (m, 2H), 1.07 (t, J = 7.2 Hz, 3H). |
| 79 | 6-(3-ethylureido)-N-(5-methoxypyridin-3-yl)-4-(phenylamino)nicotinamide | 407.24 | (400 MHz, DMSO-$d_6$): δ 10.45 (s, 1H), 9.83 (s, 1H), 9.15 (s, 1H), 8.60 (s, 1H), 8.51 (s, 1H), 8.06 (d, J = 2.4 Hz, 1H), 7.89 (br s, 1H), 7.80 (s, 1H), 7.41 (t, J = 7.6 Hz, 2H), 7.27-7.28 (m, 3H), 7.16 (t, J = 7.2 Hz, 1H), 3.83 (s, 3H), 3.10-3.15 (m, 2H), 1.06 (t, J = 7.2 Hz, 3H). |
| 80 | 6-(3-ethylureido)-N-(2-methyl-4-oxo-4H-chromen-7-yl)-4-(phenylamino)nicotinamide | 458.18 | (400 MHz, DMSO-$d_6$): δ 10.71 (s, 1H), 9.78 (s, 1H), 9.16 (s, 1H), 8.61 (s, 1H), 8.10 (s, 1H), 7.97 (d, J = 8.8 Hz, 1H), 7.89 (br, s, 1H), 7.71 (d, J = 8.8 Hz, 1H), 7.41 (t, J = 7.6 Hz, 2H), 7.28-7.30 (m, 3H), 7.17 (t, J = 8.0 Hz, 1H), 6.19 (s, 1H), 3.13-3.16 (m, 2H), 2.38 (s, 3H), 1.06 (t, J = 7.2 Hz, 3H). |
| 81 | 6-(3-ethylureido)-N-(6-methylpyridin-3-yl)-4-(phenylamino)nicotinamide | 391.2 | (400 MHz, DMSO-$d_6$): δ 10.38 (s, 1H), 9.91 (s, 1H), 9.14 (s, 1H), 8.72 (s, 1H), 8.60 (s, 1H), 7.98-8.00 (m, 1H), 7.91 (br, s, 1H), 7.40 (t, J = 7.6 Hz, 2H), 7.23-7.28 (m, 4H), 7.15 (t, J = 7.2 Hz, 1H), 3.12-3.15 (m, 2H), 2.43 (s, 3H), 1.06 (t, J = 7.2 Hz, 3H). |
| 82 | 6-(3-ethylureido)-N-(6-(4-fluorophenoxy)pyridin-3-yl)-4-(phenylamino)nicotinamide | 487.16 | (400 MHz, DMSO-$d_6$ -$D_2O$): δ 8.46 (s, 1H), 8.36 (s, 1H), 8.12 (d, J = 8.0 Hz, 1H), 7.48 (t, J = 7.6 Hz, 2H), 7.28-7.33 (m, 3H), 7.21-7.25 (m, 2H), 7.13-7.16 (m, 2H), 7.09 (d, J = 8.8 Hz, 1H), 6.69 (br, s, 1H), 3.10-3.15 (m, 2H), 1.05 (t, J = 7.2 Hz, 3H). |
| 83 | 6-(3-ethylureido)-N-methoxy-N-methyl-4-(phenylamino)nicotinamide | 344.28 | (400 MHz, DMSO-$d_6$): δ 9.00 (s, 1H), 8.58 (s, 1H), 8.11 (s, 1H), 8.01 (br s, 1H), 7.36 (t, J = 7.6 Hz, 2H), 7.19-7.21 (m, 3H), 7.09 (d, J = 7.2 Hz, 1H), 3.57 (s, 3H), 3.24 (s, 3H), 3.10-3.14 (m, 2H), 1.05 (t, J = 7.2 Hz, 3H). |
| 84 | 5-(6-(3-ethylureido)-4-(phenylamino)nicotinamido)nicotinic acid | 421.17 | (400 MHz, DMSO-$d_6$): δ 11.27 (br, s, 1H), 10.60 (br, s, 1H), 10.09 (s, 1H), 9.09 (s, 1H), 8.83 (s, 1H), 8.72 (s, 1H), 8.59 (s, 1H), 7.48 (t, J = 7.6 Hz, 3H), 7.36 (d, J = 8.0 Hz, 2H), 7.30 (t, J = 7.6 Hz, 1H), 6.79 (br s, 1H), 3.13-3.18 (m, 2H), 1.06 (t, J = 7.2 Hz, 3H). |
| 85 | 6-(3-ethylureido)-N-(5-fluoropyridin-3-yl)-4-(phenylamino)nicotinamide | 395.21 | (400 MHz, DMSO-$d_6$): δ 10.66 (s, 1H), 9.78 (s, 1H), 9.16 (s, 1H), 8.72 (s, 1H), 8.61 (s, 1H), 8.33 (d, J = 2.4 Hz, 1H), 8.14 (d, J = 11.2 Hz, 1H), 7.85 (br, s, 1H), 7.41 (t, J = 8.0 Hz, 2H), 7.28 (d, J = 8.0 Hz, 3H), 7.18 (t, J = 7.2 Hz, 1H), 3.12-3.17 (m, 2H), 1.06 (t, J = 7.2 Hz, 3H) |
| 86 | methyl 4-(6-(3-ethylureido)-4-(phenylamino)nicotinamido)-1-methyl-1H-pyrrole-2-carboxylate | 437.2 | (400 MHz, DMSO-$d_6$): δ 10.38 (s, 1H), 10.19 (s, 1H), 9.10 (s, 1H), 8.53 (s, 1H), 7.94 (br, s, 1H), 7.50 (s, 1H), 7.40 (t, J = 7.6 Hz, 2H), 7.25-7.27 (m, 3H), 7.15 (t, J = 7.2 Hz, 1H), 6.94 (s, 1H), 3.85 (s, 3H), 3.74 (s, 3H), 3.13-3.16 (m, 2H), 1.06 (t, J = 7.2 Hz, 3H). |
| 87 | 3-(2-(3-ethylureido)-5-(pyridin-3-ylcarbamoyl)pyridin-4-ylamino)benzoic acid | 421.14 | (400 MHz, DMSO-$d_6$): δ 10.49 (s, 1H), 9.87 (s, 1H), 9.21 (s, 1H), 8.87 (d, J = 2.5 Hz, 1H), 8.61 (s, 1H), 8.32 (dd, J = 4.7, 1.5 Hz, 1H), 8.12 (ddd, J = 8.4, 2.5, 1.5 Hz, 1H), 8.02 (br s, 1H), 7.80-7.78 (m, 1H), 7.75-7.69 (m, 1H), 7.54-7.51 (m, 2H), 7.39 (ddd, J = 8.5, 4.7, 0.6 Hz, 1H), 7.22 (s, 1H), 3.15 (qd, J = 7.2, 5.7 Hz, 2H), 1.07 (t, J = 7.2 Hz, 3H). |
| 88 | 6-(3-ethylureido)-N-(3-methyl-3H-imidazo[4,5-b]pyridin-6-yl)-4-(phenylamino)nicotinamide | 431.21 | (400 MHz, DMSO-$d_6$): δ 10.48 (s, 1H), 9.97 (s, 1H), 9.14 (s, 1H), 8.65 (s, 1H), 8.61 (s, 1H), 8.41 (s, 1H), 8.38 (s, 1H), 7.93 (br, s, 1H), 7.41 (t, J = 7.6 Hz, 2H), 7.27-7.29 (m, 3H), 7.15 (t, J = 7.2 Hz, 1H), 3.84 (s, 3H), 3.13-3.16 (m, 2H), 1.06 (t, J = 7.2 Hz, 3H). |
| 89 | methyl 5-(6-(3-ethylureido)-4-(phenylamino)nicotinamido)nicotinate | 433.18 [M − H]− | (400 MHz, DMSO-$d_6$): δ 10.66 (s, 1H), 9.81 (s, 1H), 9.15 (s, 1H), 9.09 (d, J = 2.0 Hz, 1H), 8.82 (s, 1H), 8.74 (s, 1H), 8.64 (s, 1H), 7.86 (br s, 1H), 7.43 (t, J = 8.0 Hz, 2H), 7.28-7.30 (m, 3H), 7.17 (t, J = 7.2 Hz, 1H), 3.90 (s, 3H), 3.11-3.17 (m, 2H), 1.06 (t, J = 7.2 Hz, 3H). |

TABLE 1-continued

Compounds and characterisation data

| No | Name | Observed LCMS [M + H]+ | $^1$H NMR |
|---|---|---|---|
| 90 | 6-(3-ethylureido)-N-(2-methylpyridin-4-yl)-4-(phenylamino)nicotinamide | 391.2 | (400 MHz, DMSO-$d_6$): δ 10.48 (s, 1H), 9.78 (s, 1H), 9.15 (s, 1H), 8.58 (s, 1H), 8.33 (br, s, 1H), 7.88 (br, s, 1H), 7.62 (s, 1H), 7.50 (br, s, 1H), 7.41 (t, J = 7.2 Hz, 2H), 7.27-7.29 (m, 3H), 7.18 (t, J = 7.6 Hz, 1H), 3.12-3.15 (m, 2H), 2.43 (s, 3H), 1.06 (t, J = 7.2 Hz, 3H). |
| 91 | 6-(3-ethylureido)-N-(5-methylpyridin-3-yl)-4-(phenylamino)nicotinamide | 391.24 | (400 MHz, DMSO-$d_6$): δ 10.40 (s, 1H), 9.88 (s, 1H), 9.14 (s, 1H), 8.65 (s, 1H), 8.60 (s, 1H), 8.16 (s, 1H), 7.98 (s, 1H), 7.90 (br, s, 1H), 7.41 (t, J = 7.6 Hz, 2H), 7.27-7.29 (m, 3H), 7.16 (t, J = 7.2 Hz, 1H), 3.11-3.16 (m, 2H), 2.31 (s, 3H), 1.08 (t, J = 7.2 Hz, 3H). |
| 92 | 6-(3-ethylureido)-4-(phenylamino)-N-(quinolin-3-yl)nicotinamide | 427.25 | (400 MHz, DMSO-$d_6$): δ 10.71 (s, 1H), 9.93 (s, 1H), 9.17 (s, 1H), 9.10 (d, J = 2.4 Hz, 1H), 8.78 (d, J = 2.4 Hz, 1H), 8.70 (s, 1H), 7.97 (t, J = 7.6 Hz, 2H), 7.90 (br, s, 1H), 7.65-7.69 (m, 1H), 7.59 (t, J = 7.6 Hz, 1H), 7.42 (t, J = 7.6 Hz, 2H), 7.31-7.32 (m, 3H), 7.15-7.29 (m, 1H), 3.12-3.18 (m, 2H), 1.07 (t, J = 7.2 Hz, 3H). |
| 93 | 6-(3-ethylureido)-N-(3-fluoro-5-methylphenyl)-4-(phenylamino)nicotinamide | 408.2 | (400 MHz, DMSO-$d_6$): δ 10.37 (s, 1H), 9.83 (s, 1H), 9.14 (s, 1H), 8.55 (s, 1H), 7.92 (br, s, 1H), 7.36-7.46 (m, 4H), 7.21-7.28 (m, 3H), 7.16 (t, J = 7.2 Hz, 1H), 6.78 (d, J = 8.6 Hz, 1H), 3.12-3.16 (m, 2H), 2.31 (s, 3H), 1.06 (t, J = 7.2 Hz, 3H). |
| 94 | 6-(3-ethylureido)-N-(1-methyl-1H-indol-4-yl)-4-(phenylamino)nicotinamide | 429.24 | (400 MHz, DMSO-$d_6$): δ 10.19 (s, 1H), 10.04 (s, 1H), 9.11 (s, 1H), 8.66 (s, 1H), 8.02 (br, s, 1H), 7.39 (t, J = 8.0 Hz, 2H), 7.34 (d, J = 7.2 Hz, 1H), 7.25-7.29 (m, 5H), 7.14 (t, J = 7.6 Hz, 2H), 6.58 (d, J = 2.8 Hz, 1H), 3.79 (s, 3H), 3.12-3.19 (m, 2H), 1.07 (t, J = 7.2 Hz, 3H) |
| 95 | 6-(3-ethylureido)-N-(6-(isopropylamino)pyridin-3-yl)-4-(phenylamino)nicotinamide | 434.26 | (400 MHz, DMSO-$d_6$): δ 10.08 (s, 1H), 10.03 (s, 1H), 9.10 (s, 1H), 8.55 (s, 1H), 8.17 (d, J = 6.0 Hz, 1H), 7.95 (br, s, 1H), 7.61 (dd, J = 8.8 and 2.0 Hz respectively, 1H), 7.39 (t, J = 7.6 Hz, 2H), 7.24-7.26 (m, 3H), 7.14 (t, J = 7.2 Hz, 1H), 6.43 (d, J = 8.8 Hz, 1H), 6.25 (d, J = 7.6 Hz, 1H), 3.94 (hept, J = 6.4 Hz, 1H), 3.12-3.16 (m, 2H), 1.13 (d, J = 6.4 Hz, 6H), 1.06 (t, J = 7.2 Hz, 3H). |
| 96 | methyl 4-(2-(3-ethylureido)-5-(pyridin-3-ylcarbamoyl)pyridin-4-ylamino)benzoate | 435.16 | (400 MHz, DMSO-$d_6$): δ 10.54 (s, 1H), 10.06 (s, 1H), 9.25 (s, 1H), 8.86 (d, J = 2.2 Hz, 1H), 8.64 (s, 1H), 8.32 (dd, J = 4.7, 1.4 Hz, 1H), 8.11 (ddd, J = 8.3, 2.5, 1.5 Hz, 1H), 7.95 (d, J = 8.8 Hz, 2H), 7.84 (br s, 1H), 7.55 (s, 1H), 7.42-7.38 (m, 1H), 7.39 (d, J = 8.7 Hz, 2H), 3.84 (s, 3H), 3.21-3.12 (m, 2H), 1.07 (t, J = 7.2 Hz, 3H). |
| 97 | methyl 3-(2-(3-ethylureido)-5-(pyridin-3-ylcarbamoyl)pyridin-4-ylamino)benzoate | 435.17 | (400 MHz, DMSO-$d_6$): δ 10.50 (s, 1H), 9.88 (s, 1H), 9.21 (s, 1H), 8.87 (d, J = 2.3 Hz, 1H), 8.61 (s, 1H), 8.32 (dd, J = 4.7, 1.5 Hz, 1H), 8.12 (ddd, J = 8.4, 2.5, 1.5 Hz, 1H), 8.02 (br s, 1H), 7.82-7.79 (m, 1H), 7.73 (dt, J = 6.6, 1.8 Hz, 1H), 7.60-7.52 (m, 2H), 7.39 (dd, J = 8.5, 4.5 Hz, 1H), 7.23 (s, 1H), 3.86 (s, 3H), 3.19-3.11 (m, 2H), 1.07 (t, J = 7.2 Hz, 3H). |
| 98 | N-(6-(dimethylamino)pyridin-3-yl)-6-(3-ethylureido)-4-(phenylamino)nicotinamide | 420.24 | (400 MHz, DMSO-$d_6$): δ 10.12 (s, 1H), 10.07 (s, 1H), 9.12 (s, 1H), 8.57 (s, 1H), 8.31 (s, 1H), 7.94 (br, s, 1H), 7.80 (d, J = 8.4 Hz, 1H), 7.40 (t, J = 7.6 Hz, 2H), 7.25-7.27 (m, 3H), 7.15 (t, J = 7.2 Hz, 1H), 6.66 (d, J = 9.2 Hz, 1H), 3.13-3.16 (m, 2H), 3.00 (s, 6H), 1.06 (t, J = 7.2 Hz, 3H). |
| 99 | 6-(3-ethylureido)-N-(1-methyl-6-oxo-1,6-dihydropyridin-3-yl)-4-(phenylamino)nicotinamide | 407.2 | (400 MHz, DMSO-$d_6$): δ 10.06 (s, 1H), 9.98 (s, 1H), 9.11 (s, 1H), 8.54 (s, 1H), 8.13 (s, 1H), 7.88 (br s, 1H), 7.57 (d, J = 7.6 Hz, 1H), 7.40 (br, s, 1H), 7.26-7.29 (m, 3H), 7.15 (br, s, 1H), 6.43 (d, J = 10.0 Hz, 1H), 3.44 (s, 3H), 3.14 (m, 2H), 1.05 (m, 3H). |
| 100 | 6-(3-ethylureido)-N-(6-(4-hydroxypiperidin-1-yl)pyridin-3-yl)-4-(phenylamino)nicotinamide | 476.31 | (400 MHz, DMSO-$d_6$): δ 10.14 (s, 1H), 10.04 (s, 1H), 9.11 (s, 1H), 8.57 (s, 1H), 8.34 (d, J = 2.4 Hz, 1H), 7.95 (br, s, 1H), 7.84 (dd, J = 9.2 & 2.8 Hz respectively, 1H), 7.40 (t, J = 7.6 Hz, 2H), 7.25-7.27 (m, 3H), 7.15 (t, J = 7.2 Hz, 1H), 6.86 (d, J = 9.2 Hz, 1H), 4.69 (d, J = 4.4 Hz, 1H), 3.97 (d, J = 13.2 Hz, 2H), 3.65-3.70 (m, 1H), 3.11-3.17 (m, 2H), 3.00-3.06 (m, 2H), 1.75-1.78 (m, 2H), 1.30-1.39 (m, 2H), 1.06 (t, J = 7.2 Hz, 3H). |

TABLE 1-continued

Compounds and characterisation data

| No | Name | Observed LCMS [M + H]$^+$ | $^1$H NMR |
|---|---|---|---|
| 101 | 6-(3-ethylureido)-N-(6-methoxyquinolin-3-yl)-4-(phenylamino)nicotinamide | 457.23 | (400 MHz, DMSO-d$_6$): δ 10.62 (s, 1H), 9.97 (s, 1H), 9.16 (s, 1H), 9.02 (s, 1H), 8.68 (d, J = 4.8 Hz, 2H), 7.86-7.89 (m, 2H), 7.37-7.43 (m, 3H), 7.24-7.32 (m, 4H), 7.16 (t, J = 6.4 Hz, 1H), 3.91 (s, 3H), 3.13-3.17 (m, 2H), 1.08 (t, J = 7.2 Hz, 3H). |
| 102 | methyl 2-(6-(3-ethylureido)-4-(phenylamino)nicotinamido)benzo[d]thiazole-6-carboxylate | 491.19 | (400 MHz, TFA-d): δ 8.87 (s, 1H), 8.73 (s, 1H), 8.40 (d, J = 6.4 Hz, 1H), 7.97 (d, J = 6.4 Hz, 1H), 7.41-7.47 (m, 3H), 7.20-7.22 (m, 2H), 6.29 (br, s, 1H), 4.04 (s, 3H), 3.26 (m, 2H), 1.13 (m, 3H). |
| 103 | 4-(6-(3-ethylureido)-4-(phenylamino)nicotinamido)-1-methyl-1H-pyrrole-2-carboxylic acid | 423.19 | (400 MHz, DMSO-d$_6$): δ 12.20 (br s, 1H), 10.35 (s, 1H), 10.22 (s, 1H), 9.11 (s, 1H), 8.53 (s, 1H), 7.96 (br s, 1H), 7.45 (s, 1H), 7.40 (t, J = 7.6 Hz, 2H), 7.25-7.27 (m, 3H), 7.14 (t, J = 7.2 Hz, 1H), 6.86 (s, 1H), 3.84 (s, 3H), 3.11-3.17 (m, 2H), 1.06 (t, J = 7.2 Hz, 3H). |
| 104 | N-(6-cyanopyridin-3-yl)-6-(3-ethylureido)-4-(phenylamino)nicotinamide | 402.19 | (400 MHz, DMSO-d$_6$): δ 10.82 (s, 1H), 9.72 (s, 1H), 9.18 (s, 1H), 9.03 (s, 1H), 8.63 (s, 1H), 8.37 (dd, J = 8.8 and 2.0 Hz respectively, 1H), 8.04 (d, J = 8.8 Hz, 1H), 7.82 (br s, 1H), 7.41 (t, J = 7.6 Hz, 2H), 7.27-7.30 (m, 3H), 7.17 (t, J = 7.2 Hz, 1H), 3.12-3.15 (m, 2H), 1.05 (t, J = 7.2 Hz, 3H). |
| 105 | 4-(2-chlorophenylamino)-6-(3-ethylureido)-N-(pyridin-3-yl)nicotinamide | 411.16 | (400 MHz, DMSO-d$_6$): δ 10.52 (s, 1H), 10.10 (s, 1H), 9.20 (s, 1H), 8.85 (s, 1H), 8.67 (s, 1H), 8.33 (m, 1H), 8.13 (d, J = 8.0 Hz, 1H), 7.80 (br, s, 1H), 7.60-7.55 (m, 2H), 7.42 (t, J = 6.4 Hz, 2H), 7.23-7.18 (m, 2H), 3.17 (m, 2H), 1.07 (t, J = 6.8 Hz, 3H). |
| 106 | 4-(4-chlorophenylamino)-6-(3-ethylureido)-N-(pyridin-3-yl)nicotinamide | 411.16 | (400 MHz, DMSO-d$_6$): δ 10.48 (s, 1H), 9.85 (s, 1H), 9.23 (s, 1H), 8.86 (s, 1H), 8.61 (s, 1H), 8.32 (d, J = 8.0 Hz, 1H), 8.12 (d, J = 8.4 Hz, 1H), 7.97 (br, s, 1H), 7.43 (t, J = 7.6 Hz, 3H), 7.29 (s, 1H), 7.19 (d, J = 7.6 Hz, 2H), 3.17 (m, 2H), 1.08 (t, J = 6.8 Hz, 3H). |
| 107 | 4-(3-chlorophenylamino)-6-(3-ethylureido)-N-(pyridin-3-yl)nicotinamide | 411.16 | (400 MHz, DMSO-d$_6$): δ 10.46 (s, 1H), 9.81 (s, 1H), 9.14 (s, 1H), 8.69 (s, 1H), 8.61 (s, 1H), 8.32 (d, J = 4.4 Hz, 1H), 8.12 (d, J = 8.4 Hz, 1H), 7.86 (br s, 1H), 7.46 (d, J = 8.8 Hz, 2H), 7.41-7.37 (m, 1H), 7.31 (d, J = 8.8 Hz, 2H), 7.26 (s, 1H), 3.18 (m, 2H), 1.08 (t, J = 7.2 Hz, 3H). |
| 108 | 6-(3-ethylureido)-4-(1-methyl-6-oxo-1,6-dihydropyridin-3-ylamino)-N-(pyridin-3-yl)nicotinamide | 408.2 | (400 MHz, DMSO-d$_6$): δ 10.40 (s, 1H), 9.23 (s, 1H), 9.07 (s, 1H), 8.87 (s, 1H), 8.58 (s, 1H), 8.31 (s, 1H), 8.11 (d, J = 7.2 Hz, 2H), 7.80 (s, 1H), 7.40 (s, 2H), 6.71 (s, 1H), 6.46 (d, J = 8.8 Hz, 1H), 3.42 (s, 3H), 3.14 (s, 2H), 1.05 (s, 3H). |
| 109 | 6-(3-ethylureido)-4-(2-methoxyphenylamino)-N-(pyridin-3-yl)nicotinamide | 407.22 | (400 MHz, DMSO-d$_6$): δ 10.45 (s, 1H), 9.85 (s, 1H), 9.15 (s, 1H), 8.85 (s, 1H), 8.61 (s, 1H), 8.31 (s, 1H), 8.12 (s, 1H), 7.96 (br s, 1H), 7.39 (s, 2H), 7.24 (s, 1H), 7.12 (s, 2H), 6.98 (s, 1H), 3.83 (s, 3H), 3.15 (m, 2H), 1.06 (s, 3H). |
| 110 | ethyl 2-(4-(2-(3-ethylureido)-5-(pyridin-3-ylcarbamoyl)pyridin-4-ylamino)phenyl)acetate | 463.24 | (400 MHz, DMSO-d$_6$): δ 10.45 (s, 1H), 9.85 (s, 1H), 9.14 (s, 1H), 8.86 (s, 1H), 8.61 (s, 1H), 8.32 (d, J = 4.8 Hz, 1H), 8.12 (d, J = 8.8 Hz, 1H), 7.90 (br s, 1H), 7.41-7.37 (m, 1H), 7.30 (t, J = 7.2 Hz, 3H), 7.24 (d, J = 8.4 Hz, 2H), 4.11-4.06 (m, 2H), 3.66 (s, 2H), 3.18-3.11 (m, 2H), 1.21 (t, J = 6.8 Hz, 3H), 1.08 (t, J = 7.2 Hz, 3H). |
| 111 | 6-(3-ethylureido)-4-(3-methoxyphenylamino)-N-(pyridin-3-yl)nicotinamide | 407.25 | (400 MHz, DMSO-d$_6$): δ 10.50 (s, 1H), 9.87 (s, 1H), 9.19 (s, 1H), 8.67 (s, 1H), 8.61 (s, 1H), 8.32 (d, J = 3.6 Hz, 1H), 8.12 (d, J = 8.4 Hz, 1H), 7.94 (br s, 1H), 7.41-7.39 (m, 1H), 7.38 (s, 1H), 7.31 (t, J = 8.0 Hz, 1H), 6.86 (t, J = 8.0 Hz, 2H), 6.76 (dd, J = 8.4 Hz, 1H), 3.78 (s, 3H), 3.18 (m, 2H), 1.08 (t, J = 7.6 Hz, 3H). |
| 112 | 1-(5-benzoyl-4-(phenylamino)pyridin-2-yl)-3-ethylurea | 361.13 | (400 MHz, CD$_3$CN): δ 10.42 (s, 1H), 8.56 (s, 1H), 8.27 (s, 1H), 7.70-7.65 (m, 3H), 7.65-7.59 (m, 1H), 7.57-7.51 (m, 2H), 7.49-7.43 (m, 2H), 7.36 (dd, J = 8.4, 0.9 Hz, 2H), 7.29-7.24 (m, 1H), 6.76 (s, 1H), 3.21 (qd, J = 7.2, 5.6 Hz, 2H), 1.10 (t, J = 7.2 Hz, 3H). |
| 113 | 6-(3-ethylureido)-4-(1-methyl-1H-pyrazol-4-ylamino)-N-(pyridin-3-yl)nicotinamide | 381.19 | (400 MHz, DMSO-d$_6$): δ 10.39 (s, 1H), 9.40 (s, 1H), 9.10 (s, 1H), 8.86 (s, 1H), 8.58 (s, 1H), 8.31 (s, 1H), 8.11 (d, J = 8.0 Hz, 2H), 7.78 (s, 1H), 7.46 (s, 1H), 7.40-7.37 (m, 1H), 6.94 (s, 1H), 3.84 (s, 3H), 3.19-3.12 (m, 2H), 1.09 (t, J = 7.2 Hz, 3H). |

TABLE 1-continued

Compounds and characterisation data

| No | Name | Observed LCMS [M + H]+ | $^1$H NMR |
|---|---|---|---|
| 114 | 2-(4-(2-(3-ethylureido)-5-(pyridin-3-ylcarbamoyl)pyridin-4-ylamino)phenyl)acetic acid | 435.22 | (400 MHz, DMSO-d$_6$): δ 10.47 (s, 1H), 9.85 (s, 1H), 9.14 (s, 1H), 8.86 (s, 1H), 8.62 (s, 1H), 8.32 (d, J = 5.2 Hz, 1H), 8.12 (d, J = 7.2 Hz, 1H), 7.93 (m, 1H), 7.40-7.37 (m, 1H), 7.28 (m, 3H), 7.22 (d, J = 8.0 Hz, 2H), 3.54 (s, 2H), 3.16 (m, 2H), 1.08 (t, J = 6.8 Hz, 3H). |
| 115 | 4-(3,5-dimethylisoxazol-4-ylamino)-6-(3-ethylureido)-N-(pyridin-3-yl)nicotinamide | 396.23 | (400 MHz, DMSO-d$_6$): δ 10.40 (s, 1H), 9.15 (s, 1H), 9.08 (s, 1H), 8.88 (s, 1H), 8.59 (s, 1H), 8.31 (d, J = 4.4 Hz, 1H), 8.12 (m, 1H), 7.92 (br s, 1H), 7.41-7.37 (m, 1H), 6.51 (s, 1H), 3.15 (m, 2H), 2.26 (s, 3H), 2.07 (s, 3H), 1.07 (t, J = 7.2 Hz, 3H). |
| 116 | 6-(3-ethylureido)-4-(1-methyl-1H-pyrazol-3-ylamino)-N-(pyridin-3-yl)nicotinamide | 381.19 | (400 MHz, DMSO-d$_6$): δ 10.45 (br s, 1H), 10.21 (br s, 1H), 9.28 (s, 1H), 8.86 (s, 1H), 8.63 (s, 1H), 8.32 (d, J = 4.4 Hz, 1H), 8.12 (d, J = 8.0 Hz, 2H), 7.69 (s, 1H), 7.60 (s, 1H), 7.41-7.38 (m, 1H), 6.13 (d, J = 2.0 Hz, 1H), 3.78 (s, 3H), 3.21-3.15 (m, 2H), 1.10 (t, J = 7.2 Hz, 3H). |
| 117 | 6-(3-ethylureido)-N-(4-(3-hydroxypropyl)phenyl)-4-(phenylamino)nicotinamide | 434.18 | (400 MHz, Acetone-d$_6$): δ 10.13 (s, 1H), 9.52 (s, 1H), 8.77 (s, 1H), 8.60 (s, 1H), 8.46 (s, 1H), 7.71 (dd, J = 8.6, 2.2 Hz, 2H), 7.42 (t, J = 7.9 Hz, 2H), 7.33 (d, J = 7.6 Hz, 2H), 7.23 (d, J = 8.5 Hz, 2H), 7.17 (t, J = 7.3 Hz, 1H), 7.00 (d, J = 5.2 Hz, 1H), 3.57 (t, J = 6.0 Hz, 2H), 3.50 (t, J = 5.4 Hz, 1H), 3.28 (qd, J = 7.2, 5.7 Hz, 2H), 2.73-2.65 (m, 2H), 1.82 (dq, J = 9.3, 6.4 Hz, 2H), 1.15 (t, J = 7.2 Hz, 3H). |
| 118 | N-(4-(3-amino-3-oxopropyl)phenyl)-6-(3-ethylureido)-4-(phenylamino)nicotinamide | 447.16 | (400 MHz, MeOD): δ 8.50 (s, 1H), 7.56 (d, J = 8.5 Hz, 2H), 7.40 (tt, J = 3.9, 1.9 Hz, 2H), 7.27 (dd, J = 8.5, 1.1 Hz, 2H), 7.23 (d, J = 8.6 Hz, 2H), 7.20-7.13 (m, 1H), 6.86 (s, 1H), 3.30-3.25 (m, 2H), 2.91 (t, J = 7.8 Hz, 2H), 2.51 (dd, J = 8.5, 7.1 Hz, 2H), 1.18 (t, J = 7.2 Hz, 3H). |
| 119 | N-(4-(3-(dimethylamino)-3-oxopropyl)phenyl)-6-(3-ethylureido)-4-(phenylamino)nicotinamide | 475.17 | (400 MHz, MeOD): δ 8.50 (s, 1H), 7.57 (d, J = 8.5 Hz, 2H), 7.41 (t, J = 7.9 Hz, 2H), 7.27 (dd, J = 8.5, 1.1 Hz, 2H), 7.24 (d, J = 8.6 Hz, 2H), 7.20-7.15 (m, 1H), 6.86 (s, 1H), 3.30-3.25 (m, 2H), 2.97 (s, 3H), 2.94-2.87 (m, 5H), 2.68 (t, J = 7.6 Hz, 2H), 1.18 (t, J = 7.2 Hz, 3H). |
| 120 | 6-(3-ethylureido)-N-(4-(3-(methylamino)-3-oxopropyl)phenyl)-4-(phenylamino)nicotinamide | 461.16 | (400 MHz, MeOD): δ 8.50 (s, 1H), 7.56 (d, J = 8.5 Hz, 2H), 7.45-7.37 (m, 2H), 7.28 (dd, J = 8.6, 1.1 Hz, 2H), 7.24-7.14 (m, 3H), 6.86 (s, 1H), 3.27 (d, J = 7.2 Hz, 2H), 2.90 (t, J = 7.6 Hz, 2H), 2.69 (d, J = 3.8 Hz, 3H), 2.47 (t, J = 7.7 Hz, 2H), 1.19 (t, J = 7.2 Hz, 3H). |
| 121 | 6-(3-ethylureido)-N-methyl-N-phenyl-4-(phenylamino)nicotinamide | 390.15 | (400 MHz, DMSO-d$_6$): δ 8.76 (s, 1H), 8.39 (s, 1H), 7.82 (s, 1H), 7.67 (s, 1H), 7.39-7.04 (m, 10H), 6.98 (s, 1H), 3.36 (s, 3H), 3.13-3.02 (m, 2H), 1.00 (t, J = 7.2 Hz, 3H). |
| 122 | 6-(3-ethylureido)-N-(4-(3-oxobutyl)phenyl)-4-(phenylamino)nicotinamide | 446.2 | (400 MHz, Acetone-d$_6$): δ 10.12 (s, 1H), 9.53 (s, 1H), 8.77 (s, 1H), 8.59 (s, 1H), 8.47 (s, 1H), 7.74-7.67 (m, 2H), 7.45-7.38 (m, 2H), 7.32 (d, J = 7.6 Hz, 2H), 7.26-7.14 (m, 3H), 7.01-6.98 (m, 1H), 3.28 (qd, J = 7.2, 5.6 Hz, 2H), 2.88-2.74 (m, 4H), 2.11 (s, 3H), 1.14 (t, J = 7.2 Hz, 3H). |
| 123 | 6-(3-ethylureido)-N-(4-(3-(methoxy(methyl)amino)-3-oxopropyl)phenyl)-4-(phenylamino)nicotinamide | 491.19 | (400 MHz, MeOD): δ 8.50 (s, 1H), 7.61-7.53 (m, 2H), 7.44-7.37 (m, 2H), 7.31-7.13 (m, 5H), 6.86 (s, 1H), 3.64 (s, 3H), 3.30-3.25 (m, 2H), 3.17 (s, 3H), 2.92 (t, J = 7.5 Hz, 2H), 2.82-2.70 (m, 2H), 1.18 (t, J = 7.2 Hz, 3H). |
| 124 | 4-(4-(dimethylcarbamoyl)phenylamino)-6-(3-ethylureido)-N-(pyridin-3-yl)nicotinamide | 448.14 | (400 MHz, MeOD): δ 8.87 (d, J = 2.3 Hz, 1H), 8.60 (s, 1H), 8.31 (dd, J = 4.8, 1.3 Hz, 1H), 8.23 (ddd, J = 8.4, 2.5, 1.5 Hz, 1H), 7.52-7.48 (m, 2H), 7.45 (dd, J = 8.1, 4.5 Hz, 1H), 7.40-7.35 (m, 2H), 7.06 (s, 1H), 3.33-3.29 (obscured by solvent, m, 2H), 3.09 (d, J = 11.8 Hz, 6H), 1.20 (t, J = 7.2 Hz, 3H). |
| 125 | 4-(4-carbamoylphenylamino)-6-(3-ethylureido)-N-(pyridin-3-yl)nicotinamide | 420.15 | (400 MHz, DMSO): δ 10.51 (s, 1H), 10.01 (s, 1H), 9.20 (s, 1H), 8.87 (d, J = 2.3 Hz, 1H), 8.64 (s, 1H), 8.32 (dd, J = 4.6, 1.3 Hz, 1H), 8.12 (ddd, J = 8.4, 2.5, 1.5 Hz, 1H), 7.91 (d, J = 8.7 Hz, 2H), 7.49 (s, 1H), 7.40 (dd, J = 8.2, 4.7 Hz, 1H), 7.33 (d, J = 8.7 Hz, 2H), 3.15 (q, J = 7.2 Hz, 2H), 1.07 (t, J = 7.2 Hz, 3H). |

TABLE 1-continued

Compounds and characterisation data

| No | Name | Observed LCMS [M + H]+ | ¹H NMR |
|----|------|------------------------|--------|
| 126 | 6-(3-ethylureido)-4-(4-(methylcarbamoyl)phenylamino)-N-(pyridin-3-yl)nicotinamide | 434.14 | (400 MHz, DMSO): δ 10.51 (s, 1H), 10.01 (s, 1H), 9.20 (s, 1H), 8.87 (d, J = 2.3 Hz, 1H), 8.64 (s, 1H), 8.39 (q, J = 4.1 Hz, 1H), 8.32 (dd, J = 4.7, 1.4 Hz, 1H), 8.12 (ddd, J = 8.3, 2.5, 1.5 Hz, 1H), 7.86 (d, J = 8.7 Hz, 2H), 7.82 (s, 1H), 7.49 (d, J = 3.6 Hz, 1H), 7.40 (ddd, J = 8.4, 4.7, 0.6 Hz, 1H), 7.34 (d, J = 8.7 Hz, 2H), 3.21-3.09 (m, 2H), 2.79 (d, J = 3.8 Hz, 3H), 1.07 (t, J = 7.2 Hz, 3H). |
| 127 | 1-ethyl-3-(5-(2-phenylacetyl)-4-(phenylamino)pyridin-2-yl)urea | 375.17 | (400 MHz, DMSO-d₆): δ 10.74 (s, 1H), 9.15 (s, 1H), 8.94 (s, 1H), 7.76 (s, 1H), 7.42 (t, J = 7.9 Hz, 2H), 7.36-7.17 (m, 9H), 4.37 (s, 2H), 3.20-3.05 (m, 2H), 1.05 (t, J = 7.2 Hz, 3H). |
| 128 | 6-(3-ethylureido)-4-(4-(hydroxymethyl)phenylamino)-N-(pyridin-3-yl)nicotinamide | 407.13 | (400 MHz, Acetone-d₆): δ 10.01 (s, 1H), 9.73 (s, 1H), 8.94 (d, J = 2.1 Hz, 1H), 8.66 (s, 2H), 8.47 (s, 1H), 8.35 (d, J = 3.4 Hz, 1H), 8.24 (d, J = 7.7 Hz, 1H), 7.54-7.21 (m, 5H), 6.99 (s, 1H), 4.65 (d, J = 5.3 Hz, 2H), 4.23 (t, J = 5.4 Hz, 1H), 3.34-3.21 (m, 2H), 1.15 (t, J = 7.2 Hz, 3H). |
| 129 | methyl 3-(4-(6-(3-ethylureido)-4-(phenylamino)nicotinamido)phenyl)-2,2-dimethylpropanoate | 490.22 | (400 MHz, Acetone-d₆): δ 10.08 (s, 1H), 9.53 (s, 1H), 8.78 (s, 1H), 8.59 (s, 1H), 8.48 (s, 1H), 7.73-7.68 (m, 2H), 7.45-7.38 (m, 2H), 7.33 (dd, J = 5.3, 3.3 Hz, 2H), 7.20-7.11 (m, 3H), 7.00 (dd, J = 5.1, 1.2 Hz, 1H), 3.65 (s, 3H), 3.36-3.21 (m, 2H), 2.86 (s, 2H), 1.18 (s, 6H), 1.15 (t, J = 7.2 Hz, 3H). |
| 130 | 3-(4-(6-(3-ethylureido)-4-(phenylamino)nicotinamido)phenyl)-2,2-dimethylpropanoic acid | 476.22 | (400 MHz, DMSO-d₆): δ 10.35 (s, 1H), 10.01 (s, 1H), 9.16 (s, 1H), 8.60 (s, 1H), 8.12 (s, 1H), 7.52 (d, J = 8.5 Hz, 2H), 7.43-7.36 (m, 2H), 7.30-7.23 (m, 3H), 7.17-7.09 (m, 3H), 3.21-3.07 (m, 2H), 2.67 (s, 2H), 1.06 (t, J = 7.2 Hz, 3H), 0.90 (s, 6H). |
| 131 | ethyl 3-(4-(2-(3-ethylureido)-5-(pyridin-3-ylcarbamoyl)pyridin-4-ylamino)phenyl)propanoate | 477.3 | (400 MHz, DMSO-d₆): δ 10.44 (s, 1H), 9.82 (s, 1H), 9.13 (s, 1H), 8.86 (s, 1H), 8.60 (s, 1H), 8.30 (s, 1H), 8.12 (d, J = 8.4 Hz, 1H), 7.90 (br s, 1H), 7.40 (br s, 1H), 7.27 (d, J = 8.4 Hz, 3H), 7.19 (d, J = 8.0 Hz, 2H), 4.08 (dd, J = 14.0 Hz, 2H), 3.15 (t, J = 6.0 Hz, 2H), 2.87 (t, J = 7.2 Hz, 2H), 2.64 (t, J = 7.2 Hz, 2H), 1.18 (t, J = 7.2 Hz, 3H), 1.07 (t, J = 7.2 Hz, 3H). |
| 137 | (2E)-3-{4-[({6-[(ethylcarbamoyl)amino]-4-(phenylamino)pyridin-3-yl}carbonyl)amino]phenyl}prop-2-enoic acid | 446.19 | (400 MHz, DMSO) δ 10.35 (s, 1H), 9.92 (s, 1H), 9.18 (s, 1H), 8.58 (s, 1H), 8.02 (s, 1H), 7.69 (d, J = 8.6 Hz, 2H), 7.46 (d, J = 8.6 Hz, 2H), 7.40 (t, J = 7.9 Hz, 2H), 7.31-7.25 (m, 3H), 7.15 (t, J = 7.4 Hz, 1H), 7.07 (d, J = 15.8 Hz, 1H), 6.32 (d, J = 15.8 Hz, 1H), 3.20-3.09 (m, 2H), 1.07 (t, J = 7.2 Hz, 3H). |
| 138 | 3-[4-({2-[(ethylcarbamoyl)amino]-5-(pyridin-3-ylcarbamoyl)pyridin-4-yl}amino)phenyl]propanoic acid | 449.20 | (400 MHz, DMSO-d₆): δ 12.12 (br s, 1H), 10.44 (br s, 1H), 9.82 (s, 1H), 9.12 (s, 1H), 8.86 (br s, 1H), 8.60 (s, 1H), 8.31 (m, 1H), 8.10 (d, J = 8.40 Hz, 1H), 7.93 (m, 1H), 7.39 (m, 1H), 7.17-7.29 (m, 4H), 3.13-3.16 (m, 2H), 2.82 (t, J = 6.80 Hz, 2H), 2.56 (m, 2H) and 1.06 (t, J = 7.20 Hz, 3H) |
| 139 | 6-[(ethylcarbamoyl)amino]-4-[(4-fluorophenyl)amino]-N-(pyridin-3-yl)pyridine-3-carboxamide | 395.21 | (400 MHz, DMSO-d₆): δ 10.44 (s, 1H), 9.73 (s, 1H), 9.11 (s, 1H), 8.86 (br s, 1H), 8.60 (s, 1H), 8.31 (m, 1H), 8.12 (d, J = 8.40 Hz, 1H), 7.88 (m, 1H), 7.38 (m, 1H), 7.23-7.31 (m, 4H), 7.11 (s, 1H), 3.12-3.15 (m, 2H) and 1.05 (t, J = 7.20 Hz, 3H) |
| 140 | 6-[(ethylcarbamoyl)amino]-4-[(4-methylphenyl)amino]-N-(pyridin-3-yl)pyridine-3-carboxamide | 391.19 | (400 MHz, DMSO- d₆): δ 10.44 (s, 1H), 9.77 (br s, 1H), 9.11 (s, 1H), 8.86 (br s, 1H), 8.60 (s, 1H), 8.31 (m, 1H), 8.12 (d, J = 7.20 Hz, 1H), 7.87 (m, 1H), 7.39 (m, 1H), 7.15-7.21 (m, 5H), 3.13-3.15 (m, 2H), 2.31 (s, 3H) and 1.07 (m, 3H) |
| 141 | 6-[(ethylcarbamoyl)amino]-N-(pyridin-3-yl)-4-{[3-(trifluoromethyl)phenyl]amino}pyridine-3-carboxamide | 445.17 | (400 MHz, DMSO- d₆): δ 10.50 (br s, 1H), 9.90 (br s, 1H), 9.25 (s, 1H), 8.87 (br s, 1H), 8.61 (s, 1H), 8.32 (m, 1H), 8.12 (d, J = 8.40 Hz, 1H), 7.94 (m, 1H), 7.60 (m, 3H), 7.45 (m, 1H), 7.40 (m, 1H), 7.30 (s, 1H), 3.13-3.17 (m, 2H) and 1.06 (t, J = 7.20 Hz, 3H) |
| 142 | 6-[(ethylcarbamoyl)amino]-N-(pyridin-3-yl)-4-{[4-(trifluoromethyl)phenyl]amino}pyridine-3-carboxamide | 445.16 | (400 MHz, DMSO- d₆): δ 10.53 (br s, 1H), 10.0 (br s, 1H), 9.23 (s, 1H), 8.86 (br s, 1H), 8.63 (s, 1H), 8.32 (m, 1H), 8.12 (d, J = 8.40 Hz, 1H), 7.83 (m, 1H), 7.73 (d J = 8.0 Hz, 2H), 7.46-7.48 (m, 3H), 7.38-7.41 (m, 1H), 3.12-3.19 (m, 2H) and 1.07 (t, J = 7.20 Hz, 3H) |

TABLE 1-continued

Compounds and characterisation data

| No | Name | Observed LCMS [M + H]+ | $^1$H NMR |
|---|---|---|---|
| 143 | 6-[(ethylcarbamoyl)amino]-4-[(3-fluorophenyl)amino]-N-(pyridin-3-yl)pyridine-3-carboxamide | 395.19 | (400 MHz, DMSO-$d_6$): δ 10.47 (br s, 1H), 9.91 (br s, 1H), 9.19 (s, 1H), 8.86 (br s, 1H), 8.62 (s, 1H), 8.32 (m, 1H), 8.12 (d, J = 8.40 Hz, 1H), 7.92 (m, 1H), 7.36-7.44 (m, 3H), 7.10-7.17 (m, 2H), 6.95 (t, J = 8.0 Hz, 1H), 3.13-3.18 (m, 2H) and 1.07 (t, J = 7.20 Hz, 3H) |
| 144 | 6-[(ethylcarbamoyl)amino]-4-[(2-fluorophenyl)amino]-N-(pyridin-3-yl)pyridine-3-carboxamide | 395.16 | (400 MHz, DMSO-$d_6$): δ 10.50 (br s, 1H), 9.88 (br s, 1H), 9.19 (s, 1H), 8.86 (s, 1H), 8.65 (s, 1H), 8.32 (m, 1H), 8.12 (d, J = 8.40 Hz, 1H), 7.85 (m, 1H), 7.49 (m, 1H), 7.33-7.42 (m, 2H), 7.24-7.28 (m, 2H), 7.11 (m, 1H), 3.11-3.17 (m, 2H) and 1.06 (t, J = 7.20 Hz, 3H) |
| 145 | 6-[(ethylcarbamoyl)amino]-4-[(6-methoxypyridin-3-yl)amino]-N-(pyridin-3-yl)pyridine-3-carboxamide | 408.19 | (400 MHz, DMSO-$d_6$): δ 10.43 (br s, 1H), 9.58 (s, 1H), 9.08 (s, 1H), 8.87 (s, 1H), 8.59 (s, 1H), 8.31 (m, 1H), 8.11 (m, 2H), 7.91 (m, 1H), 7.65 (dd, J = 2.40 and 8.80 Hz respectively, 1H), 7.39 (m, 1H), 6.88-6.90 (m, 2H), 3.87 (s, 3H), 3.11-3.14 (m, 2H) and 1.05 (t, J = 7.20 Hz, 3H) |
| 146 | ethyl {4-[({6-[(ethylcarbamoyl)amino]-4-(phenylamino)pyridin-3-yl}carbonyl)amino]phenoxy}acetate | 478.2 | (400 MHz, DMSO) δ 10.19 (s, 1H), 9.99 (s, 1H), 9.10 (s, 1H), 8.56 (s, 1H), 8.05-7.87 (m, 1H), 7.59 (d, J = 9.1 Hz, 2H), 7.40 (t, J = 7.9 Hz, 2H), 7.26 (d, J = 7.4 Hz, 3H), 7.15 (t, J = 7.4 Hz, 1H), 6.92 (d, J = 9.1 Hz, 2H), 4.75 (s, 2H), 4.17 (q, J = 7.1 Hz, 2H), 3.19-3.10 (m, 2H), 1.25-1.19 (m, 3H), 1.07 (t, J = 7.2 Hz, 3H). |
| 147 | methyl 3-{4-[({6-[(ethylcarbamoyl)amino]-4-(pyridin-3-ylamino)pyridin-3-yl}carbonyl)amino]phenyl}propanoate | 463.21 | (400 MHz, DMSO-$d_6$): δ 10.27 (br s, 1H), 9.92 (s, 1H), 9.15 (s, 1H), 8.57 (s, 1H), 8.53 (s, 1H), 8.35 (m, 1H), 7.94 (m, 1H), 7.73 (m, 1H), 7.61 (d, J = 8.0 Hz, 2H), 7.41-7.44 (m, 1H), 7.23 (s, 1H), 7.21 (d, J = 8.40 Hz, 2H), 3.57 (s, 3H), 3.13-3.16 (m, 2H), 2.82 (t, J = 7.20 Hz, 2H), 2.62 (t, J = 7.60 Hz, 2H) and 1.06 (t, J = 7.20 Hz, 3H) |
| 148 | methyl 3-{4-[({4-[(4-chlorophenyl)amino]-6-[(ethylcarbamoyl)amino]pyridin-3-yl}carbonyl)amino] phenyl}propanoate | 496.17 | (400 MHz, DMSO-$d_6$): δ 10.24 (br s, 1H), 9.89 (br s, 1H), 9.12 (s, 1H), 8.58 (s, 1H), 7.92 (m, 1H), 7.60 (d, J = 8.40 Hz, 2H), 7.45 (d, J = 8.80 Hz, 2H), 7.30 (d, J = 8.40 Hz, 2H), 7.24 (s, 1H), 7.20 (d, J = 8.40 Hz, 2H), 3.57 (s, 3H), 3.11-3.16 (m, 2H), 2.82 (t, J = 7.60 Hz, 2H), 2.62 (t, J = 7.60 Hz, 2H) and 1.06 (t, J = 7.20 Hz, 3H) |
| 149 | 3-{4-[({4-[(4-chlorophenyl)amino]-6-[(ethylcarbamoyl)amino]pyridin-3-yl}carbonyl)amino] phenyl}propanoic acid | 482.17 | (400 MHz, DMSO-$d_6$): δ 12.12 (br s, 1H), 10.24 (br s, 1H), 9.90 (br s, 1H), 9.12 (s, 1H), 8.56 (s, 1H), 7.92 (m, 1H), 7.60 (d, J = 8.0 Hz, 2H), 7.45 (d, J = 8.40 Hz, 2H), 7.30 (d, J = 8.80 Hz, 2H), 7.24 (s, 1H), 7.20 (d, J = 8.40 Hz, 2H), 3.11-3.18 (m, 2H), 2.79 (t, J = 7.20 Hz, 2H), 2.53 (m, 2H) and 1.08 (t, J = 7.20 Hz, 3H) |
| 150 | {4-[({6-[(ethylcarbamoyl)amino]-4-(phenylamino)pyridin-3-yl}carbonyl)amino]phenoxy}acetic acid | 450.26 | (400 MHz, DMSO) δ 10.17 (s, 1H), 10.05 (s, 1H), 9.15 (s, 1H), 8.57 (s, 1H), 8.04 (s, 1H), 7.54-7.47 (m, 2H), 7.44-7.36 (m, 2H), 7.31-7.23 (m, 3H), 7.14 (dt, J = 8.5, 1.1 Hz, 1H), 6.81-6.75 (m, 2H), 4.09 (s, 2H), 3.20-3.07 (m, 2H), 1.06 (t, J = 7.2 Hz, 3H). |
| 151 | N-(6-chloropyridin-3-yl)-6-[(ethylcarbamoyl)amino]-4-(pyridin-3-ylamino)pyridine-3-carboxamide | 412.2 | (400 MHz, Acetone) δ 10.01 (s, 1H), 9.88 (s, 1H), 8.79-8.77 (m, 1H), 8.69 (s, 1H), 8.60 (d, J = 2.6 Hz, 1H), 8.52 (s, 1H), 8.46 (s, 1H), 8.40 (dd, J = 4.7, 1.3 Hz, 1H), 8.33-8.28 (m, 1H), 7.80-7.75 (m, 1H), 7.48 (dd, J = 8.7, 0.5 Hz, 1H), 7.45-7.41 (m, 1H), 7.03 (dd, J = 5.1, 2.0 Hz, 1H), 3.31-3.23 (m, 2H), 1.14 (t, J = 7.2 Hz, 3H). |
| 152 | 6-[(ethylcarbamoyl)amino]-N-[2-(3-hydroxyazetidin-1-yl)pyrimidin-5-yl]-4-(pyridin-3-ylamino)pyridine-3-carboxamide | 450.22 | (400 MHz, Acetone) δ 10.22 (s, 1H), 9.59 (s, 1H), 8.70 (d, J = 1.6 Hz, 1H), 8.68 (d, J = 2.3 Hz, 2H), 8.61 (d, J = 2.6 Hz, 2H), 8.52 (s, 1H), 8.41 (dd, J = 4.7, 1.3 Hz, 1H), 7.81-7.76 (m, 1H), 7.45 (ddd, J = 8.2, 4.7, 0.6 Hz, 1H), 7.08-7.03 (m, 1H), 4.79-4.70 (m, 1H), 4.36-4.30 (m, 2H), 3.94-3.88 (m, 2H), 3.34-3.26 (m, 2H), 1.17 (t, J = 7.2 Hz, 3H). |
| 153 | 3-{4-[({6-[(ethylcarbamoyl)amino]-4-(pyridin-3-ylamino)pyridin-3-yl}carbonyl)amino]phenyl}propanoic acid | 449.20 | (400 MHz, DMSO-$d_6$): δ 10.27 (br s, 1H), 9.93 (br s, 1H), 9.15 (s, 1H), 8.57 (s, 1H), 8.53 (br s, 1H), 8.35 (d, J = 4.40 Hz, 1H), 7.95 (m, 1H), 7.73 (d, J = 8.40 Hz, 1H), 7.61 (d, J = 8.40 Hz, 2H), 7.41-7.44 (m, 1H), 7.19-7.23 (m, 3H), 3.11-3.18 (m, 2H), 2.79 (t, J = 7.20 Hz, 2H), 2.52 (m, 2H) and 1.06 (t, J = 7.20 Hz, 3H) |

TABLE 1-continued

Compounds and characterisation data

| No | Name | Observed LCMS [M + H]+ | 1H NMR |
|---|---|---|---|
| 154 | methyl 1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylate | 520.3 | (400 MHz, Acetone) δ 10.19 (s, 1H), 9.50 (s, 1H), 8.66 (d, J = 1.0 Hz, 1H), 8.59 (d, J = 2.4 Hz, 2H), 8.58-8.54 (m, 1H), 8.49 (s, 1H), 8.38 (dd, J = 4.7, 1.4 Hz, 1H), 7.78-7.74 (m, 1H), 7.42 (ddd, J = 8.2, 4.7, 0.7 Hz, 1H), 7.02 (dd, J = 4.9, 1.7 Hz, 1H), 6.23 (t, J = 6.3 Hz, 1H), 3.88 (d, J = 6.5 Hz, 2H), 3.67 (s, 3H), 3.31-3.23 (m, 2H), 2.43-2.33 (m, 2H), 2.14-1.96 (m, 2H), 1.95-1.84 (m, 2H), 1.14 (t, J = 7.2 Hz, 3H). |
| 155 | 1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylic acid | 506.26 | (400 MHz, DMSO) δ 10.17 (s, 1H), 9.99 (s, 1H), 9.13 (s, 1H), 8.60 (s, 1H), 8.53 (d, J = 2.5 Hz, 1H), 8.50 (s, 2H), 8.35 (dd, J = 4.7, 1.4 Hz, 1H), 7.84 (s, 1H), 7.74-7.70 (m, 1H), 7.43 (ddd, J = 8.3, 4.7, 0.4 Hz, 1H), 7.25 (s, 1H), 6.98 (t, J = 6.3 Hz, 1H), 3.68 (d, J = 6.3 Hz, 2H), 3.18-3.10 (m, 2H), 2.28-2.19 (m, 2H), 2.08-1.99 (m, 2H), 1.89-1.71 (m, 2H), 1.06 (t, J = 7.2 Hz, 3H). |
| 156 | methyl 1-[({5-[({6-[(ethylcarbamoyl)amino]-4-(pyridin-3-ylamino)pyridin-3-yl}carbonyl)amino]pyridin-2-yl}amino)methyl]cyclobutane carboxylate | 519.33 | (400 MHz, Acetone) δ 10.28 (s, 1H), 9.47 (s, 1H), 8.74-8.64 (m, 2H), 8.61 (d, J = 2.7 Hz, 1H), 8.55 (s, 1H), 8.40 (dd, J = 4.7, 1.4 Hz, 1H), 8.36 (t, J = 2.5 Hz, 1H), 7.83-7.76 (m, 2H), 7.44 (ddd, J = 8.2, 4.7, 0.6 Hz, 1H), 7.03 (dd, J = 4.8, 1.5 Hz, 1H), 6.61 (dd, J = 8.9, 0.5 Hz, 1H), 5.76 (t, J = 6.2 Hz, 1H), 3.88-3.84 (m, 2H), 3.65 (s, 3H), 3.34-3.26 (m, 2H), 2.45-2.34 (m, 2H), 2.17-1.98 (m, 3H), 1.97-1.85 (m, 1H), 1.17 (t, J = 7.2 Hz, 3H). |
| 157 | 6-[(ethylcarbamoyl)amino]-4-[(5-methylpyridin-3-yl)amino]-N-(pyridin-3-yl)pyridine-3-carboxamide | 392.17 | (400 MHz, DMSO-$d_6$): δ 10.50 (br s, 1H), 9.83 (s, 1H), 9.21 (s, 1H), 8.87 (m, 1H), 8.65 (s, 1H), 8.31-8.34 (m, 2H), 8.20 (s, 1H), 8.12 (d, J = 8.40 Hz, 1H), 7.98 (m, 1H), 7.55 (s, 1H), 7.38-7.41 (m, 1H), 7.19 (s, 1H), 3.12-3.19 (m, 2H), 2.31 (s, 3H) and 1.06 (t, J = 7.20 Hz, 3H) |
| 158 | 1-[({5-[({6-[(ethylcarbamoyl)amino]-4-(pyridin-3-ylamino)pyridin-3-yl}carbonyl)amino]pyridin-2-yl}amino)methyl]cyclobutane carboxylic acid | 505.25 | (400 MHz, DMSO) δ 10.11-10.03 (m, 2H), 9.12 (s, 1H), 8.59 (s, 1H), 8.53 (d, J = 2.6 Hz, 1H), 8.35 (dd, J = 4.7, 1.4 Hz, 1H), 8.19 (d, J = 2.6 Hz, 1H), 7.91 (bs, 1H), 7.74-7.69 (m, 1H), 7.63 (dd, J = 8.9, 2.6 Hz, 1H), 7.43 (dd, J = 8.1, 4.7 Hz, 1H), 7.24 (s, 1H), 6.58 (d, J = 8.9 Hz, 1H), 6.35 (s, 1H), 3.65 (s, 2H), 3.20-3.11 (m, 2H), 2.31-2.21 (m, 2H), 2.03-1.97 (m, 2H), 1.94-1.77 (m, 2H), 1.07 (t, J = 7.2 Hz, 3H). |
| 159 | methyl 3-{4-[({4-[(4-chlorophenyl)amino]-6-[(ethylcarbamoyl)amino]pyridin-3-yl}carbonyl)amino]phenyl}-2,2-dimethylpropanoate | 524.21 | (400 MHz, DMSO-$d_6$): δ 10.26 (br s, 1H), 9.86 (br s, 1H), 9.12 (s, 1H), 8.55 (s, 1H), 7.92 (m, 1H), 7.60 (d, J = 7.60 Hz, 2H), 7.45 (d, J = 7.60 Hz, 2H), 7.30 (d, J = 8.0 Hz, 2H), 7.24 (s, 1H), 7.06 (d, J = 8.0 Hz, 2H), 3.60 (s, 3H), 3.13-3.16 (m, 2H), 2.77 (s, 2H), 1.11 (s, 6H) and 1.06 (t, J = 7.20 Hz, 3H) |
| 160 | 3-{4-[({4-[(4-chlorophenyl)amino]-6-[(ethylcarbamoyl)amino]pyridin-3-yl}carbonyl)amino]phenyl}-2,2-dimethylpropanoic acid | 510.29 | (400 MHz, DMSO-$d_6$): δ 12.24 (br s, 1H), 10.26 (br s, 1H), 9.87 (br s, 1H), 9.12 (s, 1H), 8.55 (s, 1H), 7.93 (m, 1H), 7.59 (d, J = 8.0 Hz, 2H), 7.45 (d, J = 8.80 Hz, 2H), 7.30 (d, J = 8.80 Hz, 2H), 7.24 (s, 1H), 7.10 (d, J = 8.40 Hz, 2H), 3.11-3.18 (m, 2H), 2.75 (s, 2H) and 1.04-1.07 (m, 9H) |
| 161 | 4-(3,5-difluoroanilino)-6-(ethylcarbamoylamino)-N-[4-[2-(1H-tetrazol-5-yl)ethyl]phenyl]pyridine-3-carboxamide | 508.12 | 1H NMR (400 MHz, DMSO) δ 10.28 (s, 1H), 10.01 (s, 1H), 9.22 (s, 1H), 8.57 (s, 1H), 8.01 (s, 1H), 7.58 (d, J = 8.5 Hz, 2H), 7.40 (s, 1H), 7.18 (d, J = 8.5 Hz, 2H), 7.03 (dd, J = 9.3, 2.1 Hz, 2H), 6.92 (tt, J = 9.3, 2.2 Hz, 1H), 3.17 (ddd, J = 18.1, 14.0, 7.6 Hz, 4H), 3.00 (t, J = 7.7 Hz, 2H), 1.08 (t, J = 7.2 Hz, 3H). |
| 162 | 6-[(ethylcarbamoyl)amino]-4-[(2-methylpyridin-4-yl)amino]-N-(pyridin-3-yl)pyridine-3-carboxamide | 392.17 | (400 MHz, DMSO-$d_6$): δ 10.55 (br s, 1H), 9.99 (s, 1H), 9.34 (s, 1H), 8.85 (m, 1H), 8.64 (s, 1H), 8.29-8.33 (m, 2H), 8.11 (d, J = 8.40 Hz, 1H), 7.97 (m, 1H), 7.56 (s, 1H), 7.38-7.41 (m, 1H), 7.10 (s, 1H), 7.06 (m, 1H), 3.17-3.20 (m, 2H), 2.41 (s, 3H) and 1.09 (t, J = 7.20 Hz, 3H) |
| 163 | 6-[(ethylcarbamoyl)amino]-4-[(2-methoxypyridin-4-yl)amino]-N-(pyridin-3-yl)pyridine-3-carboxamide | 408.18 | (400 MHz, DMSO-$d_6$): δ 10.55 (br s, 1H), 9.99 (s, 1H), 9.34 (s, 1H), 8.85 (m, 1H), 8.63 (s, 1H), 8.32 (d, J = 4.40 Hz, 1H), 8.11 (d, J = 8.40 Hz, 1H), 8.03 (d, J = 6.0 Hz, 1H), 7.85 (m, 1H), 7.61 (s, 1H), 7.38-7.41 (m, 1H), 6.85 (d, J = 5.60 Hz, 1H), 6.62 (s, 1H), 3.83 (s, 3H), 3.15-3.21 (m, 2H) and 1.08 (t, J = 7.20 Hz, 3H) |

TABLE 1-continued

Compounds and characterisation data

| No | Name | Observed LCMS [M + H]+ | 1H NMR |
|---|---|---|---|
| 164 | ethyl 1-({5-[({4-[(4-chlorophenyl)amino]-6-[(ethylcarbamoyl)amino]pyridin-3-yl}carbonyl)amino]pyrimidin-2-yl}amino)cyclobutanecarboxylate | 553.31 | (400 MHz, DMSO) δ 10.13 (s, 1H), 9.94 (s, 1H), 9.11 (s, 1H), 8.57 (s, 1H), 8.46 (s, 2H), 7.91 (s, 1H), 7.82 (s, 1H), 7.52-7.39 (m, 2H), 7.31-7.24 (m, 3H), 4.04 (q, J = 7.1 Hz, 2H), 3.19-3.10 (m, 2H), 2.62-2.55 (m, 2H), 2.25-2.15 (m, 2H), 2.01-1.86 (m, 2H), 1.10-1.02 (m, 6H). |
| 165 | 1-({5-[({4-[(4-chlorophenyl)amino]-6-[(ethylcarbamoyl)amino]pyridin-3-yl}carbonyl)amino]pyrimidin-2-yl}amino)cyclobutanecarboxylic acid | 525.21 | (400 MHz, MeOD) δ 8.54 (s, 1H), 8.53 (s, 2H), 7.43-7.38 (m, 2H), 7.29-7.25 (m, 2H), 6.89 (s, 1H), 3.29-3.25 (partially obscured by solvent peak, m, 2H), 2.78-2.69 (m, 2H), 2.35-2.26 (m, 2H), 2.08 (dd, J = 8.5, 5.1 Hz, 2H), 1.18 (t, J = 7.2 Hz, 3H). |
| 166 | 3-{5-[({6-[(ethylcarbamoyl)amino]-4-(phenylamino)pyridin-3-yl}carbonyl)amino]pyridin-2-yl}propanoic acid | 449.2 | (400 MHz, DMSO) δ 10.38 (s, 1H), 9.90 (s, 1H), 9.12 (s, 1H), 8.74 (d, J = 2.2 Hz, 1H), 8.60 (s, 1H), 8.01 (dd, J = 8.4, 2.6 Hz, 1H), 7.91 (s, 1H), 7.45-7.36 (m, 2H), 7.27 (d, J = 7.9 Hz, 4H), 7.20-7.11 (m, 1H), 3.19-3.09 (m, 2H), 2.95 (t, J = 7.3 Hz, 2H), 2.65 (t, J = 7.4 Hz, 2H), 1.06 (t, J = 7.2 Hz, 3H). |
| 167 | 6-[(ethylcarbamoyl)amino]-4-[(6-methylpyridin-3-yl)amino]-N-(pyridin-3-yl)pyridine-3-carboxamide | 392.18 | (400 MHz, DMSO- d6): δ 10.46 (br s, 1H), 9.71 (s, 1H), 9.11 (s, 1H), 8.87 (d, J = 2.0 Hz, 1H), 8.61 (s, 1H), 8.39 (d, J = 2.40 Hz, 1H), 8.32 (m, 1H), 8.12 (d, J = 8.0 Hz, 1H), 7.83 (m, 1H), 7.60 (dd, J = 2.40 and 8.40 Hz respectively, 1H), 7.37-7.41 (m, 1H), 7.31 (d, J = 8.40 Hz, 1H), 7.15 (s, 1H), 3.12-3.15 (m, 2H), 2.47 (s, 3H) and 1.05 (t, J = 7.20 Hz, 3H) |
| 168 | 1-[({5-[({6-[(ethylcarbamoyl)amino]-4-(phenylamino)pyridin-3-yl}carbonyl)amino]pyrimidin-2-yl}amino)methyl]cyclobutanecarboxylic acid | 505.26 | (400 MHz, Acetone) δ 10.16 (s, 1H), 10.06 (s, 1H), 9.13 (s, 1H), 8.60 (s, 1H), 8.51 (s, 2H), 7.93 (s, 1H), 7.44-7.37 (m, 2H), 7.32-7.24 (m, 3H), 7.15 (t, J = 7.2 Hz, 1H), 6.94 (s, 1H), 3.68 (d, J = 5.0 Hz, 2H), 3.19-3.11 (m, 2H), 2.25 (dd, J = 18.6, 9.4 Hz, 2H), 2.11-1.97 (m, 2H), 1.93-1.73 (m, 2H), 1.07 (t, J = 7.2 Hz, 3H). |
| 169 | (1R,2R)-2-{4-[({6-[(ethylcarbamoyl)amino]-4-(phenylamino)pyridin-3-yl}carbonyl)amino]phenyl}cyclopropanecarboxylic acid | 460.26 | (400 MHz, DMSO) δ 10.25 (s, 1H), 9.95 (s, 1H), 9.18 (s, 1H), 8.56 (s, 1H), 8.05 (s, 1H), 7.57 (d, J = 8.6 Hz, 2H), 7.40 (t, J = 7.9 Hz, 2H), 7.32-7.22 (m, 3H), 7.19-7.10 (m, 1H), 7.05 (d, J = 8.6 Hz, 2H), 3.21-3.06 (m, 2H), 2.22-2.07 (m, 1H), 1.66-1.50 (m, 1H), 1.33-1.16 (m, 1H), 1.06 (t, J = 7.2 Hz, 3H), 0.99 (dd, J = 10.0, 7.4 Hz, 1H). |
| 170 | methyl 3-{4-[({6-[(ethylcarbamoyl)amino]-4-(pyridin-3-ylamino)pyridin-3-yl}carbonyl)amino]phenyl}-2,2-dimethylpropanoate | 491.24 | (400 MHz, DMSO- d6): δ 10.28 (br s, 1H), 9.89 (br s, 1H), 9.14 (s, 1H), 8.57 (s, 1H), 8.53 (d, J = 2.40 Hz, 1H), 8.35 (d, J = 3.60 Hz, 1H), 7.94 (m, 1H), 7.73 (d, J = 8.40 Hz, 1H), 7.60 (d, J = 8.40 Hz, 1H), 7.41-7.44 (m, 1H), 7.23 (s, 1H), 7.06 (d, J = 8.40 Hz, 2H), 3.60 (s, 3H), 3.11-3.18 (m, 2H), 2.77 (s, 2H), 1.11 (s, 6H) and 1.06 (t, J = 7.20 Hz, 3H) |
| 171 | 3-{4-[({6-[(ethylcarbamoyl)amino]-4-(pyridin-3-ylamino)pyridin-3-yl}carbonyl)amino]phenyl}-2,2-dimethylpropanoic acid | 477.24 | (400 MHz, DMSO- d6): δ 12.33 (br s, 1H), 10.28 (br s, 1H), 9.89 (br s, 1H), 9.15 (s, 1H), 8.53-8.57 (m, 2H), 8.35 (d, J = 4.40 Hz, 1H), 7.94 (m, 1H), 7.73 (d, J = 8.40 Hz, 1H), 7.59 (d, J = 8.0 Hz, 2H), 7.38-7.44 (m, 1H), 7.23 (s, 1H), 7.13 (m, 2H), 3.13-3.18 (m, 2H), 2.75 (s, 2H) and 1.04-1.07 (m, 9H) |
| 172 | 4-{[6-(acetylamino)pyridin-3-yl]amino}-6-[(ethylcarbamoyl)amino]-N-(pyridin-3-yl)pyridine-3-carboxamide | 435.21 | (400 MHz, DMSO- d6): δ 10.55 (br s, 1H), 10.46 (br s, 1H), 9.69 (s, 1H), 9.12 (s, 1H), 8.88 (s, 1H), 8.60 (s, 1H), 8.32 (d, J = 5.20 Hz, 1H), 8.25 (s, 1H), 8.12 (m, 2H), 7.91 (m, 1H), 7.71 (m, 1H), 7.39-7.41 (m, 1H), 7.05 (s, 1H), 3.12-3.15 (m, 2H), 2.10 (s, 3H) and 1.05 (t, J = 7.20 Hz, 3H) |
| 173 | 6-[(ethylcarbamoyl)amino]-N-(pyridin-3-yl)-4-(pyrimidin-5-ylamino)pyridine-3-carboxamide | 379.18 | (400 MHz, DMSO- d6): δ 10.53 (br s, 1H), 9.80 (s, 1H), 9.20 (s, 1H), 8.95 (s, 1H), 8.88 (d, J = 2.0 Hz, 1H), 8.81 (s, 2H), 8.63 (s, 1H), 8.33 (m, 1H), 8.12 (d, J = 8.0 Hz, 1H), 7.88 (m, 1H), 7.41 (dd, J = 4.40 and 8.0 Hz respectively, 1H), 7.25 (s, 1H), 3.12-3.18 (m, 2H) and 1.06 (t, J = 7.20 Hz, 3H) |
| 174 | 6-[(ethylcarbamoyl)amino]-4-[(5-methoxypyridin-3-yl)amino]-N-(pyridin-3-yl)pyridine-3-carboxamide | 408.19 | (400 MHz, DMSO- d6): δ 10.50 (br s, 1H), 9.87 (s, 1H), 9.22 (s, 1H), 8.87 (s, 1H), 8.63 (s, 1H), 8.32 (d, J = 5.60 Hz, 1H), 8.07-8.14 (m, 3H), 7.92 (m, 1H), 7.34-7.41 (m, 3H), 3.85 (s, 3H), 3.15-3.17 (m, 2H) and 1.07 (t, J = 7.20 Hz, 3H) |

TABLE 1-continued

Compounds and characterisation data

| No | Name | Observed LCMS [M + H]+ | 1H NMR |
|---|---|---|---|
| 175 | 3-{4-[({6-[(ethylcarbamoyl)amino]-4-[(4-fluorophenyl)amino]pyridin-3-yl}carbonyl)amino]phenyl}-2,2-dimethylpropanoic acid | 494.25 | (400 MHz, DMSO- $d_6$): δ 12.21 (br s, 1H), 10.23 (br s, 1H), 9.80 (s, 1H), 9.08 (br s, 1H), 8.54 (s, 1H), 7.95 (m, 1H), 7.59 (d, J = 8.40 Hz, 2H), 7.22-7.32 (m, 4H), 7.08-7.12 (m, 3H), 3.10-3.17 (m, 2H), 2.75 (s, 2H) and 1.04-1.07 (m, 9H) |
| 176 | 3-[4-[[6-(ethylcarbamoylamino)-4-[4-(trifluoromethyl)anilino]pyridine-3-carbonyl]amino]phenyl]propanoic acid | 516.19 | 1H NMR (400 MHz, DMSO) δ 10.60 (s, 1H), 10.27 (s, 1H), 8.53 (s, 1H), 7.79 (d, J = 8.5 Hz, 2H), 7.62-7.51 (m, 5H), 7.22 (d, J = 8.6 Hz, 2H), 7.07 (s, 1H), 3.21-3.12 (m, 2H), 2.80 (t, J = 7.5 Hz, 2H), 2.56-2.50 (m, 2H), 1.08 (t, J = 7.2 Hz, 3H). |
| 177 | 3-{4-[({4-[(3-chlorophenyl)amino]-6-[(ethylcarbamoyl)amino]pyridin-3-yl}carbonyl)amino]phenyl}-2,2-dimethylpropanoic acid | 510.22 | (400 MHz, DMSO- $d_6$): δ 12.22 (br s, 1H), 10.26 (br s, 1H), 9.92 (s, 1H), 9.19 (s, 1H), 8.56 (s, 1H), 8.06 (m, 1H), 7.59 (d, J = 8.40 Hz, 2H), 7.35-7.42 (m, 3H), 7.10-7.27 (m, 4H), 3.12-3.19 (m, 2H), 2.75 (s, 2H) and 1.05-1.09 (m, 9H) |
| 178 | 3-{4-[({6-[(ethylcarbamoyl)amino]-4-[(3-methoxyphenyl)amino]pyridin-3-yl}carbonyl)amino]phenyl}-2,2-dimethylpropanoic acid | 506.28 | (400 MHz, DMSO- $d_6$): δ 12.22 (br s, 1H), 10.24 (br s, 1H), 9.93 (s, 1H), 9.16 (s, 1H), 8.55 (s, 1H), 8.0 (m, 1H), 7.59 (d, J = 8.80 Hz, 2H), 7.26-7.33 (m, 2H), 7.13 (d, J = 8.40 Hz, 2H), 6.81-6.85 (m, 2H), 6.71 (m, 1H), 3.78 (s, 3H), 3.14-3.17 (m, 2H), 2.76 (s, 2H) and 1.05-1.08 (m, 9H) |
| 179 | methyl 3-{5-[({6-[(ethylcarbamoyl)amino]-4-(phenylamino)pyridin-3-yl}carbonyl)amino]pyridin-2-yl}propanoate | 463.26 | (400 MHz, DMSO) δ 10.39 (s, 1H), 9.90 (s, 1H), 9.12 (s, 1H), 8.73 (d, J = 2.4 Hz, 1H), 8.60 (s, 1H), 8.01 (dd, J = 8.4, 2.6 Hz, 1H), 7.92 (s, 1H), 7.44-7.37 (m, 2H), 7.27 (dd, J = 7.7, 1.3 Hz, 4H), 7.16 (t, J = 7.4 Hz, 1H), 3.58 (s, 3H), 3.20-3.08 (m, 2H), 2.98 (t, J = 7.3 Hz, 2H), 2.74 (t, J = 7.3 Hz, 2H), 1.06 (t, J = 7.2 Hz, 3H). |
| 180 | ethyl (1R,2R)-2-{4-[({6-[(ethylcarbamoyl)amino]-4-(phenylamino)pyridin-3-yl}carbonyl)amino]phenyl}cyclopropanecarboxylate | 488.28 | (400 MHz, DMSO) δ 10.26 (s, 1H), 9.96 (s, 1H), 9.12 (s, 1H), 8.59 (s, 1H), 7.98 (s, 1H), 7.63 (d, J = 8.6 Hz, 2H), 7.46-7.38 (m, 2H), 7.32-7.25 (m, 3H), 7.21-7.14 (m, 3H), 4.16-4.08 (m, 2H), 3.21-3.11 (m, 2H), 2.47-2.38 (m, 1H), 1.96-1.89 (m, 1H), 1.51-1.43 (m, 1H), 1.39 (ddd, J = 8.4, 6.6, 4.4 Hz, 1H), 1.22 (t, J = 7.1 Hz, 3H), 1.08 (t, J = 7.2 Hz, 3H). |
| 181 | 3-{4-[({6-[(ethylcarbamoyl)amino]-4-[(3-fluorophenyl)amino]pyridin-3-yl}carbonyl)amino]phenyl}-2,2-dimethylpropanoic acid | 494.30 | (400 MHz, DMSO- $d_6$): δ 12.18 (br s, 1H), 10.26 (br s, 1H), 9.98 (br s, 1H), 9.16 (s, 1H), 8.57 (s, 1H), 7.99 (m, 1H), 7.59 (d, J = 8.40 Hz, 2H), 7.38-7.44 (m, 1H), 7.34 (s, 1H), 7.09-7.16 (m, 4H), 6.94 (t, J = 8.40 Hz, 1H), 3.13-3.20 (m, 2H), 2.76 (s, 2H) and 1.07-1.09 (m, 9H) |
| 182 | 3-{4-[({6-[(ethylcarbamoyl)amino]-4-[(2-fluorophenyl)amino]pyridin-3-yl}carbonyl)amino]phenyl}-2,2-dimethylpropanoic acid | 494.23 | (400 MHz, DMSO- $d_6$): δ 12.25 (br s, 1H), 10.27 (br s, 1H), 9.94 (br s, 1H), 9.14 (s, 1H), 8.59 (s, 1H), 7.92 (m, 1H), 7.59 (d, J = 8.80 Hz, 2H), 7.47-7.51 (m, 1H), 7.32-7.37 (m, 1H), 7.21-7.27 (m, 2H), 7.11-7.13 (m, 3H), 3.13-3.16 (m, 2H), 2.76 (s, 2H) and 1.04-1.07 (m, 9H) |
| 183 | 3-{4-[({4-[(2-chlorophenyl)amino]-6-[(ethylcarbamoyl)amino]pyridin-3-yl}carbonyl)amino]phenyl}-2,2-dimethylpropanoic acid | 510.25 | (400 MHz, DMSO- $d_6$): δ 12.24 (br s, 1H), 10.30 (br s, 1H), 10.15 (br s, 1H), 9.17 (s, 1H), 8.61 (s, 1H), 7.90 (m, 1H), 7.54-7.59 (m, 4H), 7.37-7.41 (m, 1H), 7.11-7.22 (m, 4H), 3.13-3.16 (m, 2H), 2.75 (s, 2H) and 1.04-1.06 (m, 9H) |
| 184 | 3-{4-[({6-[(ethylcarbamoyl)amino]-4-[(4-fluoro-3-methoxyphenyl)amino]pyridin-3-yl}carbonyl)amino]phenyl}-2,2-dimethylpropanoic acid | 524.24 | (400 MHz, DMSO- $d_6$): δ 12.22 (br s, 1H), 10.23 (br s, 1H), 9.84 (s, 1H), 9.13 (br s, 1H), 8.55 (s, 1H), 8.03 (m, 1H), 7.59 (d, J = 8.80 Hz, 2H), 7.20-7.25 (m, 2H), 7.08-7.13 (m, 3H), 6.81 (m, 1H), 3.86 (s, 3H), 3.13-3.16 (m, 2H), 2.75 (s, 2H) and 1.02-1.07 (m, 9H) |
| 185 | 4-[(4-chlorophenyl)amino]-6-[(ethylcarbamoyl)amino]-N-[4-(3-hydroxy-3-methylbut-1-yn-1-yl)phenyl]pyridine-3-carboxamide | 492.11 | (400 MHz, DMSO) δ 10.39 (s, 1H), 9.79 (s, 1H), 9.11 (s, 1H), 8.56 (s, 1H), 7.88 (s, 1H), 7.72 (d, J = 8.7 Hz, 2H), 7.55-7.16 (m, 7H), 5.42 (s, 1H), 3.21-3.04 (m, 2H), 1.46 (s, 6H), 1.06 (t, J = 7.2 Hz, 3H). |
| 186 | 3-{4-[({6-[(methylcarbamoyl)amino]-4-(phenylamino)pyridin-3-yl}carbonyl)amino]phenyl}propanoic acid | 434.13 | (400 MHz, Acetone) δ 10.09 (s, 1H), 9.54 (s, 1H), 8.66 (s, 1H), 8.59 (s, 1H), 8.50 (s, 1H), 7.76-7.68 (m, 2H), 7.45-7.39 (m, 2H), 7.35-7.30 (m, 2H), 7.29-7.25 (m, 2H), 7.17 (t, J = 7.3 Hz, 1H), 7.02-6.98 (m, 1H), 2.91 (t, J = 7.6 Hz, 2H), 2.80 (d, J = 4.1 Hz, 3H), 2.62 (t, J = 7.6 Hz, 2H). |

TABLE 1-continued

Compounds and characterisation data

| No | Name | Observed LCMS [M + H]+ | 1H NMR |
|---|---|---|---|
| 187 | 3-{4-[({6-[(ethylcarbamoyl)amino]-4-[(2-methoxypyridin-4-yl)amino]pyridin-3-yl}carbonyl)amino]phenyl}-2,2-dimethylpropanoic acid | 507.35 | (400 MHz, DMSO- $d_6$): δ 12.21 (br s, 1H), 10.34 (br s, 1H), 10.08 (s, 1H), 9.31 (s, 1H), 8.58 (s, 1H), 8.03 (d, J = 6.0 Hz, 1H), 7.92 (m, 1H), 7.55-7.58 (m, 3H), 7.13 (d, J = 8.40 Hz, 2H), 6.82 (m, 1H), 6.65 (s, 1H), 3.83 (s, 3H), 3.16-3.20 (m, 2H), 2.75 (s, 2H) and 1.06-1.10 (m, 9H) |
| 188 | 3-{4-[({4-[(4-cyanophenyl)amino]-6-[(ethylcarbamoyl)amino]pyridin-3-yl}carbonyl)amino]phenyl}-2,2-dimethylpropanoic acid | 501.27 | (400 MHz, DMSO- $d_6$): δ 12.22 (br s, 1H), 10.32 (br s, 1H), 10.12 (s, 1H), 9.23 (s, 1H), 8.58 (s, 1H), 7.89 (m, 1H), 7.81 (d, J = 8.0 Hz, 2H), 7.58 (d, J = 8.40 Hz, 2H), 7.53 (s, 1H), 7.43 (d, J = 8.80 Hz, 2H), 7.12 (d, J = 8.0 Hz, 2H), 3.15-3.18 (m, 2H), 2.75 (s, 2H) and 1.06-1.10 (m, 9H) |
| 189 | 3-[4-[[6-(ethylcarbamoylamino)-4-(3,4,5-trifluoroanilino)pyridine-3-carbonyl]amino]phenyl]propanoic acid | 502.13 | 1H NMR (400 MHz, DMSO) δ 10.40 (s, 1H), 10.00 (s, 1H), 8.57 (s, 1H), 7.89 (s, 1H), 7.61 (d, J = 8.5 Hz, 2H), 7.36 (dd, J = 9.4, 6.3 Hz, 2H), 7.23 (d, J = 8.6 Hz, 2H), 7.18 (s, 1H), 3.23-3.15 (m, 2H), 2.82 (t, J = 7.5 Hz, 2H), 2.59-2.52 (m, 2H), 1.10 (t, J = 7.2 Hz, 3H). |
| 190 | 3-{4-[({6-[(ethylcarbamoyl)amino]-4-[(3-fluoro-4-methoxyphenyl)amino]pyridin-3-yl}carbonyl)amino]phenyl}-2,2-dimethylpropanoic acid | 524.28 | (400 MHz, DMSO- $d_6$): δ 12.24 (br s, 1H), 10.21 (br s, 1H), 9.74 (s, 1H), 9.07 (s, 1H), 8.54 (s, 1H), 8.02 (m, 1H), 7.59 (d, J = 8.40 Hz, 2H), 7.03-7.22 (m, 6H), 3.85 (s, 3H), 3.11-3.18 (m, 2H), 2.75 (s, 2H) and 1.04-1.07 (m, 9H) |
| 191 | 4-[(4-chlorophenyl)amino]-6-[(ethylcarbamoyl)amino]-N-[4-(pyridin-2-ylethynyl)phenyl]pyridine-3-carboxamide | 511 | (400 MHz, DMSO) δ 10.49 (br s, 1H), 9.79 (br s, 1H), 9.12 (s, 1H), 8.63-8.57 (m, 2H), 7.90 (br s, 1H), 7.87-7.79 (m, 3H), 7.65-7.57 (m, 3H), 7.48-7.42 (m, 2H), 7.40 (ddd, J = 7.6, 4.9, 1.2 Hz, 1H), 7.35-7.28 (m, 2H), 7.25 (br s, 1H), 3.21-3.10 (m, 2H), 1.07 (t, J = 7.2 Hz, 3H). |
| 192 | (1R,2R)-2-{4-[({4-[(4-chlorophenyl)amino]-6-[(ethylcarbamoyl)amino]pyridin-3-yl}carbonyl)amino]phenyl}cyclopropanecarboxylic acid | 494.12 | (400 MHz, DMSO) δ 10.24 (s, 1H), 9.92 (s, 1H), 9.17 (s, 1H), 8.56 (s, 1H), 7.99 (s, 1H), 7.57 (d, J = 8.6 Hz, 2H), 7.46-7.41 (m, 2H), 7.32-7.23 (m, 3H), 7.05 (d, J = 8.7 Hz, 2H), 3.18-3.10 (m, 2H), 2.18-2.11 (m, 1H), 1.62-1.55 (m, 1H), 1.28-1.21 (m, 1H), 1.06 (t, J = 7.2 Hz, 3H), 1.02-0.96 (m, 1H). |
| 193 | (1R,2R)-2-{4-[({6-[(ethylcarbamoyl)amino]-4-(pyridin-3-ylamino)pyridin-3-yl}carbonyl)amino]phenyl}cyclopropanecarboxylic acid | 461.13 | (400 MHz, DMSO) δ 10.27 (s, 1H), 9.92 (s, 1H), 9.14 (s, 1H), 8.58 (s, 1H), 8.53 (d, J = 2.3 Hz, 1H), 8.35 (dd, J = 4.7, 1.4 Hz, 1H), 7.94 (s, 1H), 7.74-7.69 (m, 1H), 7.61 (d, J = 8.6 Hz, 2H), 7.45-7.40 (m, 1H), 7.23 (s, 1H), 7.13 (d, J = 8.7 Hz, 2H), 3.19-3.10 (m, 2H), 2.36-2.29 (m, 1H), 1.78-1.72 (m, 1H), 1.41-1.35 (m, 1H), 1.29-1.23 (m, 1H), 1.06 (t, J = 7.2 Hz, 3H). |
| 194 | N-{4-[4-(aminomethyl)-1H-1,2,3-triazol-1-yl]phenyl}-4-[(4-chlorophenyl)amino]-6-[(ethylcarbamoyl)amino]pyridine-3-carboxamide | 506.05 | (400 MHz, DMSO) δ 10.52 (s, 1H), 9.84 (s, 1H), 9.14 (s, 1H), 8.62 (s, 1H), 8.58 (br s, 1H), 7.96-7.83 (m, 5H), 7.48-7.42 (m, 2H), 7.34-7.29 (m, 2H), 7.27 (s, 1H), 3.21-3.09 (m, 4H), 1.07 (t, J = 7.2 Hz, 3H). |
| 195 | tert-butyl 1-{4-[({6-[(ethylcarbamoyl)amino]-4-(phenylamino)pyridin-3-yl}carbonyl)amino]phenyl}-L-prolinate | 545.19 | (400 MHz, DMSO) δ 10.08 (s, 1H), 10.02 (s, 1H), 9.07 (s, 1H), 8.55 (s, 1H), 7.99 (s, 1H), 7.47 (d, J = 9.0 Hz, 2H), 7.43-7.37 (m, 2H), 7.28-7.23 (m, 3H), 7.17-7.11 (m, 3H), 6.47 (d, J = 9.1 Hz, 2H), 4.12 (dd, J = 8.6, 1.7 Hz, 1H), 3.44-3.34 (m, 1H), 3.19-3.10 (m, 2H), 2.32-2.20 (m, 1H), 2.05-1.95 (m, 3H), 1.38 (s, 9H), 1.07 (t, J = 7.2 Hz, 3H). |
| 196 | 3-(4-{[(6-[(ethylcarbamoyl)amino]-4-{[4-(methoxycarbonyl)phenyl]amino}pyridin-3-yl)carbonyl]amino}phenyl)-2,2-dimethylpropanoic acid | 534.31 | (400 MHz, DMSO- $d_6$): δ 10.31 (br s, 1H), 10.15 (br s, 1H), 9.23 (s, 1H), 8.59 (s, 1H), 7.92-7.94 (m, 3H), 7.58 (d, J = 8.0 Hz, 2H), 7.52 (s, 1H), 7.38 (d, J = 8.40 Hz, 2H), 7.14 (d, J = 8.0 Hz, 2H), 3.83 (s, 3H), 3.13-3.20 (m, 2H), 2.74 (s, 2H) and 1.04-1.09 (m, 9H) |
| 197 | methyl 1-{4-[({4-[(4-chlorophenyl)amino]-6-[(ethylcarbamoyl)amino]pyridin-3-yl}carbonyl)amino]phenyl}-1H-pyrrole-2-carboxylate | 533.12 | (400 MHz, DMSO) δ 10.44 (s, 1H), 9.86 (s, 1H), 9.13 (s, 1H), 8.61 (s, 1H), 7.91 (br s, 1H), 7.77 (d, J = 8.8 Hz, 2H), 7.45 (d, J = 8.7 Hz, 2H), 7.31 (br d, J = 7.4 Hz, 4H), 7.27 (s, 1H), 7.23-7.20 (m, 1H), 7.03 (dd, J = 3.9, 1.8 Hz, 1H), 6.31 (dd, J = 3.8, 2.7 Hz, 1H), 3.63 (s, 3H), 3.20-3.11 (m, 2H), 1.07 (t, J = 7.2 Hz, 3H). |

TABLE 1-continued

Compounds and characterisation data

| No | Name | Observed LCMS [M + H]+ | 1H NMR |
|----|------|------------------------|--------|
| 198 | 1-{4-[({6-[(ethylcarbamoyl)amino]-4-(phenylamino)pyridin-3-yl}carbonyl)amino]phenyl}-1H-pyrrole-2-carboxylic acid | 485.11 | (400 MHz, DMSO) δ 10.37 (br s, 1H), 9.99 (br s, 1H), 9.17 (br s, 1H), 8.61 (s, 1H), 8.06 (br s, 1H), 7.63 (d, J = 7.6 Hz, 2H), 7.46-7.35 (m, 2H), 7.34-7.25 (m, 3H), 7.25-7.18 (m, 2H), 7.18-7.10 (m, 1H), 6.68 (s, 1H), 6.38 (dd, J = 3.4, 1.9 Hz, 1H), 6.01-5.95 (m, 1H), 3.20-3.11 (m, 2H), 1.07 (t, J = 7.2 Hz, 3H). |
| 199 | 3-{4-[({4-[(3-cyanophenyl)amino]-6-[(ethylcarbamoyl)amino]pyridin-3-yl}carbonyl)amino]phenyl}-2,2-dimethylpropanoic acid | 501.21 | (400 MHz, DMSO- d$_6$): δ 10.30 (br s, 1H), 9.98 (s, 1H), 9.20 (s, 1H), 8.57 (s, 1H), 8.10 (br s, 1H), 7.73 (s, 1H), 7.56-7.62 (m, 5H), 7.25 (s, 1H), 7.13 (d, J = 8.80 Hz, 2H), 3.15-3.18 (m, 2H), 2.75 (s, 2H) and 1.05-1.09 (m, 9H). |
| 200 | 6-[(ethylcarbamoyl)amino]-4-[(4-fluorophenyl)amino]-N-[4-(pyrrolidin-1-ylmethyl)phenyl]pyridine-3-carboxamide | 477.32 | (400 MHz, DMSO- d$_6$): δ 10.23 (br s, 1H), 9.81 (s, 1H), 9.07 (s, 1H), 8.56 (s, 1H), 7.95 (br s, 1H), 7.64 (d, J = 8.40 Hz, 2H), 7.22-7.32 (m, 6H), 7.09 (s, 1H), 3.52 (s, 2H), 3.10-3.17 (m, 2H), 2.40 (br s, 4H), 1.68 (br s, 4H) and 1.06 (t, J = 7.20 Hz, 3H). |
| 201 | 6-[(ethylcarbamoyl)amino]-4-[(4-fluorophenyl)amino]-N-[4-(morpholin-4-ylmethyl)phenyl]pyridine-3-carboxamide | 493.35 | (400 MHz, DMSO- d$_6$): δ 10.26 (br s, 1H), 9.82 (s, 1H), 9.09 (s, 1H), 8.55 (s, 1H), 7.97 (br s, 1H), 7.66 (d, J = 8.40 Hz, 2H), 7.22-7.32 (m, 6H), 7.09 (s, 1H), 3.56 (br s, 4H), 3.42 (s, 2H), 3.12-3.15 (m, 2H), 2.33 (br s, 4H) and 1.05 (t, J = 7.20 Hz, 3H). |
| 202 | 6-[(ethylcarbamoyl)amino]-4-[(4-fluorophenyl)amino]-N-{4-[(4-methylpiperazin-1-yl)methyl]phenyl}pyridine-3-carboxamide | 506.29 | (400 MHz, DMSO- d$_6$): δ 10.25 (br s, 1H), 9.80 (s, 1H), 9.08 (s, 1H), 8.55 (s, 1H), 7.95 (br s, 1H), 7.66 (d, J = 8.40 Hz, 2H), 7.22-7.32 (m, 6H), 7.10 (s, 1H), 3.44 (s, 2H), 3.12-3.17 (m, 2H), 2.38-2.50 (m, 8H), 2.27 (s, 3H) and 1.05 (t, J = 7.20 Hz, 3H) |
| 203 | 4-[(4-cyanophenyl)amino]-6-[(ethylcarbamoyl)amino]-N-[4-(pyrrolidin-1-ylmethyl)phenyl]pyridine-3-carboxamide | 484.15 | (400 MHz, DMSO- d$_6$): δ 10.37 (br s, 1H), 10.13 (s, 1H), 9.24 (s, 1H), 8.60 (s, 1H), 7.83 (br s, 1H), 7.81 (d, J = 8.40 Hz, 2H), 7.66 (d, J = 8.0 Hz, 2H), 7.53 (s, 1H), 7.43 (d, J = 8.40 Hz, 2H), 7.30-7.32 (m, 2H), 3.65 (br s, 2H), 3.15-3.18 (m, 2H), 2.50 (br s, 4H), 1.73 (br s, 4H) and 1.07 (t, J = 7.20 Hz, 3H) |
| 204 | 4-[(4-cyanophenyl)amino]-6-[(ethylcarbamoyl)amino]-N-[4-(morpholin-4-ylmethyl)phenyl]pyridine-3-carboxamide | 500.15 | (400 MHz, DMSO- d$_6$): δ 10.36 (br s, 1H), 10.13 (s, 1H), 9.24 (s, 1H), 8.59 (s, 1H), 7.84 (br s, 1H), 7.81 (d, J = 8.40 Hz, 2H), 7.65 (d, J = 8.40 Hz, 2H), 7.53 (s, 1H), 7.43 (d, J = 8.80 Hz, 2H), 7.28 (d, J = 8.40 Hz, 2H), 3.56 (br s, 4H), 3.42 (s, 2H), 3.13-3.20 (m, 2H), 2.33 (br s, 4H) and 1.07 (t, J = 7.20 Hz, 3H) |
| 205 | 4-[(4-cyanophenyl)amino]-6-[(ethylcarbamoyl)amino]-N-{4-[(4-methylpiperazin-1-yl)methyl]phenyl}pyridine-3-carboxamide | 513.22 | (400 MHz, DMSO- d$_6$): δ 10.35 (br s, 1H), 10.13 (s, 1H), 9.24 (s, 1H), 8.59 (s, 1H), 7.83 (br s, 1H), 7.81 (d, J = 8.80 Hz, 2H), 7.64 (d, J = 8.40 Hz, 2H), 7.53 (s, 1H), 7.43 (d, J = 8.80 Hz, 2H), 7.26 (d, J = 8.40 Hz, 2H), 3.41 (s, 2H), 3.13-3.20 (m, 2H), 2.31-2.41 (m, 8H), 2.18 (s, 3H) and 1.07 (t, J = 7.20 Hz, 3H) |
| 206 | diethyl {4-[({6-[(ethylcarbamoyl)amino]-4-(phenylamino)pyridin-3-yl}carbonyl)amino]benzyl}phosphonate | 526.12 | (400 MHz, CDCl$_3$) δ 9.76 (s, 1H), 9.21 (t, J = 4.9 Hz, 1H), 8.39 (s, 1H), 8.35 (s, 1H), 7.55 (d, J = 8.3 Hz, 2H), 7.48 (s, 1H), 7.37 (t, J = 7.9 Hz, 2H), 7.29 (dd, J = 8.6, 2.4 Hz, 2H), 7.23-7.14 (m, 3H), 6.31 (s, 1H), 4.09-3.94 (m, 4H), 3.38-3.29 (m, 2H), 3.14 (d, J = 21.5 Hz, 2H), 1.26 (t, J = 7.1 Hz, 6H), 1.20 (t, J = 7.2 Hz, 3H). |
| 207 | {4-[({6-[(ethylcarbamoyl)amino]-4-(phenylamino)pyridin-3-yl}carbonyl)amino]benzyl}phosphonic acid | 469.92 | (400 MHz, DMSO) δ 10.56 (s, 1H), 10.17 (s, 1H), 8.48 (s, 1H), 7.57 (d, J = 8.3 Hz, 2H), 7.49 (t, J = 7.6 Hz, 2H), 7.39-7.22 (m, 5H), 3.16 (dt, J = 12.9, 7.2 Hz, 2H), 2.94 (d, J = 21.3 Hz, 2H), 1.07 (t, J = 7.2 Hz, 3H). |
| 208 | 3-{4-[({6-[(ethylcarbamoyl)amino]-4-[(4-methoxyphenyl)amino]pyridin-3-yl}carbonyl)amino]phenyl}-2,2-dimethylpropanoic acid | 506.29 | (400 MHz, DMSO- d$_6$): δ 12.07 (br s, 1H), 10.18 (br s, 1H), 9.70 (s, 1H), 9.02 (s, 1H), 8.53 (s, 1H), 7.99 (br s, 1H), 7.59 (d, J = 8.40 Hz, 2H), 7.19 (d, J = 8.80 Hz, 2H), 7.12 (d, J = 8.0 Hz, 2H), 6.96-6.99 (m, 3H), 3.77 (s, 3H), 3.09-3.16 (m, 2H), 2.75 (s, 2H) and 1.03-1.07 (m, 9H) |
| 209 | 4-(3,5-difluoroanilino)-6-(ethylcarbamoylamino)-N-[4-(1H-tetrazol-5-ylmethyl)phenyl]pyridine-3-carboxamide | 493.99 | |
| 210 | 6-[(ethylcarbamoyl)amino]-N-{4-[(methylsulfamoyl)methyl]phenyl}-4-(phenylamino)pyridine-3-carboxamide | 483.1 | (400 MHz, MeOD) δ 8.52 (s, 1H), 7.72-7.68 (m, 2H), 7.45-7.38 (m, 4H), 7.28 (dd, J = 8.5, 1.1 Hz, 2H), 7.21-7.16 (m, 1H), 6.87 (s, 1H), 4.32 (s, 2H), 3.30-3.24 (m, 2H), 2.66 (s, 3H), 1.19 (t, J = 7.2 Hz, 3H). |

TABLE 1-continued

Compounds and characterisation data

| No | Name | Observed LCMS [M + H]+ | 1H NMR |
|---|---|---|---|
| 211 | 5-[(ethylcarbamoyl)amino]-3-(phenylamino)-N-(pyridin-3-yl)pyrazine-2-carboxamide | 378.05 | (400 MHz, DMSO) δ 10.81 (s, 1H), 10.70 (s, 1H), 9.72 (s, 1H), 9.01 (dd, J = 2.5, 0.5 Hz, 1H), 8.32 (dd, J = 4.7, 1.5 Hz, 1H), 8.30 (s, 1H), 8.27-8.23 (m, 1H), 7.58 (dt, J = 8.4, 4.3 Hz, 3H), 7.44-7.37 (m, 3H), 7.18-7.12 (m, 1H), 3.17-3.00 (m, 2H), 0.96 (t, J = 7.2 Hz, 3H). |
| 212 | 6-[(ethylcarbamoyl)amino]-N-phenyl-4-(phenylamino)pyridazine-3-carboxamide | 377.11 | (400 MHz, Acetone) δ 10.59 (s, 1H), 10.36 (s, 1H), 8.73 (s, 1H), 7.95 (d, J = 8.5 Hz, 2H), 7.78 (bs, 1H), 7.61-7.56 (m, 1H), 7.49 (t, J = 7.9 Hz, 2H), 7.45-7.38 (m, 4H), 7.27 (t, J = 7.3 Hz, 1H), 7.17 (t, J = 7.4 Hz, 1H), 3.34-3.25 (m, 2H), 1.16 (t, J = 7.2 Hz, 3H). |
| 213 | 6-[(ethylcarbamoyl)amino]-N-[4-(methylcarbamoyl)phenyl]-4-(phenylamino)pyridine-3-carboxamide | 433.11 | (400 MHz, DMSO) δ 10.45 (s, 1H), 9.86 (s, 1H), 9.14 (s, 1H), 8.59 (s, 1H), 8.35 (q, J = 4.3 Hz, 1H), 7.93 (s, 1H), 7.88-7.69 (m, 4H), 7.48-7.35 (m, 2H), 7.31-7.25 (m, 3H), 7.19-7.13 (m, 1H), 3.19-3.10 (m, 2H), 2.78 (d, J = 4.5 Hz, 3H), 1.06 (t, J = 7.2 Hz, 3H). |
| 214 | N-{4-[(1,1-dioxidothiomorpholin-4-yl)methyl]phenyl}-6-[(ethylcarbamoyl)amino]-4-(phenylamino)pyridine-3-carboxamide | 523.1 | (400 MHz, DMSO) δ 10.29 (s, 1H), 9.92 (s, 1H), 9.12 (s, 1H), 8.57 (s, 1H), 7.97 (s, 1H), 7.67 (d, J = 8.5 Hz, 2H), 7.48-7.35 (m, 2H), 7.29 (dd, J = 13.9, 7.9 Hz, 5H), 7.15 (t, J = 7.4 Hz, 1H), 3.64 (s, 2H), 3.19-3.07 (m, 6H), 2.89-2.82 (m, 4H), 1.06 (t, J = 7.2 Hz, 3H). |
| 215 | ethyl 3-{4-[({4-[(3,4-difluorophenyl)amino]-6-[(ethylcarbamoyl)amino]pyridin-3-yl}carbonyl)amino]phenyl}propanoate | 512.13 | (400 MHz, DMSO) δ 10.25 (s, 1H), 9.89 (s, 1H), 9.14 (s, 1H), 8.58 (s, 1H), 8.01 (br s, 1H), 7.64-7.59 (m, 2H), 7.52-7.46 (m, 2H), 7.46-7.39 (m, 1H), 7.21 (d, J = 8.7 Hz, 3H), 7.16-7.10 (m, 1H), 4.06 (q, J = 7.1 Hz, 2H), 3.25-3.08 (m, 2H), 2.84 (t, J = 7.5 Hz, 2H), 2.62 (t, J = 7.5 Hz, 2H), 1.18 (t, J = 7.1 Hz, 3H), 1.09 (t, J = 7.2 Hz, 3H). |
| 216 | ethyl 3-{4-[({6-[(ethylcarbamoyl)amino]-4-[(3-fluorophenyl)amino]pyridin-3-yl}carbonyl)amino]phenyl}propanoate | 494.14 | (400 MHz, DMSO) δ 10.27 (s, 1H), 10.02 (s, 1H), 9.19 (s, 1H), 8.59 (s, 1H), 8.01 (br s, 1H), 7.66-7.56 (m, 2H), 7.43 (td, J = 8.2, 6.9 Hz, 1H), 7.36 (s, 1H), 7.22 (d, J = 8.6 Hz, 2H), 7.19-7.08 (m, 2H), 6.96 (ddd, J = 8.3, 2.5, 1.2 Hz, 1H), 4.06 (dt, J = 7.1, 5.4 Hz, 2H), 3.22-3.13 (m, 2H), 2.84 (t, J = 7.5 Hz, 2H), 2.62 (t, J = 7.5 Hz, 2H), 1.18 (t, J = 7.1 Hz, 3H), 1.09 (t, J = 7.2 Hz, 3H). |
| 217 | ethyl 3-{4-[({6-[(ethylcarbamoyl)amino]-4-[(3-fluoro-4-methylphenyl)amino]pyridin-3-yl}carbonyl)amino]phenyl}propanoate | 508.14 | (400 MHz, DMSO) δ 10.22 (s, 1H), 9.91 (s, 1H), 9.12 (s, 1H), 8.56 (s, 1H), 7.96 (s, 1H), 7.59 (d, J = 8.5 Hz, 2H), 7.32-7.24 (m, 2H), 7.19 (d, J = 8.6 Hz, 2H), 7.09 (dd, J = 11.4, 2.1 Hz, 1H), 7.00 (dd, J = 8.1, 2.1 Hz, 1H), 4.04 (q, J = 7.1 Hz, 2H), 3.19-3.11 (m, 2H), 2.82 (t, J = 7.5 Hz, 2H), 2.60 (t, J = 7.5 Hz, 2H), 2.22 (d, J = 1.1 Hz, 3H), 1.16 (t, J = 7.1 Hz, 3H), 1.07 (t, J = 7.2 Hz, 3H). |
| 218 | ethyl 3-{4-[({6-[(ethylcarbamoyl)amino]-4-[(4-fluoro-3-methylphenyl)amino]pyridin-3-yl}carbonyl)amino]phenyl}propanoate | 508.16 | (400 MHz, DMSO) δ 10.22 (s, 1H), 9.82 (s, 1H), 9.11 (s, 1H), 8.57 (s, 1H), 8.11 (br s, 1H), 7.61 (d, J = 8.5 Hz, 2H), 7.21 (dd, J = 8.8, 4.4 Hz, 4H), 7.15-7.09 (m, 1H), 7.07 (s, 1H), 4.11-4.00 (m, 2H), 3.22-3.11 (m, 2H), 2.84 (t, J = 7.5 Hz, 2H), 2.62 (dd, J = 9.7, 5.4 Hz, 2H), 2.26 (d, J = 1.7 Hz, 3H), 1.21-1.16 (m, 3H), 1.08 (t, J = 7.2 Hz, 3H). |
| 219 | ethyl 3-{4-[({4-[(4-chloro-2-fluorophenyl)amino]-6-[(ethylcarbamoyl)amino]pyridin-3-yl}carbonyl)amino]phenyl}propanoate | 528.1 | (400 MHz, DMSO) δ 10.28 (s, 1H), 9.93 (s, 1H), 9.14 (s, 1H), 8.61 (s, 1H), 7.90 (br s, 1H), 7.64-7.58 (m, 3H), 7.53 (d, J = 8.7 Hz, 1H), 7.39-7.32 (m, 1H), 7.22 (d, J = 8.6 Hz, 2H), 7.08 (s, 1H), 4.06 (dt, J = 7.1, 4.3 Hz, 2H), 3.22-3.11 (m, 2H), 2.84 (t, J = 7.5 Hz, 2H), 2.62 (t, J = 7.5 Hz, 2H), 1.18 (dd, J = 10.0, 4.2 Hz, 3H), 1.08 (t, J = 7.2 Hz, 3H). |
| 220 | 3-{4-[({4-[(3,4-difluorophenyl)amino]-6-[(ethylcarbamoyl)amino]pyridin-3-yl}carbonyl)amino]phenyl}propanoic acid | 484.09 | (400 MHz, DMSO) δ 12.12 (br s, 1H), 10.41 (br s, 1H), 9.99 (br s, 1H), 8.55 (s, 1H), 7.80 (br s, 1H), 7.61 (d, J = 8.5 Hz, 2H), 7.57-7.43 (m, 2H), 7.30-7.13 (m, 3H), 7.01 (br s, 1H), 3.22-3.14 (m, 2H), 2.82 (t, J = 7.5 Hz, 2H), 2.58-2.53 (m, 2H), 1.09 (t, J = 7.2 Hz, 3H). |
| 221 | 3-{4-[({6-[(ethylcarbamoyl)amino]-4-[(3-fluorophenyl)amino]pyridin-3-yl}carbonyl)amino]phenyl}propanoic acid | 466.11 | (400 MHz, DMSO) δ 12.05 (br s, 1H), 10.58 (br s, 1H), 10.17 (s, 1H), 8.53 (s, 1H), 7.66-7.57 (m, 3H), 7.50 (dd, J = 15.0, 8.0 Hz, 1H), 7.27-7.22 (m, 3H), 7.22-7.17 (m, 1H), 7.10 (t, J = 7.9 Hz, 1H), 6.99 (br s, 1H), 3.22-3.14 (m, 2H), 2.82 (t, J = 7.5 Hz, 2H), 2.58-2.54 (m, 2H), 1.10 (t, J = 7.2 Hz, 3H). |

TABLE 1-continued

Compounds and characterisation data

| No | Name | Observed LCMS [M + H]+ | 1H NMR |
|---|---|---|---|
| 222 | 3-{4-[({6-[(ethylcarbamoyl)amino]-4-[(3-fluoro-4-methylphenyl)amino]pyridin-3-yl}carbonyl)amino]phenyl}propanoic acid | 480.09 | (400 MHz, DMSO) δ 12.12 (br s, 1H), 10.63 (br s, 1H), 10.14 (s, 1H), 8.50 (s, 1H), 7.67-7.54 (m, 2H), 7.52-7.32 (m, 2H), 7.27-7.17 (m, 3H), 7.11 (dd, J = 8.1, 1.7 Hz, 1H), 6.81 (br s, 1H), 3.22-3.12 (m, 2H), 2.82 (t, J = 7.5 Hz, 2H), 2.59-2.54 (m, 2H), 2.27 (s, 3H), 1.09 (t, J = 7.2 Hz, 3H). |
| 223 | 3-{4-[({6-[(ethylcarbamoyl)amino]-4-[(4-fluoro-3-methylphenyl)amino]pyridin-3-yl}carbonyl)amino]phenyl}propanoic acid | 480.11 | (400 MHz, DMSO) δ 12.20 (br s, 1H), 10.67 (br s, 1H), 10.08 (s, 1H), 8.48 (s, 1H), 7.60 (d, J = 8.5 Hz, 2H), 7.48-7.11 (m, 6H), 6.59 (s, 1H), 3.22-3.13 (m, 2H), 2.82 (t, J = 7.5 Hz, 2H), 2.58-2.54 (m, 2H), 2.28 (d, J = 1.6 Hz, 3H), 1.12-1.05 (m, 3H). |
| 224 | 3-{4-[({4-[(4-chloro-2-fluorophenyl)amino]-6-[(ethylcarbamoyl)amino]pyridin-3-yl}carbonyl)amino]phenyl}propanoic acid | 500.08 | (400 MHz, DMSO) δ 10.64 (s, 1H), 10.29 (bs, 1H), 10.07 (s, 1H), 8.54 (s, 1H), 8.54 (s, 1H), 7.67 (dd, J = 10.3, 2.2 Hz, 1H), 7.59 (d, J = 8.5 Hz, 2H), 7.56-7.45 (m, 2H), 7.40 (dd, J = 8.6, 1.4 Hz, 1H), 7.23 (d, J = 8.6 Hz, 2H), 6.61 (bs, 1H), 3.20-3.11 (m, 2H), 2.81 (t, J = 7.5 Hz, 2H), 2.53 (dd, J = 7.1, 4.3 Hz, 2H), 1.07 (t, J = 7.2 Hz, 3H). |
| 225 | ethyl 3-{4-[({4-[(3,5-dichlorophenyl)amino]-6-[(ethylcarbamoyl)amino]pyridin-3-yl}carbonyl)amino]phenyl}propanoate | 544.09 | (400 MHz, DMSO) δ 10.29 (s, 1H), 9.97 (s, 1H), 9.29 (s, 1H), 8.59 (s, 1H), 8.12 (br s, 1H), 7.61 (d, J = 8.5 Hz, 2H), 7.36 (d, J = 1.8 Hz, 2H), 7.33-7.27 (m, 2H), 7.21 (d, J = 8.6 Hz, 2H), 4.06 (q, J = 7.1 Hz, 2H), 3.24-3.15 (m, 2H), 2.84 (t, J = 7.5 Hz, 2H), 2.62 (t, J = 7.5 Hz, 2H), 1.18 (t, J = 7.1 Hz, 3H), 1.10 (t, J = 7.2 Hz, 3H). |
| 226 | ethyl 3-{4-[({4-[(3-chloro-4-fluorophenyl)amino]-6-[(ethylcarbamoyl)amino]pyridin-3-yl}carbonyl)amino]phenyl}propanoate | 528.17 | (400 MHz, DMSO) δ 10.24 (s, 1H), 9.85 (s, 1H), 9.16 (s, 1H), 8.58 (s, 1H), 8.05 (br s, 1H), 7.64-7.59 (m, 2H), 7.54 (dd, J = 6.6, 2.6 Hz, 1H), 7.46 (t, J = 9.0 Hz, 1H), 7.30 (ddd, J = 8.9, 4.2, 2.7 Hz, 1H), 7.21 (d, J = 8.6 Hz, 2H), 7.14 (s, 1H), 4.06 (q, J = 7.1 Hz, 2H), 3.21-3.12 (m, 2H), 2.84 (t, J = 7.5 Hz, 2H), 2.62 (t, J = 7.5 Hz, 2H), 1.18 (t, J = 7.1 Hz, 3H), 1.09 (t, J = 7.2 Hz, 3H). |
| 227 | ethyl 3-{4-[({4-[(2,4-difluorophenyl)amino]-6-[(ethylcarbamoyl)amino]pyridin-3-yl}carbonyl)amino]phenyl}propanoate | 512.11 | (400 MHz, DMSO) δ 10.25 (s, 1H), 9.76 (s, 1H), 9.10 (s, 1H), 8.60 (s, 1H), 7.93 (br s, 1H), 7.62 (d, J = 8.5 Hz, 2H), 7.56-7.41 (m, 2H), 7.22 (d, J = 8.6 Hz, 2H), 7.20-7.15 (m, 1H), 6.91 (s, 1H), 4.06 (q, J = 7.1 Hz, 2H), 3.21-3.10 (m, 2H), 2.84 (t, J = 7.5 Hz, 2H), 2.62 (t, J = 7.5 Hz, 2H), 1.18 (t, J = 7.1 Hz, 3H), 1.08 (t, J = 7.2 Hz, 3H). |
| 228 | 3-{4-[({4-[(3,5-dichlorophenyl)amino]-6-[(ethylcarbamoyl)amino]pyridin-3-yl}carbonyl)amino]phenyl}propanoic acid | [M − H]− 513.86 | (400 MHz, DMSO) δ 10.62 (s, 1H), 10.31 (s, 1H), 10.16 (s, 1H), 8.53 (s, 1H), 7.60 (d, J = 8.5 Hz, 3H), 7.52-7.41 (m, 3H), 7.24 (d, J = 8.5 Hz, 2H), 6.94 (s, 1H), 3.26-3.13 (m, 2H), 2.82 (t, J = 7.5 Hz, 2H), 2.58-2.53 (m, 2H), 1.10 (t, J = 7.2 Hz, 3H). |
| 229 | 3-{4-[({4-[(3-chloro-4-fluorophenyl)amino]-6-[(ethylcarbamoyl)amino]pyridin-3-yl}carbonyl)amino]phenyl}propanoic acid | [M − H]− 497.89 | (400 MHz, DMSO) δ 10.67 (s, 1H), 10.46 (br s, 1H), 10.11 (s, 1H), 8.51 (s, 1H), 7.66 (dd, J = 6.6, 2.4 Hz, 1H), 7.63-7.59 (m, 2H), 7.59-7.52 (m, 1H), 7.52-7.43 (m, 1H), 7.43-7.37 (m, 1H), 7.25 (d, J = 8.6 Hz, 2H), 6.69 (s, 1H), 3.23-3.11 (m, 2H), 2.82 (t, J = 7.5 Hz, 2H), 2.58-2.53 (m, 2H), 1.09 (t, J = 7.2 Hz, 3H). |
| 230 | 3-{4-[({4-[(2,4-difluorophenyl)amino]-6-[(ethylcarbamoyl)amino]pyridin-3-yl}carbonyl)amino]phenyl}propanoic acid | 484.09 | (400 MHz, DMSO) δ 10.66 (s, 1H), 10.37 (br s, 1H), 9.98 (s, 1H), 8.54 (s, 1H), 7.63-7.59 (m, 2H), 7.57-7.50 (m, 2H), 7.47 (br s, 1H), 7.30-7.21 (m, 3H), 6.49 (br s, 1H), 3.22-3.11 (m, 2H), 2.83 (t, J = 7.5 Hz, 2H), 2.58-2.54 (m, 2H), 1.09 (t, J = 7.2 Hz, 3H). |
| 231 | 6-[(ethylcarbamoyl)amino]-4-(phenylamino)-N-(4-sulfamoylphenyl)pyridine-3-carboxamide | 455.09 | (400 MHz, DMSO) δ 10.55 (s, 1H), 9.85 (s, 1H), 9.13 (s, 1H), 8.61 (s, 1H), 7.93-7.85 (m, 3H), 7.80 (d, J = 8.8 Hz, 2H), 7.41 (t, J = 7.9 Hz, 2H), 7.31-7.24 (m, 4H), 7.17 (t, J = 7.4 Hz, 2H), 3.22-3.07 (m, 2H), 1.07 (t, J = 7.2 Hz, 3H). |
| 232 | 6-[(ethylcarbamoyl)amino]-N-{4-[(methylsulfonyl)amino]phenyl}-4-(phenylamino)pyridine-3-carboxamide | 469.09 | (400 MHz, DMSO) δ 10.27 (s, 1H), 9.94 (s, 1H), 9.60 (s, 1H), 9.10 (s, 1H), 8.57 (s, 1H), 7.96 (s, 1H), 7.69-7.63 (m, 2H), 7.44-7.37 (m, 2H), 7.27 (d, J = 7.0 Hz, 3H), 7.22-7.12 (m, 3H), 3.19-3.11 (m, 2H), 2.95 (s, 3H), 1.07 (t, J = 7.2 Hz, 3H). |
| 233 | {3-[({6-[(ethylcarbamoyl)amino]-4-(phenylamino)pyridin-3-yl}carbonyl)amino]-1H-pyrazol-1-yl}acetic acid | 424.06 | (400 MHz, DMSO) δ 10.94 (s, 1H), 10.44 (s, 1H), 8.52 (s, 1H), 8.09 (s, 1H), 7.64 (s, 1H), 7.55-7.20 (m, 6H), 6.79 (s, 1H), 4.96 (s, 2H), 3.15 (dt, J = 14.1, 7.0 Hz, 2H), 1.07 (t, J = 7.2 Hz, 3H). |

TABLE 1-continued

Compounds and characterisation data

| No | Name | Observed LCMS [M + H]+ | ¹H NMR |
|---|---|---|---|
| 234 | ethyl 3-{4-[({4-[(3,5-difluorophenyl)amino]-6-[(ethylcarbamoyl)amino]pyridin-3-yl}carbonyl)amino]phenyl}propanoate | 512.27 | (400 MHz, DMSO) δ 10.28 (s, 1H), 10.03 (s, 1H), 9.23 (s, 1H), 8.58 (s, 1H), 8.01 (s, 1H), 7.62-7.55 (m, 2H), 7.40 (s, 1H), 7.20 (d, J = 8.5 Hz, 2H), 7.07-6.97 (m, 2H), 6.97-6.88 (m, 1H), 4.04 (q, J = 7.1 Hz, 2H), 3.23-3.12 (m, 2H), 2.82 (t, J = 7.5 Hz, 2H), 2.60 (t, J = 7.5 Hz, 2H), 1.16 (t, J = 7.1 Hz, 3H), 1.08 (t, J = 7.2 Hz, 3H). |
| 235 | 3-{4-[({4-[(3,5-difluorophenyl)amino]-6-[(ethylcarbamoyl)amino]pyridin-3-yl}carbonyl)amino]phenyl}propanoic acid | 484.23 | (400 MHz, DMSO) δ 10.58 (s, 1H), 10.17 (s, 1H), 8.53 (s, 1H), 7.73-7.52 (m, 3H), 7.28-7.00 (m, 6H), 3.23-3.12 (m, 2H), 2.80 (t, J = 7.5 Hz, 2H), 2.53 (d, J = 7.7 Hz, 2H), 1.09 (t, J = 7.2 Hz, 3H). |
| 236 | 3-{4-[({6-[(ethylcarbamoyl)amino]-4-[(5-fluoropyridin-3-yl)amino]pyridin-3-yl}carbonyl)amino]phenyl}propanoic acid | 467.11 | (400 MHz, DMSO) δ 10.31 (s, 1H), 10.05 (br s, 1H), 9.21 (s, 1H), 8.61 (s, 1H), 8.45 (t, J = 1.7 Hz, 1H), 8.34 (d, J = 2.5 Hz, 1H), 8.02 (br s, 1H), 7.73 (dt, J = 10.9, 2.4 Hz, 1H), 7.62 (d, J = 8.5 Hz, 2H), 7.34 (s, 1H), 7.22 (d, J = 8.6 Hz, 2H), 3.23-3.14 (m, 2H), 2.81 (t, J = 7.5 Hz, 2H), 2.57-2.53 (m, 2H), 1.10 (t, J = 7.2 Hz, 3H). |
| 237 | 3-(4-{[(6-[(ethylcarbamoyl)amino]-4-{[3-(pentafluorothio)phenyl]amino}pyridin-3-yl)carbonyl]amino}phenyl)propanoic acid | 574.06 | (400 MHz, DMSO) δ 10.55 (br s, 1H), 10.15 (br s, 1H), 9.99 (br m, 1H), 8.53 (s, 1H), 7.87 (s, 1H), 7.82-7.74 (m, 1H), 7.73-7.65 (m, 2H), 7.61 (d, J = 8.5 Hz, 3H), 7.24 (d, J = 8.5 Hz, 2H), 6.96 (br s, 1H), 3.21-3.13 (m, 2H), 2.82 (t, J = 7.5 Hz, 2H), 2.55 (d, J = 7.6 Hz, 2H), 1.09 (t, J = 7.2 Hz, 3H). |
| 238 | 2-{4-[({4-[(3,5-difluorophenyl)amino]-6-[(ethylcarbamoyl)amino]pyridin-3-yl}carbonyl)amino]phenyl}cyclopropanecarboxylic acid | 496.22 | (400 MHz, DMSO) δ 10.36 (s, 1H), 10.05 (s, 1H), 8.57 (s, 1H), 7.93 (s, 1H), 7.59 (t, J = 8.6 Hz, 2H), 7.33 (s, 1H), 7.15 (d, J = 8.7 Hz, 2H), 7.05 (d, J = 8.0 Hz, 2H), 6.96 (s, 1H), 3.23-3.13 (m, 2H), 2.41-2.34 (m, 1H), 1.84-1.73 (m, 1H), 1.48-1.36 (m, 1H), 1.32 (ddd, J = 8.3, 6.5, 4.3 Hz, 1H), 1.08 (t, J = 7.2 Hz, 3H). |
| 239 | 3-{4-[({4-[(3,5-difluorophenyl)amino]-6-[(ethylcarbamoyl)amino]pyridin-3-yl}carbonyl)amino]phenyl}-2,2-dimethyl propanoic acid | 512.22 | (400 MHz, DMSO) δ 10.38 (s, 1H), 10.05 (s, 1H), 8.56 (s, 1H), 7.90 (s, 1H), 7.58 (d, J = 8.6 Hz, 2H), 7.30 (s, 1H), 7.13 (d, J = 8.5 Hz, 2H), 7.06 (d, J = 7.2 Hz, 2H), 6.96 (d, J = 8.5 Hz, 1H), 3.24-3.12 (m, 3H), 2.76 (s, 2H), 1.09 (d, J = 7.2 Hz, 3H), 1.07 (d, J = 2.9 Hz, 6H). |
| 240 | 3-(4-{[(6-[(ethylcarbamoyl)amino]-4-{[3-(trifluoromethyl)phenyl]amino}pyridin-3-yl)carbonyl]amino}phenyl)propanoic acid | 516.22 | (400 MHz, DMSO) δ 10.56 (s, 1H), 10.18 (s, 1H), 8.50 (s, 1H), 7.68 (d, J = 5.7 Hz, 3H), 7.59 (d, J = 8.5 Hz, 3H), 7.22 (d, J = 8.5 Hz, 2H), 6.89 (s, 1H), 3.22-3.10 (m, 3H), 2.80 (t, J = 7.5 Hz, 2H), 2.53 (d, J = 7.7 Hz, 2H), 1.07 (t, J = 7.2 Hz, 3H). |
| 241 | 3-(4-{[(6-[(ethylcarbamoyl)amino]-4-{[3-(trifluoromethoxy)phenyl]amino}pyridin-3-yl)carbonyl]amino}phenyl)propanoic acid | 532.1 | (400 MHz, DMSO) δ 10.60 (br s, 1H), 10.18 (s, 1H), 8.52 (s, 1H), 7.66-7.47 (m, 4H), 7.45-7.35 (m, 2H), 7.31-7.17 (m, 3H), 6.93 (br s, 1H), 3.23-3.12 (m, 2H), 2.82 (t, J = 7.5 Hz, 2H), 2.59-2.53 (m, 2H), 1.10 (t, J = 7.2 Hz, 3H). |
| 242 | 3-(4-{[(6-[(ethylcarbamoyl)amino]-4-{[4-(trifluoromethoxy)phenyl]amino}pyridin-3-yl)carbonyl]amino}phenyl)propanoic acid | 532.25 | (400 MHz, DMSO) δ 10.60 (s, 1H), 10.14 (s, 1H), 8.49 (s, 1H), 7.58 (d, J = 8.6 Hz, 2H), 7.51-7.44 (m, 5H), 7.23 (d, J = 8.6 Hz, 2H), 6.85-6.72 (m, 1H), 3.24-3.10 (m, 2H), 2.80 (t, J = 7.6 Hz, 2H), 2.56-2.50 (m, 2H), 1.07 (t, J = 7.2 Hz, 3H). |
| 243 | 5-[(ethylcarbamoyl)amino]-3-(phenylamino)-N-(pyridin-3-yl)pyridine-2-carboxamide | 377.19 | 1H NMR (400 MHz, DMSO) δ 10.67 (s, 1H), 10.20 (s, 1H), 9.08 (s, 1H), 9.00 (d, J = 2.2 Hz, 1H), 8.30 (dd, J = 4.7, 1.4 Hz, 1H), 8.28-8.23 (m, 1H), 8.10 (d, J = 2.1 Hz, 1H), 8.00 (d, J = 2.1 Hz, 1H), 7.44-7.35 (m, 3H), 7.31-7.26 (m, 2H), 7.16-7.09 (m, 1H), 6.37 (s, 1H), 3.14-3.05 (m, 2H), 1.04 (t, J = 7.2 Hz, 3H). |
| 244 | 4-[(3,5-difluorophenyl)amino]-6-[(ethylcarbamoyl)amino]-N-[4-(morpholin-4-ylmethyl)phenyl]pyridine-3-carboxamide | 511.02 | 1H NMR (400 MHz, DMSO) δ 10.33 (s, 1H), 10.02 (s, 1H), 9.24 (s, 1H), 8.59 (s, 1H), 8.02 (s, 1H), 7.64 (d, J = 8.5 Hz, 2H), 7.40 (s, 1H), 7.27 (d, J = 8.5 Hz, 2H), 7.03 (d, J = 7.7 Hz, 2H), 6.92 (t, J = 9.3 Hz, 1H), 3.60-3.54 (m, 4H), 3.43 (s, 2H), 3.22-3.13 (m, 2H), 2.38-2.29 (m, 4H), 1.08 (t, J = 7.2 Hz, 3H). |

TABLE 1-continued

Compounds and characterisation data

| No | Name | Observed LCMS [M + H]+ | 1H NMR |
|---|---|---|---|
| 245 | 4-[(3,5-difluorophenyl)amino]-N-(4-{[(2R,6S)-2,6-dimethylmorpholin-4-yl]methyl}phenyl)-6-[(ethylcarbamoyl)amino]pyridine-3-carboxamide | 538.99 | 1H NMR (400 MHz, DMSO) δ 10.35 (s, 1H), 10.03 (s, 1H), 9.26 (s, 1H), 8.61 (s, 1H), 8.04 (bs, 1H), 7.66 (d, J = 8.5 Hz, 2H), 7.42 (s, 1H), 7.28 (d, J = 8.5 Hz, 2H), 7.08-7.00 (m, 2H), 6.98-6.90 (m, 1H), 3.57 (dqd, J = 12.4, 6.1, 1.9 Hz, 2H), 3.42 (s, 2H), 3.24-3.15 (m, 2H), 2.67 (d, J = 10.2 Hz, 2H), 1.64 (t, J = 10.7 Hz, 2H), 1.10 (t, J = 7.2 Hz, 3H), 1.04 (d, J = 6.3 Hz, 6H). |
| 246 | ethyl 3-{4-[({6-[(ethylcarbamoyl)amino]-4-[(2,3,4-trifluorophenyl)amino]pyridin-3-yl}carbonyl)amino]phenyl}propanoate | 502.06 | 1H NMR (400 MHz, DMSO) δ 10.68 (s, 1H), 10.37 (br s, 1H), 10.07 (s, 1H), 8.56 (s, 1H), 7.61 (d, J = 8.5 Hz, 2H), 7.60-7.32 (m, 3H), 7.25 (d, J = 8.5 Hz, 2H), 6.60 (s, 1H), 3.24-3.08 (m, 2H), 2.83 (t, J = 7.5 Hz, 2H), 2.58-2.54 (m, 2H), 1.09 (t, J = 7.2 Hz, 3H). |
| 247 | ethyl 2-[[4-anilino-6-(ethylcarbamoylamino)pyridine-3-carbonyl]amino]thiazole-4-carboxylate | 455.08 | |
| 248 | 4-(4-chloroanilino)-6-(ethylcarbamoylamino)-N-(2-methylpyrimidin-5-yl)pyridine-3-carboxamide | 426.06 | |
| 249 | ethyl 3-[[4-anilino-6-(ethylcarbamoylamino)pyridine-3-carbonyl]amino]benzoate | 448.28 | |
| 250 | 1-[[4-[[4-(3,5-difluoroanilino)-6-(ethylcarbamoylamino)pyridine-3-carbonyl]amino]phenyl]methyl]pyrrolidine-2-carboxylic acid | 539.03 | |
| 251 | 1-[[4-[[4-(3,5-difluoroanilino)-6-(ethylcarbamoylamino)pyridine-3-carbonyl]amino]phenyl]methyl]piperidine-2-carboxylic acid | 553.06 | |

Biological Data

On-Target Enzyme Assay: Determination of Gyrase ATPase Activity

Gyrase converts ATP into ADP and inorganic phosphate. The released phosphate can be detected by the addition of malachite green solution and measured by monitoring the increase in absorbance at 600 nm. The ATPase assay is carried out in a buffer containing 10 nM Gyrase enzyme ($A_2B_2$ complex from *Staphylococcus aureus*), 0.08 mg/mL double-stranded DNA, 40 mM HEPES.KOH pH 7.6, 500 mM K glutamate, 10 mM Mg acetate, 2 mM DTT, 0.01 mg/mL BSA, 1 mM ATP and 5% DMSO solution containing the inhibitor. Alternatively, the ATPase assay is carried out in a buffer containing 10 nM Gyrase enzyme ($A_2B_2$ complex from *Escherichia coli*), 0.08 µg/mL ssDNA, 35 mM Tris pH 7.5, 24 mM KCl, 2 mM $MgCl_2$, 6.5% Glycerol, 2 mM DTT, 0.1 mg/mL BSA, 1 mM ATP and 1% DMSO solution containing the inhibitor. The reaction is started by adding ATP to a final concentration of 1 mM and allowed to incubate at 30° C. for 60 minutes. The reaction is stopped by adding 200 µL of malachite green solution (0.034% malachite green, 10 mM ammonium molybdate, 1 M HCl, 3.4% ethanol, 0.01% tween 20). Colour is allowed to develop for 5 minutes and the absorbance at 600 nm is measured spectrophotometrically. The $IC_{50}$ values are determined from the absorbance readings using no compound and no enzyme controls.

The compounds of the invention demonstrated on target enzyme activity with the majority of compounds tested showing Gyrase ATPase activity $IC_{50}$ values equal to or less than 10 µg/mL.

Surprisingly when the comparator compounds A, B, C and D below having a phenyl core in place of a heteroaryl core were tested in the same enzyme assay they did not demonstrate any measurable on-target activity (i.e. $IC_{50} \geq 200$ µg/mL).

4-(3-Ethylureido)-N-methyl-2-(phenylamino)-N-m-tolylbenzamide (Compound A)

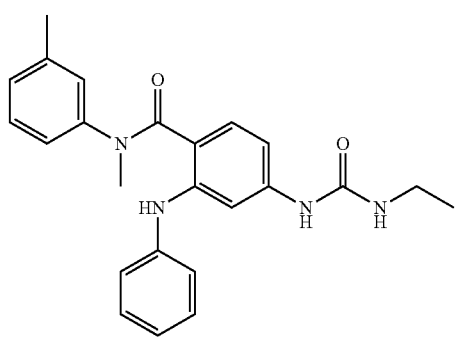 [SMILES: CCNC(=O)Nc1ccc(C(=O)N(C)c2cccc(C)c2)c(Nc2ccccc2)c1]

1H NMR (400 MHz, CDCl3) δ 7.82 (s, 1H), 7.33-7.21 (m, 2H), 7.14-7.05 (m, 4H), 6.99-6.93 (m, 2H), 6.89 (s, 1H), 6.84 (d, J=7.8 Hz, 1H), 6.80 (d, J=8.4 Hz, 1H), 6.50 (dd, J=8.5, 2.1

Hz, 1H), 6.26 (d, J=11.8 Hz, 1H), 4.68 (s, 1H), 3.43 (s, 3H), 3.24-3.15 (m, 2H), 2.25 (s, 3H), 1.07 (t, J=7.2 Hz, 3H). [M+H]+ m/z=402.93.

N-(3-Chlorophenyl)-4-(3-ethylureido)-2-(phenylamino)benzamide (Compound B)

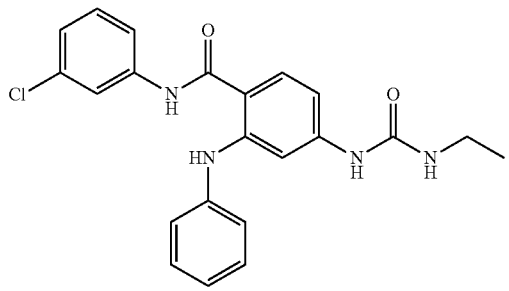 [SMILES: CCNC(=O)Nc1ccc(C(=O)Nc2cccc(Cl)c2)c(Nc2ccccc2)c1]

$^1$H NMR (400 MHz, CDCl$_3$) δ 9.24 (s, 1H), 8.03 (s, 1H), (ddd, J=8.2, 2.0, 0.9 Hz, 1H), 7.32-7.22 (m, 3H), 7.16 (d, J=7.5 Hz, 2H), 7.13-7.08 (m, 1H), 7.10 (d, J=2.1 Hz, 1H), 7.02 (t, J=7.3 Hz, 1H), 6.86 (dd, J=8.6, 2.1 Hz, 1H), 6.48 (s, 1H), 4.78 (t, J=5.4 Hz, 1H), 3.32-3.18 (m, 2H), 1.13 (t, J=7.2 Hz, 3H). [M+H]+ m/z=408.89.

4-(3-Ethylureido)-N-phenyl-2-(phenylamino)benzamide (Compound C)

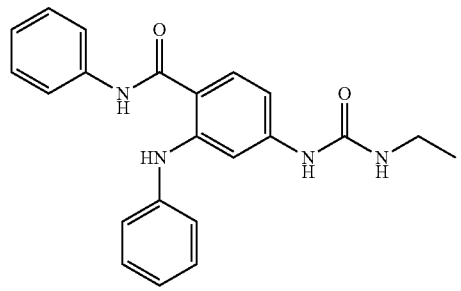 [SMILES: CCNC(=O)Nc1ccc(C(=O)Nc2ccccc2)c(Nc2ccccc2)c1]

$^1$H NMR (400 MHz, CDCl$_3$) δ 9.82 (br s, 1H), 9.41 (br s, 1H), 8.04 (br s, 1H), 7.80-7.75 (m, 2H), 7.73 (d, J=8.7 Hz, 1H), 7.55 (d, J=2.1 Hz, 1H), 7.33 (dd, J=15.5, 7.2 Hz, 4H), 7.25 (dd, J=8.6, 1.2 Hz, 2H), 7.12-7.07 (m, 1H), 7.04 (dd, J=8.7, 2.1 Hz, 1H), 7.02-6.96 (m, 1H), 5.78 (t, J=5.2 Hz, 1H), 3.21 (qd, J=7.2, 5.6 Hz, 2H), 1.09 (t, J=7.2 Hz, 3H). [M+H]+ m/z=375.

4-(3-Ethylureido)-2-(phenylamino)-N-(pyridin-3-yl)benzamide (Compound D)

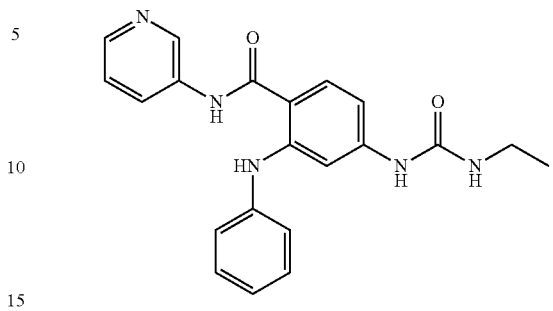

$^1$H NMR (400 MHz, DMSO-d6) δ 10.26 (s, 1H), 9.63 (s, 1H), 8.86 (d, J=2.3 Hz, 1H), 8.71 (s, 1H), 7.77 (d, J=8.8 Hz, 4.7, 1.4 Hz, 1H), 8.17-8.06 (m, 1H), 7.77 (d, J=8.8 Hz, 1H), 7.51 (d, J=2.0 Hz, 1H), 7.41-7.37 (m, 1H), 7.37-7.31 (m, 2H), 7.21 (dd, J=8.6, 1.0 Hz, 2H), 7.01 (t, J=7.3 Hz, 1H), 6.95 (dd, J=8.7, 2.1 Hz, 1H), 6.14 (t, J=5.6 Hz, 1H), 3.17-3.03 (m, 2H), 1.05 (t, J=7.2 Hz, 3H). [M+H]+ m/z=376.19.

Bacterial Assay

Determination of Antibacterial Activity

Compounds of the invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition*. Document M7-A7. CLSI, Wayne, Pa., 2006; Clinical Laboratories and Standards Institute. The Gram positive bacterial strains tested include *S. aureus* (*Staphylococcus aureus* (Isolate ID ATCC 29213)), *E. faecalis* (*Enterococcus faecalis* (Isolate ID ATCC 29212)) and *S. pyogenes* (*Streptococcus pyogenes* (Isolate ID ATCC 51339)). The Gram negative bacterial strains tested include *H. influenzae* (*Haemophilus influenzae* (Isolate ID ATCC 49247)).

Gram Positive Antibacterial Activity

Representative compounds of the invention were tested for activity against one or more Gram positive bacterial strains and the results are presented in Tables 2, 3 and 4.

TABLE 2

*S. aureus* (ATCC 29213) minimal inhibitory concentration (MIC)

| MIC (µg/mL) | Representative compound example number |
|---|---|
| ≤1 | 4, 13, 15, 17, 18, 20, 42, 48, 55, 56, 63, 66, 67, 69, 70, 77, 78, 79, 81, 85, 86, 89, 90, 91, 93, 96, 98, 105, 106, 107, 111, 117, 119, 122, 123, 130, 135, 139, 140, 141, 143, 144, 148, 149, 160, 161, 163, 170, 175, 176, 177, 178, 179, 181, 182, 183, 184, 187, 188, 189, 190, 192, 196, 204, 206, 208, 209, 215, 220, 221, 222, 223, 224, 228, 229, 230, 235, 237, 238, 239, 240 |
| 2 | 1, 23, 24, 46, 65, 76, 82, 88, 95, 97, 100, 104, 109, 118, 120, 129, 137, 142, 168, 169, 199, 201, 203, 205, 210, 226, 232 |
| 4 | 14, 32, 33, 34, 47, 60, 103, 110, 116, 134, 145, 147, 171, 174, 213, 214, 225, 231, 236 |
| 8 | 19, 59, 68, 128, 131, 132, 157, 162, 185, 194, 198, 200, 202 |
| 16 | 10, 71, 99, 153, 156, 165, 166, 167 |
| 32 | 8, 51, 52, 61, 113, 115, 186, 193 |

TABLE 3

E. faecalis (ATCC 29212) minimal inhibitory concentration (MIC)

| MIC (µg/mL) | Representative compound example number |
|---|---|
| ≤1 | 1, 4, 13, 17, 18, 19, 20, 21, 23, 24, 27, 28, 181, 187, 188, 189, 196, 198, 199, 201, 203, 204, 205, 206, 210, 213, 214, 215, 216, 217, 218, 219, 220, 221, 222, 223, 224, 225, 226, 227, 228, 229, 230, 231, 232, 234, 235, 236, 237, 238, 239, 240 |
| 2 | 25, 200, 202, 233 |
| 4 | 197 |
| 8 | 26, 207, 212 |
| 16 | — |

TABLE 4

S. pyogenes (ATCC 51339) minimal inhibitory concentration (MIC)

| MIC (µg/mL) | Representative compound example number |
|---|---|
| ≤1 | 13, 15, 16, 19, 20, 23, 24, 28, 42, 60, 63, 64, 65, 67, 68, 70, 71, 76, 77, 78, 79, 81, 85, 86, 88, 90, 91, 95, 96, 98, 99, 100, 103, 104, 105, 106, 109, 111, 116, 117, 118, 119, 120, 122, 123, 125, 128, 129, 130, 181, 188, 189, 196, 220, 221, 224, 228, 229, 235 |
| 2 | 10, 14, 17, 18, 51, 56, 59, 93, 107, 126 |
| 4 | 4, 46, 50, 55, 66, 69, 110, 113, 124, 131 |
| 8 | 25, 26, 32, 48, 52, 82, 87, 89, 114, 115 |
| 16 | 1, 8, 33, 61, 84, 108 |
| 32 | 34, 47, 97 |

Gram Negative Antibacterial Activity

Selected compounds of the invention were also tested for activity against the Gram negative bacterial strain *H. influenzae* (ATCC 49247) and the results are presented in Table 5.

TABLE 5

H. influenzae (ATCC 49247) minimal inhibitory concentration (MIC)

| MIC (µg/mL) | Representative compound example number |
|---|---|
| ≤1 | 181, 187, 188, 189, 196, 220, 221, 222, 223, 224, 228, 229, 230, 238, 239, 240 |
| 2 | 70, 71, 77, 78, 169, 180, 190, 192, 199, 237 |
| 4 | 67, 68, 103, 130, 137, 148, 149, 171, 175, 176, 177, 178, 182, 183, 184, 198, 204, 210, 231, 232, 235, 236 |
| 8 | 90, 123, 134, 160, 161, 163, 166, 168, 179 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The invention claimed is:

1. A compound of Formula (I), a racemate, an enantiomer or a salt thereof:

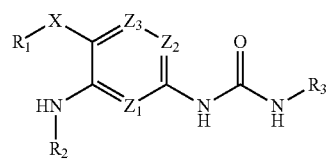

wherein

X is selected from C($=X_1$), S($=$O) and $SO_2$;

$X_1$ is selected from O, S and $NR_4$;

$R_1$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl, $CR_5(R_6)_2$, $NR_4SO_2R_5$, $OR_6$, $SR_6$, $NH_2$, $NR_5R_6$ and $NR^aR^b$ where $R^a$ and $R^b$ join with the N to which they are attached to form an optionally substituted 5-10 membered heterocyclic ring;

$R_2$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_3$ is an optionally substituted $C_{1-6}$alkyl;

$R_4$ is H or an optionally substituted $C_{1-6}$alkyl;

$R_5$ is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

Each $R_6$ is H or is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

t is an integer selected from 0, 1, 2 and 3 wherein each $(CH_2)_t$ when present may be independently optionally substituted;

$Z_1$, $Z_2$ and $Z_3$ are each independently selected from $CR_7$ and N where $R_7$ is selected from H, halo or an optional substituent and further where at least one of $Z_1$, $Z_2$ or $Z_3$ is N; and each cycloalkyl, cycloalkenyl, aryl, heterocyclyl and heteroaryl ring may be a monocyclic or fused bicyclic ring system.

2. A compound according to claim 1 wherein X is $C(=X_1)$, $X_1$ is selected from O, S and $NR_4$ and $R_1$ is selected from $NH_2$, $NR_5R_6$ and $NR^aR^b$.

3. A compound of claim 1 of Formula (Ia), a racemate, an enantiomer or a salt thereof:

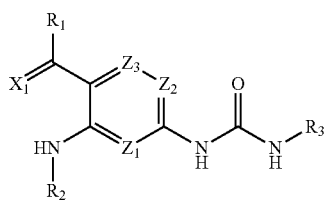

(Ia)

wherein $X_1$ is selected from O, S or $NR_4$;

$R_1$ is selected from $NH_2$, $NR_5R_6$ and $NR^aR^b$ where $R^a$ and $R^b$ join with the N to which they are attached to form an optionally substituted 5-10 membered heterocyclic ring;

$R_2$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_3$ is an optionally substituted $C_{1-6}$alkyl;

$R_4$ is H or an optionally substituted $C_{1-6}$alkyl;

$R_5$ is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_6$ is H or is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

t is an integer selected from 0, 1, 2 and 3 and wherein each $(CH_2)_t$ when present may be independently optionally substituted; and $Z_1$, $Z_2$ and $Z_3$ are each independently selected from $CR_7$ and N where each $R_7$ is independently selected from H, halo or an optional substituent and further where at least one of $Z_1$, $Z_2$ or $Z_3$ is N.

4. A compound of claim 1 wherein $X_1$ is O.

5. A compound of claim 1 wherein one of $Z_1$, $Z_2$ or $Z_3$ is N and the two remaining are each $CR_7$ where each $R_7$ is independently selected from selected from H, halo or an optional substituent.

6. A compound of claim 1 wherein two of $Z_1$, $Z_2$ or $Z_3$ are N and the one remaining is $CR_7$ where $R_7$ is independently selected from selected from H, halo or an optional substituent.

7. A compound of claim 1 wherein $R_1$ is $NR^aR^b$ and $R^a$ and $R^b$ join with the N to which they are attached to form an optionally substituted 5- or 6-membered heterocyclic ring.

8. A compound accordingly to claim 1 wherein $R_1$ is $NR_5R_6$.

9. A compound of claim 1 of Formula (Ib), a racemate, an enantiomer or a salt thereof:

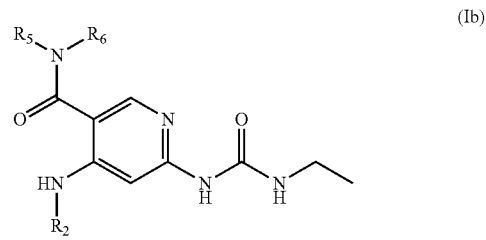

(Ib)

wherein $R_2$ is optionally substituted and selected from $C_{1-6}$alkyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_5$ is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl;

$R_6$ is H or is optionally substituted and selected from $C_{1-6}$alkyl, $C_{1-6}$alkoxyl, $C_{2-6}$alkenyl, $C_{2-6}$alkynyl, $(CH_2)_tC_{3-10}$cycloalkyl, $(CH_2)_tC_{3-10}$cycloalkenyl, $(CH_2)_tC_{6-10}$aryl, $(CH_2)_t$3-10-membered heterocyclyl and $(CH_2)_t$5-10-membered heteroaryl; and t is an integer selected from 0, 1, 2 and 3 wherein each $(CH_2)_t$ when present may be independently optionally substituted.

10. A compound of claim 1 wherein $R_2$ is selected from an optionally substituted cyclohexyl, an optionally substituted $(CH_2)_t$phenyl, an optionally substituted 5-6-membered heterocyclyl and an optionally substituted $(CH_2)_t$5-6-membered heteroaryl ring where t is 0 or 1.

11. A compound of claim 1 wherein $R_5$ is selected from an optionally substituted $C_{1-3}$alkyl, an optionally substituted $C_{3-6}$cycloalkyl, an optionally substituted $(CH_2)_t$phenyl, an optionally substituted 5-6-membered heterocyclyl, an optionally substituted $(CH_2)_t$5-6-membered heteroaryl ring and an optionally substituted 9-10-membered heteroaryl ring where t is an integer 0, 1 or 2.

12. A compound of claim 1 wherein $R_2$ and $R_5$ are each independently selected from an optionally substituted $(CH_2)_t$phenyl, an optionally substituted $(CH_2)_t$5-6-membered heterocyclyl, an optionally substituted $(CH_2)_t$5-6-membered heteroaryl ring and an optionally substituted $(CH_2)_t$9-10-membered heteroaryl ring where t is an integer 0, 1 or 2 and $R_6$ is H.

13. A compound of claim 1 selected from the group consisting of:
  6-(3-ethylureido)-N-m-tolyl-4-(m-tolylamino)nicotinamide;
  6-(3-ethylureido)-N-(thiazol-2-yl)-4-(m-tolylamino)nicotinamide;
  4-(cyclohexylamino)-6-(3-ethylureido)-N-m-tolylnicotinamide;
  N-(3-chlorophenyl)-6-(3-ethylureido)-4-(phenylamino) nicotinamide;
  2-(3-ethylureido)-N-phenyl-4-(phenylamino)pyrimidine-5-carboxamide;
  2-(3-ethylureido)-4-(phenylamino)-N-(pyridin-3-yl)pyrimidine-5-carboxamide;

N-(3-chlorophenyl)-2-(3-ethylureido)-4-(phenylamino) pyrimidine-5-carboxamide;
N-ethyl-6-(3-ethylureido)-4-(phenylamino)nicotinamide;
N-(2-chlorophenyl)-6-(3-ethylureido)-4-(phenylamino) nicotinamide;
6-(3-ethylureido)-N-(1-methyl-1H-pyrazol-5-yl)-4-(phenylamino) nicotinamide;
6-(3-ethylureido)-4-(phenylamino)-N-(2-(trifluoromethyl)phenyl) nicotinamide;
ethyl (2E)-3-{4-[({6-[(ethylcarbamoyl)amino]-4-(phenylamino)pyridin-3-yl}carbonyl)amino]phenyl}prop-2-enoate;
6-(3-ethylureido)-N-phenyl-4-(pyridin-3-ylamino)nicotinamide;
6-(3-ethylureido)-4-(4-methoxyphenylamino)-N-(pyridin-3-yl)nicotinamide;
ethyl 4-(2-(3-ethylureido)-5-(pyridin-3-ylcarbamoyl)pyridin-4-ylamino)benzoate;
4-(2-(3-ethylureido)-5-(pyridin-3-ylcarbamoyl)pyridin-4-ylamino)benzoic acid;
6-(3-ethylureido)-N-phenyl-4-(phenylamino)nicotinamide;
6-(3-ethylureido)-4-(phenylamino)-N-m-tolylnicotinamide;
6-(3-ethylureido)-N-(pyridin-3-yl)-4-(pyridin-3-ylamino) nicotinamide;
6-(3-ethylureido)-4-(phenylamino)-N-(pyridin-3-yl)nicotinamide;
methyl 4-(6-(3-ethylureido)-4-(phenylamino)nicotinamido)picolinate;
ethyl 6-(3-ethylureido)-4-(pyridin-3-ylmethylamino) nicotinate;
6-(3-ethylureido)-N-(6-morpholinopyridin-3-yl)-4-(phenylamino)nicotinamide;
N-(6-acetamidopyridin-3-yl)-6-(3-ethylureido)-4-(phenylamino) nicotinamide;
6-(3-ethylureido)-N-phenyl-4-(pyridin-3-ylmethylamino) nicotinamide;
6-(3-ethylureido)-N-(pyridin-3-yl)-4-(pyridin-3-ylmethylamino) nicotinamide;
N-(6-(1H-1,2,4-triazol-1-yl)pyridin-3-yl)-6-(3-ethylureido)-4-(phenylamino)nicotinamide;
6-(3-ethylureido)-4-(phenylamino)-N-(pyridin-3-ylmethyl)nicotinamide;
2-(3-ethylureido)-N-phenyl-4-(pyridin-3-ylamino)pyrimidine-5-carboxamide;
6-(3-ethylureido)-N,N-dimethyl-4-(phenylamino)nicotinamide;
6-(3-ethylureido)-N-(2-methoxyphenyl)-4-(phenylamino)nicotinamide;
6-(3-ethylureido)-N-(3-methoxyphenyl)-4-(phenylamino)nicotinamide;
6-(3-ethylureido)-N-(4-methoxyphenyl)-4-(phenylamino)nicotinamide;
N-(4-chlorophenyl)-6-(3-ethylureido)-4-(phenylamino) nicotinamide;
2-(3-ethylureido)-N-(pyridin-3-yl)-4-(pyridin-3-ylamino) pyrimidine-5-carboxamide;
6-(3-ethylureido)-N-isopropyl-4-(phenylamino)nicotinamide;
N-cyclopentyl-6-(3-ethylureido)-4-(phenylamino)nicotinamide;
N-cyclopropyl-6-(3-ethylureido)-4-(phenylamino)nicotinamide;
6-(3-ethylureido)-N-methyl-4-(phenylamino)nicotinamide;
6-(3-ethylureido)-N-(2-methoxyethyl)-4-(phenylamino) nicotinamide;
1-ethyl-3-(5-(morpholine-4-carbonyl)-4-(phenylamino) pyridin-2-yl)urea;
6-(3-ethylureido)-4-(phenylamino)-N-(pyridin-4-yl)nicotinamide;
6-(3-ethylureido)-N-phenethyl-4-(phenylamino)nicotinamide;
N-benzyl-6-(3-ethylureido)-4-(phenylamino)nicotinamide;
N-cyclohexyl-6-(3-ethylureido)-4-(phenylamino)nicotinamide;
6-(3-ethylureido)-4-(phenylamino)-N-p-tolylnicotinamide
6-(3-ethylureido)-4-(phenylamino)-N-(4-(trifluoromethyl)phenyl) nicotinamide;
6-(3-ethylureido)-4-(phenylamino)-N-(3-(trifluoromethyl)phenyl) nicotinamide;
6-(3-ethylureido)-4-(phenylamino)-N-(pyridin-2-yl)nicotinamide;
N-(3,5-dimethylisoxazol-4-yl)-6-(3-ethylureido)-4-(phenylamino) nicotinamide;
6-(3-ethylureido)-4-(phenylamino)-N-(pyridin-4-ylmethyl)nicotinamide;
6-(3-ethylureido)-4-(phenylamino)-N-(pyridin-2-ylmethyl)nicotinamide;
1-ethyl-3-(5-(4-methylpiperazine-1-carbonyl)-4-(phenylamino)pyridin-2-yl)urea;
1-(5-(4-acetylpiperazine-1-carbonyl)-4-(phenylamino) pyridin-2-yl)-3-ethylurea;
6-(3-ethylureido)-N-(4-fluorophenyl)-4-(phenylamino) nicotinamide;
6-(3-ethylureido)-N-(3-fluorophenyl)-4-(phenylamino) nicotinamide;
6-(3-ethylureido)-N-(2-fluorophenyl)-4-(phenylamino) nicotinamide;
6-(3-ethylureido)-4-(phenylamino)-N-o-tolylnicotinamide;
6-(3-ethylureido)-N-(1-methyl-1H-pyrazol-3-yl)-4-(phenylamino) nicotinamide;
6-(3-ethylureido)-4-(phenylamino)-N-(pyrimidin-5-yl) nicotinamide;
6-(3-ethylureido)-4-(phenylamino)nicotinamide;
6-(3-ethylureido)-4-(phenylamino)-N-(thiazol-2-yl)nicotinamide;
6-(3-ethylureido)-N-(6-methoxypyridin-3-yl)-4-(phenylamino) nicotinamide;
6-(3-ethylureido)-4-(phenylamino)-N-(pyridazin-4-yl) nicotinamide;
6-(3-ethylureido)-N-(1-methyl-1H-pyrazol-4-yl)-4-(phenylamino) nicotinamide;
N-(3,5-difluorophenyl)-6-(3-ethylureido)-4-(phenylamino)nicotinamide;
methyl 4-(6-(3-ethylureido)-4-(phenylamino)nicotinamido)benzoate;
4-(6-(3-ethylureido)-4-(phenylamino)nicotinamido)benzoic acid;
N-(3,4-difluorophenyl)-6-(3-ethylureido)-4-(phenylamino)nicotinamide;
ethyl 2-(4-(6-(3-ethylureido)-4-(phenylamino)nicotinamido)phenyl)acetate;
2-(4-(6-(3-ethylureido)-4-(phenylamino)nicotinamido) phenyl)acetic acid;
N-(benzo[d]thiazol-2-yl)-6-(3-ethylureido)-4-(phenylamino) nicotinamide;
6-(3-ethylureido)-N-(4-methylthiazol-2-yl)-4-(phenylamino) nicotinamide;

N-(3,5-dimethylphenyl)-6-(3-ethylureido)-4-(phenylamino)nicotinamide;
6-(3-ethylureido)-4-(phenylamino)-N-(6-(trifluoromethyl)pyridin-3-yl) nicotinamide;
6-(3-ethylureido)-N-(imidazo[1,2-a]pyridin-6-yl)-4-(phenylamino) nicotinamide;
methyl 3-(4-(6-(3-ethylureido)-4-(phenylamino)nicotinamido)phenyl)propanoate;
3-(4-(6-(3-ethylureido)-4-(phenylamino)nicotinamido)phenyl)propanoic acid;
6-(3-ethylureido)-N-(5-methoxypyridin-3-yl)-4-(phenylamino) nicotinamide;
6-(3-ethylureido)-N-(2-methyl-4-oxo-4H-chromen-7-yl)-4-(phenylamino)nicotinamide;
6-(3-ethylureido)-N-(6-methylpyridin-3-yl)-4-(phenylamino) nicotinamide;
6-(3-ethylureido)-N-(6-(4-fluorophenoxyl)pyridin-3-yl)-4-(phenylamino)nicotinamide
6-(3-ethylureido)-N-methoxy-N-methyl-4-(phenylamino) nicotinamide;
5-(6-(3-ethylureido)-4-(phenylamino)nicotinamido)nicotinic acid;
6-(3-ethylureido)-N-(5-fluoropyridin-3-yl)-4-(phenylamino) nicotinamide;
methyl 4-(6-(3-ethylureido)-4-(phenylamino)nicotinamido)-1-methyl-1H-pyrrole-2-carboxylate;
3-(2-(3-ethylureido)-5-(pyridin-3-ylcarbamoyl)pyridin-4-ylamino)benzoic acid;
6-(3-ethylureido)-N-(3-methyl-3H-imidazo[4,5-b]pyridin-6-yl)-4-(phenylamino)nicotinamide;
methyl 5-(6-(3-ethylureido)-4-(phenylamino)nicotinamido)nicotinate;
6-(3-ethylureido)-N-(2-methylpyridin-4-yl)-4-(phenylamino) nicotinamide;
6-(3-ethylureido)-N-(5-methylpyridin-3-yl)-4-(phenylamino) nicotinamide;
6-(3-ethylureido)-4-(phenylamino)-N-(quinolin-3-yl) nicotinamide;
6-(3-ethylureido)-N-(3-fluoro-5-methylphenyl)-4-(phenylamino) nicotinamide;
6-(3-ethylureido)-N-(1-methyl-1H-indol-4-yl)-4-(phenylamino) nicotinamide;
6-(3-ethylureido)-N-(6-(isopropylamino)pyridin-3-yl)-4-(phenylamino) nicotinamide;
methyl 4-(2-(3-ethylureido)-5-(pyridin-3-ylcarbamoyl)pyridin-4-ylamino)benzoate;
methyl 3-(2-(3-ethylureido)-5-(pyridin-3-ylcarbamoyl)pyridin-4-ylamino)benzoate;
N-(6-(dimethylamino)pyridin-3-yl)-6-(3-ethylureido)-4-(phenylamino)nicotinamide;
6-(3-ethylureido)-N-(1-methyl-6-oxo-1,6-dihydropyridin-3-yl)-4-(phenylamino)nicotinamide;
6-(3-ethylureido)-N-(6-(4-hydroxypiperidin-1-yl)pyridin-3-yl)-4-(phenylamino)nicotinamide;
6-(3-ethylureido)-N-(6-methoxyquinolin-3-yl)-4-(phenylamino) nicotinamide;
methyl 2-(6-(3-ethylureido)-4-(phenylamino)nicotinamido)benzo[d]thiazole-6-carboxylate;
4-(6-(3-ethylureido)-4-(phenylamino)nicotinamido)-1-methyl-1H-pyrrole-2-carboxylic acid;
N-(6-cyanopyridin-3-yl)-6-(3-ethylureido)-4-(phenylamino)nicotinamide;
4-(2-chlorophenylamino)-6-(3-ethylureido)-N-(pyridin-3-yl) nicotinamide;
4-(4-chlorophenylamino)-6-(3-ethylureido)-N-(pyridin-3-yl) nicotinamide;
4-(3-chlorophenylamino)-6-(3-ethylureido)-N-(pyridin-3-yl) nicotinamide;
6-(3-ethylureido)-4-(1-methyl-6-oxo-1,6-dihydropyridin-3-ylamino)-N-(pyridin-3-yl)nicotinamide;
6-(3-ethylureido)-4-(2-methoxyphenylamino)-N-(pyridin-3-yl)nicotinamide;
ethyl 2-(4-(2-(3-ethylureido)-5-(pyridin-3-ylcarbamoyl)pyridin-4-ylamino)phenyl)acetate;
6-(3-ethylureido)-4-(3-methoxyphenylamino)-N-(pyridin-3-yl)nicotinamide;
1-(5-benzoyl-4-(phenylamino)pyridin-2-yl)-3-ethylurea;
6-(3-ethylureido)-4-(1-methyl-1H-pyrazol-4-ylamino)-N-(pyridin-3-yl)nicotinamide;
2-(4-(2-(3-ethylureido)-5-(pyridin-3-ylcarbamoyl)pyridin-4-ylamino)phenyl)acetic acid;
4-(3,5-dimethylisoxazol-4-ylamino)-6-(3-ethylureido)-N-(pyridin-3-yl)nicotinamide;
6-(3-ethylureido)-4-(1-methyl-1H-pyrazol-3-ylamino)-N-(pyridin-3-yl)nicotinamide;
6-(3-ethylureido)-N-(4-(3-hydroxypropyl)phenyl)-4-(phenylamino) nicotinamide;
N-(4-(3-amino-3-oxopropyl)phenyl)-6-(3-ethylureido)-4-(phenylamino)nicotinamide;
N-(4-(3-(dimethylamino)-3-oxopropyl)phenyl)-6-(3-ethylureido)-4-(phenylamino)nicotinamide;
6-(3-ethylureido)-N-(4-(3-(methylamino)-3-oxopropyl)phenyl)-4-(phenylamino)nicotinamide;
6-(3-ethylureido)-N-methyl-N-phenyl-4-(phenylamino) nicotinamide;
6-(3-ethylureido)-N-(4-(3-oxobutyl)phenyl)-4-(phenylamino) nicotinamide;
6-(3-ethylureido)-N-(4-(3-(methoxy(methyl)amino)-3-oxopropyl)phenyl)-4-(phenylamino)nicotinamide;
4-(4-(dimethylcarbamoyl)phenylamino)-6-(3-ethylureido)-N-(pyridin-3-yl)nicotinamide;
4-(4-carbamoylphenylamino)-6-(3-ethylureido)-N-(pyridin-3-yl)nicotinamide;
6-(3-ethylureido)-4-(4-(methylcarbamoyl)phenylamino)-N-(pyridin-3-yl)nicotinamide;
1-ethyl-3-(5-(2-phenylacetyl)-4-(phenylamino)pyridin-2-yl)urea;
6-(3-ethylureido)-4-(4-(hydroxymethyl)phenylamino)-N-(pyridin-3-yl)nicotinamide;
methyl 3-(4-(6-(3-ethylureido)-4-(phenylamino)nicotinamido)phenyl)-2,2-dimethylpropanoate;
3-(4-(6-(3-ethylureido)-4-(phenylamino)nicotinamido)phenyl)-2,2-dimethylpropanoic acid;
ethyl 3-(4-(2-(3-ethylureido)-5-(pyridin-3-ylcarbamoyl)pyridin-4-ylamino)phenyl)propanoate;
N-(4-azidophenyl)-4-[(4-chlorophenyl)amino]-6-[(ethylcarbamoyl)amino]pyridine-3-carboxamide;
ethyl 1-{4-[({4-[(4-chlorophenyl)amino]-6-[(ethylcarbamoyl)amino]pyridin-3-yl}carbonyl)amino]phenyl}-1H-1,2,3-triazole-4-carboxylate;
6-[(ethylcarbamoyl)amino]-N-(1-methyl-2-oxo-1,2-dihydropyridin-4-yl)-4-(phenylamino)pyridine-3-carboxamide;
6-[(ethylcarbamoyl)amino]-N-[4-(3-hydroxyprop-1-yn-1-yl)phenyl]-4-(phenylamino)pyridine-3-carboxamide;
ethyl 1-{5-[({6-[(ethylcarbamoyl)amino]-4-(pyridin-3-ylamino)pyridin-3-yl}carbonyl)amino]pyrimidin-2-yl}-4-methylpiperidine-4-carboxylate;
(2E)-3-{4-[({6-[(ethylcarbamoyl)amino]-4-(phenylamino)pyridin-3-yl}carbonyl)amino]phenyl}prop-2-enoic acid;
3-[4-({2-[(ethylcarbamoyl)amino]-5-(pyridin-3-ylcarbamoyl)pyridin-4-yl}amino)phenyl]propanoic acid;

6-[(ethylcarbamoyl)amino]-4-[(4-fluorophenyl)amino]-Nyridin-3-yl)pyridine-3-carboxamide;
6-[(ethylcarbamoyl)amino]-4-[(4-methylphenyl)amino]-Nyridin-3-yl)pyridine-3-carboxamide;
6-[(ethylcarbamoyl)amino]-Nyridin-3-yl)-4-{[3-(trifluoromethyl)phenyl]amino}pyridine-3-carboxamide;
6-[(ethylcarbamoyl)amino]-Nyridin-3-yl)-4-{[4-(trifluoromethyl)phenyl]amino}pyridine-3-carboxamide;
6-[(ethylcarbamoyl)amino]-4-[(3-fluorophenyl)amino]-Nyridin-3-yl)pyridine-3-carboxamide;
6-[(ethylcarbamoyl)amino]-4-[(2-fluorophenyl)amino]-Nyridin-3-yl)pyridine-3-carboxamide;
6-[(ethylcarbamoyl)amino]-4-[(6-methoxypyridin-3-yl)amino]-Nyridin-3-yl)pyridine-3-carboxamide;
ethyl {4-[({6-[(ethylcarbamoyl)amino]-4-(phenylamino)pyridin-3-yl}carbonyl)amino]phenoxy}acetate;
methyl 3-{4-[({6-[(ethylcarbamoyl)amino]-4-(pyridin-3-ylamino)pyridin-3-yl}carbonyl)amino]phenyl}propanoate;
methyl 3-{4-[({4-[(4-chlorophenyl)amino]-6-[(ethylcarbamoyl)amino]pyridin-3-yl}carbonyl)amino]phenyl}propanoate;
3-{4-[({4-[(4-chlorophenyl)amino]-6-[(ethylcarbamoyl)amino]pyridin-3-yl}carbonyl)amino]phenyl}propanoic acid;
{4-[({6-[(ethylcarbamoyl)amino]-4-(phenylamino)pyridin-3-yl}carbonyl)amino]phenoxy}acetic acid;
N-(6-chloropyridin-3-yl)-6-[(ethylcarbamoyl)amino]-4-(pyridin-3-ylamino)pyridine-3-carboxamide;
6-[(ethylcarbamoyl)amino]-N-[2-(3-hydroxyazetidin-1-yl)pyrimidin-5-yl]-4-(pyridin-3-ylamino)pyridine-3-carboxamide;
3-{4-[({6-[(ethylcarbamoyl)amino]-4-(pyridin-3-ylamino)pyridin-3-yl}carbonyl)amino]phenyl}propanoic acid;
methyl 1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylate;
1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylic acid;
methyl 1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylate;
6-[(ethylcarbamoyl)amino]-4-[(5-methylpyridin-3-yl)amino]-Nyridin-3-yl)pyridine-3-carboxamide;
1-[({5-[({6-[(ethylcarbamoyl)amino]-4-(pyridin-3-ylamino)pyridin-3-yl}carbonyl)amino]pyrimidin-2-yl}amino)methyl]cyclobutanecarboxylic acid;
methyl 3-{4-[({4-[(4-chlorophenyl)amino]-6-[(ethylcarbamoyl)amino]pyridin-3-yl}carbonyl)amino]phenyl}-2,2-dimethylpropanoate;
3-{4-[({4-[(4-chlorophenyl)amino]-6-[(ethylcarbamoyl)amino]pyridin-3-yl}carbonyl)amino]phenyl}-2,2-dimethylpropanoic acid;
4-(3,5-difluoroanilino)-6-(ethylcarbamoylamino)-N-[4-[2-(1H-tetrazol-5-yl)ethyl]phenyl]pyridine-3-carboxamide;
6-[(ethylcarbamoyl)amino]-4-[(2-methylpyridin-4-yl)amino]-Nyridin-3-yl)pyridine-3-carboxamide;
6-[(ethylcarbamoyl)amino]-4-[(2-methoxypyridin-4-yl)amino]-Nyridin-3-yl)pyridine-3-carboxamide;
ethyl 1-({5-[({4-[(4-chlorophenyl)amino]-6-[(ethylcarbamoyl)amino]pyridin-3-yl}carbonyl)amino]pyrimidin-2-yl}amino)cyclobutanecarboxylate;
1-({5-[({4-[(4-chlorophenyl)amino]-6-[(ethylcarbamoyl)amino]pyridin-3-yl}carbonyl)amino]pyrimidin-2-yl}amino)cyclobutanecarboxylic acid;
3-{5-[({6-[(ethylcarbamoyl)amino]-4-(phenylamino)pyridin-3-yl}carbonyl)amino]pyridin-2-yl}propanoic acid;
6-[(ethylcarbamoyl)amino]-4-[(6-methylpyridin-3-yl)amino]-Nyridin-3-yl)pyridine-3-carboxamide;
1-[({5-[({6-[(ethylcarbamoyl)amino]-4-(phenylamino)pyridin-3-yl}carbonyl)amino]pyrimidin-2-yl}amino)methyl]cyclobutanecarboxylic acid;
(1R,2R)-2-{4-[({6-[(ethylcarbamoyl)amino]-4-(phenylamino)pyridin-3-yl}carbonyl)amino]phenyl}cyclopropanecarboxylic acid;
methyl 3-{4-[({6-[(ethylcarbamoyl)amino]-4-(pyridin-3-ylamino)pyridin-3-yl}carbonyl)amino]phenyl}-2,2-dimethylpropanoate;
3-{4-[({6-[(ethylcarbamoyl)amino]-4-(pyridin-3-ylamino)pyridin-3-yl}carbonyl)amino]phenyl}-2,2-dimethylpropanoic acid;
4-{[6-(acetylamino)pyridin-3-yl]amino}-6-[(ethylcarbamoyl)amino]-Nyridin-3-yl)pyridine-3-carboxamide;
6-[(ethylcarbamoyl)amino]-Nyridin-3-yl)-4-(pyrimidin-5-ylamino)pyridine-3-carboxamide;
6-[(ethylcarbamoyl)amino]-4-[(5-methoxypyridin-3-yl)amino]-Nyridin-3-yl)pyridine-3-carboxamide;
3-{4-[({6-[(ethylcarbamoyl)amino]-4-[(4-fluorophenyl)amino]pyridin-3-yl}carbonyl)amino]phenyl}-2,2-dimethylpropanoic acid;
3-{4-[[6-(ethylcarbamoylamino)-4-[4-(trifluoromethyl)anilino]pyridine-3-carbonyl]amino]phenyl]propanoic acid;
3-{4-[({4-[(3-chlorophenyl)amino]-6-[(ethylcarbamoyl)amino]pyridin-3-yl}carbonyl)amino]phenyl}-2,2-dimethylpropanoic acid;
3-{4-[({6-[(ethylcarbamoyl)amino]-4-[(3-methoxyphenyl)amino]pyridin-3-yl}carbonyl)amino]phenyl}-2,2-dimethylpropanoic acid;
methyl 3-{5-[({6-[(ethylcarbamoyl)amino]-4-(phenylamino)pyridin-3-yl}carbonyl)amino]pyridin-2-yl}propanoate;
ethyl (1R,2R)-2-{4-[({6-[(ethylcarbamoyl)amino]-4-(phenylamino)pyridin-3-yl}carbonyl)amino]phenyl}cyclopropanecarboxylate;
3-{4-[({6-[(ethylcarbamoyl)amino]-4-[(3-fluorophenyl)amino]pyridin-3-yl}carbonyl)amino]phenyl}-2,2-dimethylpropanoic acid;
3-{4-[({6-[(ethylcarbamoyl)amino]-4-[(2-fluorophenyl)amino]pyridin-3-yl}carbonyl)amino]phenyl}-2,2-dimethylpropanoic acid;
3-{4-[({4-[(2-chlorophenyl)amino]-6-[(ethylcarbamoyl)amino]pyridin-3-yl}carbonyl)amino]phenyl}-2,2-dimethylpropanoic acid;
3-{4-[({6-[(ethylcarbamoyl)amino]-4-[(4-fluoro-3-methoxyphenyl)amino]pyridin-3-yl}carbonyl)amino]phenyl}-2,2-dimethylpropanoic acid;
4-[(4-chlorophenyl)amino]-6-[(ethylcarbamoyl)amino]-N-[4-(3-hydroxy-3-methylbut-1-yn-1-yl)phenyl]pyridine-3-carboxamide;
3-{4-[({6-[(methylcarbamoyl)amino]-4-(phenylamino)pyridin-3-yl}carbonyl)amino]phenyl}propanoic acid;
3-{4-[({6-[(ethylcarbamoyl)amino]-4-[(2-methoxypyridin-4-yl)amino]pyridin-3-yl}carbonyl)amino]phenyl}-2,2-dimethylpropanoic acid;
3-{4-[({4-[(4-cyanophenyl)amino]-6-[(ethylcarbamoyl)amino]pyridin-3-yl}carbonyl)amino]phenyl}-2,2-dimethylpropanoic acid;

3-[4-[[6-(ethylcarbamoylamino)-4-(3,4,5-trifluoroanilino)pyridine-3-carbonyl]amino]phenyl]propanoic acid;
3-{4-[({6-[(ethylcarbamoyl)amino]-4-[(3-fluoro-4-methoxyphenyl)amino]pyridin-3-yl}carbonyl)amino]phenyl}-2,2-dimethylpropanoic acid;
4-[(4-chlorophenyl)amino]-6-[(ethylcarbamoyl)amino]-N-[4-(pyridin-2-ylethynyl)phenyl]pyridine-3-carboxamide;
(1R,2R)-2-{4-[({4-[(4-chlorophenyl)amino]-6-[(ethylcarbamoyl)amino]pyridin-3-yl}carbonyl)amino]phenyl}cyclopropanecarboxylic acid;
(1R,2R)-2-{4-[({6-[(ethylcarbamoyl)amino]-4-(pyridin-3-ylamino)pyridin-3-yl}carbonyl)amino]phenyl}cyclopropanecarboxylic acid;
N-{4-[4-(aminomethyl)-1H-1,2,3-triazol-1-yl]phenyl}-4-[(4-chloro phenyl)amino]-6-[(ethylcarbamoyl)amino]pyridine-3-carboxamide;
tert-butyl 1-{4-[({6-[(ethylcarbamoyl)amino]-4-(phenylamino)pyridin-3-yl}carbonyl)amino]phenyl}-L-prolinate;
3-(4-{[(6-[(ethylcarbamoyl)amino]-4-{[4-(methoxycarbonyl)phenyl]amino}pyridin-3-yl)carbonyl]amino}phenyl)-2,2-dimethylpropanoic acid;
methyl 1-{4-[({4-[(4-chlorophenyl)amino]-6-[(ethylcarbamoyl)amino]pyridin-3-yl}carbonyl)amino]phenyl}-1H-pyrrole-2-carboxylate;
1-{4-[({6-[(ethylcarbamoyl)amino]-4-(phenylamino)pyridin-3-yl}carbonyl)amino]phenyl}-1H-pyrrole-2-carboxylic acid;
3-{4-[({4-[(3-cyanophenyl)amino]-6-[(ethylcarbamoyl)amino]pyridin-3-yl}carbonyl)amino]phenyl}-2,2-dimethylpropanoic acid;
6-[(ethylcarbamoyl)amino]-4-[(4-fluorophenyl)amino]-N-[4-(pyrrolidin-1-ylmethyl)phenyl]pyridine-3-carboxamide;
6-[(ethylcarbamoyl)amino]-4-[(4-fluorophenyl)amino]-N-[4-(morpholin-4-ylmethyl)phenyl]pyridine-3-carboxamide;
6-[(ethylcarbamoyl)amino]-4-[(4-fluorophenyl)amino]-N-{4-[(4-methylpiperazin-1-yl)methyl]phenyl}pyridine-3-carboxamide;
4-[(4-cyanophenyl)amino]-6-[(ethylcarbamoyl)amino]-N-[4-(pyrrolidin-1-ylmethyl)phenyl]pyridine-3-carboxamide;
4-[(4-cyanophenyl)amino]-6-[(ethylcarbamoyl)amino]-N-[4-(morpholin-4-ylmethyl)phenyl]pyridine-3-carboxamide;
4-[(4-cyanophenyl)amino]-6-[(ethylcarbamoyl)amino]-N-{4-[(4-methylpiperazin-1-yl)methyl]phenyl}pyridine-3-carboxamide;
diethyl {4-[({6-[(ethylcarbamoyl)amino]-4-(phenylamino)pyridin-3-yl}carbonyl)amino]benzyl}phosphonate;
{4-[({6-[(ethylcarbamoyl)amino]-4-(phenylamino)pyridin-3-yl}carbonyl)amino]benzyl}phosphonic acid;
3-{4-[({6-[(ethylcarbamoyl)amino]-4-[(4-methoxyphenyl)amino]pyridin-3-yl}carbonyl)amino]phenyl}-2,2-dimethylpropanoic acid;
4-(3,5-difluoroanilino)-6-(ethylcarbamoylamino)-N-[4-(1H-tetrazol-5-ylmethyl)phenyl]pyridine-3-carboxamide;
6-[(ethylcarbamoyl)amino]-N-{4-[(methylsulfamoyl)methyl]phenyl}-4-(phenylamino)pyridine-3-carboxamide;
5-[(ethylcarbamoyl)amino]-3-(phenylamino)-N-(pyridin-3-yl)pyrazine-2-carboxamide;
6-[(ethylcarbamoyl)amino]-N-phenyl-4-(phenylamino)pyridazine-3-carboxamide;
6-[(ethylcarbamoyl)amino]-N-[4-(methylcarbamoyl)phenyl]-4-(phenylamino)pyridine-3-carboxamide;
N-{4-[(1,1-dioxidothiomorpholin-4-yl)methyl]phenyl}-6-[(ethylcarbamoyl)amino]-4-(phenylamino)pyridine-3-carboxamide;
ethyl 3-{4-[({4-[(3,4-difluorophenyl)amino]-6-[(ethylcarbamoyl)amino]pyridin-3-yl}carbonyl)amino]phenyl}propanoate;
ethyl 3-{4-[({6-[(ethylcarbamoyl)amino]-4-[(3-fluorophenyl)amino]pyridin-3-yl}carbonyl)amino]phenyl}propanoate;
ethyl 3-{4-[({6-[(ethylcarbamoyl)amino]-4-[(3-fluoro-4-methyl phenyl)amino]pyridin-3-yl}carbonyl)amino]phenyl}propanoate;
ethyl 3-{4-[({6-[(ethylcarbamoyl)amino]-4-[(4-fluoro-3-methylphenyl)amino]pyridin-3-yl}carbonyl)amino]phenyl}propanoate;
ethyl 3-{4-[({4-[(4-chloro-2-fluorophenyl)amino]-6-[(ethylcarbamoyl)amino]pyridin-3-yl}carbonyl)amino]phenyl}propanoate;
3-{4-[({4-[(3,4-difluorophenyl)amino]-6-[(ethylcarbamoyl)amino]pyridin-3-yl}carbonyl)amino]phenyl}propanoic acid;
3-{4-[({6-[(ethylcarbamoyl)amino]-4-[(3-fluorophenyl)amino]pyridin-3-yl}carbonyl)amino]phenyl}propanoic acid;
3-{4-[({6-[(ethylcarbamoyl)amino]-4-[(3-fluoro-4-methylphenyl)amino]pyridin-3-yl}carbonyl)amino]phenyl}propanoic acid;
3-{4-[({6-[(ethylcarbamoyl)amino]-4-[(4-fluoro-3-methylphenyl)amino]pyridin-3-yl}carbonyl)amino]phenyl}propanoic acid;
3-{4-[({4-[(4-chloro-2-fluorophenyl)amino]-6-[(ethylcarbamoyl)amino]pyridin-3-yl}carbonyl)amino]phenyl}propanoic acid;
ethyl 3-{4-[({4-[(3,5-dichlorophenyl)amino]-6-[(ethylcarbamoyl)amino]pyridin-3-yl}carbonyl)amino]phenyl}propanoate;
ethyl 3-{4-[({4-[(3-chloro-4-fluorophenyl)amino]-6-[(ethylcarbamoyl)amino]pyridin-3-yl}carbonyl)amino]phenyl}propanoate;
ethyl 3-{4-[({4-[(2,4-difluorophenyl)amino]-6-[(ethylcarbamoyl)amino]pyridin-3-yl}carbonyl)amino]phenyl}propanoate;
3-{4-[({4-[(3,5-dichlorophenyl)amino]-6-[(ethylcarbamoyl)amino]pyridin-3-yl}carbonyl)amino]phenyl}propanoic acid;
3-{4-[({4-[(3-chloro-4-fluorophenyl)amino]-6-[(ethylcarbamoyl)amino]pyridin-3-yl}carbonyl)amino]phenyl}propanoic acid;
3-{4-[({4-[(2,4-difluorophenyl)amino]-6-[(ethylcarbamoyl)amino]pyridin-3-yl}carbonyl)amino]phenyl}propanoic acid;
6-[(ethylcarbamoyl)amino]-4-(phenylamino)-N-(4-sulfamoylphenyl) pyridine-3-carboxamide;
6-[(ethylcarbamoyl)amino]-N-{4-[(methylsulfonyl)amino]phenyl}-4-(phenylamino)pyridine-3-carboxamide;
{3-[({6-[(ethylcarbamoyl)amino]-4-(phenylamino)pyridin-3-yl}carbonyl)amino]-1H-pyrazol-1-yl}acetic acid;
ethyl 3-{4-[({4-[(3,5-difluorophenyl)amino]-6-[(ethylcarbamoyl)amino]pyridin-3-yl}carbonyl)amino]phenyl}propanoate;

3-{4-[({4-[(3,5-difluorophenyl)amino]-6-[(ethylcarbamoyl)amino]pyridin-3-yl}carbonyl)amino]phenyl}propanoic acid;

3-{4-[({6-[(ethylcarbamoyl)amino]-4-[(5-fluoropyridin-3-yl)amino]pyridin-3-yl}carbonyl)amino]phenyl}propanoic acid;

3-(4-{[(6-[(ethylcarbamoyl)amino]-4-{[3-(pentafluorothio)phenyl]amino}pyridin-3-yl)carbonyl]amino}phenyl)propanoic acid;

2-{4-[({4-[(3,5-difluorophenyl)amino]-6-[(ethylcarbamoyl)amino]pyridin-3-yl}carbonyl)amino]phenyl}cyclopropanecarboxylic acid;

3-{4-[({4-[(3,5-difluorophenyl)amino]-6-[(ethylcarbamoyl)amino]pyridin-3-yl}carbonyl)amino]phenyl}-2,2-dimethylpropanoic acid;

3-(4-{[(6-[(ethylcarbamoyl)amino]-4-{[3-(trifluoromethyl)phenyl]amino}pyridin-3-yl)carbonyl]amino}phenyl)propanoic acid;

3-(4-{[(6-[(ethylcarbamoyl)amino]-4-{[3-(trifluoromethoxy)phenyl]amino}pyridin-3-yl)carbonyl]amino}phenyl)propanoic acid;

3-(4-{[(6-[(ethylcarbamoyl)amino]-4-{[4-(trifluoromethoxy)phenyl]amino}pyridin-3-yl)carbonyl]amino}phenyl)propanoic acid;

5-[(ethylcarbamoyl)amino]-3-(phenylamino)-N-(pyridin-3-yl)pyridine-2-carboxamide;

4-[(3,5-difluorophenyl)amino]-6-[(ethylcarbamoyl)amino]-N-[4-(morpholin-4-ylmethyl)phenyl]pyridine-3-carboxamide;

4-[(3,5-difluorophenyl)amino]-N-(4-{[(2R,6S)-2,6-dimethylmorpholin-4-yl]methyl}phenyl)-6-[(ethylcarbamoyl)amino]pyridine-3-carboxamide;

ethyl 3-{4-[({6-[(ethylcarbamoyl)amino]-4-[(2,3,4-trifluorophenyl)amino]pyridin-3-yl}carbonyl)amino]phenyl}propanoate;

ethyl 2-[[4-anilino-6-(ethylcarbamoylamino)pyridine-3-carbonyl]amino]thiazole-4-carboxylate;

4-(4-chloroanilino)-6-(ethylcarbamoylamino)-N-(2-methylpyrimidin-5-yl)pyridine-3-carboxamide;

ethyl 3-[[4-anilino-6-(ethylcarbamoylamino)pyridine-3-carbonyl]amino]benzoate;

1-[[4-[[4-(3,5-difluoroanilino)-6-(ethylcarbamoylamino)pyridine-3-carbonyl]amino]phenyl]methyl]pyrrolidine-2-carboxylic acid; and 1-[[4-[[4-(3,5-difluoroanilino)-6-(ethylcarbamoylamino)pyridine-3-carbonyl]amino]phenyl]methyl]piperidine-2-carboxylic acid;

a racemate, an enantiomer or a salt thereof.

14. An antibacterial agent comprising a compound according to claim 1, a racemate, an enantiomer or a pharmaceutically acceptable salt thereof.

15. A pharmaceutical composition comprising a compound according claim 1, a racemate, an enantiomer or a pharmaceutically acceptable salt thereof and a pharmaceutically acceptable excipient or carrier.

16. A method for the treatment of a bacterial infection comprising administration of a compound according to claim 1, a racemate, an enantiomer or a pharmaceutically acceptable salt thereof, to a subject suffering from said infection.

17. A method of treating bacterial contamination of a substrate comprising applying to the site of such contamination an amount of a compound according to claim 1, a racemate, an enantiomer or pharmaceutically acceptable salt thereof sufficient to inhibit bacterial growth.

18. A process for the manufacture of a compound according to claim 1 via an intermediate of formula (II):

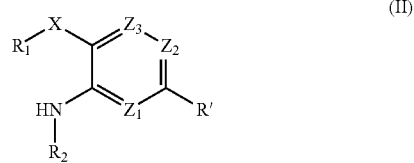

wherein R' is a halo or $NH_2$ group and $R^1$, $R^2$, $Z_1$, $Z_2$, $Z_3$ and X are as defined in claim 1; or via an intermediate of formula (III):

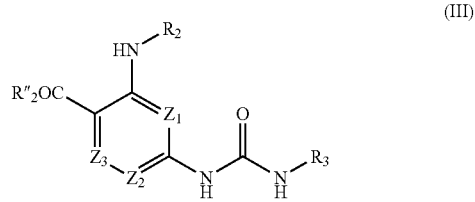

wherein R" is H or $C_{1-6}$alkyl and $R^2$, $R^3$, $Z_1$, $Z_2$ and $Z_3$ are as defined in claim 1; or via an intermediate of formula (IV):

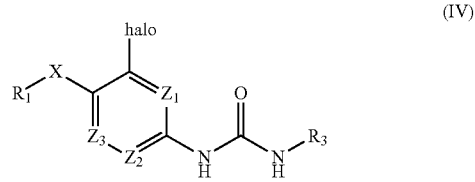

wherein X, $R_1$, $R_3$, $Z_1$, $Z_2$ and $Z_3$ are as defined in claim 1.

* * * * *